(12) United States Patent
Bergeron, Jr.

(10) Patent No.: US 10,570,104 B2
(45) Date of Patent: Feb. 25, 2020

(54) METABOLICALLY PROGRAMMED METAL CHELATORS AND USES THEREOF

(71) Applicant: University of Florida Research Foundation, Incorporated, Gainesville, FL (US)

(72) Inventor: Raymond J. Bergeron, Jr., Gainesville, FL (US)

(73) Assignee: University of Florida Research Foundation, Incorporated, Gainsville, FL (US)

( * ) Notice: Subject to any disclaimer, the term of this patent is extended or adjusted under 35 U.S.C. 154(b) by 0 days.

(21) Appl. No.: 15/569,750

(22) PCT Filed: Apr. 27, 2016

(86) PCT No.: PCT/US2016/029587
§ 371 (c)(1),
(2) Date: Oct. 26, 2017

(87) PCT Pub. No.: WO2016/176343
PCT Pub. Date: Nov. 3, 2016

(65) Prior Publication Data
US 2018/0140581 A1 May 24, 2018

Related U.S. Application Data

(60) Provisional application No. 62/153,468, filed on Apr. 27, 2015.

(51) Int. Cl.
*C07D 277/12* (2006.01)
*C07C 215/50* (2006.01)
*C07C 229/16* (2006.01)
*A61K 31/426* (2006.01)
*C07C 211/54* (2006.01)

(52) U.S. Cl.
CPC .......... *C07D 277/12* (2013.01); *A61K 31/426* (2013.01); *C07C 211/54* (2013.01); *C07C 215/50* (2013.01); *C07C 229/16* (2013.01)

(58) Field of Classification Search
CPC .................................................. C07D 277/12
See application file for complete search history.

(56) References Cited

U.S. PATENT DOCUMENTS

| | | | |
|---|---|---|---|
| 3,274,207 A | 9/1966 | Kollonitsch |
| 3,809,754 A | 5/1974 | Bertrand |
| 3,882,110 A | 5/1975 | Clemence et al. |
| 4,270,537 A | 6/1981 | Romaine |
| 4,367,233 A | 1/1983 | Clark et al. |
| 4,406,905 A | 9/1983 | Zahner et al. |
| 4,457,935 A | 7/1984 | Iwao et al. |
| 4,457,936 A | 7/1984 | Draeger et al. |
| 4,558,059 A | 12/1985 | Kawasaki et al. |
| 4,596,556 A | 6/1986 | Morrow et al. |
| 4,736,060 A | 4/1988 | Tomuro et al. |
| 4,775,675 A | 10/1988 | Gyorgydeak et al. |
| 4,790,824 A | 12/1988 | Morrow et al. |
| 4,829,072 A | 5/1989 | Hamprecht et al. |
| 4,886,499 A | 12/1989 | Cirelli et al. |
| 4,902,700 A | 2/1990 | Hayasi et al. |
| 4,914,208 A | 4/1990 | Jakob et al. |
| 4,940,460 A | 7/1990 | Casey et al. |
| 4,941,880 A | 7/1990 | Burns |
| 5,015,235 A | 5/1991 | Crossman |
| 5,064,413 A | 11/1991 | McKinnon et al. |
| 5,084,083 A | 1/1992 | Lewis et al. |
| 5,106,992 A | 4/1992 | Magnin et al. |
| 5,141,496 A | 8/1992 | Dalto et al. |
| 5,169,858 A | 12/1992 | Rubin |
| 5,182,402 A | 1/1993 | Lewis et al. |
| 5,190,521 A | 3/1993 | Hubbard et al. |
| 5,192,781 A | 3/1993 | Bru-Magniez et al. |

(Continued)

FOREIGN PATENT DOCUMENTS

| | | |
|---|---|---|
| CA | 2728636 A1 | 1/2010 |
| CS | 205217 B1 | 5/1981 |

(Continued)

OTHER PUBLICATIONS

Bergeron et al. J. Med. Chem. 2010, 53, 2843-2853 (Year: 2010).*
[No Author Listed], CHEMCATS, Accession No. 2003:2524667; TimTec Overseas Stock; May 19, 2003.
[No Author Listed], Closed head injury. Wikipedia. http://en.wikipedia.org/wiki/Close_head_injury [last accessed Nov. 28, 2011]. 7 pages.
[No Author Listed], Desferal. Product Information. Novartis Pharmaceuticals Corporation. East Hanover, NJ. 2011. Available at www.pharma.us.novartis.com/product/pi/pdf/desferal.pdf. Last accessed Jan. 25, 2013.

(Continued)

*Primary Examiner* — Matthew P Coughlin
(74) *Attorney, Agent, or Firm* — Wolf, Greenfield & Sacks, P.C.

(57) ABSTRACT

The present invention provides compounds of Formula (I), which are "metabolically programmed" metal chelators, e.g., lipophilic, absorbable (e.g., orally absorbable), and effective metal chelators that are converted in vivo to their hydrophilic, nontoxic metabolites. The present invention also provides compounds of Formula (II), which are also "metabolically programmed" metal chelators. The invention also provides pharmaceutical compositions, kits, methods, and uses that include a compound described herein. The compounds, pharmaceutical compositions, kits, and methods may be useful in treating or preventing a disease (e.g., metal overload, oxidative stress, diabetes, liver disease, heart disease, cancer, radiation injury, neurological or neurodegenerative disorder, Friedreich's ataxia (FRDA), macular degeneration, closed head injury, irritable bowel disease, reperfusion injury, metal poisoning, or infectious disease).

20 Claims, 18 Drawing Sheets

(56) References Cited

U.S. PATENT DOCUMENTS

| | | | |
|---|---|---|---|
| 5,312,335 A | 5/1994 | McKinnon et al. |
| 5,328,483 A | 7/1994 | Jacoby |
| 5,334,144 A | 8/1994 | Alchas et al. |
| 5,339,163 A | 8/1994 | Homma et al. |
| 5,383,851 A | 1/1995 | McKinnon, Jr. et al. |
| 5,385,922 A | 1/1995 | Bron et al. |
| 5,393,777 A | 2/1995 | Crosa |
| 5,417,662 A | 5/1995 | Hjertman et al. |
| 5,442,073 A | 8/1995 | Eicken et al. |
| 5,466,220 A | 11/1995 | Brenneman |
| 5,480,381 A | 1/1996 | Weston |
| 5,503,627 A | 4/1996 | McKinnon et al. |
| 5,520,639 A | 5/1996 | Peterson et al. |
| 5,527,288 A | 6/1996 | Gross et al. |
| 5,569,189 A | 10/1996 | Parsons |
| 5,599,302 A | 2/1997 | Lilley et al. |
| 5,614,520 A | 3/1997 | Kondo et al. |
| 5,649,912 A | 7/1997 | Peterson |
| 5,704,911 A | 1/1998 | Parsons |
| 5,840,739 A | 11/1998 | Bergeron, Jr. |
| 5,893,397 A | 4/1999 | Peterson et al. |
| 5,993,412 A | 11/1999 | Deily et al. |
| 6,080,764 A | 6/2000 | Chihiro et al. |
| 6,083,966 A | 7/2000 | Bergeron, Jr. |
| 6,147,070 A | 11/2000 | Facchini |
| 6,159,983 A | 12/2000 | Bergeron, Jr. |
| 6,251,927 B1 | 6/2001 | Lai et al. |
| 6,373,912 B1 | 4/2002 | Yu |
| 6,437,143 B2 | 8/2002 | Moinet et al. |
| 6,521,652 B1 | 2/2003 | Bergeron |
| 6,525,080 B1 | 2/2003 | Bergeron |
| 6,559,315 B1 | 5/2003 | Bergeron |
| 6,864,270 B2 | 3/2005 | Bergeron, Jr. |
| RE39,132 E | 6/2006 | Bergeron, Jr. |
| 7,126,004 B2 | 10/2006 | Bergeron |
| 7,144,904 B2 | 12/2006 | Bergeron, Jr. |
| 7,531,563 B2 | 5/2009 | Bergeron |
| 7,879,886 B2 | 2/2011 | Bergeron, Jr. |
| 8,008,502 B2 | 8/2011 | Bergeron |
| 8,063,227 B2 | 11/2011 | Tapper et al. |
| 8,278,458 B2 * | 10/2012 | Bergeron, Jr. | C07D 277/10 548/201 |
| 8,324,397 B2 * | 12/2012 | Bergeron, Jr. | A61K 31/426 548/201 |
| 8,604,216 B2 | 12/2013 | Bergeron, Jr. |
| 8,722,899 B2 * | 5/2014 | Bergeron, Jr. | C07D 277/10 548/201 |
| 9,096,553 B2 * | 8/2015 | Bergeron, Jr. | C07D 277/10 |
| 9,174,948 B2 * | 11/2015 | Bergeron, Jr. | A61K 31/426 |
| 9,567,309 B2 * | 2/2017 | Bergeron, Jr. | C07D 277/10 |
| 9,730,917 B2 * | 8/2017 | Bergeron, Jr. | A61K 31/426 |
| 9,994,535 B2 * | 6/2018 | Bergeron, Jr. | C07D 277/10 |
| 2002/0049316 A1 | 4/2002 | Halbert et al. |
| 2003/0083349 A1 | 5/2003 | Bergeron, Jr. |
| 2003/0236417 A1 | 12/2003 | Bergeron |
| 2004/0044220 A1 | 3/2004 | Bergeron, Jr. |
| 2004/0132789 A1 | 7/2004 | Bergeron, Jr. |
| 2005/0033057 A1 | 2/2005 | Bergeron |
| 2005/0234113 A1 | 10/2005 | Bergeron, Jr. |
| 2006/0211746 A1 | 9/2006 | Bergeron, Jr. |
| 2006/0211773 A1 | 9/2006 | Bergeron, Jr. |
| 2007/0238767 A1 | 10/2007 | Bergeron |
| 2008/0096974 A2 | 4/2008 | Bergeron, Jr. |
| 2008/0194518 A1 | 8/2008 | Mookerjee et al. |
| 2008/0214630 A1 | 9/2008 | Bergeron |
| 2008/0255081 A1 | 10/2008 | Bergeron, Jr. |
| 2010/0093812 A1 | 4/2010 | Bergeron, Jr. |
| 2010/0094016 A1 | 4/2010 | Bergeron |
| 2010/0137346 A1 | 6/2010 | Bergeron, Jr. |
| 2010/0137383 A1 * | 6/2010 | Tapper | C07D 277/12 514/365 |
| 2011/0053993 A1 | 3/2011 | McCall, Jr. et al. |
| 2011/0275636 A1 | 11/2011 | Malecha |
| 2012/0184586 A1 * | 7/2012 | Bergeron, Jr. | C07D 277/12 514/365 |
| 2013/0030028 A1 | 1/2013 | Bergeron, Jr. |
| 2013/0210870 A1 | 8/2013 | Bergeron, Jr. |
| 2014/0235680 A1 | 8/2014 | Bergeron, Jr. |
| 2014/0323534 A1 | 10/2014 | Bergeron, Jr. |
| 2014/0343110 A1 | 11/2014 | Bergeron, Jr. |
| 2015/0336911 A1 | 11/2015 | Bergeron, Jr. |
| 2016/0022645 A1 | 1/2016 | Bergeron, Jr. |
| 2016/0289223 A1 | 10/2016 | Bergeron |
| 2017/0209420 A1 | 7/2017 | Bergeron |
| 2017/0217912 A1 | 8/2017 | Bergeron |
| 2018/0290990 A1 | 10/2018 | Bergeron, Jr. |

FOREIGN PATENT DOCUMENTS

| | | |
|---|---|---|
| DE | 2245560 A1 | 3/1974 |
| DE | 3002989 A1 | 7/1981 |
| EP | 0 214 101 A2 | 3/1987 |
| EP | 0 214 933 A2 | 3/1987 |
| EP | 0 325 559 A2 | 7/1989 |
| EP | 0 513 379 A1 | 11/1992 |
| EP | 2062581 A1 | 5/2009 |
| FR | 2247243 A2 | 5/1975 |
| GB | 1292170 A | 10/1972 |
| GB | 1320534 A | 6/1973 |
| GB | 1382887 A | 2/1975 |
| JP | 57-058682 A | 4/1982 |
| JP | 2002-523500 | 7/2002 |
| JP | 2008-536833 A | 9/2008 |
| JP | 2010-521471 A | 6/2010 |
| JP | 2011-528037 | 11/2011 |
| JP | 2013-500342 A | 1/2013 |
| JP | 2013-503160 | 1/2013 |
| JP | 2013-525495 | 6/2013 |
| JP | 5909473 B2 | 4/2016 |
| WO | WO 94/11367 A1 | 5/1994 |
| WO | WO 97/13537 A1 | 4/1997 |
| WO | WO 97/36885 A1 | 10/1997 |
| WO | WO 97/37705 A1 | 10/1997 |
| WO | WO 99/34850 A1 | 7/1999 |
| WO | WO 99/53039 A1 | 10/1999 |
| WO | WO 2000/012493 A1 | 3/2000 |
| WO | WO 2000/016763 A2 | 3/2000 |
| WO | WO 2001/027119 A2 | 4/2001 |
| WO | WO 2003/078467 A1 | 9/2003 |
| WO | WO 2004/017959 A2 | 3/2004 |
| WO | WO 2005/023310 A2 | 3/2005 |
| WO | WO 2005/034949 A1 | 4/2005 |
| WO | WO 2006/055412 A1 | 5/2006 |
| WO | WO 2006/107626 A1 | 10/2006 |
| WO | WO 2008/115433 A1 | 9/2008 |
| WO | WO 2008/130395 A2 | 10/2008 |
| WO | WO 2009/053628 A2 | 4/2009 |
| WO | WO 2010/009120 A2 | 1/2010 |
| WO | WO 2011/017054 A2 | 2/2011 |
| WO | WO 2011/028255 A2 | 3/2011 |
| WO | WO-2011028255 A2 * | 3/2011 | C07D 277/12 |
| WO | WO 2012/027794 A2 | 3/2012 |
| WO | WO 2013/086312 | 6/2013 |
| WO | WO 2013/090750 A1 | 6/2013 |
| WO | WO 2013/090766 A1 | 6/2013 |
| WO | WO 2014/134701 A1 | 9/2014 |

OTHER PUBLICATIONS

[No Author Listed], Highlights of Prescribing Information: EXJADE. Novartis Pharma Stein AG. 2010. Available at http://www.pharma.us.novartis.com/product/pi/pdf/exjade.pdf. Last accessed Sep. 9, 2010. 14 pages.

[No Author Listed], Ion exchanger. Ullmanns Encyclopedia of Industrial Chemistry. 5th Ed. vol. 14A:446-56.

[No Author Listed], Irritable bowel syndrome. Wikipedia. http://en.wikipedia.org/wiki/Irritable_bowel_syndrome [last accessed Nov. 28, 2011]. 24 pages.

[No Author Listed], Macular degeneration. Wikipedia. http://en.wikipedia.org/wiki/Macular_degeneration [last accessed Nov. 28, 2011]. 14 pages.

(56) References Cited

OTHER PUBLICATIONS

[No Author Listed], Reperfusion injury. Wikipedia. http://en.wikipedia.org/wiki/Reperfusion_injury [last accessed Nov. 28, 2011]. 7 pages.
[No Author Listed], Stroke. Wikipedia. http://en.wikipedia.org/wiki/Stroke [last accessed Nov. 28, 2011]. 29 pages.
Abergel et al., Anthrax pathogen evades the mammalian immune system through stealth siderophore production. Proc Natl Acad Sci U S A. Dec. 5, 2006;103(49):18499-503. Epub Nov. 28, 2006.
Allgayer, Clinical relevance of oxygen radicals in inflammatory bowel disease—facts and fashion. Klin Wochenschr. Dec. 15, 1991;69(21-23):1001-3.
Al-Refaie et al., Zinc concentration in patients with iron overload receiving oral iron chelator 1,2-dimethyl-3-hydroxypyrid-4-one or desferrioxamine. J Clin Pathol. 1994;47:657-60.
Anderegg et al., Metal Complex Formation of a New Siderophore Desferrithiocin and of Three Related Ligands. J Chem Soc Chem Commun. 1990:1194-6.
Andrews et al., Iron homeostasis. Annu Rev Physiol. 2007;69:69-85.
Angelucci et al., Hepatic iron concentration and total body iron stores in thalassemia major. N Engl J Med. Aug. 3, 2000;343(5):327-31.
Babbs et al., Oxygen radicals in ulcerative colitis. Free Radic Biol Med. 1992;13(2):169-81.
Bailly et al., Shedding of kidney injury molecule-1, a putative adhesion protein involved in renal regeneration. J Biol Chem. Oct. 18, 2002;277(42):39739-48. Epub Jul. 23, 2002.
Baker et al., Desferrithiocin is an effective iron chelator in vivo and in vitro but ferrithiocin is toxic. Br J Haematol. Jul. 1992;81(3):424-31.
Barman-Balfour et al., Deferiprone: a review of its clinical potential in iron overload in beta-thalassaemia major and other transfusion-dependent diseases. Drugs. Sep. 1999;58(3):553-78.
Bartakke et al., Effect of Deferiprone on Urinary Zinc Excretion in Multiply Transfused Children with Thalassemia Major. Ind Ped. Feb. 17, 2005;42:150-4.
Bauer et al., Iron Complexes in Organic Chemistry. Ed:Plietker. 2008;1-27.
Bedford et al., Iron chelation in the treatment of cancer: a new role for deferasirox? J Clin Pharmacol. Sep. 2013;53(9):885-91. doi: 10.1002/jcph.113. Epub Jun. 6, 2013.
Berge et al., Pharmaceutical salts. J Pharm Sci. Jan. 1977;66(1):1-19.
Bergeron et al., (S)-4,5-dihydro-2-(2-hydroxy-4-hydroxyphenyl)-4-methyl-4-thiazolecarboxylic acid polyethers: a solution to nephrotoxicity. J Med Chem. May 4, 2006;49(9):2772-83.
Bergeron et al., A comparative evaluation of iron clearance models. Ann N Y Acad Sci. 1990;612:378-93.
Bergeron et al., A comparative study of the iron-clearing properties of desferrithiocin analogues with desferrioxamine B in a Cebus monkey model. Blood. Apr. 15, 1993;81(8):2166-73.
Bergeron et al., A comparison of the iron-clearing properties of 1,2-dimethyl-3-hydroxypyrid-4-one, 1,2-diethyl-3-hydroxypyrid-4-one, and deferoxamine. Blood. Apr. 1, 1992;79(7):1882-90.
Bergeron et al., An efficient total synthesis of Desferrioxamine B. J Organic Chemistry. 1988;53(14):3131-3134.
Bergeron et al., An investigation of desferrithiocin metabolism. J Med Chem. Sep. 2, 1994;37(18):2889-95.
Bergeron et al., Comparison of iron chelator efficacy in iron-overloaded beagle dogs and monkeys (*Cebus apella*). Comp Med. Dec. 2004;54(6):664-72.
Bergeron et al., Desazadesmethyldesferrithiocin Analogues as Orally Effective Iron Chelators. J Med Chem. 1999;42:95-108.
Bergeron et al., Desferrithiocin analogue based hexacoordinate iron(III) chelators. J Med Chem. Jan. 2, 2003;46(1):16-24.
Bergeron et al., Desferrithiocin analogue iron chelators: iron clearing efficiency, tissue distribution, and renal toxicity. Biometals. Apr. 2011;24(2):239-58. Epub Nov. 20, 2010.
Bergeron et al., Desferrithiocin analogue uranium decorporation agents. Int J Radiat Biol. Apr. 2009;85(4):348-61.
Bergeron et al., Desferrithiocin analogues and nephrotoxicity. J Med Chem. Oct. 9, 2008;51(19):5993-6004. Epub Sep. 13, 2008.
Bergeron et al., Desferrithiocin: a search for clinically effective iron chelators. J Med Chem. Nov. 26, 2014;57(22):9259-91. doi:10.1021/jm500828f. Epub Sep. 10, 2014.
Bergeron et al., Design, synthesis, and testing of non-nephrotoxic desazadesferrithiocin polyether analogues. J Med Chem. Jul. 10, 2008;51(13):3913-23. Epub Jun. 6, 2008.
Bergeron et al., Design, Synthesis, and Testing of Polyamine Vectored Iron Chelators. Synthesis (Stuttg). 2010;2010(21):3631-3636.
Bergeron et al., Effects of C-4 stereochemistry and C-4' hydroxylation on the iron clearing efficiency and toxicity of desferrithiocin analogues. J Med Chem. Jul. 1, 1999;42(13):2432-40.
Bergeron et al., Evaluation of desferrithiocin and its synthetic analogues as orally effective iron chelators. J Med Chem. Jul. 1991;34(7):2072-8.
Bergeron et al., Evaluation of the desferrithiocin pharmacophore as a vector for hydroxamates. J Med Chem. Jul. 29, 1999;42(15):2881-6.
Bergeron et al., HBED: A Potential Alternative to Deferoxamine for Iron-Chelating Therapy. Blood. 1998;91:1446-52.
Bergeron et al., Impact of the 3,6,9-Trioxadecyloxy Group on Desazadesferrithiocin Analogue Iron Clearance and Organ Distribution. J Med Chem. Jul. 12, 2007;50(14):3302-13. Epub Jun. 12, 2007.
Bergeron et al., Impact of the Lipophilicity of Desferrithiocin Analogues on Iron Clearance. Medicinal Inorg Chem. 2005:366-83.
Bergeron et al., Influence of iron on in vivo proliferation and lethality of L1210 cells. J Nutr. Mar. 1985;115(3):369-74.
Bergeron et al., Iron chelation promoted by desazadesferrithiocin analogs: An enantioselective barrier. Chirality. Aug. 2003;15(7):593-9.
Bergeron et al., Iron Chelators and Therapeutic Uses. In: Burger's Medicinal Chemistry, 6th ed. 2003:479-561.
Bergeron et al., Metabolism and pharmacokinetics of N1,N11-diethylnorspermine in a Cebus apella primate model. Cancer Res. Aug. 15, 2000;60(16):4433-9.
Bergeron et al., Metabolism and pharmacokinetics of N1,N14-diethylhomospermine. Drug Metab Dispos. Mar. 1996;24(3):334-43.
Bergeron et al., Methoxylation of desazadesferrithiocin analogues: enhanced iron clearing efficiency. J Med Chem. Apr. 10, 2003;46(8):1470-7.
Bergeron et al., Partition-variant desferrithiocin analogues: organ targeting and increased iron clearance. J Med Chem. Feb. 10, 2005;48(3):821-31.
Bergeron et al., Pharmacokinetics of orally administered desferrithiocin analogs in cebus apella primates. Drug Metab Dispos. Dec. 1999;27(12):1496-8.
Bergeron et al., Polyamine-vectored iron chelators: the role of charge. J Med Chem. Jun. 16, 2005;48(12):4120-37.
Bergeron et al., Prevention of acetic acid-induced colitis by desferrithiocin analogs in a rat model. Dig Dis Sci. Feb. 2003;48(2):399-407.
Bergeron et al., Structure-activity relationships among desazadesferrithiocin analogues. In: Iron Chelation Therapy. Hershko, ed. 2002:167-84.
Bergeron et al., Substituent effects on desferrithiocin and desferrithiocin analogue iron-clearing and toxicity profiles. J Med Chem. Aug. 23, 2012;55(16):7090-103. doi: 10.1021/jm300509y. Epub Aug. 13, 2012.
Bergeron et al., Synthesis and biological evaluation of hydroxamate-based iron chelators. J Med Chem. Nov. 1991;34(11):3182-7.
Bergeron et al., Synthesis and biological evaluation of naphthyldesferrithiocin iron chelators. J Med Chem. Apr. 12, 1996;39(8):1575-81.
Bergeron et al., Synthesis of heterobactins A and B and Nocardia heterobactin. Tetrahedron. 2011:67(18):3163-69.
Bergeron et al., The desferrithiocin pharmacophore. J Med Chem. May 13, 1994;37(10):1411-7.
Bergeron et al., The design, synthesis, and evaluation of organ-specific iron chelators. J Med Chem. Nov. 30, 2006;49(24):7032-43.

(56) References Cited

OTHER PUBLICATIONS

Bergeron et al., The impact of polyether chain length on the iron clearing efficiency and physiochemical properties of desferrithiocin analogues. J Med Chem. Apr. 8, 2010;53(7):2843-53.
Bergeron et al., The origin of the differences in (R)- and (S)-desmethyldesferrithiocin. Iron-clearing properties. Ann N Y Acad Sci. Jun. 30, 1998;850:202-16.
Bergeron et al., Vibriobactin antibodies: a vaccine strategy. J Med Chem. Jun. 25, 2009;52(12):3801-13.
Bergeron, Desferrithiocin Polyether Analogue Uranium Decorporation Agents. Quad Chart and White Paper. Research Area #4 Radiological/Nuclear Threat Medical Countermeasures. Barda CBRN BAA-11-100-SOL-00009. Oct. 27, 2011. 17 pages.
Bergeron, Iron: A Controlling Nutrient in Proliferative Processes. Trends in Biochem Sci. 1986;11:133-36.
Bickel et al., [Metabolic Properties of Actinomycetes.] Ferrioxamine B. Helv Chim Acta. 1960;43:2129-38. German.
Bierer et al., The effect of desferrithiocin, an oral iron chelator, on T-cell function. Blood. Nov. 15, 1990;76(10):2052-9.
Boddaert et al., Selective iron chelation in Friedreich ataxia: biologic and clinical implications. Blood. Jul. 1, 2007;110(1):401-8. Epub Mar. 22, 2007.
Bolli et al., Iron-mediated radical reactions upon reperfusion contribute to myocardial "stunning". Am J Physiol. Dec. 1990;259(6 Pt 2):H1901-11.
Bonkovsky et al., Iron-induced liver injury. Clin Liver Dis. May 2000;4(2):409-29, vi-vii.
Bonventre, Kidney injury molecule-1 (KIM-1): a urinary biomarker and much more. Nephrol Dial Transplant. Nov. 2009;24(11):3265-8. doi: 10.1093/ndt/gfp010. Epub Mar. 23, 2009.
Brissot et al., Non-transferrin bound iron: a key role in iron overload and iron toxicity. Biochim Biophys Acta. Mar. 2012;1820(3):403-10. doi: 10.1016/j.bbagen.2011.07.014. Epub Aug. 9, 2011.
Brittenham et al., Efficacy of deferoxamine in preventing complications of iron overload in patients with thalassemia major. N Engl J Med. Sep. 1, 1994;331(9):567-73.
Brittenham, Disorders of Iron Metabolism: Iron Deficiency and Overload. In: Hermatology: Basic Principles and Practice. 3d Ed. Hoffman et al., eds., Churchill Livingston. New York. 2000:397-428.
Brittenham, Iron chelators and iron toxicity. Alcohol. Jun. 2003;30(2):151-8.
Brittenham, Pyridoxal isonicotinoyl hydrazone. Effective iron chelation after oral administration. Ann N Y Acad Sci. 1990;612:315-26.
Brittenham, Pyridoxal isonicotinoyl hydrazone: an effective iron-chelator after oral administration. Semin Hematol. Apr. 1990;27(2):112-6.
Brunner et al., Carboplatin-containing Porphyrin-platinum Complexes as Cytotoxic and Phototoxic Antitumor Agents. Inorg Chim Acta. 2004;357:4423-51.
Budimir, Metal ions, Alzheimer's disease and chelation therapy. Acta Pharm. Mar. 2011;61(1):1-14. doi: 10.2478/v10007-011-0006-6.
Byers et al., Microbial iron transport: iron acquisition by pathogenic microorganisms. Met Ions Biol Syst. 1998;35:37-66.
Caira, Crystalline Polymorphism of Organic Compounds. Topics in Current Chemistry. 1998;198:163-208.
Cappellini et al., Oral iron chelators. Annu Rev Med. 2009;60:25-38. doi: 10.1146/annurev.med.60.041807.123243.
Cappellini, Iron-chelating therapy with the new oral agent ICL670 (Exjade). Best Pract Res Clin Haematol. Jun. 2005;18(2):289-98.
Cario et al., Insulin sensitivity and beta-cell secretion in thalassaemia major with secondary haemochromatosis: assessment by oral glucose tolerance test. Eur J Pediatr. Mar. 2003;162(3):139-46. Epub Jan. 15, 2003.
Cavaliere et al., The biofilm matrix destabilizers, EDTA and DNaseI, enhance the susceptibility of nontypeable *Hemophilus influenzae* biofilms to treatment with ampicillin and ciprofloxacin. Microbiologyopen. Aug. 2014;3(4):557-67. doi: 10.1002/mbo3.187. Epub Jul. 6, 2014.
Chua et al., Nontransferrin-bound iron uptake by hepatocytes is increased in the Hfe knockout mouse model of hereditary hemochromatosis. Blood. Sep. 1, 2004;104(5):1519-25. Epub May 20, 2004.
Conrad et al., Iron absorption and transport. Am J Med Sci. Oct. 1999;318(4):213-29.
Cragg et al., The iron chelator L1 potentiates oxidative DNA damage in iron-loaded liver cells. Blood. Jul. 15, 1998;92(2):632-8.
Cunningham et al., New developments in iron chelators. Curr Opin Hematol. Mar. 2005;12(2):129-34.
Dean et al., The Action of Nine Chelators on Iron-Dependent Radical Damage. Free Rad Res. 1994;20(2):83-101.
Dolakova et al., Synthesis of Analogues of Acyclic Nucleoside Diphosphates Containing a (Phosphonomethyl)phosphanyl Moiety and Studies of Their Phosphorylation. EurJOC. 2009;1082-1092.
Domingo et al., Comparative effects of the chelators sodium 4,5-dihydroxybenzene-1,3-disulfonate (Tiron) and diethylenetriaminepentaacetic acid (DTPA) on acute uranium nephrotoxicity in rats. Toxicology. Mar. 14, 1997;118(1):49-59.
Donovan et al., Preclinical and clinical development of deferitrin, a novel, orally available iron chelator. Ann N Y Acad Sci. 2005;1054:492-4.
Dunaief et al., Macular degeneration in a patient with aceruloplasminemia, a disease associated with retinal iron overload. Ophthalmology. Jun. 2005;112(6):1062-5.
Dunaief, Iron induced oxidative damage as a potential factor in age-related macular degeneration: the Cogan Lecture. Invest Ophthalmol Vis Sci. Nov. 2006;47(11):4660-4.
Durbin et al., Chelating agents for uranium(VI): 2. Efficacy and toxicity of tetradentate catecholate and hydroxypyridinonate ligands in mice. Health Phys. May 2000;78(5):511-21.
Durbin et al., In Vivo Chelation of Am(III), Pu(IV), Np(V), and U(VI) in Mice by TREN-(Me-3,2-HOPO). Radiat Prot Dosimetry. 1994;53:305-09.
Durbin, Lauriston S. Taylor Lecture: the quest for therapeutic actinide chelators. Health Phys. Nov. 2008;95(5):465-92.
Farcasiu et al., Geometrical inversion of methoxymethyl cations. J Chem Soc Chem Commun. 1979;24:1124-5.
Farkas et al., Structure-based differences between the metal ion selectivity of two siderophores desferrioxamine B (DFB) and desferricoprogen (DFC): Why DFC is much better Pb(II) sequestering agent than DFB? J Inorg Biochem. 2008;102;1654-9.
Feau et al., Preparation and Optical Properties of Novel 3-Alkoxycarbonyl Aza- and Diazacoumarins. Synth Commun. 2010;40:3033-45.
Fedorak et al., Misoprostol provides a colonic mucosal protective effect during acetic acid-induced colitis in rats. Gastroenterology. Mar. 1990;98(3):615-25.
Finch et al., Ferrokinetics in man. Medicine (Baltimore). Jan. 1970;49(1):17-53.
Finch et al., Iron metabolism. Clin Physiol Biochem. 1986;4(1):5-10.
Finch et al., Perspectives in iron metabolism. N Engl J Med. Jun. 24, 1982;306(25):1520-8.
Fossheim et al., Lanthanide-based susceptibility contrast agents: assessment of the magnetic properties. Magn Reson Med. Feb. 1996;35(2):201-6.
Fritsch et al., Plasmodium falciparum: inhibition in vitro with lactoferrin, desferriferrithiocin, and desferricrocin. Exp Parasitol. Feb. 1987;63(1):1-9.
Fukuda, Chelating agents used for plutonium and uranium removal in radiation emergency medicine. Curr Med Chem. 2005;12(23):2765-70.
Galanello et al., A dose escalation study of the pharmacokinetics, safety & efficacy of deferitrin, an oral iron chelator in beta thalassaemia patients. ASH Annu Meet Abstr. 2007;110: Abstract 2669.
Galanello et al., Safety, tolerability, and pharmacokinetics of ICL670, a new orally active iron-chelating agent in patients with transfusion-dependent iron overload due to beta-thalassemia. J Clin Pharmacol. Jun. 2003;43(6):565-72.

(56) References Cited

OTHER PUBLICATIONS

Galey et al., N,N'-bis-(3,4,5-trimethoxybenzyl) ethylenediamine N,N'-diacetic acid as a new iron chelator with potential medicinal applications against oxidative stress. Biochem Pharmacol. Jan. 26, 1996;51(2):103-15.
Ganguly et al., Antiviral activity of isoquinolines carbazoles and other miscellaneous synthetic chemicals in mice. Indian J Med Res. Oct. 1975;63(10):1418-25.
Gaudana et al., Ocular drug delivery. AAPS J. Sep. 2010;12(3):348-60. doi: 10.1208/s12248-010-9183-3. Epub May 1, 2010.
Gershon et al., Antifungal activity of 5-, 7-, and 5,7-substituted 2-methyl-8-quinolinols. Antimicrob Agents Chemother. May 1972;1(5):373-5.
Giardina et al., Chelation therapy in beta-thalassemia: an optimistic update. Semin Hematol. Oct. 2001;38(4):360-6.
Gkouvatsos et al., Regulation of iron transport and the role of transferrin. Biochim Biophys Acta. Mar. 2012;1820(3):188-202. doi: 10.1016/j.bbagen.2011.10.013. Epub Nov. 4, 2011.
Golub et al., Molecular classification of cancer: class discovery and class prediction by gene expression monitoring. Science. Oct. 15, 1999;286(5439):531-7.
Goodsaid et al., Novel biomarkers of acute kidney toxicity. Clin Pharmacol Ther. Nov. 2009;86(5):490-6. doi: 10.1038/clpt.2009.149. Epub Aug. 26, 2009.
Gorden et al., Rational design of sequestering agents for plutonium and other actinides.Chem Rev. Nov. 2003;103(11):4207-82.
Grady et al., HBED: a potential oral iron chelator. Ann N Y Acad Sci. 1990;612:361-8.
Grady et al., Rhodotorulic acid—investigation of its potential as an iron-chelating drug. J Pharmacol Exp Ther. Jun. 1979;209(3):342-8.
Graf et al., Iron-catalyzed hydroxyl radical formation. Stringent requirement for free iron coordination site. J Biol Chem. Mar. 25, 1984;259(6):3620-4.
Grisham et al., Neutrophil-mediated mucosal injury. Role of reactive oxygen metabolites. Dig Dis Sci. Mar. 1988;33(3 Suppl):6S-15S.
Guilmette et al., Competitive binding of Pu and Am with bone mineral and novel chelating agents. Radiat Prot Dosimetry. 2003;105(1-4):527-34.
Guterman et al., Feasibility of enterochelin as an iron-chelating drug: studies with human serum and a mouse model system. Gen Pharmacol. 1978;9(2):123-7.
Hadziahmetovic et al., The oral iron chelator deferiprone protects against iron overload-induced retinal degeneration. Invest Ophthalmol Vis Sci. Feb. 16, 2011;52(2):959-68. doi: 10.1167/iovs.10-6207.
Hahn et al., Coordination Chemistry of Microbial Iron Transport. 42. Structural and Spectroscopic Characterization of Diastereomeric Cr(III) and Co(III) Complexes of Desferriferrithiocin. J Am Chem Soc. 1990;112:1854-60.
Hallberg, Bioavailability of dietary iron in man. Ann Rev Nutr. 1981;1:123-47.
Halliwell, Free radicals and antioxidants: a personal view. Nutr Rev. Aug. 1994;52(8 Pt 1):253-65.
Halliwell, Iron, Oxidative Damage and Chelating Agents. In: The Development of Iron Chelators for Clinical Use, Bergeron, ed. 1994:33-56.
Han et al., Kidney Injury Molecule-1 (KIM-1): a novel biomarker for human renal proximal tubule injury. Kidney Int. Jul. 2002;62(1):237-44.
Hazen et al., Human neutrophils employ the myeloperoxidase-hydrogen peroxide-chloride system to oxidize alpha-amino acids to a family of reactive aldehydes. Mechanistic studies identifying labile intermediates along the reaction pathway. J Biol Chem. Feb. 27, 1998;273(9):4997-5005.
He et al., A fluorescent chemosensor for calcium with excellent storage stability in water. Anal Chim Acta. Mar. 24, 2008;611(2):197-204. doi:10.1016/j.aca.2008.01.059. Epub Feb. 2, 2008.
Henry, Chemotherapeutic nitroheterocycles. Derivatives of 5-nitrothiazole-2-carboxaldehyde and 5-nitrothiazole-2-carboxylic acid. J Med Chem. Mar. 1969;12(2):303-6.

Hoffbrand et al., Long-term trial of deferiprone in 51 transfusion-dependent iron overloaded patients. Blood. Jan. 1, 1998;91(1):295-300.
Hoffbrand, Transfusion Siderosis and Chelation Therapy. Iron in Biochemistry and Medicine. vol. II. London. 1980: 449-527.
Hoffmann et al., Evaluation of a urinary kidney biomarker panel in rat models of acute and subchronic nephrotoxicity. Toxicology. Nov. 9, 2010;277(1-3):49-58. doi: 10.1016/j.tox.2010.08.013. Epub Sep. 9, 2010.
Horackova et al., The antioxidant effects of a novel iron chelator salicylaldehyde isonicotinoyl hydrazone in the prevention of H(2)O(2) injury in adult cardiomyocytes. Cardiovasc Res. Aug. 18, 2000;47(3):529-36.
Hua et al., Long-term effects of experimental intracerebral hemorrhage: the role of iron. J Neurosurg. Feb. 2006;104(2):305-12.
Iranmanesh et al., Chelation of chromium(VI) by combining deferasirox and deferiprone in rats. Biometals. 2013;26:465-71.
Jalal et al., Structure of Anguibactin, a Unique Plasmid-Related Bacterial Siderophore from the Fish Pathogen *Vibrio anguillarum*. J Am Chem Soc. 1989;111(1):292-96.
Jarvis et al., Some correlations involving the stability of complexes of transuranium metal ions and ligands with negatively charged oxygen donors. Inorg Chim Acta. 1991;182:229-32.
Jomova et al., Advances in metal-induced oxidative stress and human disease. Toxicology. May 10, 2011;283(2-3):65-87. doi: 10.1016/j.tox.2011.03.001. Epub Mar. 23, 2011.
Joo Suk, Paradoxical hypomagnesemia caused by excessive ingestion of magnesium hydroxide. Am J Emerg Med. Sep. 2008;26(7):837.e1-2. doi:10.1016/j.ajem.2008.01.030.
Kalinowski et al., The evolution of iron chelators for the treatment of iron overload disease and cancer. Pharmacol Rev. Dec. 2005;57(4):547-83.
Kem et al., Hydroxy metabolites of the Alzheimer's drug candidate 3-[(2,4-dimethoxy)benzylidene]-anabaseine dihydrochloride (GTS-21): their molecular properties, interactions with brain nicotinic receptors, and brain penetration. Mol Pharmacol. Jan. 2004;65(1):56-67.
Kersten et al., Long-term treatment of transfusional iron overload with the oral iron chelator deferiprone (L1): a Dutch multicenter trial. Ann Hematol. Nov. 1996;73(5):247-52.
Kicic et al., The desferrithiocin (DFT) class of iron chelators: potential as antineoplastic agents. Anticancer Drug Des. Aug.-Oct. 2001;16(4-5):195-207.
Kishore et al., Synthesis of α-Poly-[Nε-2-aryl-Δ2-thiazoline-4-carbonyl-L-lysine] with Antival Activity. Ind J Chem. 1977;15B:255-57.
Kitazawa et al., Reduction of ultraviolet light-induced oxidative stress by amino acid-based iron chelators. Biochim Biophys Acta. Dec. 27, 1999;1473(2-3):400-8.
Kitto et al., Post-modification of Helical Dipeptido Polyisocyanides Using the "Click" Reaction. J Mater Chem. 2008;18:5615-24.
Kontoghiorghes et al., 1,2-Dimethyl-3-hydroxypyrid-4-one, an orally active chelator for treatment of iron overload. Lancet. Jun. 6, 1987;1(8545):1294-5.
Kontoghiorghes, New Concepts of Iron and Aluminium Chelation Therapy With Oral L1 (Deferiprone) and Other Chelators. Analyst. Mar. 1995;120:845-51.
Koppenol, Kinetics and Mechanisms of the Fenton Reaction: Implications in Iron Toxicity. In: Iron Chelators: New Development Strategies, Bergeron, ed., 2000:3-10.
Langer, Solid complexes with tetravalent metal ions and ethylenediamime tetra-acetic acid (EDTA). J Inorg Nucl Chem. 1964;26:59-72.
Levien et al., Pentetate Calcium Trisodium (Ca-DTPA) and Pentetate Zinc Trisodium (Zn-DTPA). Formulary Drug Reviews. 2005;40:65-71.
Li et al., Binding and uptake of H-ferritin are mediated by human transferrin receptor-1. Proc Natl Acad Sci U S A. Feb. 23, 2010;107(8):3505-10. doi: 10.1073/pnas.0913192107. Epub Feb. 4, 2010.
Li et al., Synthesis of Coumarin-Appended Pyridyl Tricarbonylrhenium(I) 2,2'-Bipyridyl Complexes with Oligoether

(56) References Cited

OTHER PUBLICATIONS

Spacer and Their Fluorescence Resonance Energy Transfer Studies. Organometallics. 2009;28(6):1620-1630.

Lieu et al., The roles of iron in health and disease. Mol Aspects Med. Feb.-Apr. 2001;22(1-2):1-87.

Liu et al., Nanoparticle and iron chelators as a potential novel Alzheimer therapy. Methods Mol Biol. 2010;610:123-44. doi: 10.1007/978-1-60327-029-8_8.

Lovejoy et al., Iron chelators as anti-neoplastic agents: current developments and promise of the PIH class of chelators. Curr Med Chem. Jun. 2003;10(12):1035-49.

Luciani et al., Americium in the beagle dog: biokinetic and dosimetric model. Health Phys. May 2006;90(5):459-70.

Lui et al., The iron chelator, deferasirox, as a novel strategy for cancer treatment: oral activity against human lung tumor xenografts and molecular mechanism of action. Mol Pharmacol. Jan. 2013;83(1):179-90. doi: 10.1124/mol.112.081893. Epub Oct. 16, 2012.

MacPherson et al., Experimental production of diffuse colitis in rats. Digestion. 1978;17(2):135-50.

Malcovati, Impact of transfusion dependency and secondary iron overload on the survival of patients with myelodysplastic syndromes. Leuk Res. Dec. 2007;31 Suppl 3:S2-6.

Malluche et al., The Use of Deferoxamine in the Management of Aluminum Accumulation in Bone in Patients with Renal Failure. N Engl J Med. Jul. 19, 1984;311(3):140-4.

Marriott et al., Synthesis of the farnesyl ether 2,3,5-trifluoro-6-hydroxy-4-[(E,E)-3,7,11-trimethyldodeca-2,6,10-trien-1-yloxy]nitrobenzene, and related compounds containing a substituted hydroxytrifluorophenyl residue: novel inhibitors of protein farnesyltransferase, geranylgeranyltransferase I and squalene synthase. J Chem Soc Perkin Trans 1. 2000;1(24):4265-78.

Millan et al., Biological signatures of brain damage associated with high serum ferritin levels in patients with acute ischemic stroke and thrombolytic treatment. Dis Markers. 2008;25(3):181-8.

Miller et al., Efficacy of orally administered amphipathic polyaminocarboxylic acid chelators for the removal of plutonium and americium: comparison with injected Zn-DTPA in the rat. Radiat Prot Dosimetry. 2006;118(4):412-20. Epub Dec. 6, 2005.

Mladenka et al., The fate of iron in the organism and its regulatory pathways. Acta Medica (Hradec Kralove). 2005;48(3-4):127-35.

Molina-Jijón et al., Deferoxamine pretreatment prevents Cr(VI)-induced nephrotoxicity and oxidant stress: Role of Cr(VI) chelation. Toxicol. 2012;291:93-101.

Moreau-Marquis et al., Tobramycin and FDA-approved iron chelators eliminate Pseudomonas aeruginosa biofilms on cystic fibrosis cells. Am J Respir Cell Mol Biol. Sep. 2009;41(3):305-13. doi: 10.1165/rcmb.2008-0299OC. Epub Jan. 23, 2009.

Mounsey et al., Chelators in the treatment of iron accumulation in Parkinson's disease. Int J Cell Biol. 2012;2012:983245. doi: 10.1155/2012/983245. Epub Jun. 13, 2012.

Naegeli et al., Metabolites of Microorganisms. Part 193. Ferrithiocin. Helv Chim Acta. 1980;63:1400-06. German.

Nash et al., Features of the thermodynamics of two-phase distribution reactions of americium(III) and europium(III) nitrates into solutions of 2,6-bis[(bis(2-ethylhexyl)phosphino)methyl]pyridine N,P,P'-trioxide. Inorg Chem. Nov. 4, 2002;41(22):5849-58.

Neu et al., Structural Characterization of a Plutonium(IV) Siderophore Complex: Single-Crystal Structure of Pu-Desferrioxamine E. Angew Chem Int Ed Engl. Apr. 2000;39(8):1442-1444.

Neufeld et al., A phase 2 study of the safety, tolerability, and pharmacodynamics of FBS0701, a novel oral iron chelator, in transfusional iron overload. Blood. Apr. 5, 2012;119(14):3263-8. doi: 10.1182/blood-2011-10-386268. Epub Jan. 17, 2012.

Nisbet-Brown et al., Effectiveness and safety of ICL670 in iron-loaded patients with thalassaemia: a randomised, double-blind, placebo-controlled, dose-escalation trial. Lancet. May 10, 2003;361(9369):1597-602.

O'Connell et al., The role of iron in ferritin- and haemosiderin-mediated lipid peroxidation in liposomes. Biochem J. Jul. 1, 1985;229(1):135-9.

Olivieri et al., Iron-chelating therapy and the treatment of thalassemia. Blood. Feb. 1, 1997;89(3):739-61.

Olivieri et al., Long-term safety and effectiveness of iron-chelation therapy with deferiprone for thalassemia major. N Engl J Med. Aug. 13, 1998;339(7):417-23.

Olivieri, Long-term therapy with deferiprone. Acta Haematol. 1996;95(1):37-48.

Olivieri, Progression of iron overload in sickle cell disease. Semin Hematol. Jan. 2001;38(1 Suppl 1):57-62.

Olivieri et al., Comparison of oral iron chelator L1 and desferrioxamine in iron-loaded patients. Lancet. 1990;336:1275-79.

Ornelas et al., An Efficient Synthesis of Highly Functionalized Chiral Lactams. Tetrahedron Lett. 2011;52:4760-63.

Østergaard et al., Evalution of capillary electrophoresis-frontal analysis for the study of low molecular weight drug-human serum albumin interactions. Electrophoresis. Sep. 2002;23(17):2842-53.

Panter et al., Dextran-Coupled Deferoxamine Improves Outcome in a Murine Model of Head Injury. J Neurotrauma. 1992;9(1):47-53.

Paquet et al., Efficacy of 3,4,3-LI(1,2-HOPO) for decorporation of Pu, Am and U from rats injected intramuscularly with high-fired particles of MOX. Radiat Prot Dosimetry. 2003;105(1-4):521-5.

Pashalidis et al., Effective complex formation in the interaction of 1,2-dimethyl-3-hydroxypyrid-4-one (Deferiprone or L1) with uranium (VI). J Radioanal Nucl Chem. 1999;242:181-84.

Peters et al., Diagnosis and management of thalassaemia. BMJ. Jan. 25, 2012;344:e228. doi: 10.1136/bmj.e228.

Pietrangelo, Iron chelation beyond transfusion iron overload. Am J Hematol. Dec. 2007;82(12 Suppl):1142-6.

Pietrangelo, Mechanism of iron toxicity. In: Iron Chelation Therapy. Hershko, ed. 2002:19-43.

Pippard et al., Iron chelation using subcutaneous infusions of diethylene triamine penta-acetic acid (DTPA). Scand J Haematol. May 1986;36(5):466-72.

Pippard, Desferrioxamine-induced iron excretion in humans. Baillieres Clin Haematol. Apr. 1989;2(2):323-43.

Pippard, Iron overload and iron chelation therapy in thalassaemia and sickle cell haemoglobinopathies. Acta Haematol. 1987;78(2-3):206-11.

Piyamongkol et al., Novel Synthetic Approach to 2-(1'-Hydroxyalkyl)- and 2-Amido-3-Hydroxypyridin-4-ones. Tetranderon. 2001;57:3479-86.

Platzer et al., Rate of drug metabolism in man measured by 14CO2-breath analysis. Eur J Clin Pharmacol. Dec. 1, 1978;14(4):293-9.

Ponka et al., Function and regulation of transferrin and ferritin. Semin Hematol. Jan. 1998;35(1):35-54.

Ponka et al., Mobilization of iron from reticulocytes. Identification of pyridoxal isonicotinoyl hydrazone as a new iron chelating agent. FEBS Lett. Jan. 15, 1979;97(2):317-21.

PubChem SID 241084044, Feb. 16, 2015.

Rao et al., Complexation of Thorium(IV) with Desmethyldesferrithiocin. Radiochim Acta. 2000;88:851-56.

Raymond et al., Coordination Chemistry and Microbial Iron Transport. Acc Chem Res. 1979;12:183-190.

Raymond et al., Enterobactin: an archetype for microbial iron transport. Proc Natl Acad Sci U S A. Apr. 1, 2003;100(7):3584-8. Epub Mar. 24, 2003.

Re et al., Antioxidant activity applying an improved ABTS radical cation decolorization assay. Free Radic Biol Med. May 1999;26(9-10):1231-7.

Richardson et al., Development of potential iron chelators for the treatment of Friedreich's ataxia: ligands that mobilize mitochondrial iron. Biochim Biophys Acta. May 31, 2001;1536(2-3):133-40.

Richardson, The controversial role of deferiprone in the treatment of thalassemia. J Lab Clin Med. May 2001;137(5):324-9.

Rienhoff et al., A phase 1 dose-escalation study: safety, tolerability, and pharmacokinetics of FBS0701, a novel oral iron chelator for the treatment of transfusional iron overload. Haematologica. Apr. 2011;96(4):521-5. doi: 10.3324/haematol.2010.034405. Epub Dec. 20, 2010.

(56) References Cited

OTHER PUBLICATIONS

Rosse, Metabolites of the pyrimidine amine preladenant as adenosine a2a receptor antagonists. ACS Med Chem Lett. Nov. 30, 2012;4(1):5-6. doi:10.1021/ml300397j. eCollection Jan. 10, 2013.
Saha et al., Microbial siderophores: a mini review. J Basic Microbiol. Apr. 2013;53(4):303-17. doi: 10.1002/jobm.201100552. Epub Jun. 26, 2012.
Saljooghi et al., Clinical evaluation of Deferasirox for removal of cadmium ions in rat. Biometals. 2010;23:707-12.
Saljooghi, Chelation of aluminum by combining deferasirox and deferiprone in rats. Toxicol Ind Health. 2012;28(8):740-5.
Santos et al., A cyclohexane-1, 2-diyldinitrilotetraacetate tetrahydroxamate derivative for actinide complexation: Synthesis and complexation studies. J Chem Soc Dalton Trans. 2000:4398-4402.
Seligman et al., Molecular Mechanisms of Iron Metabolism. The Molecular Basis of Blood Diseases. 1987;219-44.
Shin et al., A novel trivalent cation chelator Feralex dissociates binding of aluminum and iron associated with hyperphosphorylated τ of Alzheimer's disease. Brain Res. 2003;961:139-46.
Souillac et al., "Characterization of Deliver Systems, Differential Scanning in Calorimetry." Encyclopedia of Controlled Drug Delivery. John Wiley & Sons. 1999:212-27.
Stahel et al., Iron chelators: in vitro inhibitory effect on the liver stage of rodent and human malaria. Am J Trop Med Hyg. Sep. 1988;39(3):236-40.
Stradling et al., Recent developments in the decorpoartion of plutonium, americium and thorium. Radiat Prot Dosimetry. 1998;79:445-48.
Streiff et al., Phase 1 study of N1-N11-diethylnorspermine (DENSPM) administered TID for 6 days in patients with advanced malignancies. Invest New Drugs. 2001;19(1):29-39.
Supkowski et al., Displacement of Inner-Sphere Water Molecules from Eu(3+) Analogues of Gd(3+) MRI Contrast Agents by Carbonate and Phosphate Anions: Dissociation Constants from Luminescence Data in the Rapid-Exchange Limit. Inorg Chem. Nov. 29, 1999;38(24):5616-5619.
Taetle et al., Combination iron depletion therapy. J Natl Cancer Inst. Aug. 16, 1989;81(16):1229-35.
Tang et al., High-resolution magnetic resonance imaging tracks changes in organ and tissue mass in obese and aging rats. Am J Physiol Regul Integr Comp Physiol. Mar. 2002;282(3):R890-9.
Theil et al., Ferritin Mineralization: Ferroxidation and Beyond. J Inorg Biochem. 1997;67:30. Abstract B13.
Thomas et al., Ferritin and superoxide-dependent lipid peroxidation. J Biol Chem. Mar. 25, 1985;260(6):3275-80.
Thompson et al., Protein conformational misfolding and amyloid formation: characteristics of a new class of disorders that include Alzheimer's and Prion diseases. Curr Med Chem. Oct. 2002;9(19):1751-62.
Trokowski et al., Cyclen-based phenylboronate ligands and their Eu3+ complexes for sensing glucose by MRI. Bioconjug Chem. Nov.-Dec. 2004;15(6):1431-40.
Uhlir et al., Specific sequestering agents for the actinides. 21. Synthesis and initial biological testing of octadentate mixed catecholate-hydroxypyridinonate ligands. J Med Chem. Feb. 19, 1993;36(4):504-9.
Vaidya et al., A rapid urine test for early detection of kidney injury. Kidney Int. Jul. 2009;76(1):108-14. doi: 10.1038/ki.2009.96. Epub Apr. 22, 2009.
Vaidya et al., Urinary kidney injury molecule-1: a sensitive quantitative biomarker for early detection of kidney tubular injury. Am J Physiol Renal Physiol. Feb. 2006;290(2):F517-29. Epub Sep. 20, 2005.
Vichinsky, Current issues with blood transfusions in sickle cell disease. Semin Hematol. Jan. 2001;38(1 Suppl 1):14-22.
Vippagunta et al., Crystalline solids. Adv Drug Deliv Rev. May 16, 2001;48(1):3-26.
Weintraub et al., The treatment of hemochromatosis by phlebotomy. Med Clin North Am. Nov. 1966;50(6):1579-90.
Wen et al., High serum iron is associated with increased cancer risk. Cancer Res. Nov. 15, 2014;74(22):6589-97. doi: 10.1158/0008-5472.CAN-14-0360. Epub Sep. 16, 2014.
Whisenhunt et al., Specific Sequestering Agents for the Actinides. 29. Stability of the Thorium(IV) Complexes of Desferrioxamine B (DFO) and Three Octadentate Catecholate or Hydroxypyridinonate DFO Derivatives: DFOMTA, DFOCAMC, and DFO-1,2-HOPO. Comparative Stability of the Plutonium(IV) DFOMTA Complex(1). Inorg Chem. Jul. 3, 1996;35(14):4128-4136.
White et al., The effect of chelating agents on cellular iron metabolism. Clin Sci Mol Med. Mar. 1976;50(3):145-52.
White et al., The effect of chelating agents on iron mobilization in Chang cell cultures. Blood. Dec. 1976;48(6):923-9.
White et al., Total synthesis of geodiamolide A, a novel cyclodepsipeptide of marine origin. J Org Chem. 1989;54(4):736-738.
Whittington et al., Review article: haemochromatosis. Aliment Pharmacol Ther. Dec. 2002;16(12):1963-75.
Wilen et al., Strategies in Optical Resolution. Tetrahedron. 1977;33:2725-36.
Woessner et al., Numerical solution of the Bloch equations provides insights into the optimum design of PARACREST agents for MRI. Magn Reson Med. Apr. 2005;53(4):790-9.
Wojcik et al., Natural history of C282Y homozygotes for hemochromatosis. Can J Gastroenterol. May 2002;16(5):297-302.
Wolfe et al., A non-human primate model for the study of oral iron chelators. Br J Haematol. Jul. 1989;72(3):456-61.
Wolff et al., A Phase II study of the polyamine analog N1,N11-diethylnorspermine (DENSpm) daily for five days every 21 days in patients with previously treated metastatic breast cancer. Clin Cancer Res. Dec. 1, 2003;9(16 Pt 1):5922-8.
Wong et al., The Friedreich's ataxia mutation confers cellular sensitivity to oxidant stress which is rescued by chelators of iron and calcium and inhibitors of apoptosis. Hum Mol Genet. Mar. 1999;8(3):425-30.
Wood et al., The metabolism of iron-dextran given as a total-dose infusion to iron deficient Jamaican subjects. Br J Haematol. Feb. 1968;14(2):119-29.
Yacobovich et al., Acquired proximal renal tubular dysfunction in β-thalassemia patients treated with deferasirox. J Pediatr Hematol Oncol. Oct. 2010;32(7):564-7. doi: 10.1097/MPH.0b013e3181ec0c38.
Yamada et al., Role of neutrophil-derived oxidants in the pathogenesis of intestinal inflammation. Klin Wochenschr. Dec. 15, 1991;69(21-23):988-94.
Zacharski et al., Reduction of iron stores and cardiovascular outcomes in patients with peripheral arterial disease: a randomized controlled trial. JAMA. Feb. 14, 2007;297(6):603-10.
Zaman et al., Protection from oxidative stress-induced apoptosis in cortical neuronal cultures by iron chelators is associated with enhanced DNA binding of hypoxia-inducible factor-1 and ATF-1/CREB and increased expression of glycolytic enzymes, p21(waf1/cip1), and erythropoietin. J Neurosci. Nov. 15, 1999;19(22):9821-30.
Zecca et al., Neuromelanin can protect against iron-mediated oxidative damage in system modeling iron overload of brain aging and Parkinson's disease. J Neurochem. Aug. 2008;106(4):1866-75. Epub Jul. 4, 2008.
Zeng et al., Identification of cytochrome P4503A as the major enzyme sub-family responsible for the metabolism of 22,23-dihydro-13-O-[(2-methoxyethoxy)methyl]-avermectin B1 aglycone by rat liver microsomes. Xenobiotica. Oct. 1997;27(10):985-94.
Zhang et al., A novel europium(III)-based MRI contrast agent. J Am Chem Soc. Feb. 21, 2001;123(7):1517-8.
Zhang et al., A paramagnetic CEST agent for imaging glucose by MRI. J Am Chem Soc. Dec. 17, 2003;125(50):15288-9.
Zhao et al., Specific method for determination of OSI-774 and its metabolite OSI-420 in human plasma by using liquid chromatography-tandem mass spectrometry. J Chromatogr B Analyt Technol Biomed Life Sci. Aug. 15, 2003;793(2):413-20.
Zhou et al., Comparison of kidney injury molecule-1 and other nephrotoxicity biomarkers in urine and kidney following acute exposure to gentamicin, mercury, and chromium. Toxicol Sci. Jan. 2008;101(1):159-70. Epub Oct. 13, 2007.

(56) References Cited

OTHER PUBLICATIONS

Zurlo et al., Survival and causes of death in thalassaemia major. Lancet. Jul. 1, 1989;2(8653):27-30.
Extended European Search Report, dated Jan. 19, 2010, in connection with Application No. EP 07874513.0.
International Search Report and Written Opinion, dated Jan. 8, 2009, in connection with Application No. PCT/US2007/025377.
International Preliminary Report on Patentability, dated Jun. 23, 2009, in connection with Application No. PCT/US2007/025377.
Extended European Search Report, dated Dec. 27, 2010, in connection with Application No. EP 08742093.1.
International Search Report and Written Opinion, dated Jun. 19, 2008, in connection with Application No. PCT/US2008/003433.
International Preliminary Report on Patentability, dated Sep. 24, 2009, in connection with Application No. PCT/US2008/003433.
Supplementary European Search Report, dated Dec. 5, 2001, in connection with Application No. EP 99945267.5.
International Search Report, dated Jan. 19, 2000, in connection with Application No. PCT/US1999/019691.
Written Opinion, dated Aug. 21, 2000, in connection with Application No. PCT/US1999/019691.
International Preliminary Examination Report, dated Feb. 2, 2001, in connection with Application No. PCT/US1999/019691.
Extended European Search Report, dated Mar. 25, 2013, in connection with Application No. EP 10814064.1.
International Search Report and Written Opinion, dated May 23, 2011, in connection with Application No. PCT/US2010/002336.
International Preliminary Report on Patentability, dated Mar. 8, 2012, in connection with Application No. PCT/US2010/002336.
International Search Report and Written Opinion, dated Mar. 5, 2004, in connection with Application No. PCT/US2003/028304.
Extended European Search Report, dated Mar. 29, 2017, in connection with Application No. EP 16196408.5.
International Search Report and Written Opinion, dated Aug. 9, 2006, in connection with Application No. PCT/US2006/010945.
International Preliminary Report on Patentability, dated Oct. 18, 2007, in connection with Application No. PCT/US2006/010945.
European Search Report, dated Mar. 20, 2015, in connection with Application No. EP 12857135.3.
Extended European Search Report, dated Jul. 9, 2015, in connection with Application No. EP 12857135.3.
International Search Report and Written Opinion, dated Apr. 19, 2013, in connection with Application No. PCT/US2012/069795.
International Preliminary Report on Patentability, dated Jun. 26, 2014, in connection with Application No. PCT/US2012/069795.
International Search Report and Written Opinion, dated Apr. 12, 2013, in connection with Application No. PCT/US2012/069826.
International Preliminary Report on Patentability, dated Jun. 26, 2014, in connection with Application No. PCT/US2012/069826.
Invitation to Pay Additional Fees, mailed Jan. 27, 2015, in connection with Application No. PCT/US2014/066961.
International Search Report and Written Opinion, dated Apr. 14, 2015, in connection with Application No. PCT/US2014/066961.
Extended European Search Report, dated Mar. 29, 2017, in connection with Application No. EP 14864521.1.
Invitation to Pay Additional Fees, dated Jan. 27, 2015, in connection with Application No. PCT/US2014/066965.
International Search Report and Written Opinion, dated Apr. 14, 2015, in connection with Application No. PCT/US2014/066965.
International Search Report and Written Opinion, dated Feb. 25, 2016, in connection with Application No. PCT/US2015/065985.
International Search Report and Written Opinion, dated Jun. 17, 2016, in connection with Application No. PCT/US2016/024239.
International Preliminary Report on Patentability dated Oct. 5, 2017, in connection with Application No. PCT/US2016/024239.
International Search Report and Written Opinion, dated Sep. 23, 2016, in connection with Application No. PCT/US2016/029587.
International Preliminary Report, dated Nov. 9, 2017, in connection with Application No. PCT/US2016/029587.
Extended European Search Report, dated Oct. 8, 2018, in connection with Application No. EP 16787077.3.
07874513.0, Jan. 19, 2010, Extended European Search Report.
PCT/US2007/025377, Jan. 8, 2009, International Search Report and Written Opinion.
PCT/US2007/025377, Jun. 23, 2009, International Preliminary Report on Patentability.
EP 08742093.1, Dec. 27, 2010, Extended European Search Report.
PCT/US2008/003433, Jun. 19, 2008, International Search Report and Written Opinion.
PCT/US2008/003433, Sep. 24, 2009, International Preliminary Report on Patentability.
EP 99945267.5, Dec. 5, 2001, Supplementary European Search Report.
PCT/US1999/019691, Jan. 19, 2000, International Search Report and Written Opinion.
PCT/US1999/019691, Feb. 2, 2001, International Preliminary Examination Report.
EP 10814064.1, Mar. 25, 2013, Extended European Search Report.
PCT/US1999/019691, May 23, 2011, International Search Report and Written Opinion.
PCT/US2010/002336, Mar. 8, 2012, International Preliminary Report on Patentability.
PCT/US2003/028304, Mar. 5, 2004, International Search Report and Written Opinion.
EP 16196408.5, Mar. 29, 2017, Extended European Search Report.
PCT/US2006/010945, Aug. 9, 2006, International Search Report and Written Opinion.
PCT/US2006/010945, Oct. 18, 2007, International Preliminary Report on Patentability.
EP 12857135.3, Mar. 20, 2015, Partial Supplementary European Search Report.
EP 12857135.3, Jul. 9, 2015, Extended European Search Report.
PCT/US2012/069795, Apr. 19, 2013, International Search Report and Written Opinion.
PCT/US2012/069795, Jun. 26, 2014, International Preliminary Report on Patentability.
PCT/US2012/069826, Apr. 12, 2013, International Search Report and Written Opinion.
PCT/US2012/069826, Jun. 26, 2014, International Preliminary Report on Patentability.
PCT/US2014/066961, Jan. 27, 2015, Invitation to Pay Additional Fees.
PCT/US2014/066961, Apr. 14, 2015, International Search Report and Written Opinion.
EP 14864521.1, Mar. 29, 2017, Extended European Search Report.
PCT/US2014/066965, Jan. 27, 2015, Invitation to Pay Additional Fees.
PCT/US2014/066965, Apr. 14, 2015, International Search Report and Written Opinion.
PCT/US2016/024239, Oct. 5, 2017, International Preliminary Report on Patentability.
PCT/US2016/024239, Jun. 17, 2016, International Search Report and Written Opinion.
PCT/US2016/029587, Sep. 23, 2016, International Search Report and Written Opinion.
PCT/US2016/029587, Nov. 9, 2017, International Preliminary Report on Patentability.
U.S. Appl. No. 11/686,482, filed Mar. 15, 2007, Bergeron, Jr.
U.S. Appl. No. 12/448,237, filed Jan. 6, 2010, Bergeron, Jr.
U.S. Appl. No. 12/450,194, filed Dec. 14, 2009, Bergeron, Jr.
U.S. Appl. No. 13/683,301, filed Nov. 21, 2012, Bergeron, Jr.
U.S. Appl. No. 09/144,103, filed Aug. 31, 1998, Bergeron, Jr.
U.S. Appl. No. 09/981,586, filed Oct. 17, 2001, Bergeron, Jr.
U.S. Appl. No. 09/531,753, filed Mar. 20, 2000, Bergeron, Jr.
U.S. Appl. No. 09/531,754, filed Mar. 20, 2000, Bergeron, Jr.
U.S. Appl. No. 09/531,755, filed Mar. 20, 2000, Bergeron, Jr.
U.S. Appl. No. 10/300,071, filed Nov. 20, 2002, Bergeron, Jr.
U.S. Appl. No. 10/944,150, filed Sep. 17, 2004, Bergeron, Jr.
U.S. Appl. No. 11/522,299, filed Sep. 15, 2006, Bergeron, Jr.
U.S. Appl. No. 12/383,854, filed Mar. 27, 2009, Bergeron, Jr.
U.S. Appl. No. 13/390,951, filed Mar. 30, 2012, Bergeron, Jr.
U.S. Appl. No. 11/367,042, filed Mar. 2, 2006, Bergeron, Jr.

(56) References Cited

OTHER PUBLICATIONS

U.S. Appl. No. 11/973,001, filed Oct. 4, 2007, Bergeron, Jr.
U.S. Appl. No. 13/631,025, filed Sep. 28, 2012, Bergeron, Jr.
U.S. Appl. No. 14/264,959, filed Apr. 29, 2014, Bergeron, Jr.
U.S. Appl. No. 14/811,598, filed Jul. 28, 2015, Bergeron, Jr.
U.S. Appl. No. 14/363,886, filed Jun. 9, 2014, Bergeron, Jr.
U.S. Appl. No. 14/363,952, filed Jun. 9, 2014, Bergeron, Jr.
U.S. Appl. No. 14/875,462, filed Oct. 5, 2015, Bergeron, Jr.
U.S. Appl. No. 15/428,232, filed Feb. 9, 2017, Bergeron, Jr.
U.S. Appl. No. 16/005,483, filed Jun. 11, 2018, Bergeron, Jr.
U.S. Appl. No. 15/424,557, filed Feb. 3, 2017, Bergeron, Jr.
Shibasaki, Masakatsu, Akinori Akaike, Mitsuru Hashida, Toshiyuki Sakaeda, Ken Karasawa, Kōichi Okamoto, and Kōichi Okamoto. 2012. Seizaigaku butsuri yakuzaigaku. Tōkyō: Hirokawashoten. Published May 1, 2012. Formulations. Physical pharmacy, 2nd edition. 259-66.

\* cited by examiner

METABOLICALLY PROGRAMMED METAL CHELATORS AND USES THEREOF

RELATED APPLICATIONS

This application is a national stage filing under 35 U.S.C. § 371 of international PCT application, PCT/US2016/029587, filed Apr. 27, 2016, which claims priority under 35 U.S.C. § 119(e) to U.S. provisional application, U.S. Ser. No. 62/153,468, filed Apr. 27, 2015, each of which is incorporated herein by reference herein.

GOVERNMENT SUPPORT

This invention was made with government support under grant number R37DK049108 awarded by the National Institutes of Health. The government has certain rights in the invention.

BACKGROUND OF THE INVENTION

Nearly all life forms require iron as a micronutrient (Mladenka et al., *Acta Medica.* 2005, 48, 127-135). However, the low solubility of Fe(III) hydroxide ($K_{sp}=1\times10^{-39}$) (Raymond et al., "Coordination Chemistry and Microbial Iron Transport." *Acc. Chem. Res.* 1979, 12, 183-190), the predominant form of the metal in the biosphere, required the development of sophisticated iron storage and transport systems in nature. Microorganisms utilize low molecular weight, ferric iron-specific chelators, siderophores (Byers et al., "Microbial Iron Transport: Iron Acquisition by Pathogenic Microorganisms." *Met. Ions Biol. Syst.* 1998, 35, 37-66); eukaryotes tend to employ proteins to transport and store iron (Gkouvatsos et al., Biochim. Biophys. Acta. 2012, 1820, (2012) 188-202; Li et al., Proc. Natl. Acad. Sci. U.S.A. 107 (2010, 107) 3505-3510; Bergeron, "Iron: A Controlling Micronutrient in Proliferative Processes." *Trends Biochem. Sci.* 1986, 11, 133-136; Theil et al., "Ferritin Mineralization: Ferroxidation and Beyond." *J. Inorg. Biochem.* 1997, 67, 30; Ponka et al., "Function and Regulation of Transferrin and Ferritin." *Semin. Hematol.* 1998, 35, 35-54). Humans have evolved a highly efficient iron management system (Andrews et al., Annu. Rev. Physiol. 69 (2007) 69-85) in which we absorb and excrete only about 1 mg of the metal daily; there is no mechanism for the excretion of excess metal (Whittington et al., Review article: haemochromatosis, Aliment Pharmacol. Ther. 16 (2002) 1963-1975; Brittenham, "Disorders of Iron Metabolism: Iron Deficiency and Overload." In *Hematology: Basic Principles and Practice;* $3^{rd}$ ed.; Hoffman et al., Eds.; Churchill Livingstone: New York, 2000; pp. 397-428). Whether derived from transfused red blood cells (Peters et al., B. M. J. (2012) 344:e228. doi: 10.1136/bmj.e228; Cappellini et al., Guidelines for the Clinical Management of Thalassemia, 2nd Ed., Thalassemia International Foundation, 2008; Olivieri et al., "Iron-Chelating Therapy and the Treatment of Thalassemia." *Blood* 1997, 89, 739-761; Vichinsky, "Current Issues with Blood Transfusions in Sickle Cell Disease." *Semin. Hematol.* 2001, 38, 14-22; Kersten et al., "Long-Term Treatment of Transfusional Iron Overload with the Oral Iron Chelator Deferiprone (L1): A Dutch Multicenter Trial." *Ann. Hematol.* 1996, 73, 247-252), required in the treatment of hemolytic anemias, or from increased absorption of dietary iron (Conrad et al., "Iron Absorption and Transport." *Am. J. Med. Sci.* 1999, 318, 213-229; Lieu et al., "The Roles of Iron in Health and Disease." *Mol. Aspects Med.* 2001, 22, 1-87), without effective treatment, body iron progressively increases with deposition in the liver, heart, pancreas, and elsewhere (iron overload disease) (Lieu et al., *Mol. Aspects Med.* 22 (2001) 1-87). This can lead to liver disease (Bonkovsky et al., *Clin. Liver Dis.* 4 (2000) 409-429, vi-vii), diabetes (Wojcik et al., *Can. J. Gastroenterol.* 16 (2002) 297-302), increased risk of cancer (Wen et al., *Cancer Res.* 74 (2014) 6589-6597), and heart disease, often the cause of death in these patients (Brittenham, Disorders of iron metabolism: iron deficiency and overload, in: R. Hoffman, E. J. Benz, S. J. Shattil, B. Furie, H. J. Cohen (Eds.), *Hematology: Basic Principles and Practice,* 3rd Ed., Churchill Livingstone, New York, 2000, pp 397-428). Nontransferrin-bound plasma iron (Brissot et al., Biochim. Biophys. Acta. 2012,1820, (2012) 403-410; Chua et al., Blood 104 (2004, 104,) 1519-1525; Bolli et al., Am. J. Physiol. 259 (1990, 259,) 1901-1911) is the origin of the organ damage that develops with iron overload.

In patients with iron overload disease, the toxicity derives from iron's interaction with reactive oxygen species (Graf et al., "Iron-Catalyzed Hydroxyl Radical Formation. Stringent Requirement for Free Iron Coordination Site." *J. Biol. Chem.* 1984, 259, 3620-3624; Halliwell, "Free Radicals and Antioxidants: A Personal View." *Nutr. Rev.* 1994, 52, 253-265; Halliwell, "Oxidative Damage, and Chelating Agents." In *The Development of Iron Chelators for Clinical Use;* Bergeron et al., Eds.; CRC: Boca Raton, Fla., 1994; pp 33-56; Koppenol, "Kinetics and Mechanism of the Fenton Reaction: Implications for Iron Toxicity." In *Iron Chelators: New Development Strategies;* Badman et al., Eds.; Saratoga: Ponte Vedra Beach, Fla., 2000, pp 3-10). For example, in the presence of Fe(II), endogenous $H_2O_2$ is reduced to the hydroxyl radical (HO.), a very reactive species, and HO$^-$, in the Fenton reaction. The hydroxyl radical reacts very quickly with a variety of cellular constituents and can initiate free radicals and radical-mediated chain processes that damage DNA and membranes as well as produce carcinogens (Halliwell, "Free Radicals and Antioxidants: A Personal View." *Nutr. Rev.* 1994, 52, 253-265); Babbs, "Oxygen Radicals in Ulcerative Colitis." *Free Radical Biol. Med.* 1992, 13, 169-181; Hazen et al., "Human Neutrophils Employ the Myeloperoxidase-Hydrogen Peroxide-Chloride System to Oxidize α-Amino Acids to a Family of Reactive Aldehydes. Mechanistic Studies Identifying Labile Intermediates along the Reaction Pathway." *J. Biol. Chem.* 1998, 273, 4997-5005). The liberated Fe(III) is reduced back to Fe(II) via a variety of biological reductants (e.g., ascorbate, glutathione), creating a problematic cycle.

Iron-mediated damage can be focal, as in reperfusion damage (Millán et al., "Biological Signatures of Brain Damage Associated with High Serum Ferritin Levels in Patients with Acute Ischemic Stroke and Thrombolytic Treatment." *Dis. Markers* 2008, 25, 181-188), Parkinson's (Zecca et al., "Neuromelanin Can Protect Against Iron-Mediated Oxidative Damage in System Modeling Iron Overload of Brain Aging and Parkinson's Disease." *J. Neurochem.* 2008, 106, 1866-1875), Friedreich's ataxia (Pietrangelo, "Iron Chelation Beyond Tranfusion Iron Overload." *Am. J. Hematol.* 2007, 82, 1142-1146), macular degeneration (Dunaief, "Iron Induced Oxidative Damage as a Potential Factor in Age-Related Macular Degeneration: The Cogan Lecture" *Invest. Ophthalmol. Vis. Sci.* 2006, 47, 4660-4664), and hemorrhagic stroke (Hua et al., "Long-Term Effects of Experimental Intracerebral Hemorrhage: The Role of Iron." *J. Neurosurg.* 2006, 104, 305-312), or global, as in transfusional iron overload, e.g., thalassemia (Pippard, "Iron Overload and Iron Chelation Therapy in Thalassaemia and Sickle Cell Haemoglobinopathies." *Acta. Haematol.* 1987, 78, 206-211), sickle cell disease (Pippard, "Iron Overload and Iron Chelation Therapy in Thalassaemia and Sickle Cell Haemoglobinopathies." *Acta. Haematol.* 1987, 78, 206-211; Olivieri, "Progression of Iron Overload in Sickle Cell Disease." *Semin. Hematol.* 2001, 38, 57-62), and myelodysplasia (Malcovati, "Impact of Transfusion Dependency and Secondary Iron Overload on the Survival of Patients with Myelodysplastic Syndromes." *Leukemia Res.* 2007, 31, S2-S6), with multiple organ involvement. The solution in both scenarios is the same: chelate and promote the excretion of excess unmanaged iron.

Treatment with a chelating agent capable of sequestering iron and permitting its excretion from the body is the only therapeutic approach available. Some of the iron chelating agents that are now in use or that have been clinically evaluated include desferrioxamine B mesylate (DFO) (Desferal; Novartis Pharmaceuticals Corporation: East Hanover, N.J., 2008; www.pharma.us.novartis.com/product/pi/pdf/desferal.pdf), 1,2-dimethyl-3-hydroxy-4-pyridinone (deferiprone, L1) (Hoffbrand, "Long-Term Trial of Deferiprone in 51 Transfusion-Dependent Iron Overloaded Patients." *Blood* 1998, 91, 295-300; Olivieri, "Long-Term Therapy with Deferiprone." *Acta Haematol.* 1996, 95, 37-48; Olivieri, "Long-Term Safety and Effectiveness of Iron-Chelation Therapy with Deferiprone from Thalassemia Major." *N. Engl. J. Med.* 1998, 339, 417-423; Richardson, "The Controversial Role of Deferiprone in the Treatment of Thalassemia." *J. Lab. Clin. Med.* 2001, 137, 324-329), and 4-[3,5-bis(2-hydroxyphenyl)-1,2,4-triazol-1-yl]benzoic acid (desferasirox, ICL670A) (Nisbet-Brown et al., "Effectiveness and Safety of ICL670 in Iron-Loaded Patients with Thalassemia: A Randomised, Double-Blind, Placebo-Controlled, Dose-Escalation Trial." *Lancet,* 2003, 361, 1597-1602; Galanello et al., "Safety, Tolerability, and Pharmacokinetics of ICL670, a New Orally Active Iron-Chelating Agent in Patients with Transfusion-Dependent Iron Overload Due to β-Thalassemia." *J. Clin. Pharmacol.* 2003, 43, 565-572; Cappellini, "Iron-Chelating Therapy with the New Oral Agent ICL670 (Exjade)." *Best Pract. Res. Clin. Haematol.* 2005, 18, 289-298). Each of these compounds has shortcomings. DFO must be given subcutaneously (sc) for protracted periods of time, e.g., 12 hours a day, five days a week, a serious patient compliance issue (Olivieri et al., "Iron-Chelating Therapy and the Treatment of Thalassemia." *Blood* 1997, 89, 739-761; Pippard, "Desferrioxamine-Induced Iron Excretion in Humans." *Bailliere's Clin. Haematol.* 1989, 2, 323-343; Giardina et al., "Chelation Therapy in β-Thalassemia: An Optimistic Update." *Semin. Hematol.* 2001, 38, 360-366). Deferiprone, while orally active, simply does not remove enough iron to maintain patients in a negative iron balance (Hoffbrand, "Long-Term Trial of Deferiprone in 51 Transfusion-Dependent Iron Overloaded Patients." *Blood* 1998, 91, 295-300; Olivieri, "Long-Term Therapy with Deferiprone." *Acta Haematol.* 1996, 95, 37-48; Olivieri, "Long-Term Safety and Effectiveness of Iron-Chelation Therapy with Deferiprone from Thalassemia Major." *N. Engl. J. Med.* 1998, 339, 417-423; Richardson, "The Controversial Role of Deferiprone in the Treatment of Thalassemia." *J. Lab. Clin. Med.* 2001, 137, 324-329). Desferasirox did not show noninferiority to DFO and is associated with numerous side effects, including some renal toxicity (Nisbet-Brown et al., "Effectiveness and Safety of ICL670 in Iron-Loaded Patients with Thalassemia: A Randomised, Double-Blind, Placebo-Controlled, Dose-Escalation Trial." *Lancet,* 2003, 361, 1597-1602; Galanello et al., "Safety, Tolerability, and Pharmacokinetics of ICL670, a New Orally Active Iron-Chelating Agent in Patients with Transfusion-Dependent Iron Overload Due to β-Thalassemia." *J. Clin. Pharmacol.* 2003, 43, 565-572; Cappellini, "Iron-Chelating Therapy with the New Oral Agent ICL670 (Exjade)." *Best Pract. Res. Clin. Haematol.* 2005, 18, 289-298).

Despite the work on metal chelating agents as described above, there is still a need for other metal chelating agents with more desirable properties (e.g., metal chelating agents with balanced properties (e.g., lipophilicity, metal clearing efficiency, and toxicity)) for better treatment and/or prevention of pathological conditions in a subject.

SUMMARY OF THE INVENTION

The present invention provides desazadesferrithiocin analogs based on desferrithiocin (1, shown below) and desazadesferrithiocin (1a, shown below). In certain embodiments, the desazadesferrithiocin analogs are compounds of Formula (I), and pharmaceutically acceptable salts, solvates, hydrates, polymorphs, co-crystals, tautomers, stereoisomers, isotopically labeled derivatives, and prodrugs thereof. The desazadesferrithiocin analogs are able to chelate a metal (e.g., iron and other metals). The invention also provides compounds of Formula (II), and pharmaceutically acceptable salts, solvates, hydrates, polymorphs, co-crystals, tautomers, stereoisomers, isotopically labeled derivatives, and prodrugs thereof. The invention provides pharmaceutical compositions, kits, methods, and uses that involve or include a desazadesferrithiocin analog or compounds of Formula (I) or Formula (II) described herein. The compounds, pharmaceutical compositions, kits, and methods may be useful in chelating a metal in a subject, cell, tissue, or biological sample, treating a disease in a subject, preventing a disease in a subject, treating, reducing, or preventing the formation of biofilms in a subject, or reducing or preventing the formation of biofilms on or in an object. In certain embodiments, the disease is metal overload, oxidative stress, transfusional iron overload, thalassemia, primary hemochromatosis, secondary hemochromatosis, diabetes, liver disease, heart disease, cancer, radiation injury, neurological or neurodegenerative disorder, Friedreich's ataxia (FRDA), macular degeneration, closed head injury, irritable bowel disease, or reperfusion injury. In certain embodiments, the disease is metal poisoning. In certain embodiments, the disease is an infectious disease (e.g., malaria). Iron is usually a nutrient necessary for the growth of microorganisms. Depriving the organisms of iron by chelating and/or removing iron may contribute to the treatment and/or prevention of infectious diseases.

1

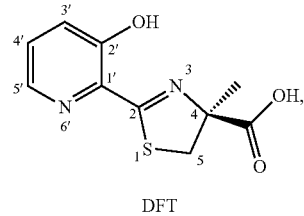

DFT

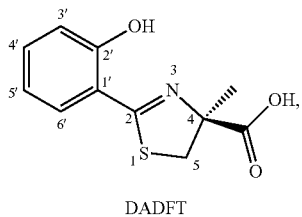

DADFT

It has been discovered that the lipophilicity of a metal chelator could have a profound effect on the metal chelator's metal clearing efficiency (MCE), organ distribution, and toxicity profile. Within a given structural family, typically the more lipophilic a metal chelator, the better the MCE. However, there also exists a second relationship: typically the greater the lipophilicity of a metal chelator, the more toxic the metal chelator. Thus, a balance between lipophilicity, MCE, and toxicity must be achieved. The compounds described herein are advantageous over known metal chelators at least because the compounds described herein are "metabolically programmed" metal chelators, e.g., they are lipophilic, absorbable (e.g., orally absorbable), and effective metal chelators, which, once absorbed, are converted to hydrophilic, nontoxic metabolites.

In one aspect, the present disclosure provides compounds of Formula (I):

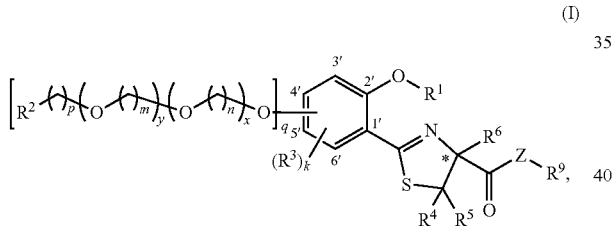

(I)

and pharmaceutically acceptable salts, solvates, hydrates, polymorphs, co-crystals, tautomers, stereoisomers, isotopically labeled derivatives, and prodrugs thereof, wherein $R^1$, $R^2$, $R^3$, $R^4$, $R^5$, $R^6$, $R^9$, Z, x, n, y, m, p, q, and k are as defined herein.

Exemplary compounds of Formula (I) include, but are not limited to:

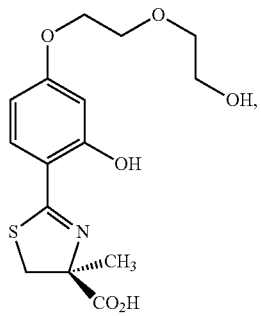

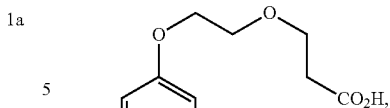

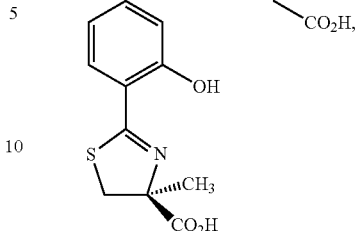

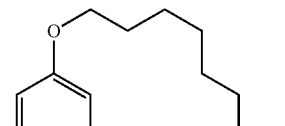

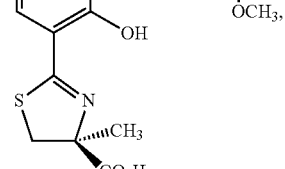

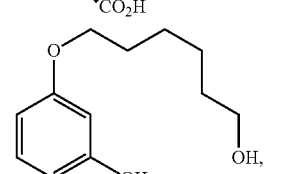

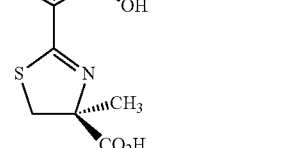

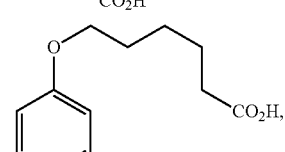

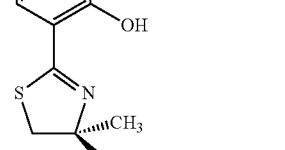

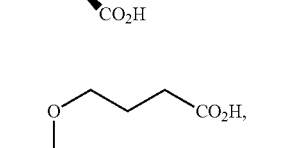

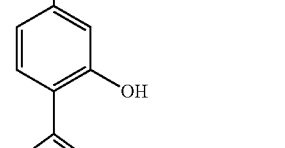

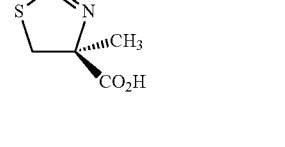

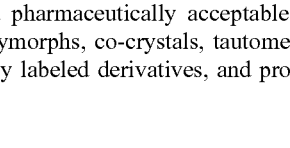

and pharmaceutically acceptable salts, solvates, hydrates, polymorphs, co-crystals, tautomers, stereoisomers, isotopically labeled derivatives, and prodrugs thereof.

In another aspect, the present disclosure provides compounds of Formula (II):

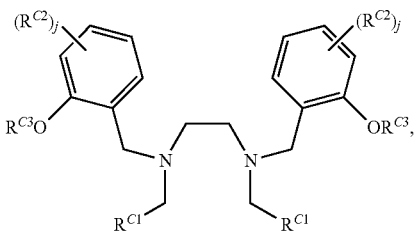

and pharmaceutically acceptable salts, solvates, hydrates, polymorphs, co-crystals, tautomers, stereoisomers, isotopically labeled derivatives, and prodrugs thereof, wherein $R^{C1}$, $C^{C2}$, $R^{C3}$, and j are as defined herein. In another aspect, described herein are pharmaceutical compositions including a compound described herein and optionally a pharmaceutically acceptable excipient. In certain embodiments, a pharmaceutical composition described herein includes an effective amount (e.g., a therapeutically or prophylactically effective amount) of a compound described herein. The pharmaceutical compositions may be useful in chelating a metal in a subject, cell, tissue, or biological sample; treating a disease in a subject (e.g., human); preventing a disease in a subject; treating, reducing, or preventing the formation of biofilms in a subject; or reducing or preventing the formation of biofilms on or in an object.

In certain embodiments, the subject is a human. In certain embodiments, the cell is in vitro. In certain embodiments, the cell is in vivo.

In certain embodiments, one of the metals chelated by the compound described herein is iron. In certain embodiments, other metals such as aluminum, thallium, chromium, magnesium, calcium, strontium, nickel, manganese, cobalt, copper, zinc, silver, sodium, potassium, cadmium, mercury, lead, antimony, molybdenum, tungsten, a lanthanide (e.g., cerium), or an actinide (e.g., uranium) are chelated by the compound.

In certain embodiments, the disease is a disease associated with the chelation of a metal. In certain embodiments, the disease is iron overload. In certain embodiments, the disease is transfusional iron overload. In certain embodiments, the disease is thalassemia, primary hemochromatosis, or secondary hemochromatosis. In certain embodiments, the disease is aluminum overload, lanthanide overload, or actinide overload. In certain embodiments, the disease is oxidative stress. In certain embodiments, the disease is diabetes, liver disease, heart disease, cancer, or neurological or neurodegenerative disorder. In certain embodiments, the disease is radiation injury, Friedreich's ataxia (FRDA), macular degeneration, closed head injury, irritable bowel disease, or reperfusion injury. In certain embodiments, the disease is metal poisoning. In certain embodiments, the disease is an infectious disease.

In still another aspect, described herein are kits including a compound or pharmaceutical composition described herein. In certain embodiments, the kit further includes instructions for using (e.g., administering) the compound or pharmaceutical composition.

In another aspect, provided herein are methods of chelating a metal in a subject, the methods including administering to the subject an effective amount of a compound or pharmaceutical composition described herein.

In another aspect, provided herein are methods of chelating a metal in a cell, tissue, or biological sample, the methods including contacting the cell, tissue, or biological sample with an effective amount of a compound or pharmaceutical composition described herein.

In another aspect, provided herein are methods of treating a disease in a subject in need thereof, the methods including administering to the subject an effective amount of a compound or pharmaceutical composition described herein.

In another aspect, provided herein are methods of preventing a disease in a subject in need thereof, the methods including administering to the subject an effective amount of a compound or pharmaceutical composition described herein.

In another aspect, provided herein are methods of treating a disease in a subject in need thereof, the methods including mixing blood or a component thereof (e.g., red blood cells) with an effective amount of a compound or pharmaceutical composition described herein to form a mixture ex vivo; and administering the mixture to the subject.

In another aspect, provided herein are methods of preventing a disease in a subject in need thereof, the methods including mixing blood or a component thereof (e.g., red blood cells) with an effective amount of a compound or pharmaceutical composition described herein to form a mixture; and administering the mixture to the subject.

In another aspect, the present disclosure provides methods of inhibiting the formation of biofilms comprising administering to a subject in need thereof an effective amount (e.g., therapeutically effective amount) of a compound or pharmaceutical composition described herein. In certain embodiments, the present invention provides methods of inhibiting the formation of biofilms comprising administering to a subject in need thereof an effective amount (e.g., therapeutically effective amount) of a compound or pharmaceutical composition described herein and an antimicrobial agent. In certain embodiments, the biofilms are produced by one or more microorganisms selected from the group consisting of bacteria, archaea, protozoa, fungi, and algae. In some embodiments, the biofilms are produced by bacteria. In some embodiments, the biofilms are produced by Gram-negative bacteria. In an embodiments, the biofilms are produced by *S. epidermidis, E. faecalis, E. coli, P. mirabilis, P. aeruginosa, K. pneumoniae, S. aureus, S. viridans, K. oxytoca, S. saprophyticus, L. pneumophila, Mycobacterium* spp., *C. freundii, A. hydrophila, F. nucleatum, A. naeslundii, P. stuartii, S. marcescens*, or a combination thereof. In some embodiments, the biofilms are produced by Gram-positive bacteria.

In another aspect, provided herein is a method for inhibiting bacterial cell growth comprising contacting bacteria with an effective amount of a compound or pharmaceutical composition described herein.

In another aspect, provided herein is a method for inducing bacterial hypersusceptibility comprising contacting a bacterium with an effective amount of a compound or pharmaceutical composition described herein. Hypersusceptibility refers to a condition of abnormal susceptibility to poisons, infective agents, or agents that are entirely innocuous in the normal subject.

In another aspect, provided are the compounds and pharmaceutical compositions described herein for use in a method described herein.

The details of one or more embodiments of the disclosure are set forth herein. Other features, objects, and advantages of the disclosure will be apparent from the Detailed Description, the Figures, the Examples, and the Claims.

Definitions

Definitions of specific functional groups and chemical terms are described in more detail below. For purposes of this invention, the chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3rd Edition, Cambridge University Press, Cambridge, 1987.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers." Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture." For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

Where an isomer/enantiomer is preferred, it may, in some embodiments, be provided substantially free of the corresponding enantiomer, and may also be referred to as "optically enriched" or "enantiomerically enriched." "Optically enriched" and "enantiomerically enriched" means that a provided compound is made up of a significantly greater proportion of one enantiomer. In certain embodiments, a compound of the present invention is made up of at least about 70% by weight of a preferred enantiomer. In certain embodiments, a compound of the present invention is made up of at least about 80% by weight of a preferred enantiomer. In certain embodiments, a compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); Wilen, *Tables of Resolving Agents and Optical Resolutions* p. 268 (E. L. Eliel, Ed., Univ. of Notre Dame Press, Notre Dame, Ind. 1972).

Unless otherwise stated, structures depicted herein are also meant to include compounds that differ only in the presence of one or more isotopically enriched atoms. For example, compounds having the depicted structures that differ only in the replacement of hydrogen by deuterium or tritium, or the replacement of a carbon by $^{13}C$ or $^{14}C$ are within the scope of this invention. Such compounds may be useful, for example, as analytical tools, as probes in biological assays, or as therapeutic agents in accordance with the present invention.

In a formula, $\sim\!\sim\!\sim$ is a single bond where the stereochemistry of the moieties immediately attached thereto is not specified, --- is absent or a single bond, and $=$ or $\equiv$ is a single or double bond.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The terms "purified," "substantially purified," and "isolated" refer to a compound useful in the present invention being free of other, dissimilar compounds with which the compound is normally associated in its natural state, so that the compound comprises at least 0.5%, 1%, 5%, 10%, 20%, 50%, 75%, 80%, 85%, 90%, 95%, 96%, 97%, 98%, 99%, 99.5%, 99.9% of the mass, by weight, of a given sample or composition. In one embodiment, these terms refer to the compound comprising at least 95%, 98%, 99%, or 99.9% of the mass, by weight, of a given sample or composition.

The term "acyl" refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, and —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "acyloxy" refers to a "substituted hydroxyl" of the formula (—OR$^i$), wherein R$^i$ is an optionally substituted acyl group, as defined herein, and the oxygen moiety is directly attached to the parent molecule.

The term "aliphatic" includes both saturated and unsaturated, nonaromatic, straight chain (e.g., unbranched), branched, acyclic, and cyclic (e.g., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkyl" refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-20 carbon atoms. In another embodiment, the alkyl group employed contains 1-15 carbon atoms. In another embodiment, the alkyl group employed contains 1-10 carbon atoms. In another embodiment, the alkyl group employed contains 1-8 carbon atoms. In another embodiment, the alkyl group employed contains 1-5 carbon atoms. Examples of alkyl radicals include, but are not limited to, methyl (e.g., unsubstituted methyl (Me)), ethyl (e.g., unsubstituted ethyl (Et)), propyl (e.g., unsubstituted propyl (Pr)), n-propyl, isopropyl, butyl (e.g., unsubstituted butyl (Bu)), n-butyl, iso-butyl, sec-butyl, sec-pentyl, iso-pentyl, tert-butyl, n-pentyl, neo-pentyl, n-hexyl, sec-hexyl, n-heptyl, n-octyl, n-decyl, n-undecyl, dodecyl, and the like, which may bear one or more sustitutents. Alkyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkenyl" denotes a monovalent group derived from a straight- or branched-chain hydrocarbon moiety having at least one carbon-carbon double bond by the removal of a single hydrogen atom. In certain embodiments, the alkenyl group employed in the invention contains 2-20 carbon atoms. In some embodiments, the alkenyl group employed in the invention contains 2-15 carbon atoms. In another embodiment, the alkenyl group employed contains 2-10 carbon atoms. In still other embodiments, the alkenyl group contains 2-8 carbon atoms. In yet other embodiments, the alkenyl group contains 2-5 carbons. Alkenyl groups include, for example, ethenyl, propenyl, butenyl, 1-methyl-2-buten-1-yl, and the like, which may bear one or more substituents. Alkenyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkynyl" refers to a monovalent group derived from a straight- or branched-chain hydrocarbon having at least one carbon-carbon triple bond by the removal of a single hydrogen atom. In certain embodiments, the alkynyl group employed in the invention contains 2-20 carbon atoms. In some embodiments, the alkynyl group employed in the invention contains 2-15 carbon atoms. In another embodiment, the alkynyl group employed contains 2-10 carbon atoms. In still other embodiments, the alkynyl group contains 2-8 carbon atoms. In still other embodiments, the alkynyl group contains 2-5 carbon atoms. Representative alkynyl groups include, but are not limited to, ethynyl, 2-propynyl (propargyl), 1-propynyl, and the like, which may bear one or more substituents. Alkynyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

Exemplary carbon atom substituents include, but are not limited to, halogen, —CN, —NO$_2$, —N$_3$, —SO$_2$H, —SO₃H, —OH, —OR$^{aa}$, —ON(R$^{bb}$)₂, —N(R$^{bb}$)₂, —N(R$^{bb}$)₃⁺X⁻, —N(OR$^{cc}$)R$^{bb}$, —SH, —SR$^{aa}$, —SSR$^{cc}$, —C(=O)R$^{aa}$, —CO₂H, —CHO, —C(OR$^{cc}$)₂, —CO₂R$^{aa}$, —OC(=O)R$^{aa}$, —OCO₂R$^{aa}$, —C(=O)N(R$^{bb}$)₂, —OC(=O)N(R$^{bb}$)₂, —NR$^{bb}$C(=O)R$^{aa}$, —NR$^{bb}$CO₂R$^{aa}$, —NR$^{bb}$C(=O)N(R$^{bb}$)₂, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(NR$^{bb}$)N(R$^{bb}$)₂, —OC(=NR$^{bb}$)N(R$^{bb}$)₂, —NR$^{bb}$C(=NR$^{bb}$)N(R$^{bb}$)₂, —C(=O)NR$^{bb}$SO₂R$^{aa}$, —NR$^{bb}$SO₂R$^{aa}$, —SO₂N(R$^{bb}$)₂, —SO₂R$^{aa}$, —SO₂OR$^{aa}$, —OSO₂R$^{aa}$, —S(=O)R$^{aa}$, —OS(=O)R$^{aa}$, —Si(R$^{aa}$)₃, —OSi(R$^{aa}$)₃ —C(=S)N(R$^{bb}$)₂, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)₂, —P(=O)(OR$^{cc}$)₂, —OP(=O)(R$^{aa}$)₂, —OP(=O)(OR$^{cc}$)₂, —P(=O)(N(R$^{bb}$)₂)₂, —OP(=O)(N(R$^{bb}$)₂)₂, —NR$^{bb}$P(=O)(R$^{aa}$)₂, —NR$^{bb}$P(=O)(OR$^{cc}$)₂, —NR$^{bb}$P(=O)(N(R$^{bb}$)₂)₂, —P(R$^{cc}$)₂, —P(OR$^{cc}$)₂, —P(R$^{cc}$)₃⁺X⁻, —P(OR$^{cc}$)₃⁺X⁻, —P(R$^{cc}$)₄, —P(OR$^{cc}$)₄, —OP(R$^{cc}$)₂, —OP(R$^{cc}$)₃⁺X⁻, —OP(OR$^{cc}$)₂, —OP(OR$^{cc}$)₃⁺X⁻, —OP(R$^{cc}$)₄, —OP(OR$^{cc}$)₄, —B(R$^{aa}$)₂, —B(OR$^{cc}$)₂, —BR$^{aa}$(OR$^{cc}$), $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X⁻ is a counterion;

or two geminal hydrogens on a carbon atom are replaced with the group =O, =S, =NN(R$^{bb}$)₂, =NNR$^{bb}$C(=O)R$^{aa}$, =NNR$^{bb}$C(=O)OR$^{aa}$, =NNR$^{bb}$S(=O)₂R$^{aa}$, =NR$^{bb}$, or =NOR$^{cc}$;

each instance of R$^{aa}$ is, independently, selected from $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$alkenyl, heteroC$_{2-10}$alkynyl, $C_{3-10}$ carbocyclyl, 3-14 membered heterocyclyl, $C_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of e is, independently, selected from hydrogen, —OH, —OR$^{aa}$, —N(R$^{cc}$)₂, —CN, —C(=O)R$^{aa}$, —C(=O)N(R$^{cc}$)₂, —CO₂R$^{aa}$, —SO₂R$^{aa}$, —C(=NR$^{cc}$)OR$^{aa}$, —C(=NR$^{cc}$)N(R$^{cc}$)₂, —SO₂N(R$^{cc}$)₂, —SO₂R$^{cc}$, —SO₂OR$^{cc}$, —SOR$^{aa}$, —C(=S)N(R$^{cc}$)₂, —C(=O)SR$^{cc}$, —C(=S)SR$^{cc}$, —P(=O)(R$^{aa}$)₂, —P(=O)(OR$^{cc}$)₂, —P(=O)(N(R$^{cc}$)₂)₂, $C_{1-10}$ alkyl, $C_{1-10}$ perhaloalkyl, $C_{2-10}$ alkenyl, $C_{2-10}$ alkynyl, heteroC$_{1-10}$alkyl, heteroC$_{2-10}$alkenyl, heteroC$_{2-10}$alkynyl, $C_{3-10}$ carbocyclyl, 3-14 membered heterocyclyl, $C_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X⁻ is a counterion;

each instance of R$^{cc}$ is, independently, selected from hydrogen, $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$alkynyl, $C_{3-10}$ carbocyclyl, 3-14 membered heterocyclyl, $C_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO₂, —N₃, —SO₂H, —SO₃H, —OH, —OR$^{ee}$, —ON(R$^{ff}$)₂, —N(R$^{ff}$)₂, —N(R$^{ff}$)₃⁺X⁻, —N(OR$^{ee}$)R$^{ff}$, —SH, —SR$^{ee}$, —SSR$^{ee}$, —C(=O)R$^{ee}$, —CO₂H, —CO₂R$^{ee}$, —OC(=O)R$^{ee}$, —OCO₂R$^{ee}$, —C(=O)N(R$^{ff}$)₂, —OC(=O)N(R$^{ff}$)₂, —NR$^{ff}$C(=O)R$^{ee}$, —NR$^{ff}$CO₂R$^{ee}$, —NR$^{ff}$C(=O)N(R$^{ff}$)₂, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)₂, —OC(=NR$^{ff}$)N(R$^{ff}$)₂, —NR$^{ff}$C(=NR$^{ff}$)N(R$^{ff}$)₂, —NR$^{ff}$SO₂R$^{ee}$, —SO₂N(R$^{ff}$)₂, —SO₂R$^{ee}$, —SO₂OR$^{ee}$, —OSO₂R$^{ee}$, —S(=O)R$^{ee}$, —Si(R$^{ee}$)₃, —OSi(R$^{ee}$)₃, —C(=S)N(R$^{ff}$)₂, —C(=O)SR$^{ee}$, —C(=S)SR$^{ee}$, —SC(=S)SR$^{ee}$, —P(=O)(OR$^{ee}$)₂, —P(=O)(R$^{ee}$)₂, —OP(=O)(R$^{ee}$)₂, —OP(=O)(OR$^{ee}$)₂, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X⁻ is a counterion;

each instance of R$^{ee}$ is, independently, selected from $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$alkenyl, heteroC$_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, 3-10 membered heterocyclyl, $C_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ roups; and each instance of R$^{gg}$ is, independently, halogen, —CN, —NO₂, —N₃, —SO₂H, —SO₃H, —OH, —OC$_{1-6}$ alkyl, —ON(C$_{1-6}$ alkyl)₂, —N(C$_{1-6}$ alkyl)₂, —N(C$_{1-6}$ alkyl)₃⁺X⁻, —NH(C$_{1-6}$ alkyl)₂⁺X⁻, —NH₂(C$_{1-6}$ alkyl)⁺X⁻, —NH₃⁺X⁻, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO₂H, —CO₂(C$_{1-6}$ alkyl), —OC(=O)(C$_{1-6}$ alkyl), —OCO₂(C$_{1-6}$ alkyl), —C(=O)NH₂, —C(=O)N(C$_{1-6}$ alkyl)₂, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO₂(C$_{1-6}$ alkyl), —NHC(=O)N(C$_{1-6}$ alkyl)₂, —NHC(=O)NH(C$_{1-6}$ alkyl), —NHC(=O)NH₂, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)₂, —C(=NH)NH(C$_{1-6}$ alkyl), —C(=NH)NH₂, —OC(=NH)N(C$_{1-6}$ alkyl)₂, —OC(NH)NH(C$_{1-6}$ alkyl), —OC(NH)NH₂, —NHC(NH)N(C$_{1-6}$ alkyl)₂, —NHC(=NH)NH₂, —NHSO₂(C$_{1-6}$ alkyl), —SO₂N(C$_{1-6}$ alkyl)₂, —SO₂NH(C$_{1-6}$ alkyl), —SO₂NH₂, —SO₂C$_{1-6}$ alkyl, —SO₂OC$_{1-6}$ alkyl, —OSO₂C$_{1-6}$ alkyl, —SOC$_{1-6}$ alkyl, —Si(C$_{1-6}$ alkyl)₃, —OSi(C$_{1-6}$ alkyl)₃, —C(=S)N(C$_{1-6}$ alkyl)₂, C(=S)NH(C$_{1-6}$ alkyl), C(=S)NH₂, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)₂, —P(=O)(C$^{1-6}$ alkyl)₂, —OP(=O)(C$_{1-6}$ alkyl)₂, —OP(=O)(OC$_{1-6}$ alkyl)₂, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

The term "amino" refers to a group of the formula (—NH$_2$). A "substituted amino" refers either to a monosubstituted amine (—NHR$^h$) of a disubstituted amine (—NR$^h_2$), wherein the R$^h$ substituent is any substituent as described herein that results in the formation of a stable moiety (e.g., a suitable amino protecting group; aliphatic, alkyl, alkenyl, alkynyl, heteroaliphatic, heterocyclic, aryl, heteroaryl, acyl, amino, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted). In certain embodiments, the R$^h$ substituents of the disubstituted amino group(—NR$^h_2$) form a 5- to 6-membered heterocyclic ring.

The term "alkoxy" refers to a "substituted hydroxyl" of the formula (—OR$^i$), wherein R$^i$ is an optionally substituted alkyl group as defined herein, and the oxygen moiety is directly attached to the parent molecule.

The term "alkylthioxy" refers to a "substituted thiol" of the formula (—SR$^r$), wherein R$^r$ is an optionally substituted alkyl group as defined herein, and the sulfur moiety is directly attached to the parent molecule.

The term "alkylamino" refers to a "substituted amino" of the formula (—NR$^h_2$), wherein R$^h$ is, independently, a hydrogen or an optionally substituted alkyl group as defined herein, and the nitrogen moiety is directly attached to the parent molecule.

The term "aryl" refer to stable aromatic mono- or polycyclic ring system having 3-20 ring atoms, of which all the ring atoms are carbon, and which may be substituted or unsubstituted. In certain embodiments of the present invention, "aryl" refers to a mono, bi, or tricyclic C$_4$-C$_{20}$ aromatic ring system having one, two, or three aromatic rings which include, but not limited to, phenyl, biphenyl, naphthyl, and the like, which may bear one or more substituents. Aryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "arylalkyl" refers to an aryl substituted alkyl group, wherein the terms "aryl" and "alkyl" are defined herein, and wherein the aryl group is attached to the alkyl group, which in turn is attached to the parent molecule. Exemplary arylalkyl groups are benzyl and phenethyl.

The term "aryloxy" refers to a "substituted hydroxyl" of the formula (—OR$^i$), wherein R$^i$ is an optionally substituted aryl group as defined herein, and the oxygen moiety is directly attached to the parent molecule.

The term "arylamino," refers to a "substituted amino" of the formula (—NR$^h_2$), wherein R$^h$ is, independently, a hydrogen or an optionally substituted aryl group as defined herein, and the nitrogen moiety is directly attached to the parent molecule.

The term "arylthioxy" refers to a "substituted thiol" of the formula (—SR$^r$), wherein R$^r$ is an optionally substituted aryl group as defined herein, and the sulfur moiety is directly attached to the parent molecule.

The terms "halo" and "halogen" refer to an atom selected from fluorine (fluoro, —F), chlorine (chloro, —Cl), bromine (bromo, —Br), and iodine (iodo, —I).

The term "heteroaliphatic" refers to an aliphatic moiety, as defined herein, which includes both saturated and unsaturated, nonaromatic, straight chain (i.e., unbranched), branched, acyclic, cyclic (e.g., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl", "heteroalkynyl", and the like. Furthermore, the terms "heteroalkyl", "heteroalkenyl", "heteroalkynyl", and the like encompass both substituted and unsubstituted groups. In certain embodiments, "heteroaliphatic" is used to indicate those heteroaliphatic groups (cyclic, acyclic, substituted, unsubstituted, branched or unbranched) having 1-20 carbon atoms. Heteroaliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroalkyl" refers to an alkyl moiety, as defined herein, which contain one or more oxygen, sulfur, nitrogen, phosphorus, or silicon atoms, e.g., in place of carbon atoms.

The term "heteroalkenyl" refers to an alkenyl moiety, as defined herein, which contain one or more oxygen, sulfur, nitrogen, phosphorus, or silicon atoms, e.g., in place of carbon atoms.

The term "heteroalkynyl" refers to an alkynyl moiety, as defined herein, which contain one or more oxygen, sulfur, nitrogen, phosphorus, or silicon atoms, e.g., in place of carbon atoms.

The term "heteroalkylamino" refers to a "substituted amino" of the formula (—NR$^h_2$), wherein R$^h$ is, independently, a hydrogen or an optionally substituted heteroalkyl group, as defined herein, and the nitrogen moiety is directly attached to the parent molecule.

The term "heteroalkyloxy" refers to a "substituted hydroxyl" of the formula (—OR$^i$), wherein R$^i$ is an optionally substituted heteroalkyl group, as defined herein, and the oxygen moiety is directly attached to the parent molecule.

The term "heteroalkylthioxy" refers to a "substituted thiol" of the formula (—SR$^r$), wherein R$^r$ is an optionally substituted heteroalkyl group, as defined herein, and the sulfur moiety is directly attached to the parent molecule.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclyl ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

The term "heterocyclic," "heterocycles," or "heterocyclyl" refers to a cyclic heteroaliphatic group. A heterocyclic group refers to a non-aromatic, partially unsaturated or fully saturated, 3- to 12-membered ring system, which includes single rings of 3 to 8 atoms in size, and bi- and tri-cyclic ring systems which may include aromatic five- or six-membered aryl or heteroaryl groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocyclyl groups include, but are not limited to, a bi- or tri-cyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Exemplary heterocycles include azacyclopropanyl, azacyclobutanyl, 1,3-diazatidinyl, piperidinyl, piperazinyl, azocanyl, thiaranyl, thietanyl, tetrahydrothiophenyl, dithiolanyl, thiacyclohexanyl, oxiranyl, oxetanyl, tetrahydrofuranyl, tetrahydropuranyl, dioxanyl, oxathiolanyl, morpholinyl, thioxanyl, tetrahydronaphthyl, and the like, which may bear one or more substituents. Substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroaryl" refer to stable aromatic mono- or polycyclic ring system having 3-20 ring atoms, of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms. Exemplary heteroaryls include, but are not limited to pyrrolyl, pyrazolyl, imidazolyl, pyridinyl (pyridyl), pyrimidinyl, pyrazinyl, pyridazinyl, triazinyl, tetrazinyl, pyyrolizinyl, indolyl, quinolinyl, isoquinolinyl, benzoimidazolyl, indazolyl, quinolinyl, isoquinolinyl, quinolizinyl, cinnolinyl, quinazolynyl, phthalazinyl, naphthridinyl, quinoxalinyl, thiophenyl, thianaphthenyl, furanyl, benzofuranyl, benzothiazolyl, thiazolynyl, isothiazolyl, thiadiazolynyl, oxazolyl, isoxazolyl, oxadiaziolyl, oxadiaziolyl, and the like, which may bear one or more substituents. Heteroaryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroarylamino" refers to a "substituted amino" of the ($-NR^h_2$), wherein $R^h$ is, independently, hydrogen or an optionally substituted heteroaryl group, as defined herein, and the nitrogen moiety is directly attached to the parent molecule.

The term "heteroaryloxy" refers to a "substituted hydroxyl" of the formula ($-OR^i$), wherein $R^i$ is an optionally substituted heteroaryl group, as defined herein, and the oxygen moiety is directly attached to the parent molecule.

The term "heteroarylthioxy" refers to a "substituted thiol" of the formula ($-SR^r$), wherein $R^r$ is an optionally substituted heteroaryl group, as defined herein, and the sulfur moiety is directly attached to the parent molecule.

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from $-OR^{aa}$, $-ON(R^{bb})_2$, $-OC(=O)SR^{aa}$, $-OC(=O)R^{aa}$, $-OCO_2R^{aa}$, $-OC(=O)N(R^{bb})_2$, $-OC(=NR^{bb})R^{aa}$, $-OC(=NR^{bb})OR^{aa}$, $-OC(=NR^{bb})N(R^{bb})_2$, $-OS(=O)R^{aa}$, $-OSO_2R^{aa}$, $-OSi(R^{aa})_3$, $-OP(R^{cc})_2$, $-OP(R^{cc})_3{}^+X^-$, $-OP(OR^{cc})_2$, $-OP(OR^{cc})_3{}^+X^-$, $-OP(=O)(R^{aa})_2$, $-OP(=O)(OR^{cc})_2$, and $-OP(=O)(N(R^{bb}))_2$, wherein $X^-$, $R^{aa}$, $R^{bb}$, and $R^{cc}$ are as defined herein.

The term "imino" refers to a group of the formula (=NR$^r$), wherein R$^r$ corresponds to hydrogen or any substituent as described herein, that results in the formation of a stable moiety (for example, a suitable amino protecting group; aliphatic, alkyl, alkenyl, alkynyl, heteroaliphatic, heterocyclic, aryl, heteroaryl, acyl, amino, hydroxyl, alkylaryl, arylalkyl, and the like, each of which may or may not be further substituted). In certain embodiments, imino refers to =NH wherein R$^r$ is hydrogen.

The term "nitro" refers to a group of the formula ($-NO_2$).

The term "oxo" refers to a group of the formula (=O).

A "protecting group" is well known in the art and include those described in detail in *Greene's Protective Groups in Organic Synthesis*, P. G. M. Wuts and T. W. Greene, 4$^{th}$ edition, Wiley-Interscience, 2006, the entirety of which is incorporated herein by reference.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, $-OR^{aa}$, $-N(R^{cc})_2$, —CN, $-C(=O)R^{aa}$, $-C(=O)N(R^{cc})_2$, $-CO_2R^{aa}$, $-SO_2R^{aa}$, $-C(=NR^{bb})R^{aa}$, $-C(=NR^{cc})OR^{aa}$, $-C(=NR^{cc})N(R^{cc})_2$, $-SO_2N(R^{cc})_2$, $-SO_2R^{cc}$, $-SO_2OR^{cc}$, $-SOR^{aa}$, $-C(=S)N(R^{cc})_2$, $-C(=O)SR^{cc}$, $-C(=S)SR^{cc}$, $-P(=O)(OR^{cc})_2$, $-P(=O)(R^{aa})_2$, $-P(=O)(N(R^{cc})_2)_2$, $C_{1-10}$ alkyl, $C_{1-10}$ perhaloalkyl, $C_{2-10}$ alkenyl, $C_{2-10}$ alkynyl, heteroC$_{1-10}$alkyl, heteroC$_{2-10}$alkenyl, heteroC$_{2-10}$alkynyl, $C_{3-10}$ carbocyclyl, 3-14 membered heterocyclyl, $C_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, $-OR^{aa}$, $-N(R^{cc})_2$, $-C(=O)R^{aa}$, $-C(=O)N(R^{cc})_2$, $-CO_2R^{aa}$, $-SO_2R^{aa}$, $-C(=NR^{cc})R^{aa}$, $-C(=NR^{cc})OR^{aa}$, $-C(=NR^{cc})N(R^{cc})_2$, $-SO_2N(R^{cc})_2$, $-SO_2R^{cc}$, $-SO_2OR^{cc}$, $-SOR^{aa}$, $-C(=S)N(R^{cc})_2$, $-C(=O)SR^{cc}$, $-C(=S)SR^{cc}$, $C_{1-10}$ alkyl, (e.g., aralkyl, heteroaralkyl), $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

For example, nitrogen protecting groups such as amide groups (e.g., $-C(=O)R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., $-C(=O)OR^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl] amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference. Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3{}^+X^-$, —$P(OR^{cc})_2$, —$P(OR^{cc})_3{}^+X^-$, —$P(=O)(R^{aa})_2$, —$P(=O)(OR^{cc})_2$, and —$P(=O)(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F, Cl, Br, I), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

The term "carbohydrate" or "saccharide" refers to an aldehydic or ketonic derivative of polyhydric alcohols. Carbohydrates include compounds with relatively small molecules (e.g., sugars) as well as macromolecular or polymeric substances (e.g., starch, glycogen, and cellulose polysaccharides). The term "sugar" refers to monosaccharides, disaccharides, or polysaccharides. Monosaccharides are the simplest carbohydrates in that they cannot be hydrolyzed to smaller carbohydrates. Most monosaccharides can be represented by the general formula $C_yH_{2y}O_y$ (e.g., $C_6H_{12}O_6$ (a hexose such as glucose)), wherein y is an integer equal to or greater than 3. Certain polyhydric alcohols not represented by the general formula described above may also be considered monosaccharides. For example, deoxyribose is of the formula $C_5H_{10}O_4$ and is a monosaccharide. Monosaccharides usually consist of five or six carbon atoms and are referred to as pentoses and hexoses, receptively. If the monosaccharide contains an aldehyde it is referred to as an aldose; and if it contains a ketone, it is referred to as a ketose. Monosaccharides may also consist of three, four, or seven carbon atoms in an aldose or ketose form and are referred to as trioses, tetroses, and heptoses, respectively. Glyceraldehyde and dihydroxyacetone are considered to be aldotriose and ketotriose sugars, respectively. Examples of aldotetrose sugars include erythrose and threose; and ketotetrose sugars include erythrulose. Aldopentose sugars include ribose, arabinose, xylose, and lyxose; and ketopentose sugars include ribulose, arabulose, xylulose, and lyxulose. Examples of aldohexose sugars include glucose (for example, dextrose), mannose, galactose, allose, altrose, talose, gulose, and idose; and ketohexose sugars include fructose, psicose, sorbose, and tagatose. Ketoheptose sugars include sedoheptulose. Each carbon atom of a monosaccharide bearing a hydroxyl group (—OH), with the exception of the first and last carbons, is asymmetric, making the carbon atom a stereocenter with two possible configurations (R or S). Because of this asymmetry, a number of isomers may exist for any given monosaccharide formula. The aldohexose D-glucose, for example, has the formula $C_6H_{12}O_6$, of which all but two of its six carbons atoms are stereogenic, making D-glucose one of the 16 (i.e., $2^4$) possible stereoisomers. The assignment of D or L is made according to the orientation of the asymmetric carbon furthest from the carbonyl group: in a standard Fischer projection if the hydroxyl group is on the right the molecule is a D sugar, otherwise it is an L sugar. The aldehyde or ketone group of a straight-chain monosaccharide will react reversibly with a hydroxyl group on a different carbon atom to form a hemiacetal or hemiketal, forming a heterocyclic ring with an oxygen bridge between two carbon atoms. Rings with five and six atoms are called furanose and pyranose forms, respectively, and exist in equilibrium with the straight-chain form. During the conversion from the straight-chain form to the cyclic form, the carbon atom containing the carbonyl oxygen, called the anomeric carbon, becomes a stereogenic center with two possible configurations: the oxygen atom may take a position either above or below the plane of the ring. The resulting possible pair of stereoisomers is called anomers. In an a anomer, the —OH substituent on the anomeric carbon rests on the opposite side (trans) of the ring from the —$CH_2OH$ side branch. The alternative form, in which the —$CH_2OH$ substituent and the anomeric hydroxyl are on the same side (cis) of the plane of the ring, is called a β anomer. A carbohydrate including two or more joined monosaccharide units is called a disaccharide or polysaccharide (e.g., a trisaccharide), respectively. The two or more monosaccharide units bound together by a covalent bond known as a glycosidic linkage formed via a dehydration reaction, resulting in the loss of a hydrogen atom from one monosaccharide and a hydroxyl group from another. Exemplary disaccharides include sucrose, lactulose, lactose, maltose, isomaltose, trehalose, cellobiose, xylobiose, laminaribiose, gentiobiose, mannobiose, melibiose, nigerose, and rutinose. Exemplary trisaccharides include, but are not limited to, isomaltotriose, nigerotriose, maltotriose, melezitose, maltotriulose, raffinose, and kestose. The term carbohydrate also includes other natural or synthetic stereoisomers of the carbohydrates described herein.

The term "pharmaceutically acceptable salt" refers to those salts which are, within the scope of sound medical judgment, suitable for use in contact with the tissues of humans and other animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable salts include inorganic acids such as hydrochloric acid, hydrobromic acid, sulfuric acid, and phosphoric acid; and organic acids such as oxalic acid, maleic acid, succinic acid, and citric acid. "Basic addition salts" refer to salts derived from appropriate bases, these salts including alkali metal, alkaline earth metal, and quaternary amine salts. Hence, the present invention contemplates sodium, potassium, magnesium, and calcium salts of the compounds disclosed herein, and the like. Basic addition salts can be prepared during the final isolation and purification of the compounds, often by reacting a carboxyl group with a suitable base such as the hydroxide, carbonate, or bicarbonate of a metal cation or with ammonia or an organic primary, secondary, or tertiary amine. The cations of therapeutically acceptable salts include lithium, sodium (by using, e.g., NaOH), potassium (by using, e.g., KOH), calcium (by using, e.g., $Ca(OH)_2$), magnesium (by using, e.g., $Mg(OH)_2$ and magnesium acetate), zinc, (by using, e.g., $Zn(OH)_2$ and zinc acetate), and aluminum, as well as non-toxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N-dibenzylethylenediamine. Other representative organic amines useful for the formation of base addition salts include ethylenediamine, ethanolamine, diethanolamine, piperidine, piperazine, choline hydroxide, hydroxyethyl morpholine, hydroxyethyl pyrrolidone, imidazole, n-methyl-d-glucamine, N,N'-dibenzylethylenediamine, N,N'-diethylethanolamine, N,N'-dimethylethanolamine, triethanolamine, and tromethamine. Basic amino acids (e.g., 1-glycine and 1-arginine) and amino acids which may be zwitterionic at neutral pH (e.g., betaine (N,N,N-trimethylglycine)) are also contemplated.

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

The term "polymorphs" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds of the invention may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R.xH$_2$O, wherein R is the compound and wherein x is a number greater than 0. A given compound may form more than one type of hydrates, including, e.g., monohydrates (x is 1), lower hydrates (x is a number greater than 0 and smaller than 1, e.g., hemihydrates (R.0.5H$_2$O)), and polyhydrates (x is a number greater than 1, e.g., dihydrates (R.2H$_2$O) and hexahydrates (R.6H$_2$)).

The term "subject" refers to any animal. In certain embodiments, the subject is a mammal. In certain embodiments, the subject is a human (e.g., a man, a woman, or a child). The human may be of either sex and may be at any stage of development. In certain embodiments, the subject has been diagnosed with the condition or disease to be treated. In other embodiments, the subject is at risk of developing the condition or disease. In certain embodiments, the subject is an experimental animal (e.g., mouse, rat, rabbit, dog, pig, or primate). The experimental animal may be genetically engineered. In certain embodiments, the subject is a domesticated animal (e.g., dog, cat, bird, horse, cow, goat, sheep).

The terms "administer," "administering," or "administration" refers to implanting, absorbing, ingesting, injecting, inhaling, or otherwise introducing an inventive compound, or a pharmaceutical composition thereof.

The terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

The terms "condition," "pathological condition," "disease," and "disorder" are used interchangeably.

An "effective amount" of a compound of the present invention or a pharmaceutical composition thereof refers to an amount sufficient to elicit the desired biological response, e.g., treating the condition. As will be appreciated by those of ordinary skill in this art, the effective amount of a compound of the invention may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound of the present invention or a pharmaceutical composition thereof is an amount sufficient to provide a therapeutic benefit in the treatment of a condition, e.g., iron overload, or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, and/or enhances the therapeutic efficacy of another therapeutic agent. In certain embodiments, a therapeutically effective amount is an amount sufficient for chelating a metal described herein. In certain embodiments, a therapeutically effective amount is an amount sufficient for treating a pathological condition described herein. In certain embodiments, a therapeutically effective amount is an amount sufficient for chelating a metal described herein and for treating a pathological condition described herein.

A "prophylactically effective amount" of a compound of the present invention is an amount sufficient to prevent a condition, e.g., iron overload, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is an amount sufficient for chelating a metal described herein. In certain embodiments, a prophylactically effective amount is an amount sufficient for preventing a pathological condition described herein. In certain embodiments, a prophylactically effective amount is an amount sufficient for chelating a metal described herein and for preventing a pathological condition described herein.

The term "biological sample" refers to any sample including tissue samples (such as tissue sections and needle biopsies of a tissue); cell samples (e.g., cytological smears (such as Pap or blood smears) or samples of cells obtained by microdis section); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

"Chelation," "chelating," "sequestration," or "sequestering" is the formation or presence of two or more separate coordinate bonds between a polydentate (multiple-bonded) compound and a single central atom. The polydentate compound is typically an organic compound and referred to as a "chelator," "chelant," "chelating agent," "sequestrator," "sequestering agent," or "ligand." The central atom is usually a metal atom or metal ion (e.g., a metal atom or metal ion described herein, such as iron (e.g., Fe(III)), Al(III), chromium (e.g., Cr(III) or Cr(VI)), and uranium (e.g., U(VI)), etc.). The chelator may form a stable complex with the central atom through coordinate bonds, inactivating the central atom so that the central atom is less likely to react with other molecules or atoms.

The term "metal-clearing efficiency" or "MCE" refers to the efficacy of a given concentration of chelator in clearing a metal atom or metal ion (e.g., a metal atom or metal ion described herein, such as iron (e.g., Fe(III)), Al(III), chromium (e.g., Cr(III) or Cr(VI)), and uranium (e.g., U(VI)) from the body or one of its organs or parts. Efficaciousness in turn concerns quantity of the metal atom or metal ion removed from a target system (e.g., a whole body, an organ, or a tissue) in a unit of time. Chelators of a metal atom or metal ion are needed in one or more of three clinical situations: (1) for acute metal toxicity from ingestion or infusion of the metal atom or metal ion; (2) to reduce total body metal secondary to transfusion or excess metal absorption; and (3) for the maintenance of metal balance after total body metal has been satisfactorily reduced and only daily dietary metal needs to be excreted. In practical terms, therefore, for chronic metal overload secondary to transfusion, the recommendation is that 0.3-0.5 mg/kg/d (i.e., mg iron per kg body weight of the subject per day) need be excreted. For the maintenance treatment, 0.25-1 mg/kg/d is sufficient. Other ranges are also possible. In certain embodiments, the metal-clearing efficiency is iron-clearing efficiency or "ICE." In certain embodiments, the metal-clearing efficiency is aluminum-clearing efficiency. In certain embodiments, the metal-clearing efficiency is chromium-clearing efficiency. In certain embodiments, the metal-clearing efficiency is uranium-clearing efficiency.

The term "focal iron overload" refers to any disease or condition that involves the accumulation of unmanaged iron in a tissue or organ. Focal iron overload typically involves less than the subject's whole body but may involve more than one organ or tissue. Unmanaged iron in any tissue or organ is typically undesired and can be the focus of the treatments of the present invention. The treatment may involve the removal of as much iron as possible from the tissue or organ or may only involve the removal of excess iron. Examples of disease and conditions associated with focal iron overload include, but are not limited to, macular degeneration, IBD, reperfusion injury, stroke including hemorrhagic stroke, and closed head injury; however, any disease or condition of focal iron overload may be treated as described herein. In certain embodiments, the term "focal iron overload" does not include diseases or conditions associated with global iron overload (e.g., global iron overload associated with chronic transfusion therapy, hereditary hemochromatosis, etc.). The treatment of focal iron overload may be systemic or local administration of an effective amount of an inventive compound, or a pharmaceutical composition thereof.

The term "reactive oxygen species" or "ROS" refers to molecules or ions formed by the incomplete reduction of oxygen. Reactive oxygen species include superoxide anion ($O_2.^-$), peroxides such as hydrogen peroxide ($H_2O_2$), hydroxyl radical (HO.), and hypochlorous acid (HClO). These molecules are typically chemically reactive. Reactive oxygen species may be formed by any number of mechanisms (e.g., enzymatically, by ionizing radiation, by reaction oxygen with a metal). In certain embodiments, the reactive oxygen species are formed by the reduction of oxygen by an iron ion, such as $Fe^{+2}$.

"Primary hemochromatosis" is a genetic disorder characterized by excessive iron accumulation that results in tissue damage. Manifestations include systemic symptoms, liver disorders, cardiomyopathy, diabetes, erectile dysfunction, and arthropathy. Normal total body iron content is about 2.5 g in women and 3.5 g in men. Because symptoms may be delayed until iron accumulation is excessive, hemochromatosis may not be recognized until total body iron content is >10 g, or often several times greater. In women, clinical manifestations are uncommon before menopause because iron loss due to menses (and sometimes pregnancy and childbirth) tends to offset iron accumulation. One mechanism for iron overload is increased iron absorption from the gastrointestinal tract, leading to chronic deposition of iron in the tissues. Hepcidin, a liver-derived peptide, is the critical control mechanism for iron absorption. Hepcidin, along with the normal HFE gene, prevents excessive iron absorption and storage in normal people. Tissue injury in a subject with primary hemochromatosis may result from reactive free hydroxyl radicals generated when iron deposition in tissues catalyzes their formation. Other mechanisms may affect particular organs (e.g., skin hyperpigmentation can result from increased melanin as well as iron accumulation).

"Secondary hemochromatosis" is a condition acquired as a consequence of another disease that causes iron overload, or blood transfusions, or both, and typically characterized by increased hepatic and total body iron content and unequivocal portal cirrhosis of the liver. Secondary hemochromatosis is usually caused by disorders of erythropoiesis (e.g., thalassemia, sickle cell anemia, X-linked sideroblastic anemia, pyruvate kinase deficiency, hereditary spherocytosis, and congenital dyserythropoietic anemia (CDA)) and the treatment of these diseases with blood transfusions. After damaging the transfused erythrocytes by macrophages, iron freed from the heme is accumulated in the body (e.g., in the liver, heart, or skin).

"Diabetes" or "diabetes mellitus" is a metabolic disorder in which there are high levels of glucose in the blood. Diabetes can be caused by insufficient amount of insulin (a hormone produced by the pancreas to control blood glucose) or resistance to insulin in a subject, or both. There are three major types of diabetes: Type 1, Type 2, and gestational diabetes. Type 1 diabetes is usually diagnosed in children and young adults, and was previously known as juvenile diabetes. In Type 1 diabetes, the body does not produce insulin, which may be a result of the destruction of islet cells in the pancreas. Type 2 diabetes, or non-insulin-dependent diabetes mellitus (NIDDM) or adult-onset diabetes, is the most common form of diabetes. Type 2 diabetes is characterized by high blood glucose in the context of insulin resistance and relative insulin deficiency. This is in contrast to Type 1 diabetes in which there is an absolute insulin deficiency. Obesity is thought to be one of the primary causes of Type 2 diabetes in subjects who are genetically predisposed to obesity. Gestational diabetes is characterized by high blood glucose that develops during pregnancy in a woman who does not have diabetes prior to the pregnancy. Gestational diabetes may be caused by various pregnancy hormones that may interfere with the body's response to insulin.

The term "closed head injury" refers to any injury to the head that does not penetrate the skull. Closed head injuries may result from falls, blasts, accidents including vehicular accidents, and assaults. Closed head injuries can lead to hemorrhage or brain swelling, which can result in increased intracranial pressure, which can in turn lead to permanent brain damage or even death. Various types of closed head injury include concussions, brain contusions, diffuse axonal injury, and hematomas.

"Thalassemia" is a group of inherited autosomal recessive blood disorders that originated in the Mediterranean region. In a subject with thalassemia, the genetic defect, which could be either mutation or deletion, results in reduced rate of synthesis or no synthesis of one of the globin chains that make up hemoglobin. This can cause the formation of abnormal hemoglobin molecules, thus causing anemia. There are two main types of thalassemia: alpha and beta thalassemias. Alpha thalassemia occurs when a gene or genes related to the alpha globin protein are missing or changed (i.e., mutated). Beta thalassemia occurs when similar gene defects affect production of the beta globin protein. Each of alpha and beta thalassemias includes two forms: thalassemia major and thalassemia minor. Beta thalassemia major is also referred to as Cooley's anemia or Mediterranean anemia.

"Friedreich's ataxia" or "FRDA" is an inherited disease that causes progressive damage to the nervous system of a subject resulting in symptoms including muscle weakness, speech problems, and heart disease. In a subject with Friedreich's ataxia, the spinal cord and peripheral nerves degenerate and become thinner. The cerebellum, part of the brain that coordinates balance and movement, also degenerates to a lesser extent. This damage results in awkward, unsteady movements and impaired sensory functions. Friedreich's ataxia also causes problems in the heart and spine, and some subjects with the condition develop diabetes. However, this disorder usually does not affect cognitive functions, such as thinking and reasoning. Friedreich's ataxia is caused by a defect, which may be a result of mutation, in a gene labeled as FXN. This disorder is recessive, meaning it occurs only in someone who inherits two defective copies of the gene, one from each parent.

"Macular degeneration" is a disease that affects the retina of a subject. The retina is a thin tissue lining the back of the eye. Light-sensitive cells in the retina are responsible for converting light into electrical impulses, which are then sent via the optic nerve to the brain for interpretation. In the center of the retina is the macula. The macula contains the highest concentration of the light-sensitive cells, called cones, which are responsible for sharp, detailed, and central vision. In macular degeneration, cells in the macular region begin to die, which results in blind spots and distorted vision. Macular degeneration is the leading cause of vision loss in humans over the age of 60. There are two forms of macular degeneration: dry and wet macular degenerations. It is possible for a subject to suffer from both forms, for it to affect one or both eyes, and for the disease to progress slowly or rapidly. Dry macular degeneration is the most common type of macular degeneration, in which the photosensitive cells of the macula slowly break down. Yellow deposits called drusen (extracellular waste products from metabolism) form and accumulate under the retina between the retinal pigmented epithelium (RPE) layer and the Bruch's membrane, which supports the retina. Over time, drusen are associated with deterioration of the macula and the death of RPE and photoreceptor cells, resulting in a blurring or spotty loss of clear, straight-ahead vision. This process does not cause any pain. In the early stages of the disease, the subject may notice slightly blurry vision. However, as more and more of the cells die, central vision worsens. Dry macular degeneration may advance and cause loss of vision without turning into the wet form of the disease. However, it is also possible for the early-stage dry form to change into the wet form of macular degeneration. Wet macular degeneration occurs when abnormal blood vessels grow behind the macula as RPE and photoreceptor cells die. The Bruch's membrane begins to break down, usually near drusen deposits, and new blood vessels grow. These vessels are very fragile and can leak fluid and blood. Scarring of and severe damage to the macula may result. Straight-ahead vision can become distorted or lost entirely in a short period of time.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include, but are not limited to, hematological malignancies. Hematological malignancies are tumors that affect blood, bone marrow, and/or lymph nodes. Exemplary hematological malignancies include, but are not limited to, leukemia, such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma, such as Hodgkin lymphoma (HL) (e.g., B-cell HL, T-cell HL) and non-Hodgkin lymphoma (NHL) (e.g., B-cell NHL, such as diffuse large cell lymphoma (DLCL) (e.g., diffuse large B-cell lymphoma (DLBCL, e.g., activated B-cell (ABC) DLBCL (ABC-DLBCL))), follicular lymphoma, chronic lymphocytic leukemia/small lymphocytic lymphoma (CLL/SLL), mantle cell lymphoma (MCL), marginal zone B-cell lymphoma (e.g., mucosa-associated lymphoid tissue (MALT) lymphoma, nodal marginal zone B-cell lymphoma, splenic marginal zone B-cell lymphoma), primary mediastinal B-cell lymphoma, Burkitt lymphoma, Waldenstrom's macroglobulinemia (WM, lymphoplasmacytic lymphoma), hairy cell leukemia (HCL), immunoblastic large cell lymphoma, precursor B-lymphoblastic lymphoma, central nervous system (CNS) lymphoma (e.g., primary CNS lymphoma and secondary CNS lymphoma); and T-cell NHL, such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); lymphoma of an immune privileged site (e.g., cerebral lymphoma, ocular lymphoma, lymphoma of the placenta, lymphoma of the fetus, testicular lymphoma); a mixture of one or more leukemia/lymphoma as described above; myelodysplasia; and multiple myeloma (MM). Additional exemplary cancers include, but are not limited to, lung cancer (e.g., bronchogenic carcinoma, small cell lung cancer (SCLC), non-small cell lung cancer (NSCLC), adenocarcinoma of the lung); kidney cancer (e.g., nephroblastoma, a.k.a. Wilms' tumor, renal cell carcinoma); acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; liver cancer (e.g., hepatocellular cancer (HCC), malignant hepatoma); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g.,bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

A "preneoplastic disease" is a disease that precedes the formation of a benign or malignant neoplasm. A precancerous lesion typically forms before a malignant neoplasm. Preneoplastic diseases include, but are not limited to, photodermatitis, x-ray dermatitis, tar dermatitis, arsenic dermatitis, lupus dermatitis, senile keratosis, Paget disease, condylomata, burn scar, syphilitic scar, fistula scar, ulcus cruris scar, chronic ulcer, varicose ulcer, bone fistula, rectal fistula, Barrett esophagus, gastric ulcer, gastritis, cholelithiasis, kraurosis vulvae, nevus pigmentosus, Bowen dermatosis, xeroderma pigmentosum, erythroplasia, leukoplakia, Paget disease of bone, exostoses, ecchondroma, osteitis fibrosa, leontiasis ossea, neurofibromatosis, polyposis, hydatidiform mole, adenomatous hyperplasia, and struma nodosa.

DETAILED DESCRIPTION OF CERTAIN EMBODIMENTS OF THE INVENTION

Figure 1:
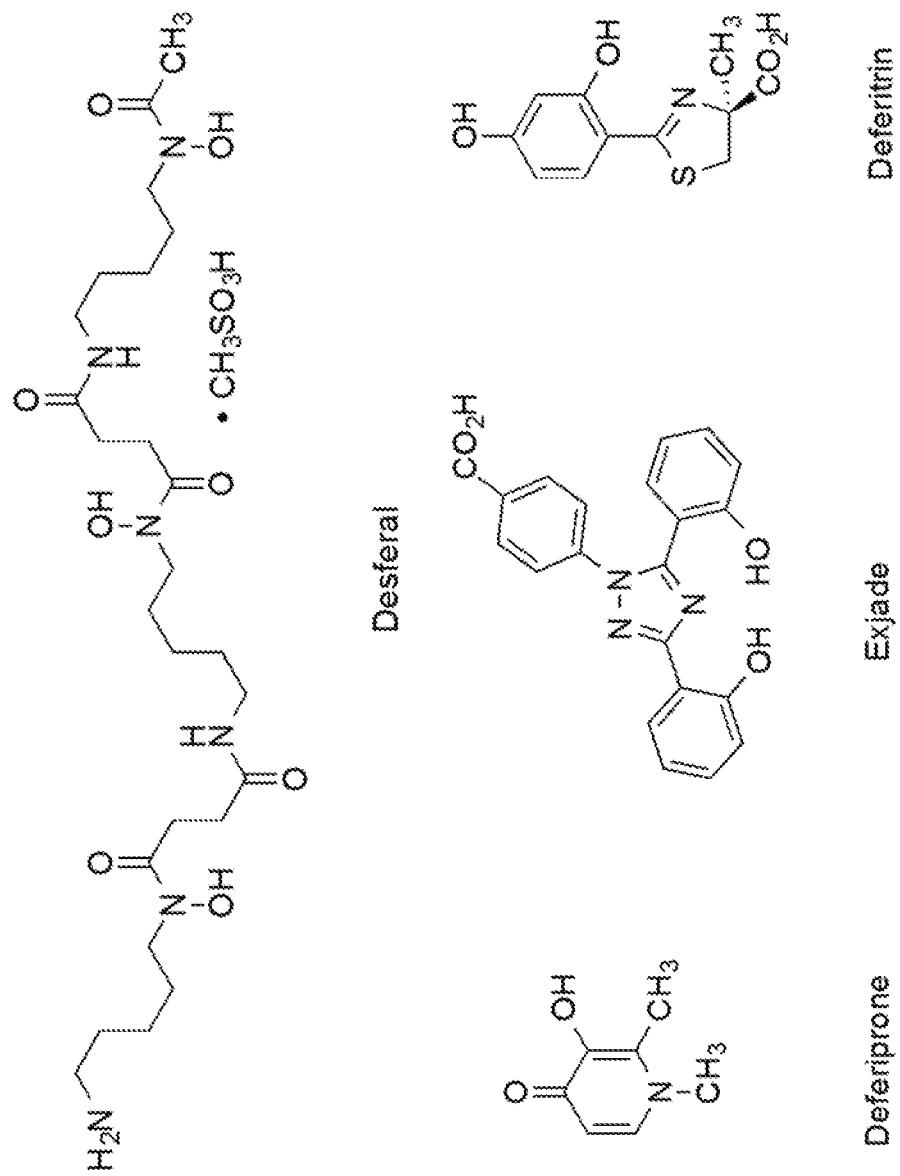
FIG. 1 shows the structures of some iron chelators evaluated clinically in humans.

The present invention provides, in one aspect, compounds of Formula (I), and pharmaceutically acceptable salts, solvates, hydrates, polymorphs, co-crystals, tautomers, stereoisomers, isotopically labeled derivatives, and prodrugs thereof. The desazadesferrithiocin analogs are able to chelate a metal (e.g., iron and other metals). The invention also provides pharmaceutical compositions, kits, methods, and uses that involve or include a desazadesferrithiocin analog described herein. The present invention provides, in another aspect, compounds of Formula (II), and pharmaceutically acceptable salts, solvates, hydrates, polymorphs, co-crystals, tautomers, stereoisomers, isotopically labeled derivatives, and prodrugs thereof. The invention also provides pharmaceutical compositions, kits, methods, and uses that involve or include a compound of Formula (I) or Formula (II) described herein. The compounds, pharmaceutical compositions, kits, and methods may be useful in chelating a metal in a subject, cell, tissue, or biological sample. The compounds, pharmaceutical compositions, kits, and methods may also be useful in treating a disease in a subject, preventing a disease in a subject, treating, reducing, or preventing the formation of biofilms in a subject, or reducing or preventing the formation of biofilms on or in an object. In certain embodiments, the disease is a metal overload, oxidative stress, transfusional iron overload, thalassemia, primary hemochromatosis, secondary hemochromatosis, diabetes, liver disease, heart disease, cancer, radiation injury, neurological or neurodegenerative disorder, Friedreich's ataxia (FRDA), macular degeneration, closed head injury, irritable bowel disease, or reperfusion injury. In certain embodiments, the disease is metal poisoning. In certain embodiments, the disease is an infectious disease (e.g., malaria).

Compounds

Desferrithiocin (DFT) 1 is a natural product iron chelator isolated from *Streptomyces antibioticus* (Naegeli et al., "Metabolites of Microorganisms. Part 193. Ferrithiocin." *Helv. Chim. Acta* 1980, 63, 1400-1406). It forms a 2:1 complex with Fe(III) with a cumulative formation constant of $4 \times 10^{29}$ $M^{-1}$ (Hahn et al., "Coordination Chemistry of Microbial Iron Transport. 42. Structural and Spectroscopic Characterization of Diastereomeric Cr(III) and Co(III) Complexes of Desferriferrithiocin." *J. Am. Chem. Soc.* 1990, 112, 1854-1860; Anderegg et al., "Metal Complex Formation of a New Siderophore Desferrithiocin and of Three Related Ligands." *J. Chem. Soc., Chem. Commun.* 1990, 1194-1196). Although the compound was shown to be an excellent deferration agent when administered orally (po) to rats (Bergeron et al., "Evaluation of Desferrithiocin and Its Synthetic Analogs as Orally Effective Iron Chelators." *J. Med. Chem.* 1991, 34, 2072-2078) and primates (Bergeron et al., "A Comparative Evaluation of Iron Clearance Models." *Ann. N.Y. Acad. Sci.* 1990, 612, 378-393; Wolfe et al., "A Non-Human Primate Model for the Study of Oral Iron Chelators." *Br. J. Haematol.* 1989, 72, 456-461), it caused severe nephrotoxicity in rats (Bergeron et al., "A Comparative Study of the Iron-Clearing Properties of Desferrithiocin Analogs with Desferrioxamine B in a Cebus Monkey Model." *Blood* 1993, 81, 2166-2173). However, the compound's oral activity spurred SAR studies focused on DFT aimed at identifying an orally active and safe DFT analog (Bergeron et al., "Effects of C-4 Stereochemistry and C-4' Hydroxylation on the Iron Clearing Efficiency and Toxicity of Desferrithiocin Analogs." *J. Med. Chem.* 1999, 42, 2432-2440; Bergeron et al., "Methoxylation of Desazadesferrithiocin Analogs: Enhanced Iron Clearing Efficiency." *J. Med. Chem.* 2003, 46, 1470-1477; Bergeron et al., "Desazadesmethyldesferrithiocin Analogs as Orally Effective Iron Chelators." *J. Med. Chem.* 1999, 42, 95-108). Various desazadesferrithiocin analogs have been developed that effectively chelate and remove metals from biological systems. See International PCT Application Publications, WO 1997/036885, published Oct. 9, 1997; WO 2000/016763, published Mar. 30, 2000; WO 2000/012493, published Mar. 9, 2000; WO 2004/017959, published Mar. 4, 2004; WO 2005/034949, published Apr. 21, 2005; WO 2005/023310, published Mar. 17, 2005; WO 2006/107626, published Oct. 12, 2006; WO 2008/130395, published Oct. 30, 2008; WO 2008/115433, published Sep. 25, 2008; WO 2011/028255, published Mar. 10, 2011; WO 2013/090750, published Jun. 20, 2013; and WO 2013/090766, published Jun. 20, 2013; each of which is incorporated herein by reference. Also see U.S. Pat. Nos. 5,840,739; 6,864,270; 7,144,904; 7,879,886; US Reissue 39,132; U.S. Pat. Nos. 6,083,966; 6,521,652; 6,525,080; 6,559,315; 8,278,458; and 8,324,397; each of which is incorporated herein by reference. Also see U.S. Patent Application Publications, US 2004/044220, US 2004/132789, US 2005/234113, US 2008/255081, US 2006/211746, US 2006/211773, US 2008/096974, US 2013/030028, US 2010/137346, US 2013/210870, and US 2012/184586, each of which is incorporated herein by reference.

Removal of the pyridine nitrogen of 1 provided 1a, the parent compound of the desazadesferrithiocin (DADFT) series (Bergeron et al., "Desazadesmethyldesferrithiocin Analogs as Orally Effective Iron Chelators." *J. Med. Chem.* 1999, 42, 95-108). Interestingly, although 1a was not overtly nephrotoxic, it elicited serious gastrointestinal (GI) problems (Bergeron et al., "A Comparative Study of the Iron-Clearing Properties of Desferrithiocin Analogs with Desferrioxamine B in a Cebus Monkey Model." *Blood* 1993, 81, 2166-2173; Bergeron et al., "Effects of C-4 Stereochemistry and C-4' Hydroxylation on the Iron Clearing Efficiency and Toxicity of Desferrithiocin Analogs." *J. Med. Chem.* 1999, 42, 2432-2440; Bergeron et al., "Desazadesmethyldesferrithiocin Analogs as Orally Effective Iron Chelators." *J. Med. Chem.* 1999, 42, 95-108). In spite of its GI toxicity, the compound's excellent iron-clearing efficiency (ICE) and the absence of nephrotoxicity prompted further SAR studies predicated on this pharmacophore. This led to the discovery that the lipophilicity (partition between octanol and water, expressed as the log of the fraction in the octanol layer, log $P_{app}$) (Sangster, *Octanol-Water Partition Coefficients: Fundamentals and Physical Chemistry*; John Wiley and Sons: West Sussex, England, 1997; Vol. 2) of DADFT analogs could have a profound effect on a compound's ICE, organ distribution, and toxicity profile (Bergeron et al., "Effects of C-4 Stereochemistry and C-4' Hydroxylation on the Iron Clearing Efficiency and Toxicity of Desferrithiocin Analogs." *J. Med. Chem.* 1999, 42, 2432-2440; Bergeron et al., "Iron Chelators and Therapeutic Uses." In: Abraham, ed.

Burger's Medicinal Chemistry. 6th. Wiley; N.Y.: 2003. pp. 479-561; Bergeron et al., "Desferrithiocin Analogs and Nephrotoxicity." *J. Med. Chem.* 2008, 51, 5993-6004). Desferrithiocin analogs have been reported to chelate and remove iron or other metals. See International PCT Application Publications, WO 1997/036885, published Oct. 9, 1997; WO 2000/016763, published Mar. 30, 2000; WO 2000/012493, published Mar. 9, 2000; and WO 2004/017959, published Mar. 4, 2004; each of which is incorporated herein by reference. Also see U.S. Pat. Nos. 5,840,739; 6,864,270; 7,144,904; 7,879,886; U.S. Reissue 39,132; U.S. Pat. Nos. 6,083,966; 6,521,652; 6,525,080; and 6,559,315; each of which is incorporated herein by reference. Also see U.S. Patent Application Publications, US 2004/044220, US 2004/132789, US 2005/234113, and US 2008/255081, each of which is incorporated herein by reference.

The toxicity associated with excess iron derives from its interaction with reactive oxygen species, for instance, endogenous hydrogen peroxide ($H_2O_2$).[20-22] In the presence of Fe(II), $H_2O_2$ is reduced to the hydroxyl radical (HO.) and $HO^-$, a process known as the Fenton reaction (shown below). The hydroxyl radical reacts very quickly with a variety of cellular constituents and can initiate radical-mediated chain processes that damage DNA and membranes, as well as produce carcinogens.[23] The cyclic nature of the Fenton reaction adds to the potential danger. The Fe(III) liberated in this reaction is converted back to Fe(II) via a variety of biological reductants, e.g., ascorbate or glutathione.

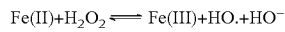

In the majority of patients with thalassemia major or other transfusion-dependent refractory anemias, treatment with a chelating agent capable of sequestering iron and permitting its excretion from the body is the only therapeutic option available. Current choices (FIG. 1) include Desferal, the mesylate[24] salt of desferrioxamine B (DFO), 1,2-dimethyl-3-hydroxypyridin-4-one (deferiprone, L1),[25,26] and 4-[3,5-bis(2-hydroxyphenyl)-1,2,4-triazol-1-yl]benzoic acid (deferasirox, ICL670A).[27,28] Each has shortcomings[29] and in some cases, serious toxicity issues. DFO, a hexacoordinate hydroxamate iron chelator produced by *Streptomyces pilosus*,[30] a siderophore, is not orally active and is best administered subcutaneously (sc) by continuous infusion over long periods of time,[31] which presents a patient compliance issue. Deferiprone, while orally active, does not remove enough iron to keep patients in a negative iron balance, and has been associated with agranulocytosis (Ferriprox Prescribing Information, Apotex Inc., Toronto, Ontario, Canada, April, 2015; www.ferriprox.com/us/pdf/ferriprox_full_pi.pdf). Novartis's drug deferasirox did not show noninferiority to DFO, is associated with a number of serious side effects, and, unfortunately, has a narrow therapeutic window.[28,33] Our pursuit of an efficient orally active iron chelator with an acceptable toxicity profile began with desferrithiocin, (S)-4,5-dihydro-2-(3-hydroxy-2-pyridinyl)-4-methyl-4-thiazolecarboxylic acid (DFT, 1, Table 1). DFT is a tridentate siderophore[34,35] excreted by *Streptomyces antibioticus*[34] that forms a stable 2:1 complex with Fe(III); the cumulative formation constant is $4 \times 10^{29}$.[35] Initial animal trials with DFT in rodents[36] and primates[37-39] revealed it to be orally active and highly efficient at removing iron. Its iron clearing efficiency (ICE) was 5.5±3.2% in rodents,[36] and 16.1±8.5% in primates[38] (Bergeron et al., *Ann N.Y. Acad. Sci.* 612 (1990, 612,) 378-393; Wolfe et al., *Br. J. Hematol.* 72 (1989, 72,) 456-461) (Table 1). ICE is calculated as (ligand-induced iron excretion/theoretical iron excretion)×100, expressed as a percent. However, DFT has unacceptable renal toxicity in rats.[40,41] Nevertheless, the ligand's remarkable oral bioavailability and ICE drove a successful structure-activity study aimed at ameliorating DFT-induced nephrotoxicity.[37,42-45] The outcome revealed that removal of the desferrithiocin aromatic nitrogen, providing (S)-4,5-dihydro-2-(2-hydroxyphenyl)-4-methyl-4-thiazolecarboxylic acid (desazadesferrithiocin, DADFT), and introduction of a hydroxyl at either the 4'-aromatic to yield (S)-2-(2,4-dihydroxyphenyl)-4,5-dihydro-4-methyl-4-thiazolecarboxylic acid[37] [(S)-4'-(HO)-DADFT, deferitrin, 2] or the 3'-aromatic to afford (S)-2-(2,3-dihydroxyphenyl)-4,5-dihydro-4-methyl-4-thiazolecarboxylic acid[37] [(S)-3'-(OH)-DADFT, 3] led to chelators with good ICE values (Table 1) and a remarkable reduction in toxicity. Deferitrin (2, FIG. 1), was taken into human clinical trials by Genzyme. Chelator 2 was well tolerated in patients at doses of 5, 10, or 15 mg/kg/day once daily (s.i.d) for up to 12 weeks,[46] and iron clearance levels were approaching the requisite 450 µg/kg/d.[47] However, when the drug was given twice daily (b.i.d) at a dose of 12.5 mg/kg (25 mg/kg/d), unacceptable renal toxicity, e.g., increases in blood urea nitrogen (BUN) and serum creatinine (SCr), were observed in three patients after only 4-5 weeks of treatment and the study was terminated.[48] Nevertheless, the results were attractive enough to compel us to reengineer deferitrin in an attempt to ameliorate the its toxicity.

The redesign of 2 was predicated on the observation that both ligands 2 and 3 were orally active iron chelators in rodents and primates (Table 1), and that when the 4'-(OH) of 2 was methylated, providing (S)-4,5-dihydro-2-(2-hydroxy-4-methoxyphenyl)-4-methyl-4-thiazolecarboxylic acid[43] [(S)-4'-(CH$_3$O)-DADFT, 4], there was a remarkable enhancement in both ICE and lipophilicity (log $P_{app}$). The log $P_{app}$ data are expressed as the log of the fraction of the chelator seen in the octanol layer; measurements were done in TRIS buffer, pH 7.4, using a "shake flask" direct method.[49] The more negative the log $P_{app}$, the less chelator is in the octanol phase, the less lipophilic. Unfortunately, the increase in ICE of 4 came with a concomitant increase in toxicity.[50] Thus, the delicate balance between the increase in ICE and toxicity with enhanced lipophilicity needed to be understood and exploited. It was determined that introducing polyether fragments at the 4'-(OH) of 2 to produce (S)-4,5-dihydro-2-[2-hydroxy-4-(3,6,9-trioxadecyloxy)phenyl]-4-methyl-4-thiazolecarboxylic acid[50] [(S)-4'-(HO)-DADFT-PE, 5] or the 3'-(OH) of 3, yielding (S)-4,5-dihydro-2-[2-hydroxy-3-(3,6,9-trioxadecyloxy)phenyl]-4-methyl-4-thiazolecarboxylic acid[51] [(S)-3'-(OH)-DADFT-PE, 6] led to less lipophilic, e.g., lower log $P_{app}$, remarkably efficient iron chelators (Table 1). Unlike deferitrin, there was no renal toxicity, seen with either 5 or 6, even when the chelators were administered b.i.d.[50,52]

A magnesium salt of ligand 6 (SPD602, deferitazole magnesium, CAS #1173092-59-5) was evaluated in clinical trials by Shire.[53,54] Since 6 is an oil, and its sodium salt is hygroscopic, dosage form issues may have driven their choice of a magnesium salt. It is interesting to speculate as to whether or not the gastrointestinal (GI) and other side effects observed with the magnesium salt of 6[53,54] derive from the magnesium itself.[55-57] All of our studies with 6 were conducted with the monosodium salt.[41,51,52,58] It remains to be seen how well the magnesium salt will perform in patients.

There were two properties of the (S)-3'-(HO)-DADFT-PE (6) that needed attention. The parent drug was an oil, and the dose response curve in rats plateaued very quickly. For example, when 6 was given orally (po) to bile duct-cannulated rats at a dose of 150 μmol/kg, the drug decorporated 0.782±0.121 mg/kg of iron; the ICE was 18.7±2.9%.[45,58] However, when the dose of the chelator was further increased to 300 μmol/kg, the quantity of iron excreted, 0.887±0.367 mg/kg, was within error of that induced by the drug at 150 μmol/kg (p>0.05), and the ICE was 10.6±4.4%.[45,58] Thus, the deferration induced by 6 was saturable over a fairly narrow dose range. Additional structure activity relationship (SAR) studies were carried out to search for a chelator that had better physicochemical properties, e.g., a solid that retained its ICE over a wider range of doses. The answer would come with a simple structural modification of (S)-4'-(HO)-DADFT-PE (5): the 3,6,9-trioxadecyloxy polyether moiety was replaced with a 3,6-dioxaheptyloxy function, providing (S)-4,5-dihydro-2-[2-hydroxy-4-(3,6-dioxaheptyloxy)phenyl]-4-methyl-4-thiazolecarboxylic acid[58,59] [(S)-4'-(HO)-DADFT-norPE, 7]. Both acid 7 (Table 1) and its ester precursor[59] were crystalline solids and could be given very effectively in capsules to both rodents and primates. Ligand 7 has excellent ICE properties (~26%) in rodents and primates. It also has a much better dose response in rodents than 6.[58]

Because of the problems with b.i.d. deferitrin, the toxicity issue of most concern with 7 was related to renal proximal tubule damage. A series of tolerability studies focusing on (S)-4'-(HO)-DADFT-norPE's impact on renal function were carried out.[58] The drug was given orally to rats s.i.d. for 28 d (56.9, 113.8, or 170.7 μmol/kg/day); s.i.d. for 10 d (384 μmol/kg/d), and b.i.d. at 237 μmol/kg/dose (474 μmol/kg/d)×7 d.[58] Blood was collected immediately prior to sacrifice and was submitted for a complete blood count (CBC) and serum chemistries, including the determination of the animals' blood urea nitrogen (BUN) and serum creatinine (SCr). No drug-related abnormalities were found, and the rats' BUN and SCr levels were within the normal range.[59] In addition, an assessment of the drug's effect on urinary kidney injury molecule-1 (Kim-1)[60,61] excretion was determined. Kim-1 is a type 1 transmembrane protein located in the epithelial cells of proximal tubules.[60,61] The ectodomain of the Kim-1 proximal tubule protein is released into the urine very early after exposure to a nephrotoxic agent or ischemia; it appears far sooner than increases in BUN or SCr are detected in the serum.[62,63] Administration of 7 to rats for up to 28 days did not elicit any increases in urinary Kim-1 excretion.[58] Extensive tissues were submitted for histopathology; no drug-related abnormalities were identified. This SAR success set the stage for a closer look at how best to further exploit the relationship between lipophilicity, ICE, and ligand toxicity. The design strategies would weigh heavily on how a chelator's substituents are potentially metabolized.

Although DFT and DADFT analogs as a class of compounds appear promising as metal chelating agents, work may be done to improve these compounds' physicochemical, pharmacokinetic, pharmacodynamic, and/or toxicological properties, such as absorption, distribution, metal-clearing efficiency, and toxicity, for the purpose of providing safe and effective compounds for a better treatment and/or prevention of pathological conditions in a subject.

One aspect of the present disclosure relates to compounds of Formula (I):

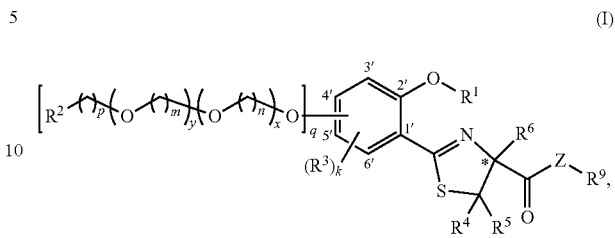

(I)

and pharmaceutically acceptable salts, solvates, hydrates, polymorphs, co-crystals, tautomers, stereoisomers, isotopically labeled derivatives, and prodrugs thereof, wherein:

$R^1$ is hydrogen, substituted or unsubstituted alkyl, substituted or unsubstituted acyl, an oxygen protecting group,

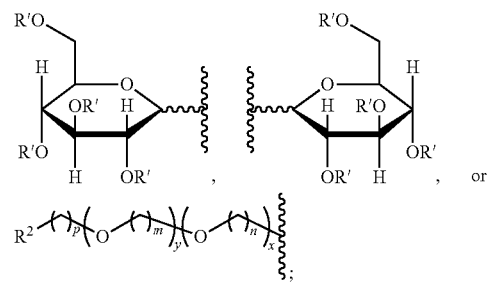

each instance of R' is independently hydrogen, substituted or unsubstituted alkyl, or an oxygen protecting group;

each instance of n is independently an integer from 1 to 8, inclusive;

each instance of x is independently an integer between 0 and 8, inclusive;

each instance of m is independently an integer from 1 to 8, inclusive;

each instance of y is independently an integer from 0 to 8, inclusive;

each instance of p is independently an integer between 1 and 10, inclusive;

q is 0 or 1, provided that when q is 0, then $R^1$ is of the formula:

each instance of $R^2$ is independently $—CH_2OR^{2a}$, $—CH_2OH$, $—C(=\!)OH$, or $—C(=\!O)OR^{2a}$, wherein each instance of $R^{2a}$ is independently substituted or unsubstituted alkyl or an oxygen protecting group;

each instance of $R^3$ is independently halogen, substituted or unsubstituted alkyl, or $—OR^8$, wherein each instance of $R^8$ is independently hydrogen, substituted or unsubstituted alkyl, substituted or unsubstituted acyl, an oxygen protecting group,

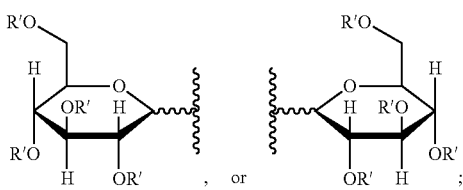, or k is 0, 1, 2, 3, or 4;

$R^4$ is hydrogen or substituted or unsubstituted alkyl;

$R^5$ is hydrogen or substituted or unsubstituted alkyl;

$R^6$ is hydrogen or substituted or unsubstituted alkyl;

Z is —O— or —S—; and $R^9$ is hydrogen, substituted or unsubstituted alkyl,

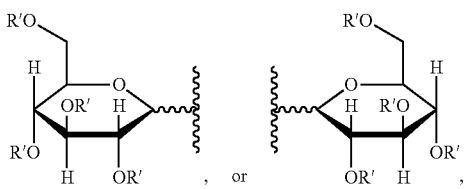, or an oxygen protecting group when attached to an oxygen atom, or a sulfur protecting group when attached to a sulfur atom.

Formula (I) includes substituent —O—$R^1$ at the 2'-position of the phenyl ring. In certain embodiments, $R^1$ is H. In certain embodiments, $R^1$ is substituted or unsubstituted alkyl (e.g., substituted or unsubstituted $C_{1-6}$ alkyl). In certain embodiments, $R^1$ is Me. In certain embodiments, $R^1$ is Et, Pr, Bu, unsubstituted pentyl, or unsubstituted hexyl. In certain embodiments, $R^1$ is substituted methyl (e.g., —$CF_3$, or Bn), substituted ethyl (e.g., perfluoroethyl), substituted propyl (e.g., perfluoropropyl), substituted butyl (e.g., perfluorobutyl), substituted pentyl (e.g., perfluoropentyl), or substituted hexyl (e.g., perflourohexyl). In certain embodiments, $R^1$ is substituted or unsubstituted acyl. In certain embodiments, $R^1$ is —C(=O)$R^a$, optionally wherein $R^a$ is substituted or unsubstituted $C_{1-6}$ alkyl (e.g., Me). In certain embodiments, $R^1$ is —C(=O)O$R^a$, optionally wherein $R^a$ is H, substituted or unsubstituted $C_{1-6}$ alkyl (e.g., Me), or an oxygen protecting group (e.g., silyl, TBDPS, TBDMS, TIPS, TES, TMS, MOM, THP, t-Bu, Bn, allyl, acetyl, pivaloyl, or benzoyl). In certain embodiments, $R^1$ is —C(=O)N($R^a$)$_2$, optionally wherein each instance of $R^a$ is independently H, substituted or unsubstituted $C_{1-6}$ alkyl (e.g., Me), or a nitrogen protecting group (e.g., Bn, Boc, Cbz, Fmoc, trifluoroacetyl, triphenylmethyl, acetyl, or Ts). In certain embodiments, $R^1$ is an oxygen protecting group (e.g., silyl, TBDPS, TBDMS, TIPS, TES, TMS, MOM, THP, t-Bu, Bn, allyl, acetyl, pivaloyl, or benzoyl). In certain embodiments, $R^1$ is

 (e.g., 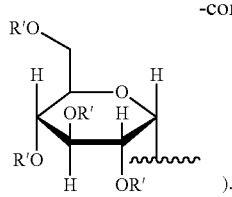).

In certain embodiments, $R^1$ is

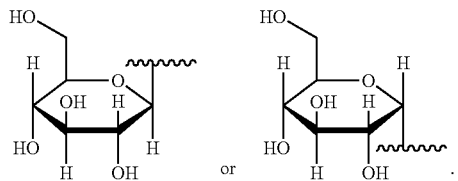.

In certain embodiments, $R^1$ is

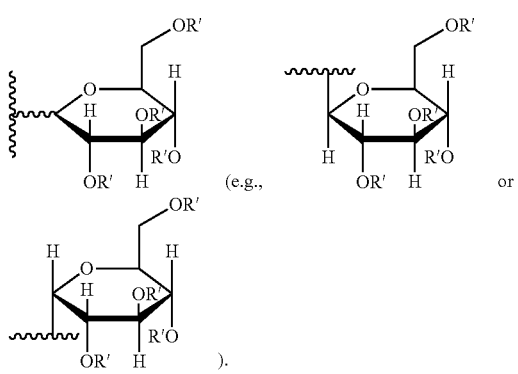.

In certain embodiments, $R^1$ is

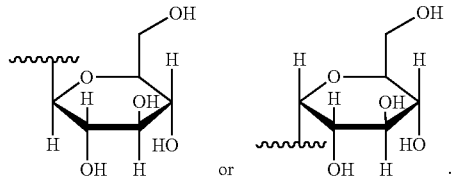.

In certain embodiments, $R^1$ is of the formula:

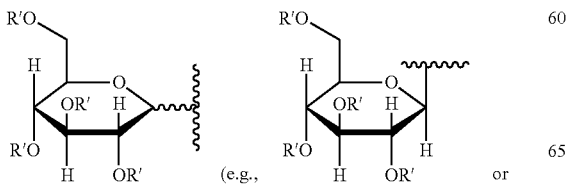.

In certain embodiments, —O—$R^1$ is of the formula:

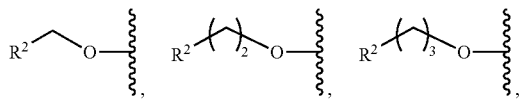

-continued
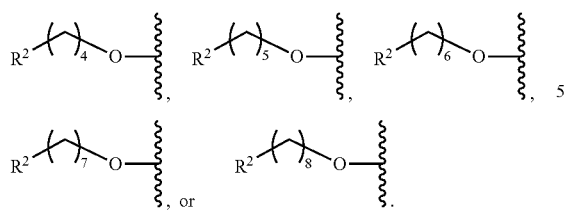
In certain embodiments, —O—R¹ is of the formula:
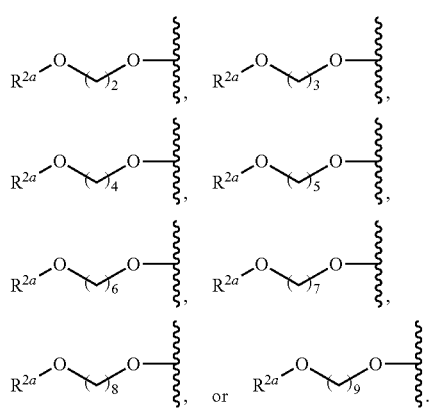
In certain embodiments, —O—R¹ is of the formula:
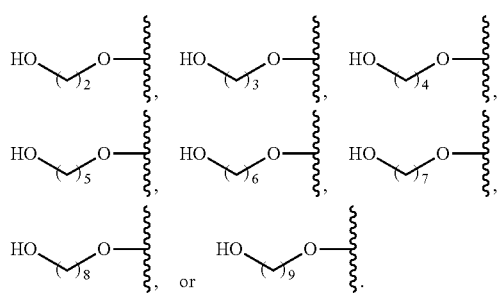
In certain embodiments, —O—R¹ is of the formula:
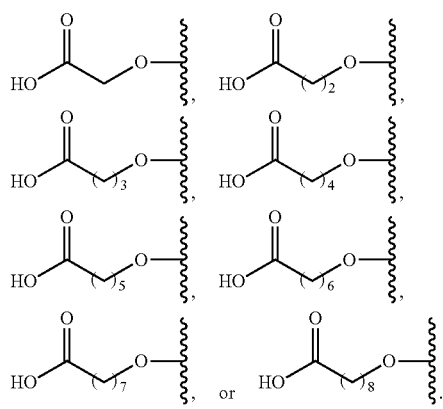
In certain embodiments, —O—R¹ is of the formula:
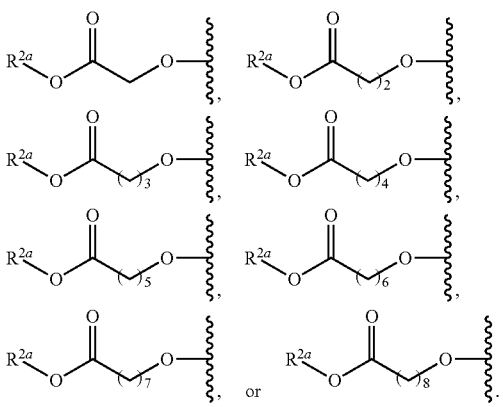
In certain embodiments, —O—R¹ is of the formula:
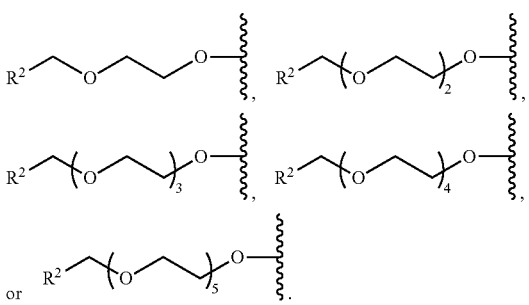
In certain embodiments, —O—R¹ is of the formula:
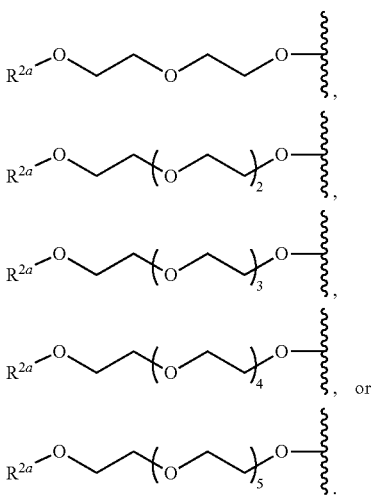
In certain embodiments, —O—R¹ is of the formula:
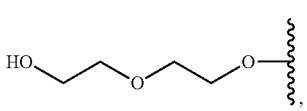

-continued

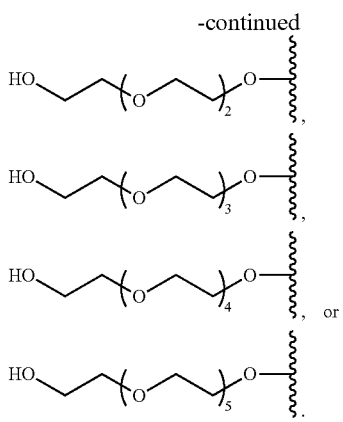

In certain embodiments, —O—R¹ is of the formula:

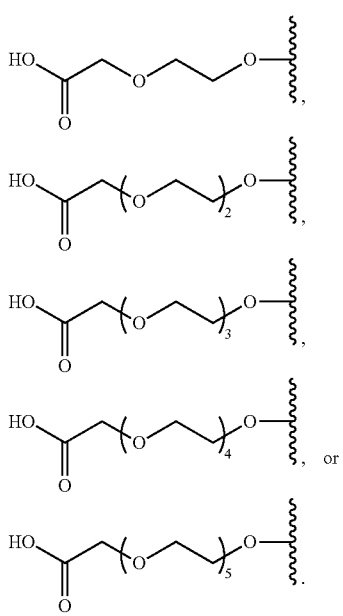

In certain embodiments, —O—R¹ is of the formula:

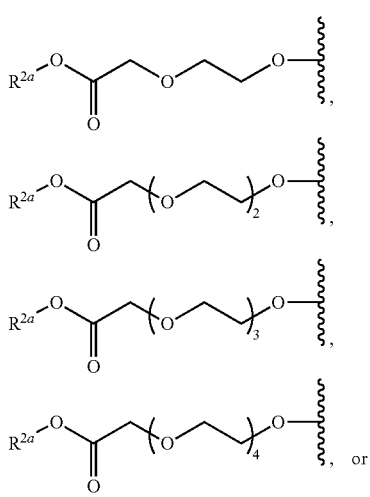

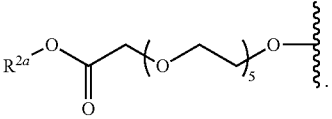

Formula (I) may include one or more instances of substituent R'. When Formula (I) includes two or more instances of R', any two instances of $R^a$ may independently be the same or different from each other. In certain embodiments, at least one instance of R' is H. In certain embodiments, each instance of R' is H. In certain embodiments, at least one instance of R' is substituted or unsubstituted alkyl (e.g., substituted or unsubstituted $C_{1-6}$ alkyl). In certain embodiments, at least one instance of R' is Me. In certain embodiments, at least one instance of R' is Et, Pr, Bu, unsubstituted pentyl, or unsubstituted hexyl. In certain embodiments, at least one instance of R' is substituted methyl (e.g., —$CF_3$, or Bn), substituted ethyl (e.g., perfluoroethyl), substituted propyl (e.g., perfluoropropyl), substituted butyl (e.g., perfluorobutyl), substituted pentyl (e.g., perfluoropentyl), or substituted hexyl (e.g., perflourohexyl). In certain embodiments, at least one instance of R' is an oxygen protecting group (e.g., acyl, silyl, TBDPS, TBDMS, TIPS, TES, TMS, MOM, THP, t-Bu, Bn, allyl, acetyl, pivaloyl, or benzoyl).

Formula (I) may include moiety

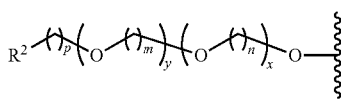

at the 3',4',5', or 6'-position of the phenyl ring. In certain embodiments, q is 0. In certain embodiments, q is 1. When Formula (I) includes two or more instances of n, any two instances of n may independently be the same or different from each other. In certain embodiments, at least one instance of n is 1. In certain embodiments, at least one instance of n is 2. In certain embodiments, each instance of n is 2. In certain embodiments, at least one instance of n is 3, 4, 5, 6, 7, or 8.

When Formula (I) includes two or more instances of x, any two instances of x may independently be the same or different from each other. In certain embodiments, at least one instance of x is 0. In certain embodiments, at least one instance of x is 1. In certain embodiments, at least one instance of x is 2. In certain embodiments, each instance of x is 2. In certain embodiments, at least one instance of x is 3. In certain embodiments, at least one instance of x is 4. In certain embodiments, at least one instance of x is 5, 6, 7, or 8.

When Formula (I) includes two or more instances of m, any two instances of m may independently be the same or different from each other. In certain embodiments, at least one instance of m is 1. In certain embodiments, at least one instance of m is 2. In certain embodiments, each instance of m is 2. In certain embodiments, at least one instance of m is 3, 4, 5, 6, 7, or 8.

When Formula (I) includes two or more instances of y, any two instances of y may independently be the same or different from each other. In certain embodiments, at least one instance of y is 0. In certain embodiments, at least one instance of y is 1. In certain embodiments, at least one instance of y is 2. In certain embodiments, at least one instance of y is 3. In certain embodiments, at least one instance of y is 4. In certain embodiments, at least one instance of y is 5, 6, 7, or 8.

In certain embodiments, each of x and y is 0. In certain embodiments, each instance of x is 1, 2, 3, or 4; each instance of n is 2; and each instance of y is 0. In certain embodiments, each instance of x is 1; each instance of n is 2; and each instance of y is 0. In certain embodiments, each instance of x is 2; each instance of n is 2; and each instance of y is 0. In certain embodiments, each instance of x is 3; each instance of n is 2; and each instance of y is 0. In certain embodiments, each instance of x is 4; each instance of n is 2; and each instance of y is 0.

When Formula (I) includes two or more instances of p, any two instances of p may independently be the same or different from each other. In certain embodiments, at least one instance of p is 1. In certain embodiments, at least one instance of p is 2. In certain embodiments, at least one instance of p is 3. In certain embodiments, at least one instance of p is 4. In certain embodiments, at least one instance of p is 5. In certain embodiments, at least one instance of p is 6, 7, 8, 9, or 10.

In certain embodiments, each of x and y is 0; and at least one instance of p is 1, 2, 3, 4, or 5. In certain embodiments, each instance of x is 1, 2, 3, or 4; each instance of n is 2; each instance of y is 0; and at least one instance of p is 1, 2, 3, 4, or 5. In certain embodiments, each instance of x is 1; each instance of n is 2; each instance of y is 0; and at least one instance of p is 1, 2, 3, 4, or 5. In certain embodiments, each instance of x is 2; each instance of n is 2; each instance of y is 0; and at least one instance of p is 1, 2, 3, 4, or 5. In certain embodiments, each instance of x is 3; each instance of n is 2; each instance of y is 0; and at least one instance of p is 1, 2, 3, 4, or 5. In certain embodiments, each instance of x is 4; each instance of n is 2; each instance of y is 0; and at least one instance of p is 1, 2, 3, 4, or 5.

In certain embodiments, $R^1$ is not of the formula:

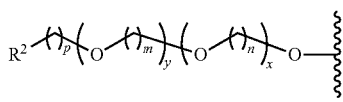

and q is 1. In certain embodiments, $R^1$ is hydrogen; and q is 1. In certain embodiments, $R^1$ is of the formula:

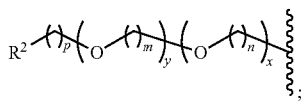

and q is 1.

In certain embodiments, at least one moiety

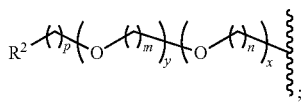

is at the 3'-position of the phenyl ring. In certain embodiments, at least one moiety

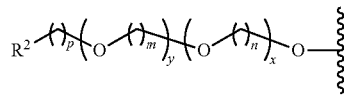

is at the 4'-position of the phenyl ring. In certain embodiments, at least one moiety

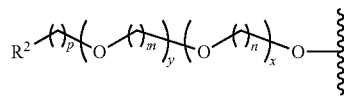

is at the 5'-position of the phenyl ring. In certain embodiments, at least one moiety

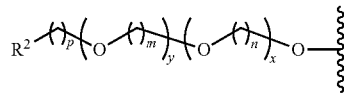

is at the 6'-position of the phenyl ring. In certain embodiments, the moiety

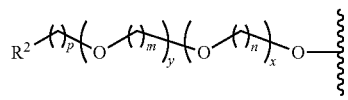

at the 3', 4',5', or 6'-position of the phenyl ring is of the formula:

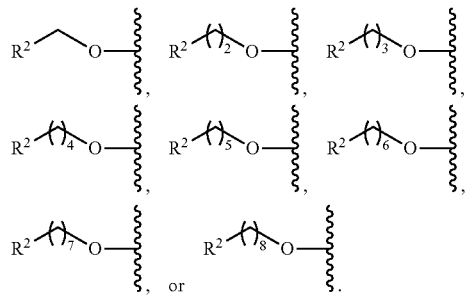

In certain embodiments, the moiety

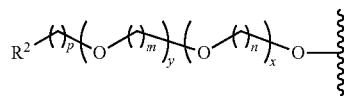

at the 3',4',5', or 6'-position of the phenyl ring is of the formula:

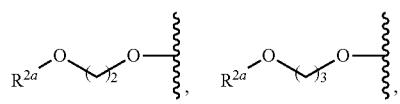

-continued

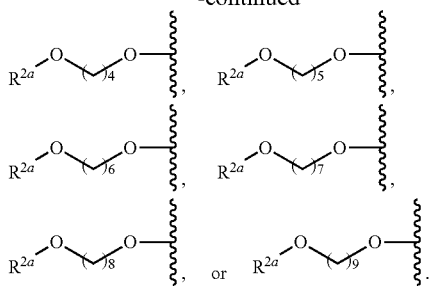

In certain embodiments, the moiety

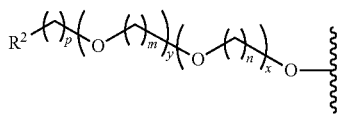

at the 3',4',5', or 6'-position of the phenyl ring is of the formula:

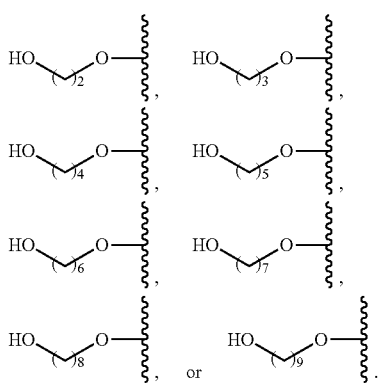

In certain embodiments, the moiety

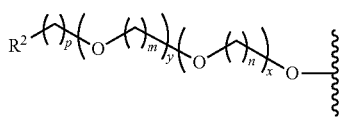

at the 3',4',5', or 6'-position of the phenyl ring is of the formula:

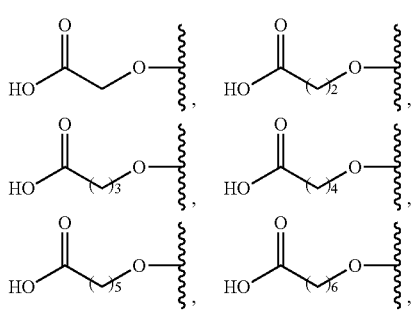

-continued

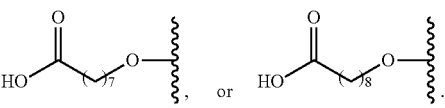

In certain embodiments, the moiety

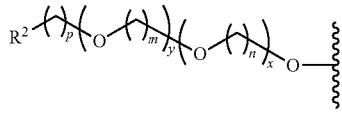

at the 3',4',5', or 6'-position of the phenyl ring is of the formula:

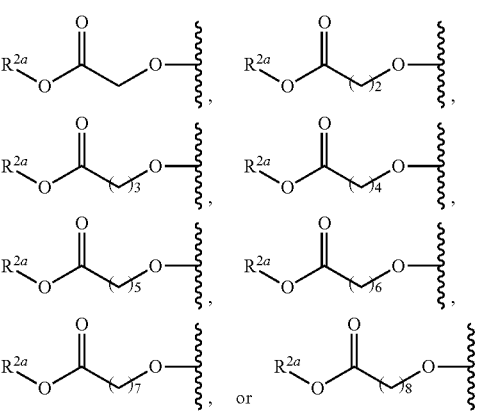

In certain embodiments, the moiety

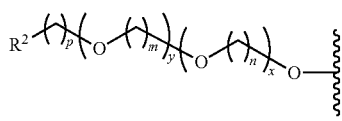

at the 3',4',5', or 6'-position of the phenyl ring is of the formula:

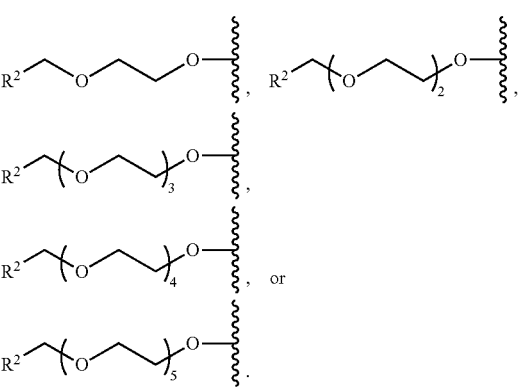

In certain embodiments, the moiety

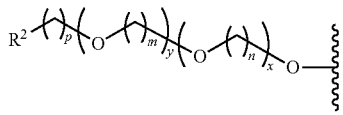

at the 3',4',5', or 6'-position of the phenyl ring is of the formula:

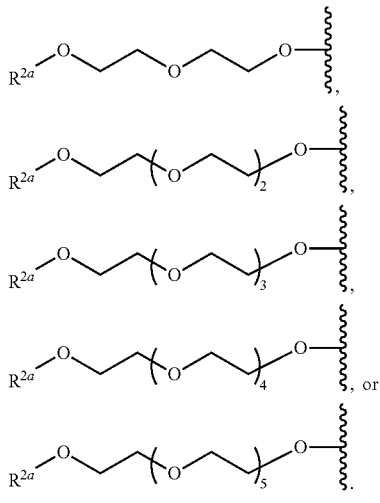

In certain embodiments, the moiety

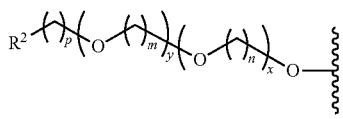

at the 3',4',5', or 6'-position of the phenyl ring is of the formula:

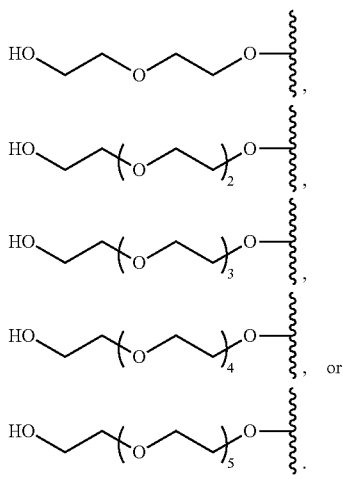

In certain embodiments, the moiety

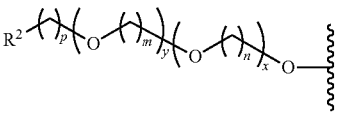

at the 3',4',5', or 6'-position of the phenyl ring is of the formula:

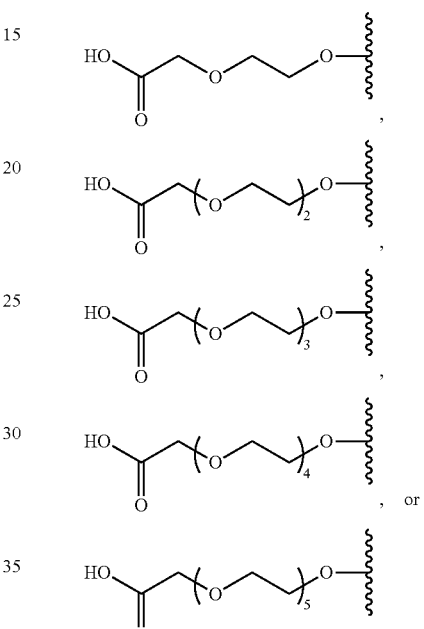

In certain embodiments, the moiety

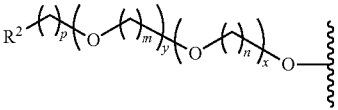

at the 3',4',5', or 6'-position of the phenyl ring is of the formula:

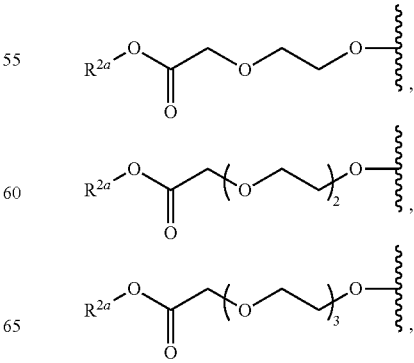

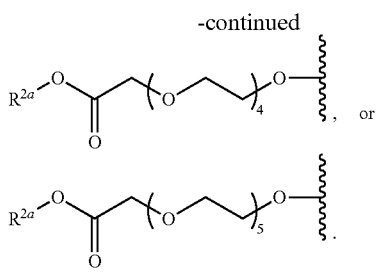

When Formula (I) includes two or more instances of $R^2$, any two instances of $R^2$ may independently be the same or different from each other. In certain embodiments, at least one instance of $R^2$ is —$CH_2OR^{2a}$. In certain embodiments, at least one instance of $R^2$ is —$CH_2OR^{2a}$, wherein $R^{2a}$ is substituted or unsubstituted alkyl (e.g., substituted or unsubstituted $C_{1-6}$ alkyl). In certain embodiments, at least one instance of $R^2$ is —$CH_2OMe$. In certain embodiments, at least one instance of $R^2$ is —$CH_2OEt$, —$CH_2OPr$, —$CH_2OBu$, —$CH_2O$(unsubstituted pentyl), or —$CH_2O$(unsubstituted hexyl). In certain embodiments, at least one instance of $R^2$ is —$CH_2O$(substituted methyl) (e.g., —$CH_2OCF_3$ or —$CH_2OBn$), —$CH_2O$(substituted ethyl) (e.g., —$CH_2O$(perfluoroethyl)), —$CH_2O$(substituted propyl) (e.g., —$CH_2O$(perfluoropropyl)), —$CH_2O$(substituted butyl) (e.g., —$CH_2O$(perfluorobutyl)), —$CH_2O$(substituted pentyl) (e.g., —$CH_2O$(perfluoropentyl)), or —$CH_2O$(substituted hexyl) (e.g., —$CH_2O$(perfluorohexyl)). In certain embodiments, at least one instance of $R^2$ is —$CH_2OR^{2a}$, wherein $R^{2a}$ is an oxygen protecting group (e.g., acyl, silyl, TBDPS, TBDMS, TIPS, TES, TMS, MOM, THP, t-Bu, Bn, allyl, acetyl, pivaloyl, or benzoyl).

In certain embodiments, at least one instance of $R^2$ is —$CH_2OH$

In certain embodiments, at least one instance of $R^2$ is —$C(═)OH$.

In certain embodiments, at least one instance of $R^2$ is —$C(═O)OR^{2a}$. In certain embodiments, at least one instance of $R^2$ is —$C(═O)OR^{2a}$, wherein $R^{2a}$ is substituted or unsubstituted alkyl (e.g., substituted or unsubstituted $C_{1-6}$ alkyl). In certain embodiments, at least one instance of $R^2$ is —$C(═)OMe$. In certain embodiments, at least one instance of $R^2$ is —$C(═)OEt$, —$C(═)OPr$, —$C(═)OBu$, —$C(═)O$ (unsubstituted pentyl), or —$C(═O)O$ (unsubstituted hexyl). In certain embodiments, at least one instance of $R^2$ is —$C(═O)O$ (substituted methyl) (e.g., —$C(═)OCF_3$ or —$C(═)OBn$), —$C(═)O$(substituted ethyl) (e.g., —$C(═)O$ (perfluoroethyl)), —$C(═O)O$(substituted propyl) (e.g., —$C(═O)O$ (perfluoropropyl)), —$C(═)O$(substituted butyl) (e.g., —$C(═)O$(perfluorobutyl)), —$C(═O)O$ (substituted pentyl) (e.g., —$C(═)O$(perfluoropentyl)), or —$C(═)O$(substituted hexyl) (e.g., —$C(═)O$(perfluorohexyl)). In certain embodiments, at least one instance of $R^2$ is —$C(═O)OR^{2a}$, wherein $R^{2a}$ is an oxygen protecting group (e.g., acyl, silyl, TBDPS, TBDMS, TIPS, TES, TMS, MOM, THP, t-Bu, Bn, allyl, acetyl, pivaloyl, or benzoyl).

Formula (I) may include one or more substituents $R^3$ at the 3',4',5', and/or 6'-position of the phenyl ring. When Formula (I) includes two or more instances of $R^3$, any two instances of $R^3$ may independently be the same or different from each other.

In certain embodiments, at least one instance of $R^3$ is halogen (e.g., F, Cl, Br, or I). In certain embodiments, at least one instance of $R^3$ is substituted or unsubstituted alkyl (e.g., substituted or unsubstituted $C_{1-6}$ alkyl). In certain embodiments, at least one instance of $R^3$ is Me. In certain embodiments, at least one instance of $R^3$ is Et, Pr, Bu, unsubstituted pentyl, or unsubstituted hexyl. In certain embodiments, at least one instance of $R^3$ is substituted methyl (e.g., —$CF_3$, or Bn), substituted ethyl (e.g., perfluoroethyl), substituted propyl (e.g., perfluoropropyl), substituted butyl (e.g., perfluorobutyl), substituted pentyl (e.g., perfluoropentyl), or substituted hexyl (e.g., perfluorohexyl). In certain embodiments, at least one instance of $R^3$ is —$OR^8$. In certain embodiments, at least one instance of $R^3$ is —OH. In certain embodiments, no instance of $R^3$ is —OH.

In certain embodiments, at least one instance of $R^3$ is —$OR^8$, wherein $R^8$ is substituted or unsubstituted alkyl (e.g., substituted or unsubstituted $C_{1-6}$ alkyl). In certain embodiments, at least one instance of $R^3$ is —OMe. In certain embodiments, no instance of $R^3$ is —OMe. In certain embodiments, at least one instance of $R^3$ is —OEt, —OPr, —OBu, —O (unsubstituted pentyl), or —O(unsubstituted hexyl). In certain embodiments, at least one instance of $R^3$ is —O(substituted methyl) (e.g., —$OCF_3$ or —OBn), —O(substituted ethyl) (e.g., —O (perfluoroethyl)), —O(substituted propyl) (e.g., —O(perfluoropropyl)), —O(substituted butyl) (e.g., —O(perfluorobutyl)), —O(substituted pentyl) (e.g., —O(perfluoropentyl)), or —O (substituted hexyl) (e.g., —O(perfluorohexyl)). In certain embodiments, at least one instance of $R^3$ is substituted or unsubstituted acyl. In certain embodiments, at least one instance of $R^3$ is —$C(═O)R^a$, optionally wherein $R^a$ is substituted or unsubstituted $C_{1-6}$ alkyl (e.g., Me). In certain embodiments, at least one instance of $R^3$ is —$C(═O)OR^a$, optionally wherein $R^a$ is H, substituted or unsubstituted $C_{1-6}$ alkyl (e.g., Me), or an oxygen protecting group (e.g., silyl, TBDPS, TBDMS, TIPS, TES, TMS, MOM, THP, t-Bu, Bn, allyl, acetyl, pivaloyl, or benzoyl). In certain embodiments, at least one instance of $R^3$ is —$C(═O)N(R^a)_2$, optionally wherein each instance of $R^a$ is independently H, substituted or unsubstituted $C_{1-6}$ alkyl (e.g., Me), or a nitrogen protecting group (e.g., Bn, Boc, Cbz, Fmoc, trifluoroacetyl, triphenylmethyl, acetyl, or Ts). In certain embodiments, at least one instance of $R^3$ is —$OR^8$, wherein $R^8$ is an oxygen protecting group (e.g., silyl, TBDPS, TBDMS, TIPS, TES, TMS, MOM, THP, t-Bu, Bn, allyl, acetyl, pivaloyl, or benzoyl). In certain embodiments, at least one instance of $R^3$ is —$OR^8$, wherein $R^8$ is (e.g., 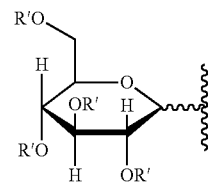 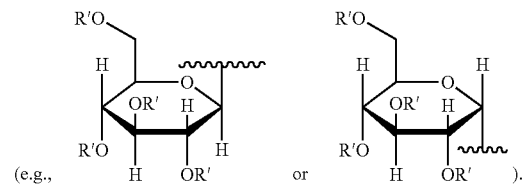 ).

In certain embodiments, at least one instance of $R^3$ is $-OR^8$, wherein $R^8$ is

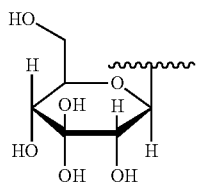 or 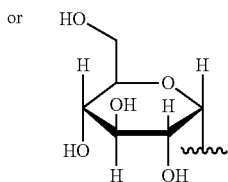

In certain embodiments, at least one instance of $R^3$ is $-OR^8$, wherein $R^8$ is

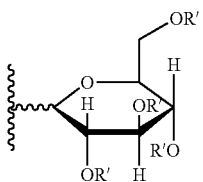

(e.g.,  or )

In certain embodiments, at least one instance of $R^3$ is $-OR^8$, wherein $R^8$ is

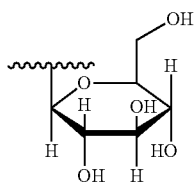 or 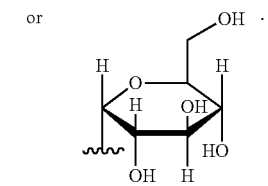.

In certain embodiments, k is 0. In certain embodiments, k is 1. In certain embodiments, k is 2. In certain embodiments, k is 3. In certain embodiments, k is 4.

Formula (I) includes substituent $R^4$ at the 5-position of the thiazolinyl ring. In certain embodiments, $R^4$ is H. In certain embodiments, $R^4$ is substituted or unsubstituted alkyl (e.g., substituted or unsubstituted $C_{1-6}$ alkyl). In certain embodiments, $R^4$ is Me. In certain embodiments, $R^4$ is Et, Pr, Bu, unsubstituted pentyl, or unsubstituted hexyl. In certain embodiments, $R^4$ is substituted methyl (e.g., $-CF_3$, or Bn), substituted ethyl (e.g., perfluoroethyl), substituted propyl (e.g., perfluoropropyl), substituted butyl (e.g., perfluorobutyl), substituted pentyl (e.g., perfluoropentyl), or substituted hexyl (e.g., perflourohexyl).

Formula (I) includes substituent $R^5$ at the 5-position of the thiazolinyl ring. In certain embodiments, $R^5$ is H. In certain embodiments, $R^5$ is substituted or unsubstituted alkyl (e.g., substituted or unsubstituted $C_{1-6}$ alkyl). In certain embodiments, $R^5$ is Me. In certain embodiments, $R^5$ is Et, Pr, Bu, unsubstituted pentyl, or unsubstituted hexyl. In certain embodiments, $R^5$ is substituted methyl (e.g., $-CF_3$, or Bn), substituted ethyl (e.g., perfluoroethyl), substituted propyl (e.g., perfluoropropyl), substituted butyl (e.g., perfluorobutyl), substituted pentyl (e.g., perfluoropentyl), or substituted hexyl (e.g., perflourohexyl).

In certain embodiments, each of $R^4$ and $R^5$ is hydrogen. In certain embodiments, each of $R^4$ and $R^5$ is independently substituted or unsubstituted alkyl (e.g., substituted or unsubstituted $C_{1-6}$ alkyl). In certain embodiments, each of $R^4$ and $R^5$ is Me.

Formula (I) includes substituent $R^6$ at the 4-position of the thiazolinyl ring. In certain embodiments, $R^6$ is H. In certain embodiments, $R^6$ is substituted or unsubstituted alkyl (e.g., substituted or unsubstituted $C_{1-6}$ alkyl). In certain embodiments, $R^6$ is Me. In certain embodiments, $R^6$ is Et, Pr, Bu, unsubstituted pentyl, or unsubstituted hexyl. In certain embodiments, $R^6$ is substituted methyl (e.g., $-CF_3$, or Bn), substituted ethyl (e.g., perfluoroethyl), substituted propyl (e.g., perfluoropropyl), substituted butyl (e.g., perfluorobutyl), substituted pentyl (e.g., perfluoropentyl), or substituted hexyl (e.g., perflourohexyl).

In certain embodiments, each of $R^4$ and $R^5$ is hydrogen, and $R^6$ is substituted or unsubstituted alkyl (e.g., substituted or unsubstituted $C_{1-6}$ alkyl). In certain embodiments, each of $R^4$ and $R^5$ is hydrogen, and $R^6$ is Me.

In certain embodiments, Z is $-O-$. In certain embodiments, Z is $-S-$.

In certain embodiments, $R^9$ is H. In certain embodiments, $R^9$ is substituted or unsubstituted alkyl (e.g., substituted or unsubstituted $C_{1-6}$ alkyl). In certain embodiments, $R^9$ is Me. In certain embodiments, $R^9$ is Et, Pr, Bu, unsubstituted pentyl, or unsubstituted hexyl. In certain embodiments, $R^9$ is substituted methyl (e.g., $-CF_3$, or Bn), substituted ethyl (e.g., perfluoroethyl), substituted propyl (e.g., perfluoropropyl), substituted butyl (e.g., perfluorobutyl), substituted pentyl (e.g., perfluoropentyl), or substituted hexyl (e.g., perflourohexyl). In certain embodiments, $R^9$ is

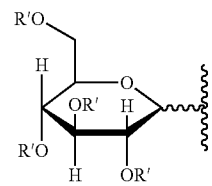

(e.g., 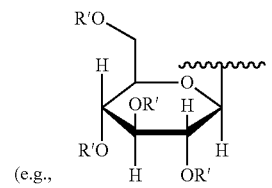).

In certain embodiments, $R^9$ is

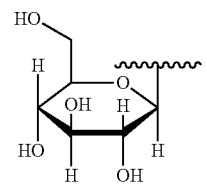 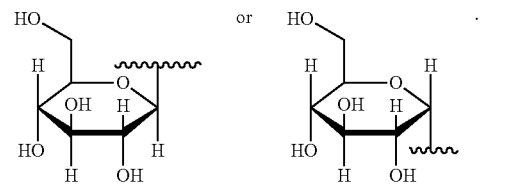

In certain embodiments, $R^9$ is

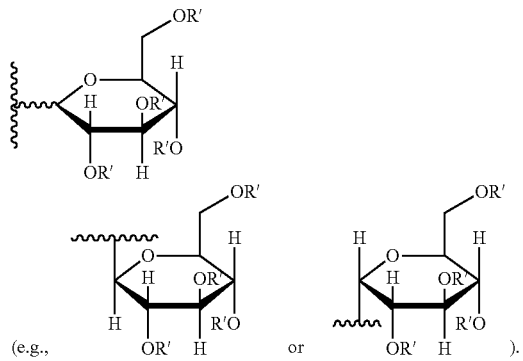

(e.g.,

In certain embodiments, $R^9$ is

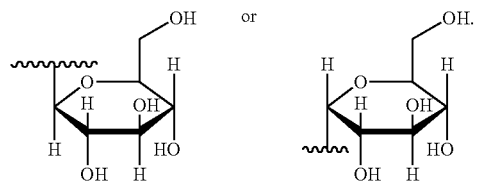

In certain embodiments, $R^9$ is an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom. In certain embodiments, $R^9$ is a sulfur protecting group (e.g., acetamidomethyl, t-Bu, 3-nitro-2-pyridine sulfenyl, 2-pyridine-sulfenyl, or triphenylmethyl) when attached to a sulfur atom.

In certain embodiments, —Z—$R^9$ is —OH. In certain embodiments, —Z—$R^9$ is —O (unsubstituted $C_{1-6}$ alkyl).

Formula (I) includes a chiral carbon atom (the carbon atom labeled with "*") at the 4-position of the thiazolinyl ring. In certain embodiments, the carbon atom labeled with "*" is of the S configuration. In certain embodiments, the carbon atom labeled with "*" is of the R configuration.

In certain embodiments, the moiety

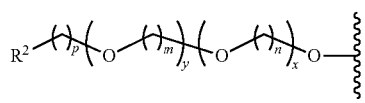

at the 3',4',5', or 6'-position of the phenyl ring is not of the formula:

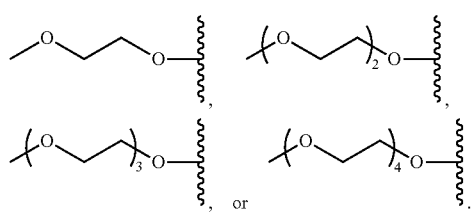

In certain embodiments, when the moiety

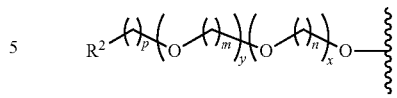

at the 3',4',5', or 6'-position of the phenyl ring is of the formula:

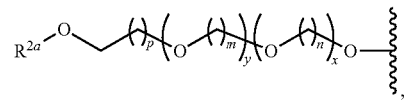

$R^{2a}$ is not Me. In certain embodiments, when the moiety

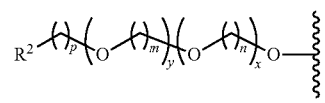

at the 3',4',5', or 6'-position of the phenyl ring is of the formula:

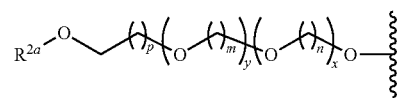

$R^{2a}$ is not substituted or unsubstituted methyl. In certain embodiments, when the moiety

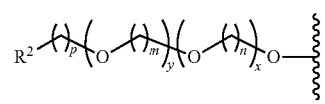

at the 3',4', 5', or 6'-position of the phenyl ring is of the formula:

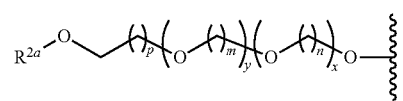

$R^{2a}$ is not unsubstituted $C_{1-6}$ alkyl. In certain embodiments, when each instance of x is 1, 2, 3, or 4, each instance of n is 2, and each instance of y is 0, then each instance of $R^2$ is —$CH_2OH$, —C(=)OH, or —C(=O)$OR^{2a}$. In certain embodiments, when the 4'-position of the phenyl ring is substituted with the moiety

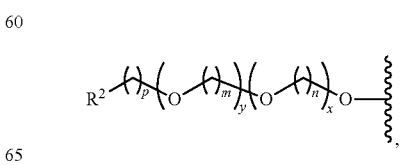

$R^2$ is —$CH_2OR^{2a}$, —C(=)OH, or —C(=O)$OR^{2a}$.

In certain embodiments, the compound of Formula (I) is of the formula:

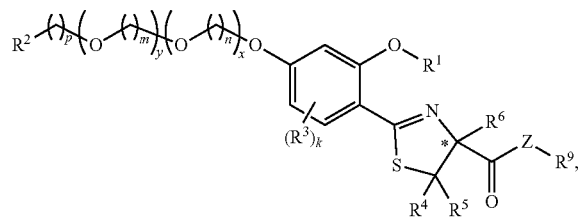

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

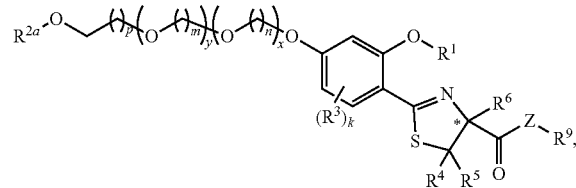

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

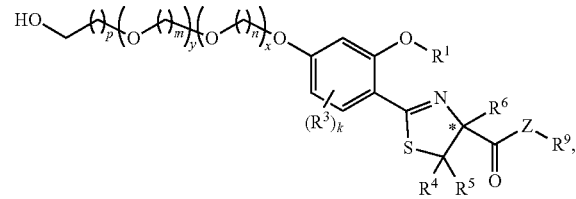

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

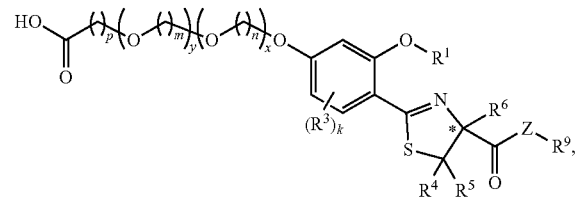

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

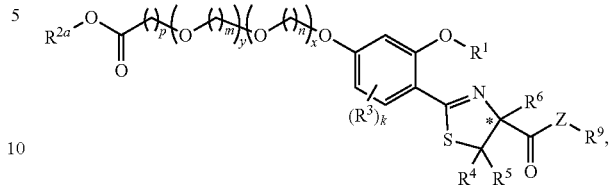

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

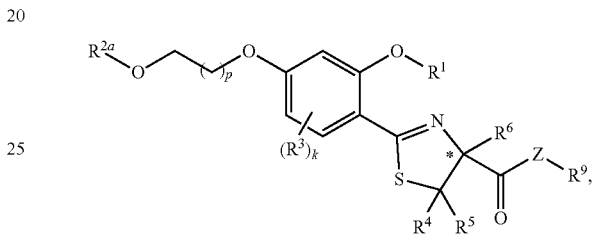

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

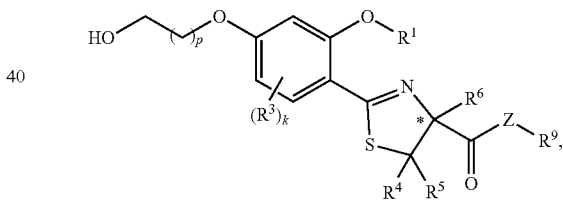

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

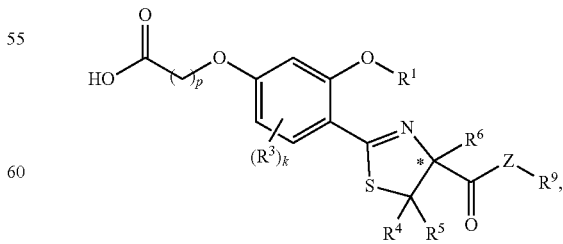

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

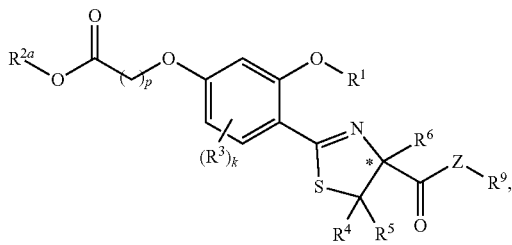

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

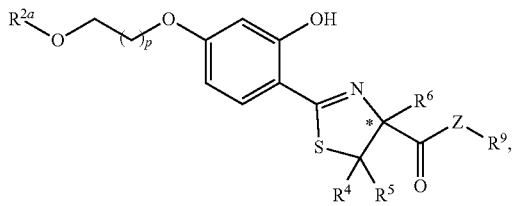

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

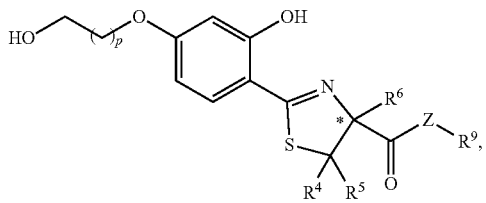

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

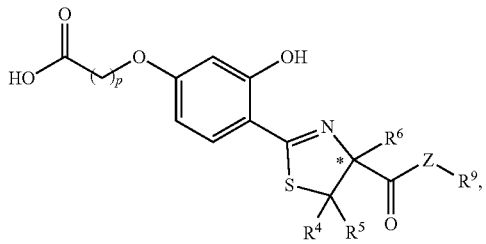

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

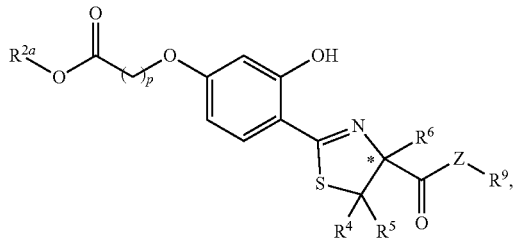

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

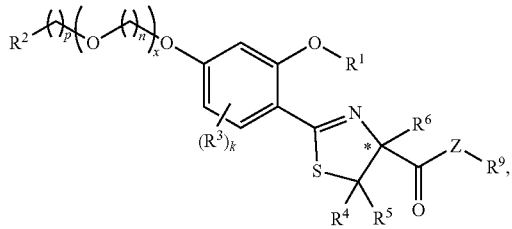

or a pharmaceutically acceptable salt, solvate, hydrate, polymorph, co-crystal, tautomer, stereoisomer, isotopically labeled derivative, or prodrug thereof, wherein x is 1, 2, 3, 4, 5, 6, 7, or 8.

In certain embodiments, the compound of Formula (I) is of the formula:

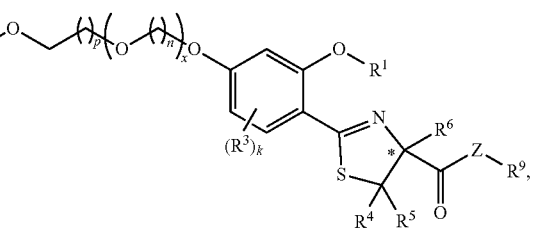

or a pharmaceutically acceptable salt, solvate, hydrate, polymorph, co-crystal, tautomer, stereoisomer, isotopically labeled derivative, or prodrug thereof, wherein x is 1, 2, 3, 4, 5, 6, 7, or 8.

In certain embodiments, the compound of Formula (I) is of the formula:

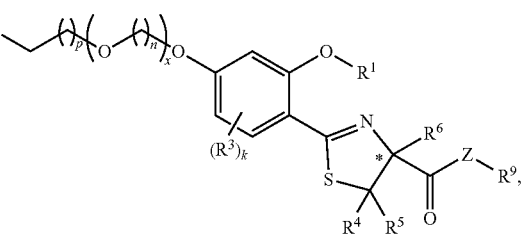

or a pharmaceutically acceptable salt, solvate, hydrate, polymorph, co-crystal, tautomer, stereoisomer, isotopically labeled derivative, or prodrug thereof, wherein x is 1, 2, 3, 4, 5, 6, 7, or 8.

In certain embodiments, the compound of Formula (I) is of the formula:

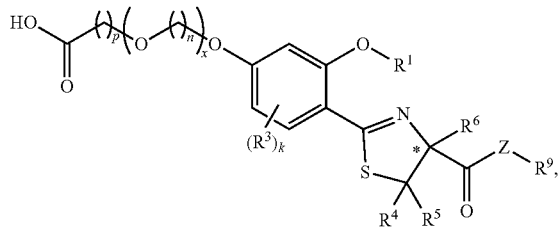

or a pharmaceutically acceptable salt, solvate, hydrate, polymorph, co-crystal, tautomer, stereoisomer, isotopically labeled derivative, or prodrug thereof, wherein x is 1, 2, 3, 4, 5, 6, 7, or 8.

In certain embodiments, the compound of Formula (I) is of the formula:

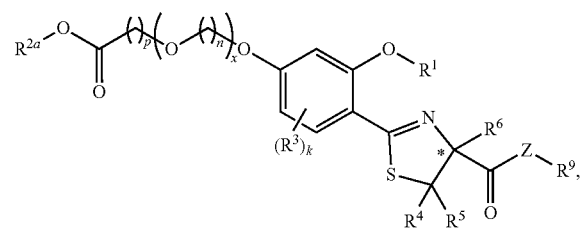

or a pharmaceutically acceptable salt, solvate, hydrate, polymorph, co-crystal, tautomer, stereoisomer, isotopically labeled derivative, or prodrug thereof, wherein x is 1, 2, 3, 4, 5, 6, 7, or 8.

In certain embodiments, the compound of Formula (I) is of the formula:

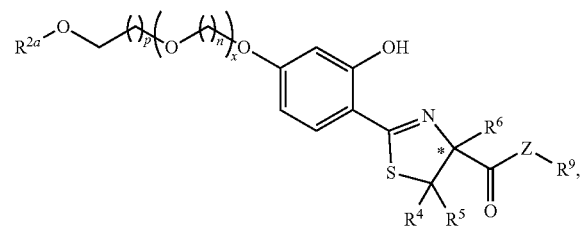

or a pharmaceutically acceptable salt, solvate, hydrate, polymorph, co-crystal, tautomer, stereoisomer, isotopically labeled derivative, or prodrug thereof, wherein x is 1, 2, 3, 4, 5, 6, 7, or 8.

In certain embodiments, the compound of Formula (I) is of the formula:

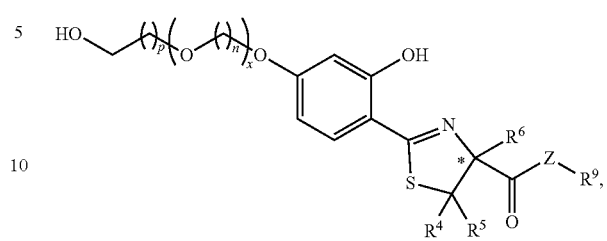

or a pharmaceutically acceptable salt, solvate, hydrate, polymorph, co-crystal, tautomer, stereoisomer, isotopically labeled derivative, or prodrug thereof, wherein x is 1, 2, 3, 4, 5, 6, 7, or 8.

In certain embodiments, the compound of Formula (I) is of the formula:

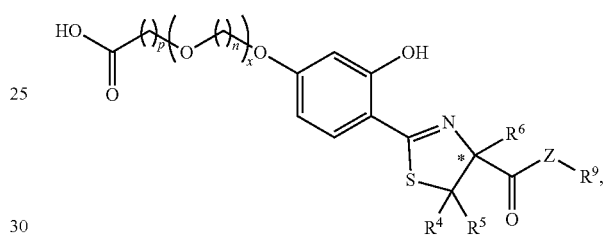

or a pharmaceutically acceptable salt, solvate, hydrate, polymorph, co-crystal, tautomer, stereoisomer, isotopically labeled derivative, or prodrug thereof, wherein x is 1, 2, 3, 4, 5, 6, 7, or 8.

In certain embodiments, the compound of Formula (I) is of the formula:

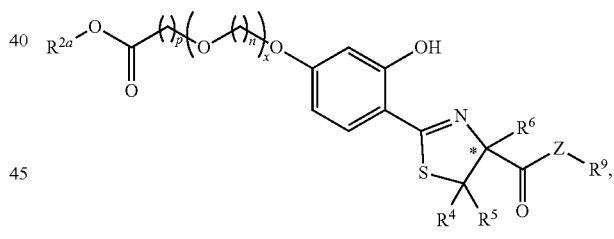

or a pharmaceutically acceptable salt, solvate, hydrate, polymorph, co-crystal, tautomer, stereoisomer, isotopically labeled derivative, or prodrug thereof, wherein x is 1, 2, 3, 4, 5, 6, 7, or 8.

In certain embodiments, the compound of Formula (I) is of the formula:

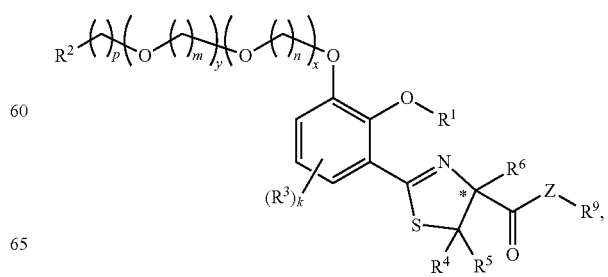

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

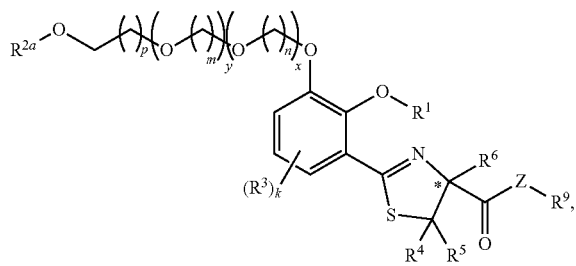

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

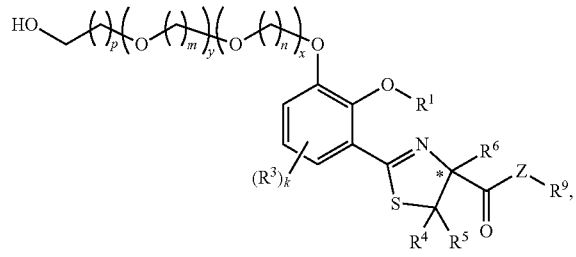

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

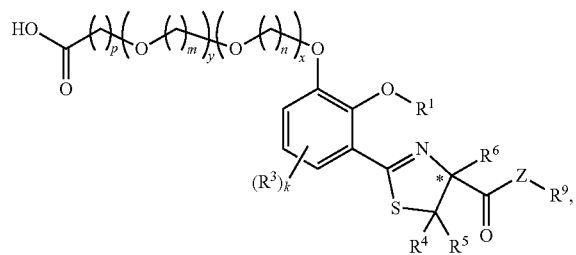

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

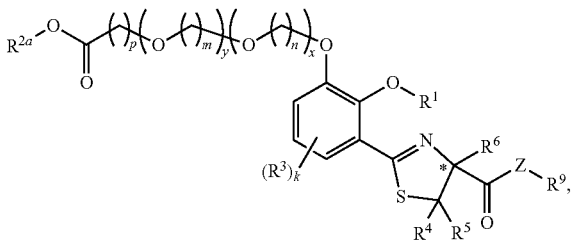

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

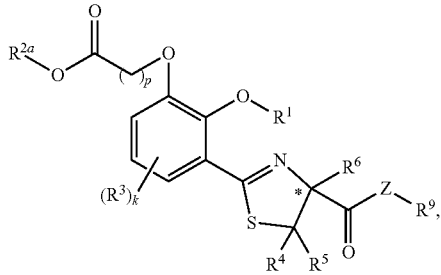

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

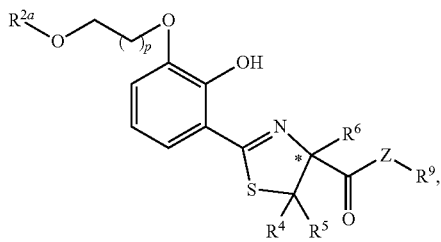

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

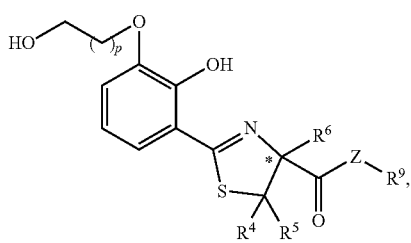

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

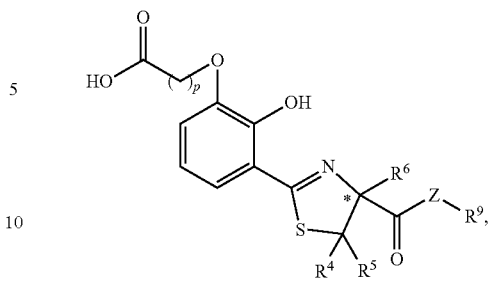

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

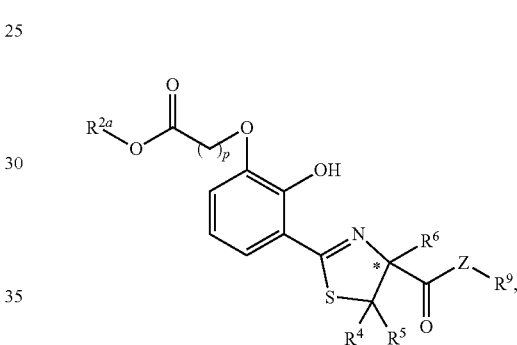

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

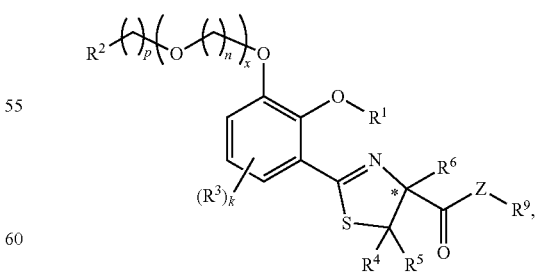

or a pharmaceutically acceptable salt, solvate, hydrate, polymorph, co-crystal, tautomer, stereoisomer, isotopically labeled derivative, or prodrug thereof, wherein x is 1, 2, 3, 4, 5, 6, 7, or 8.

In certain embodiments, the compound of Formula (I) is of the formula:

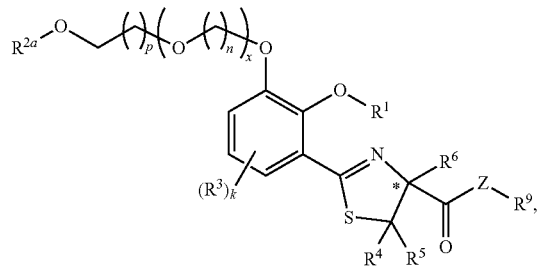

or a pharmaceutically acceptable salt, solvate, hydrate, polymorph, co-crystal, tautomer, stereoisomer, isotopically labeled derivative, or prodrug thereof, wherein x is 1, 2, 3, 4, 5, 6, 7, or 8.

In certain embodiments, the compound of Formula (I) is of the formula:

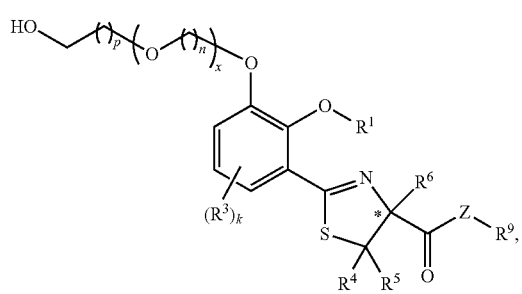

or a pharmaceutically acceptable salt, solvate, hydrate, polymorph, co-crystal, tautomer, stereoisomer, isotopically labeled derivative, or prodrug thereof, wherein x is 1, 2, 3, 4, 5, 6, 7, or 8.

In certain embodiments, the compound of Formula (I) is of the formula:

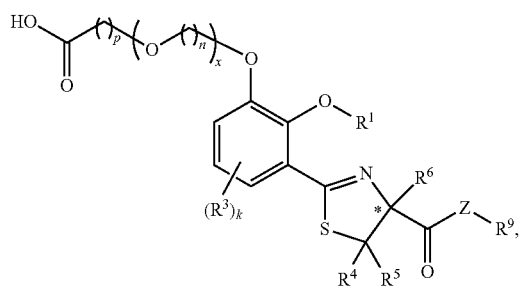

or a pharmaceutically acceptable salt, solvate, hydrate, polymorph, co-crystal, tautomer, stereoisomer, isotopically labeled derivative, or prodrug thereof, wherein x is 1, 2, 3, 4, 5, 6, 7, or 8.

In certain embodiments, the compound of Formula (I) is of the formula:

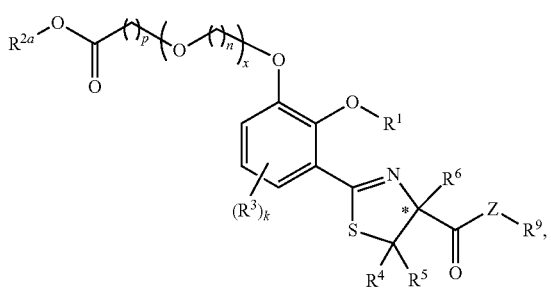

or a pharmaceutically acceptable salt, solvate, hydrate, polymorph, co-crystal, tautomer, stereoisomer, isotopically labeled derivative, or prodrug thereof, wherein x is 1, 2, 3, 4, 5, 6, 7, or 8.

In certain embodiments, the compound of Formula (I) is of the formula:

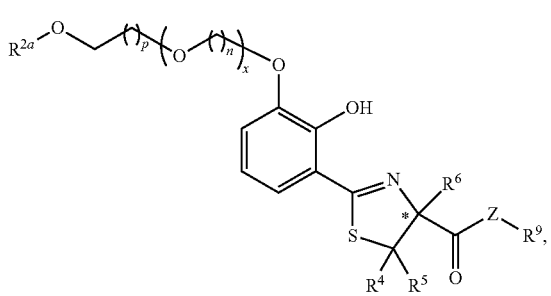

or a pharmaceutically acceptable salt, solvate, hydrate, polymorph, co-crystal, tautomer, stereoisomer, isotopically labeled derivative, or prodrug thereof, wherein x is 1, 2, 3, 4, 5, 6, 7, or 8.

In certain embodiments, the compound of Formula (I) is of the formula:

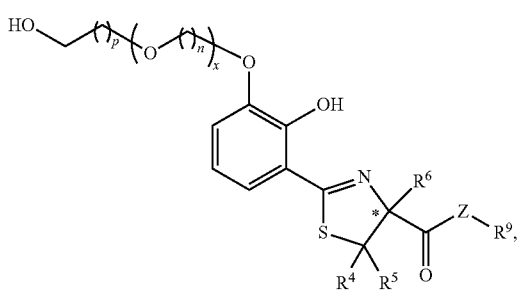

or a pharmaceutically acceptable salt, solvate, hydrate, polymorph, co-crystal, tautomer, stereoisomer, isotopically labeled derivative, or prodrug thereof, wherein x is 1, 2, 3, 4, 5, 6, 7, or 8.

In certain embodiments, the compound of Formula (I) is of the formula:

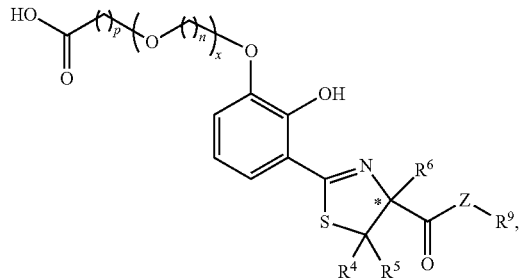

or a pharmaceutically acceptable salt, solvate, hydrate, polymorph, co-crystal, tautomer, stereoisomer, isotopically labeled derivative, or prodrug thereof, wherein x is 1, 2, 3, 4, 5, 6, 7, or 8.

In certain embodiments, the compound of Formula (I) is of the formula:

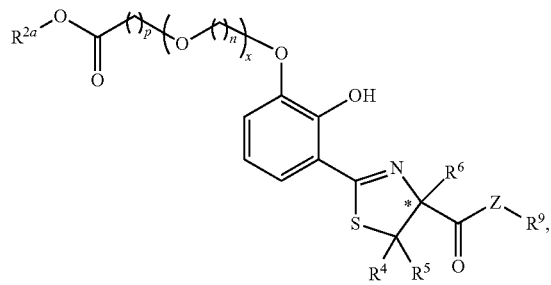

or a pharmaceutically acceptable salt, solvate, hydrate, polymorph, co-crystal, tautomer, stereoisomer, isotopically labeled derivative, or prodrug thereof, wherein x is 1, 2, 3, 4, 5, 6, 7, or 8.

In certain embodiments, the compound of Formula (I) is of the formula:

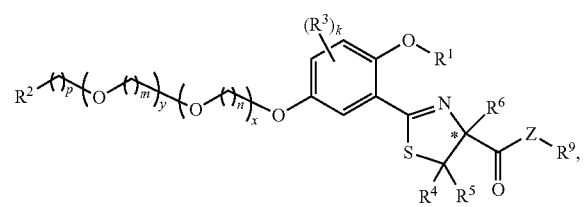

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

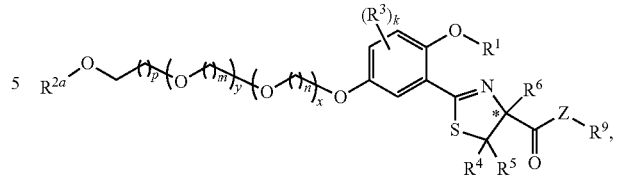

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

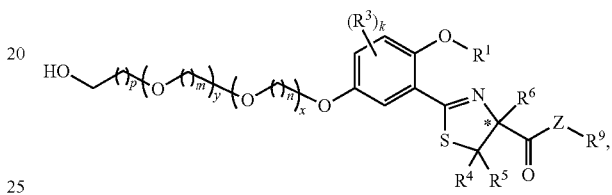

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

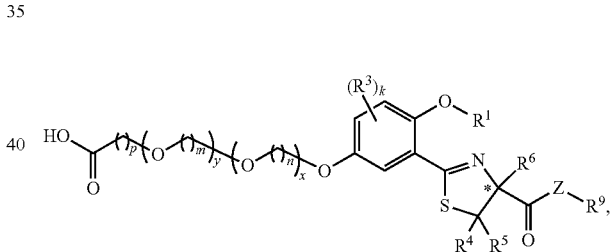

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

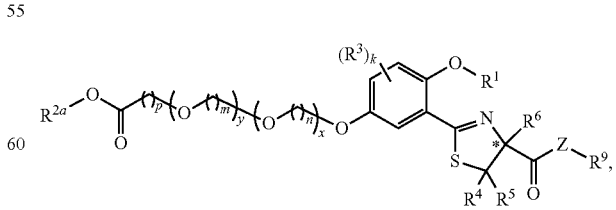

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

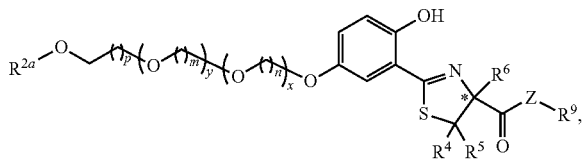

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

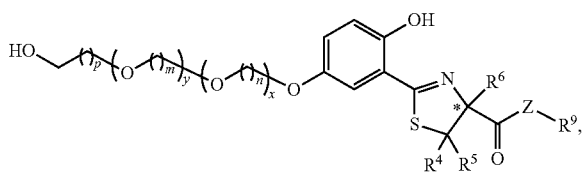

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

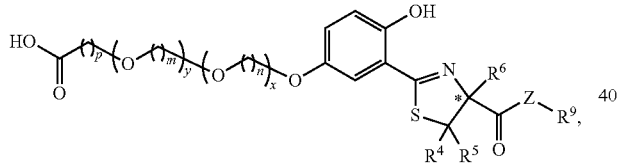

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

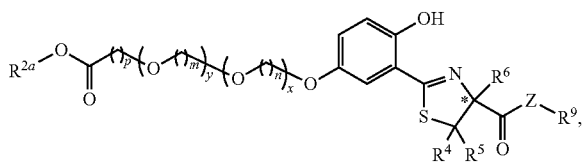

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

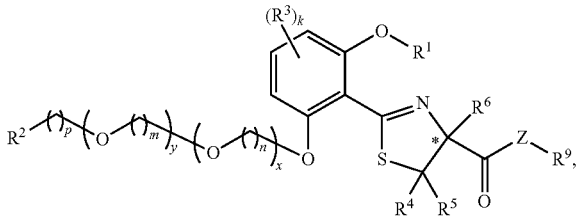

or a pharmaceutically acceptable salt, solvate, hydrate, polymorph, co-crystal, tautomer, stereoisomer, isotopically labeled derivative, or prodrug thereof.

Exemplary compounds of Formula (I) include, but are not limited to:

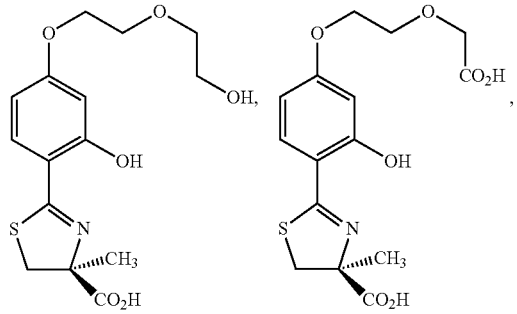

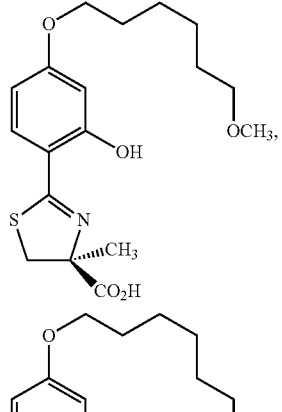

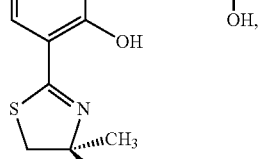

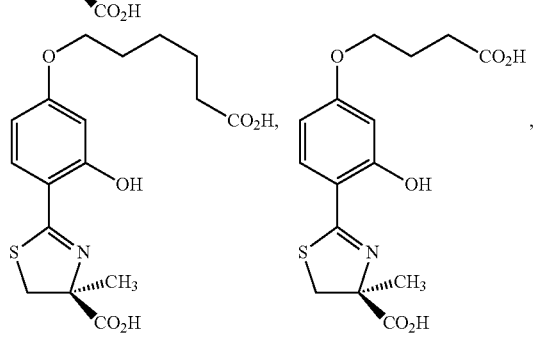

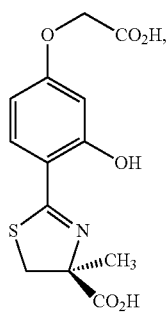

and pharmaceutically acceptable salts, solvates, hydrates, polymorphs, co-crystals, tautomers, stereoisomers, isotopically labeled derivatives, and prodrugs thereof.

Additional exemplary compounds of Formula (I) include, but are not limited to:

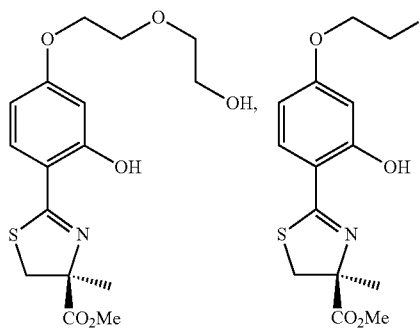

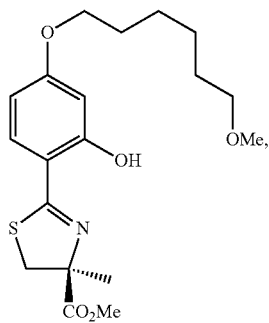

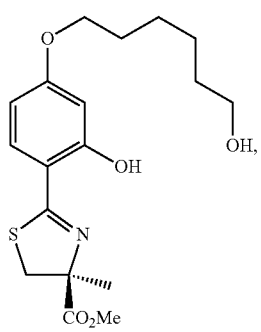

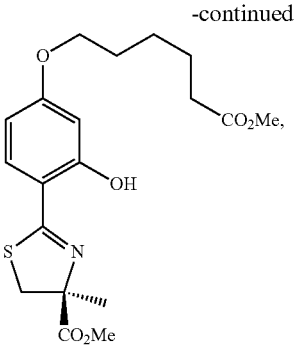

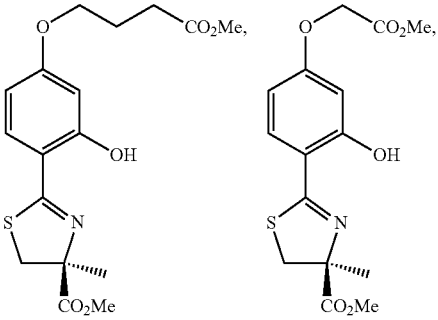

and pharmaceutically acceptable salts, solvates, hydrates, polymorphs, co-crystals, tautomers, stereoisomers, isotopically labeled derivatives, and prodrugs thereof.

Additional exemplary compounds of Formula (I) include, but are not limited to:

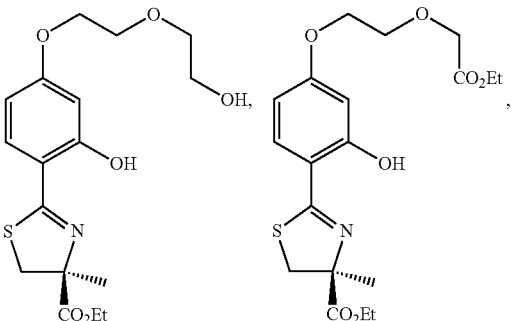

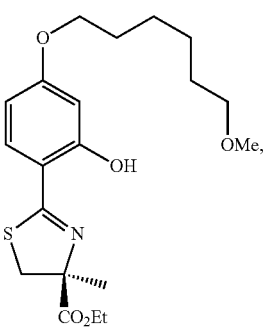

77

-continued

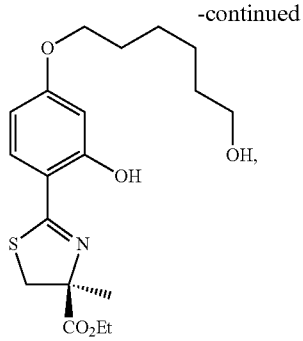

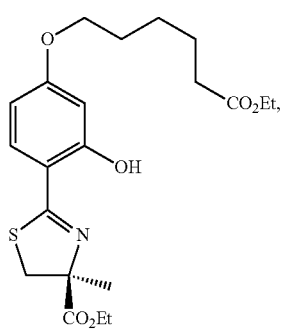

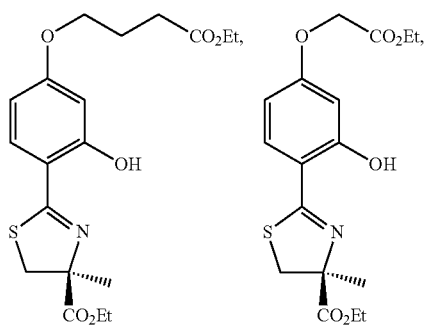

and pharmaceutically acceptable salts, solvates, hydrates, polymorphs, co-crystals, tautomers, stereoisomers, isotopically labeled derivatives, and prodrugs thereof.

Additional exemplary compounds of Formula (I) include, but are not limited to:

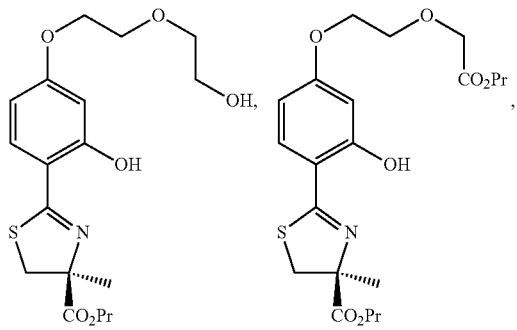

78

-continued

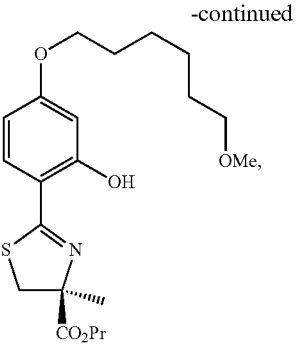

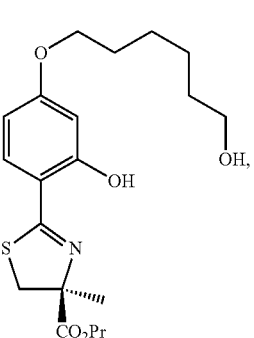

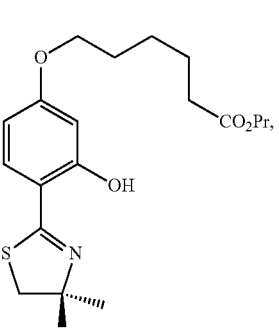

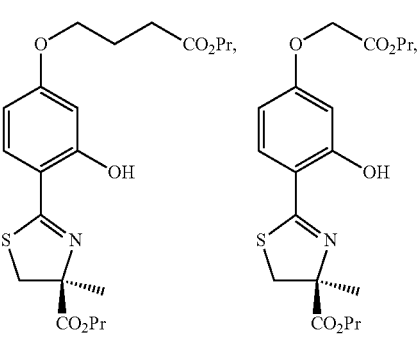

and pharmaceutically acceptable salts, solvates, hydrates, polymorphs, co-crystals, tautomers, stereoisomers, isotopically labeled derivatives, and prodrugs thereof.

Additional exemplary compounds of Formula (I) include, but are not limited to:

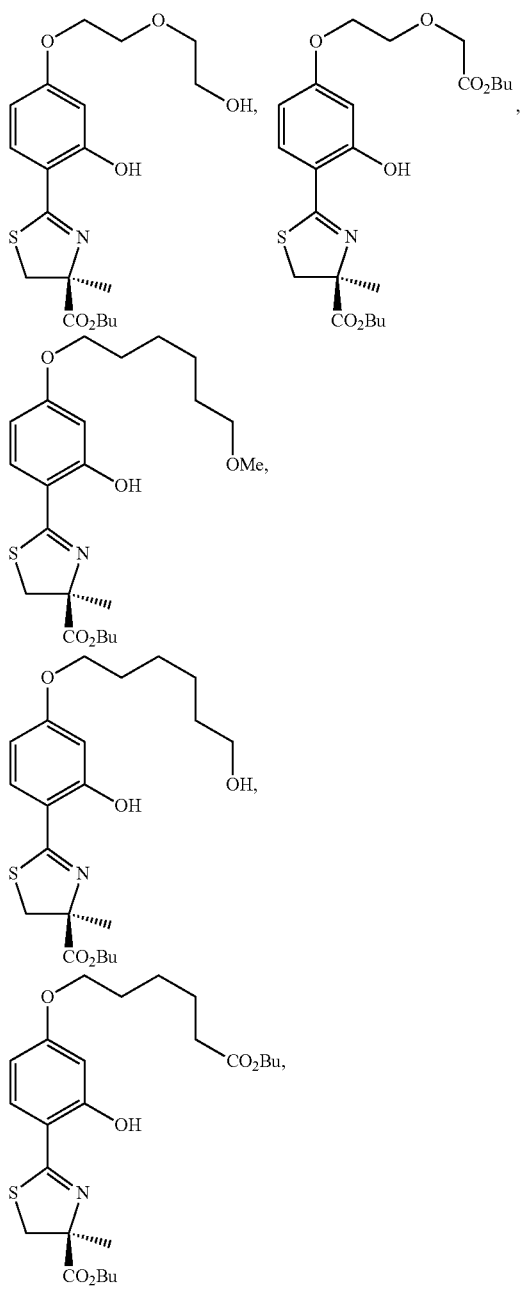

and pharmaceutically acceptable salts, solvates, hydrates, polymorphs, co-crystals, tautomers, stereoisomers, isotopically labeled derivatives, and prodrugs thereof.

The compounds of the invention may be provided in various salts forms. In certain embodiments, the inventive compounds are provided as alkali metal salts. In certain embodiments, the inventive compounds are provided as alkaline earth metal salts. In certain embodiments, when a compound described herein includes one or more —C(=)OH or —C(=O)SH moieties (e.g., —Z—$R_9$ is —OH or —SH, $R^2$ is —C(=)OH), the compound may be provided as a carboxylate salt or thiocarboxylate salt with a base. In certain embodiments, the base is betaine, choline hydroxide, diethanolamine, diethylamine, ethanolamine, hydroxyethyl-morpholine, 4-(2-hydroxyethyl morpholine), 1-(2-hydroxyethyl pyrrolidine), 1-(2-hydroxyethyl)-piperidine, hydroxyethyl pyrroldine, imidazone, lysine (e.g., L-lysine), arginine (e.g., L-arginine), histidine (e.g., L-histidine), N-methyl-D-glucamine (NMG), N,N'-dibenzyl-ethylenediamine, N,N'-diethyl-ethanolamine, triethanolamine, tromethamine, $Ca(OH)_2$, $Mg(OH)_2$, magnesium acetate, LiOH, KOH, potassium 2-ethylhexanoate, NaOH, sodium acetate, sodium 2-ethylhexanoate, $Zn(OH)_2$, zinc acetate, a mixture of $Zn(OH)_2$ and $Mg(OH)_2$, or piperazine. In certain embodiments, a salt described herein is a lithium salt (e.g., mono-lithium salt or di-lithium salt). In certain embodiments, a salt described herein is a sodium salt (e.g., mono-sodium salt or di-sodium salt). In certain embodiments, a salt described herein is a potassium salt (e.g., mono-potassium salt or di-potassium salt). In certain embodiments, a salt described herein is a zinc salt (e.g., hemi-zinc salt or mono-zinc salt). In certain embodiments, a salt described herein is a magnesium salt (e.g., hemi-megnesium salt or mono-magnesium salt). In certain embodiments, a salt described herein is a calcium salt (e.g., hemi-calcium salt or mono-calcium salt).

The cation (e.g., $Li^+$, $Na^+$, $K^+$, $Mg^{2+}$, $Mg(OH)^+$, $Ca^{2+}$, $Ca(OH)^+$, $Zn^{2+}$, or $Zn(OH)^+$) and anion (e.g., a compound described herein that includes one or more —C(=)OH or —C(=O)SH moieties (e.g., —Z—$R_9$ is —OH or —SH, $R^2$ is —C(=)OH)) in a salt described herein may combine in a 1:1 molar ratio. Other molar ratios (e.g., 1:1.5, 1:2, 1:3, and 2:1 (cation:anion)) are also possible, as long as the sum of the formal charges of the cation and anion in the salt is about zero.

Additional exemplary compounds of Formula (I) include, but are not limited to:

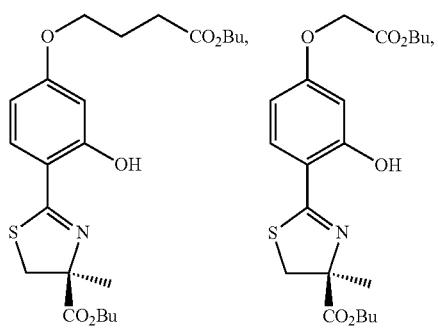

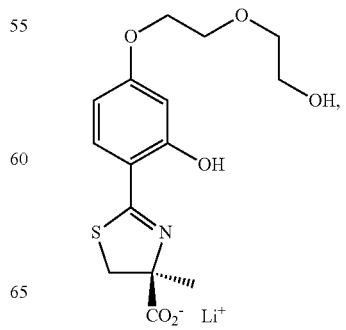

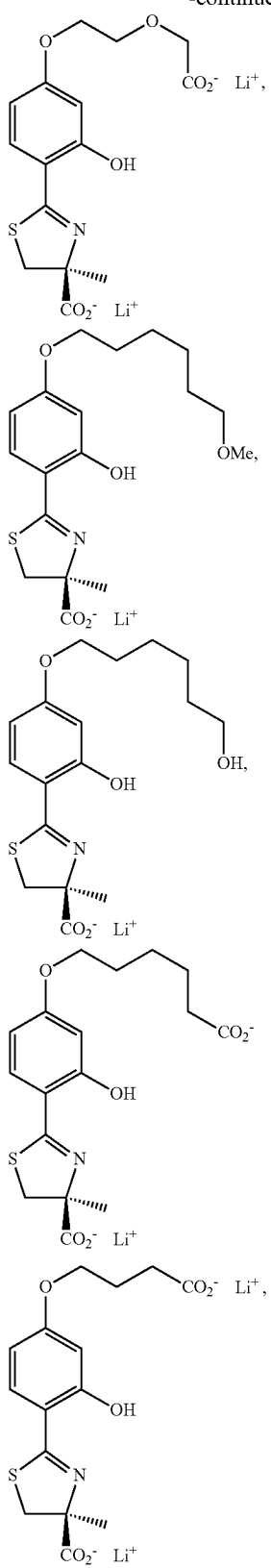
and pharmaceutically acceptable solvates, hydrates, polymorphs, co-crystals, tautomers, stereoisomers, isotopically labeled derivatives, and prodrugs thereof.
Additional exemplary compounds of Formula (I) include, but are not limited to:
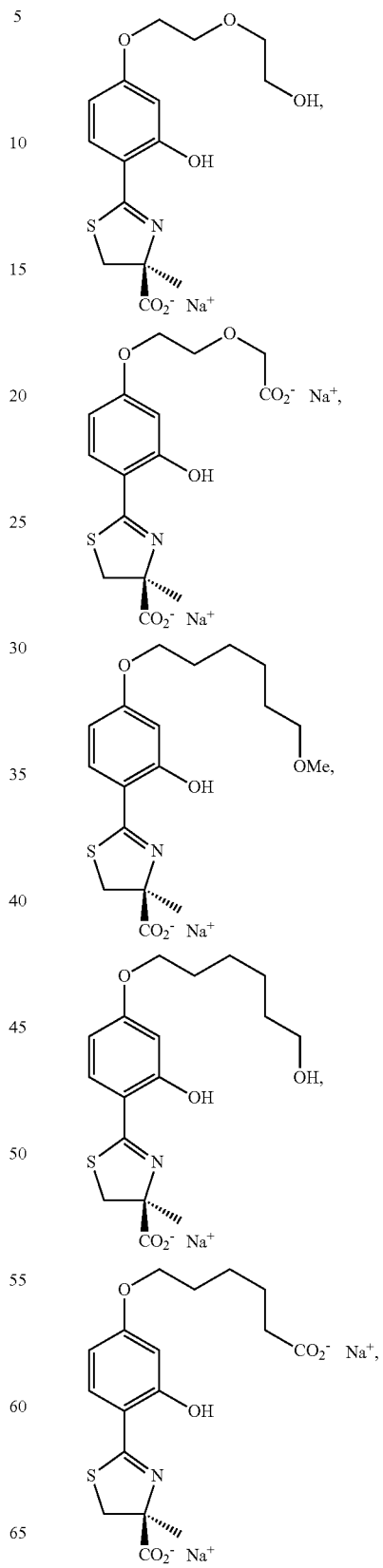

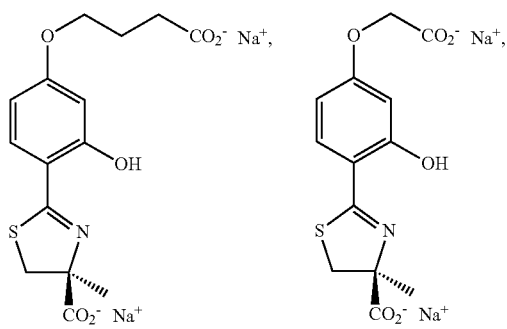

and pharmaceutically acceptable solvates, hydrates, polymorphs, co-crystals, tautomers, stereoisomers, isotopically labeled derivatives, and prodrugs thereof.

Additional exemplary compounds of Formula (I) include, but are not limited to:

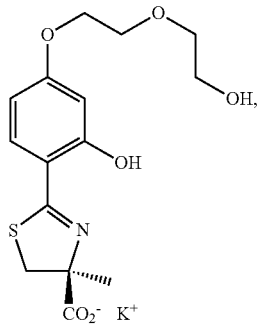

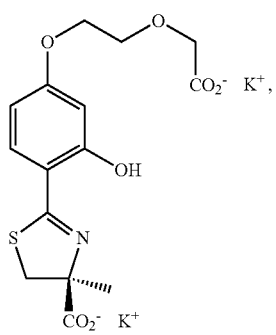

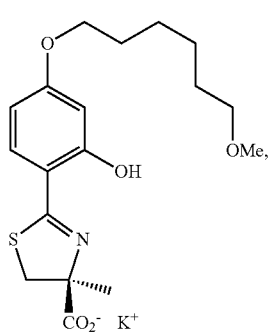

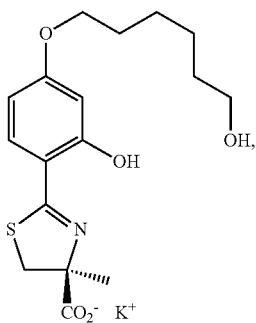

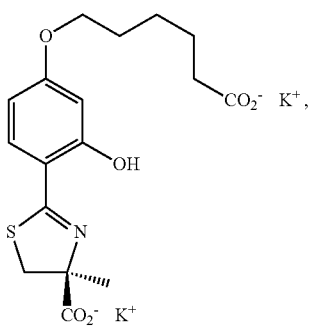

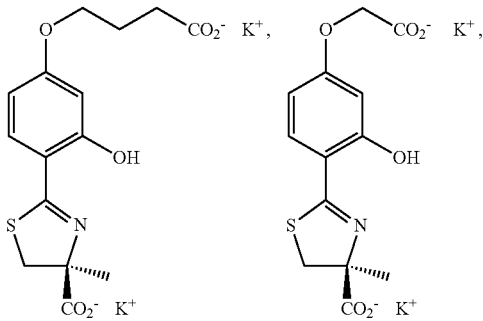

and pharmaceutically acceptable solvates, hydrates, polymorphs, co-crystals, tautomers, stereoisomers, isotopically labeled derivatives, and prodrugs thereof.

Additional exemplary compounds of Formula (I) include, but are not limited to:

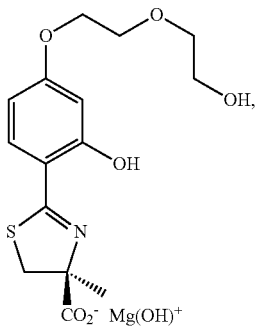

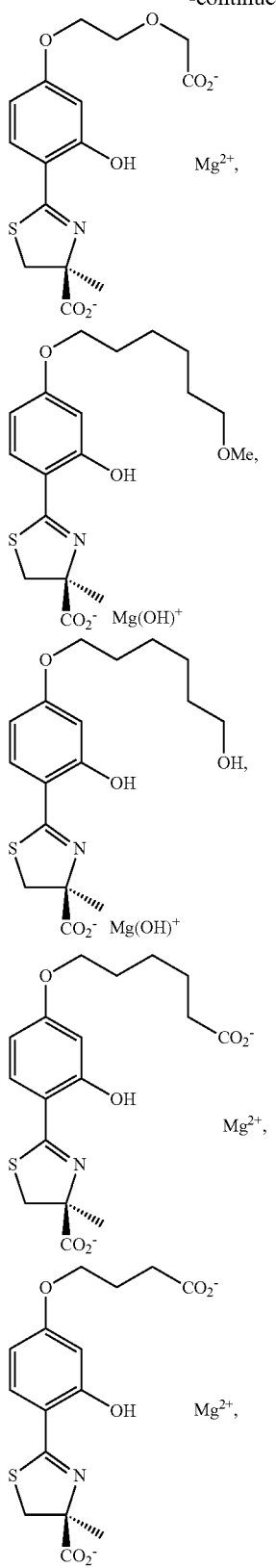
and pharmaceutically acceptable solvates, hydrates, polymorphs, co-crystals, tautomers, stereoisomers, isotopically labeled derivatives, and prodrugs thereof.
Additional exemplary compounds of Formula (I) include, but are not limited to:
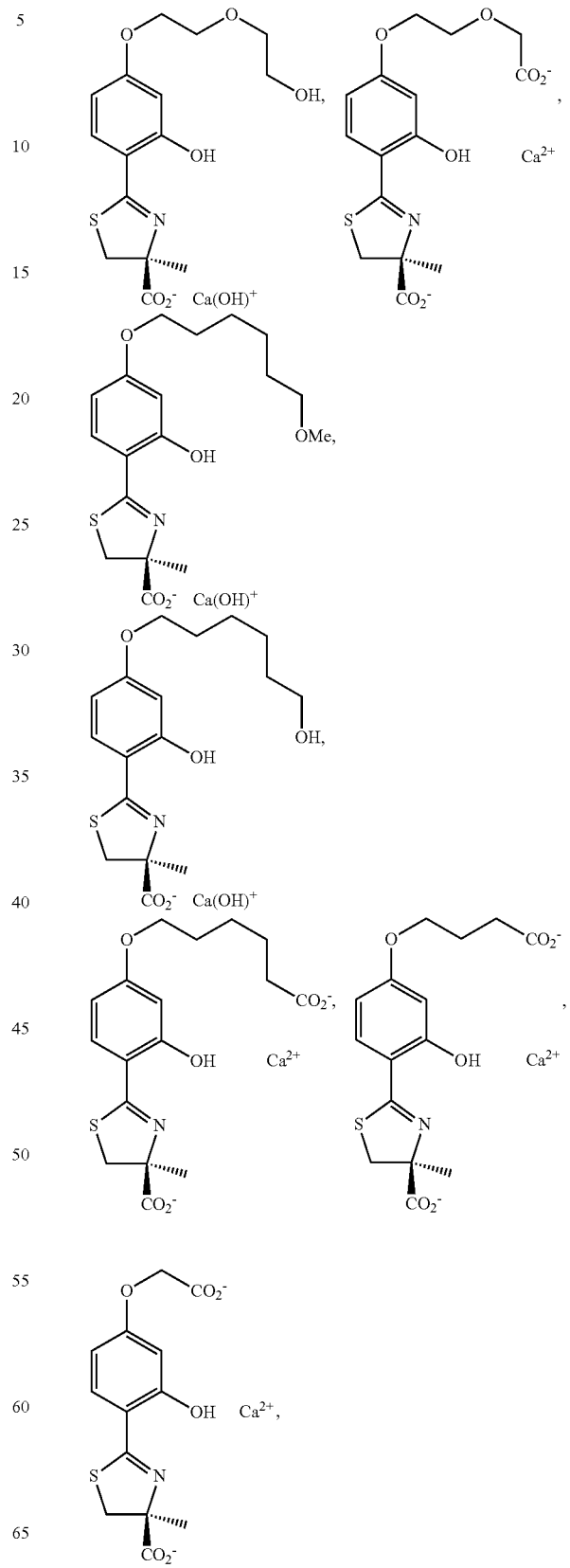

and pharmaceutically acceptable solvates, hydrates, polymorphs, co-crystals, tautomers, stereoisomers, isotopically labeled derivatives, and prodrugs thereof.

Additional exemplary compounds of Formula (I) include, but are not limited to:

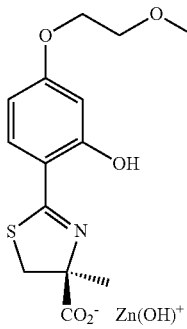 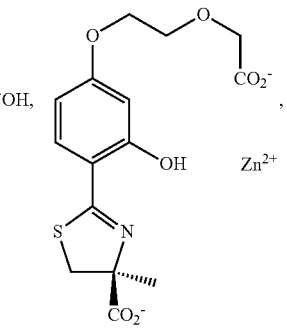

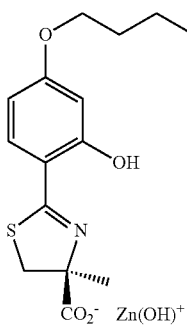

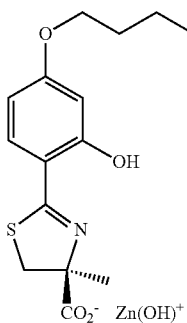

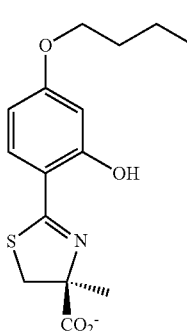 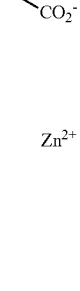

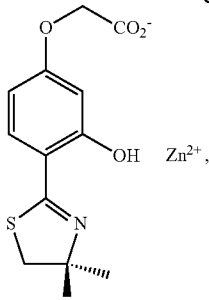

and pharmaceutically acceptable solvates, hydrates, polymorphs, co-crystals, tautomers, stereoisomers, isotopically labeled derivatives, and prodrugs thereof.

In certain embodiments, a compound described herein is a compound of Formula (I), or a pharmaceutically acceptable salt, solvate, hydrate, polymorph, co-crystal, tautomer, stereoisomer, isotopically labeled derivative, or prodrug thereof. In certain embodiments, a compound described herein is a compound of Formula (I), or a pharmaceutically acceptable salt or stereoisomer thereof. In certain embodiments, a compound described herein is a compound of Formula (I), or a pharmaceutically acceptable salt thereof.

Another aspect of the present disclosure relates to compounds of Formula (II):

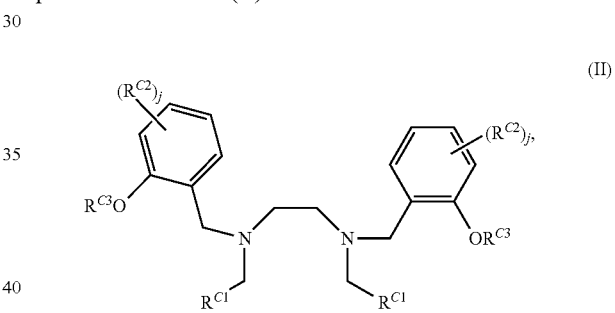

(II)

or a pharmaceutically acceptable salt thereof, wherein:
each instance of $R^{C1}$ is independently $-(CH_2)_hOR^{A1}$, or $-(CH_2)_hC(=O)OR^{A1}$, wherein each instance of $R^{A1}$ is independently hydrogen, substituted or unsubstituted alkyl, or an oxygen protecting group, provided that h is not 0, and $R^{A1}$ is not hydrogen when $R^{C1}$ is $-(CH_2)_hC(=O)OR^{A1}$;
each instance of $R^{C2}$ is independently hydrogen, halogen, substituted or unsubstituted $C_{1-6}$ alkyl, $-CN$, $-NO_2$, $-OR^X$, or $-N(R^Y)_2$;
each instance of $R^{C3}$ is independently hydrogen, alkyl, or an oxygen protecting group;
$R^X$ is hydrogen, substituted or unsubstituted $C_{1-6}$ alkyl, or oxygen protecting group;
each instance of $R^Y$ is independently hydrogen, substituted or unsubstituted $C_{1-6}$ alkyl, a nitrogen protecting group, or optionally two $R^Y$ are taken together with the intervening atoms to form substituted or unsubstituted heterocyclyl or substituted or unsubstituted heteroaryl;
each instance of h is independently 0, 1, 2, 3, 4, 5, 6, 7, or 8; and
each instance of j is independently 0, 1, 2, 3, or 4.

Formula (II) includes one or more instances of substituent $R^{C1}$. In certain embodiments, at least one instance of $R^{C1}$ is of the formula: $-(CH_2)_hOR^{A1}$, wherein each instance of $R^{A1}$ is independently hydrogen, substituted or unsubstituted alkyl, or an oxygen protecting group. In certain embodiments, at least one instance of $R^{C1}$ is —$(CH_2)_hOH$, wherein: h is 0, 1, 2, 3, 4, 5, 6, 7, or 8. In certain embodiments, h is 0. In certain embodiments, h is 1. In certain embodiments, h is 2. In certain embodiments, h is 3. In certain embodiments, h is 4. In certain embodiments, h is 5. In certain embodiments, h is 6. In certain embodiments, h is 7. In certain embodiments, h is 8. In certain embodiments, at least one instance of $R^{C1}$ is —OH. In certain embodiments, $R^{A1}$ is hydrogen. In certain embodiments, $R^{A1}$ is substituted or unsubstituted $C_{1-6}$ alkyl (e.g., methyl or ethyl). In certain embodiments, at least one instance of $R^{A1}$ is methyl. In certain embodiments, at least one instance of $R^{A1}$ is substituted methyl (e.g., —$CF_3$, —$CH_2OH$, or Bn). In certain embodiments, at least one instance of $R^{A1}$ is unsubstituted ethyl, substituted ethyl (e.g., perfluoroethyl), unsubstituted propyl (e.g., n-Pr or i-Pr), substituted propyl (e.g., perfluoropropyl), unsubstituted butyl, or substituted butyl (e.g., perfluorobutyl). In certain embodiments, at least one instance of $R^{C1}$ is —OMe or —OEt. In certain embodiments, $R^{A1}$ is an oxygen protecting group (e.g., silyl, TBDPS, TBDMS, TIPS, TES, TMS, MOM, THP, t-Bu, Bn, allyl, acetyl, pivaloyl, or benzoyl). In certain embodiments, at least one instance of $R^{C1}$ is of the formula: —$(CH_2)_hC(=O)OR^{A1}$, wherein each instance of $R^{A1}$ is independently hydrogen, substituted or unsubstituted alkyl, or an oxygen protecting group, provided that h is not 0, and $R^{A1}$ is not hydrogen when $R^{C1}$ is —$(CH_2)_hC(=O)OR^{A1}$. In certain embodiments, at least one instance of $R^{A1}$ is —$(CH_2)C(=O)OR^{A1}$ (e.g., —$(CH_2)C(=O)OH$, —$(CH_2)C(=O)O$(substituted or unsubstituted $C_{1-6}$ alkyl) (e.g., —OMe, —$OCF_3$, —OEt, —OPr, —OBu, or —OBn), or —$(CH_2)C(=O)O$(substituted or unsubstituted phenyl) (e.g., —$(CH_2)C(=O)OPh$)). In certain embodiments, at least one instance of $R^{C1}$ is —$(CH_2)C(=O)OMe$. In certain embodiments, at least one instance of $R^{C1}$ is —$(CH_2)C(=O)OEt$.

Formula (II) includes one or more instances of substituent $R^{C2}$. In certain embodiments, j is 0. In certain embodiments, j is 1. In certain embodiments, j is 2. In certain embodiments, j is 3. In certain embodiments, j is 4. In certain embodiments, at least one instance of $R^{C2}$ is hydrogen. In certain embodiments, at least one instance of $R^{C2}$ is halogen (e.g., F, Cl, Br, or I). In certain embodiments, at least one instance of $R^{C2}$ is F. In certain embodiments, at least one instance of $R^{C2}$ is Cl. In certain embodiments, at least one instance of $R^{C2}$ is substituted or unsubstituted $C_{1-6}$ alkyl. In certain embodiments, at least one instance of $R^{C2}$ is methyl. In certain embodiments, at least one instance of $R^{C2}$ is substituted methyl (e.g., —$CF_3$, —$CH_2OH$, or Bn). In certain embodiments, at least one instance of $R^{C2}$ is unsubstituted ethyl, substituted ethyl (e.g., perfluoroethyl), unsubstituted propyl (e.g., n-Pr or i-Pr), substituted propyl (e.g., perfluoropropyl), unsubstituted butyl, or substituted butyl (e.g., perfluorobutyl). In certain embodiments, at least one instance of $R^{C2}$ is —CN. In certain embodiments, at least one instance of $R^{C2}$ is —$NO_2$. In certain embodiments, at least one instance of $R^{C2}$ is —$OR^X$ (e.g., —OH, —O(substituted or unsubstituted $C_{1-6}$ alkyl) (e.g., —OMe, —$OCF_3$, —OEt, —OPr, —OBu, or —OBn), or —O(substituted or unsubstituted phenyl) (e.g., —OPh)), wherein $R^X$ is hydrogen, substituted or unsubstituted $C_{1-6}$ alkyl, or oxygen protecting group. In certain embodiments, at least one instance of $R^{C2}$ is —OH. In certain embodiments, at least one instance of $R^{C2}$ is —OMe. In certain embodiments, at least one instance of $R^{C2}$ is —OEt. In certain embodiments, at least one instance of $R^{C2}$ is —$N(R^Y)_2$ (e.g., —$NH_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)), wherein each instance of $R^Y$ is independently hydrogen, substituted or unsubstituted $C_{1-6}$ alkyl, a nitrogen protecting group, or optionally two $R^Y$ are taken together with the intervening atoms to form substituted or unsubstituted heterocyclyl or substituted or unsubstituted heteroaryl. In certain embodiments, at least one instance of $R^{C2}$ is —$NMe_2$. In certain embodiments, at least one instance of $R^{C2}$ is —$NEt_2$. In certain embodiments, two instances of $R^Y$ are taken together with the intervening atoms to form a substituted or unsubstituted, 5- to 14-membered, monocyclic or bicyclic heterocyclic ring comprising zero, one, or two double bonds in the heterocyclic ring, wherein one, two, or three atoms of the heterocyclic ring are independently nitrogen, oxygen, or sulfur.

Formula (II) includes one or more instances of substituent $R^{C3}$. In certain embodiments, at least one instance of $R^{C3}$ is hydrogen. In certain embodiments, at least one instance of $R^{C3}$ is substituted or unsubstituted alkyl. In certain embodiments, at least one instance of $R^{C3}$ is substituted or unsubstituted $C_{1-6}$ alkyl. In certain embodiments, at least one instance of $R^{C3}$ is Me. In certain embodiments, at least one instance of $R^{C3}$ is substituted methyl (e.g., —$CF_3$, —$CH_2OH$, or Bn). In certain embodiments, at least one instance of $R^{C3}$ is Et, substituted ethyl (e.g., perfluoroethyl), Pr (e.g., n-Pr or i-Pr), substituted propyl (e.g., perfluoropropyl), Bu, or substituted butyl (e.g., perfluorobutyl). In certain embodiments, at least one instance of $R^D$ is an oxygen protecting group (e.g., silyl, TBDPS, TBDMS, TIPS, TES, TMS, MOM, THP, t-Bu, Bn, allyl, acetyl, pivaloyl, or benzoyl).

In certain embodiments, the compound of Formula (II) is of the formula:

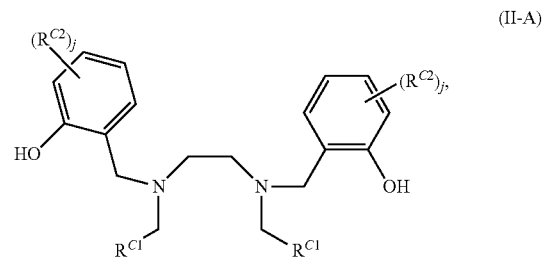

(II-A)

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

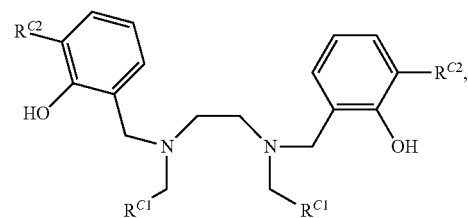

-continued

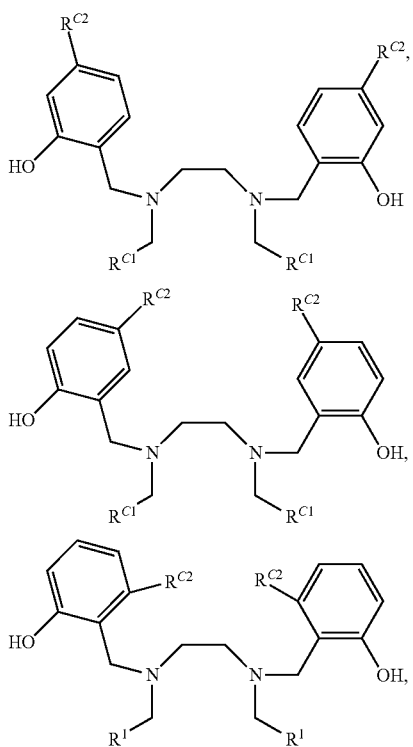

or a pharmaceutically acceptable salt, solvate, hydrate, polymorph, co-crystal, tautomer, stereoisomer, isotopically labeled derivative, or prodrug thereof.

Exemplary compounds of Formula (II) include, but are not limited to:

-continued

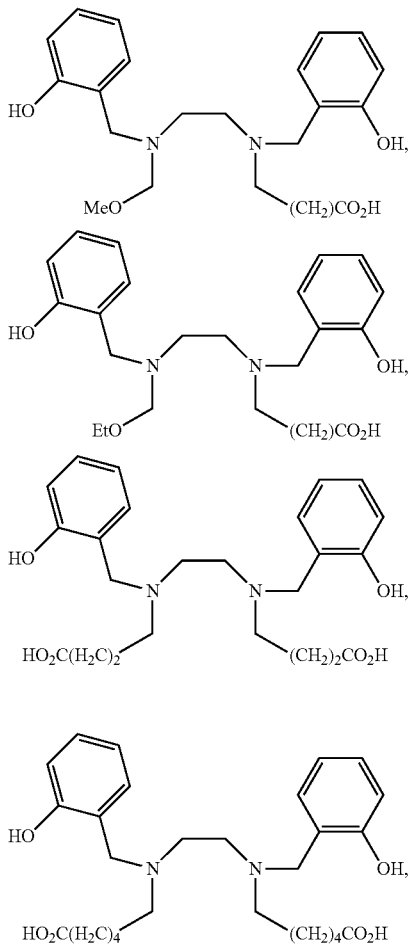

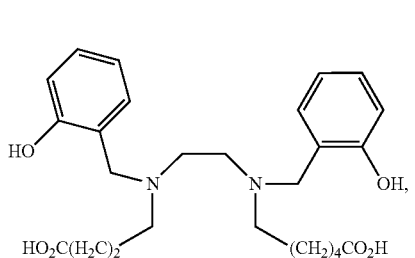

or a pharmaceutically acceptable salt, solvate, hydrate, polymorph, co-crystal, tautomer, stereoisomer, isotopically labeled derivative, or prodrug thereof.

Exemplary compounds of Formula (II) include, but are not limited to:

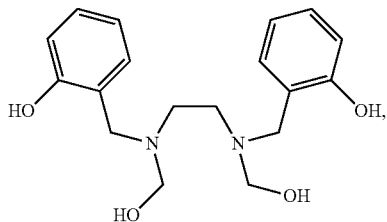

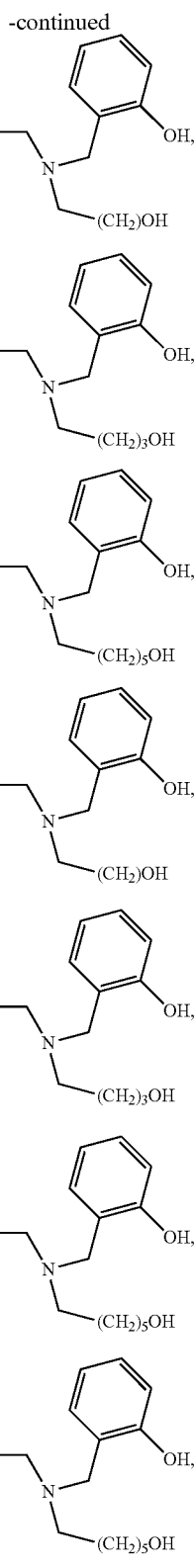

or a pharmaceutically acceptable salt, solvate, hydrate, polymorph, co-crystal, tautomer, stereoisomer, isotopically labeled derivative, or prodrug thereof.

In certain embodiments, a compound described herein is a compound of Formula (II), or a pharmaceutically acceptable salt, solvate, hydrate, polymorph, co-crystal, tautomer, stereoisomer, isotopically labeled derivative, or prodrug thereof. In certain embodiments, a compound described herein is a compound of Formula (II), or a pharmaceutically acceptable salt or stereoisomer thereof. In certain embodiments, a compound described herein is a compound of Formula (II), or a pharmaceutically acceptable salt thereof.

Pharmaceutical Compositions, Kits, and Administration

The present invention provides pharmaceutical compositions comprising a compound of the invention, and optionally a pharmaceutically acceptable excipient. The pharmaceutical compositions may be useful in chelating a metal (e.g., iron or another metal) in a subject, cell, tissue, or biological sample, treating a disease in a subject thereof, preventing a disease in a subject in need thereof, treating, reducing, or preventing the formation of biofilms in a subject, or reducing or preventing the formation of biofilms on or in an object. In certain embodiments, the compound of the present invention is a compound of Formula (I), or a pharmaceutically acceptable salt thereof. In certain embodiments, the compound of the present invention is a compound of Formula (II), or a pharmaceutically acceptable salt thereof. In certain embodiments, the compound of the present invention is provided in an effective amount in the pharmaceutical composition. In certain embodiments, the effective amount is a therapeutically effective amount. In certain embodiments, the effective amount is a prophylactically effective amount.

Pharmaceutical compositions described herein can be prepared by any method known in the art of pharmacology. In general, such preparatory methods include the steps of bringing the compound of the present invention (the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g., polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g., Cremophor™), polyoxyethylene ethers, (e.g., polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

While it may be possible for the compounds disclosed herein, or pharmaceutically acceptable salts, tautomers, stereoisomers, solvates, hydrates, or polymorphs thereof, to be administered orally as they are, it is also possible to present them as a pharmaceutical formulation or dosage. Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier or excipient and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. The inventive compounds and compositions may also be mixed with blood ex vivo, and the resulting mixture may be administered (e.g., intravenously) to a subject. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is 70 kg.

A compound or composition described herein can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, in reducing the risk to develop a disease in a subject in need thereof, and/or in inhibiting the activity of a protein kinase in a subject or cell), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which are different from the compound or composition and may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, hematological disease, neurological disease, painful condition, psychiatric disorder, or metabolic disorder). Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, and pain-relieving agents. In certain embodiments, the additional pharmaceutical agent is an anti-proliferative agent. In certain embodiments, the additional pharmaceutical agent is an anti-cancer agent. In certain embodiments, the additional pharmaceutical agent is an anti-viral agent. In certain embodiments, the additional pharmaceutical agent is a binder or inhibitor of a protein kinase. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation. In certain embodiments, the additional pharmaceutical agent is an iron chelator (e.g., desferrioxamine (DFO, DFX, deferoxamine, deferoxamine mesylate, desferrioxamine B, Desferal®), deferasirox (Exjad®), deferiprone (L1, Ferriprox®), or Feralex-G). In certain embodiments, the compounds described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy.

Also encompassed by the invention are kits (e.g., pharmaceutical packs). The kit may comprise an inventive compound or pharmaceutical composition and a first container (e.g., a vial, ampule, bottle, syringe, and/or dispenser package, or other suitable container). In some embodiments, the kit further includes a second container comprising a pharmaceutical excipient for, e.g., dilution or suspension of an inventive compound or pharmaceutical composition. In some embodiments, the inventive compound or pharmaceutical composition provided in the first container and the second container are combined to form one unit dosage form.

The kits may be useful in chelating a metal (e.g., iron or another metal) in a subject, cell, tissue, or biological sample, treating a disease in a subject thereof, preventing a disease in a subject in need thereof, treating, reducing, or preventing the formation of biofilms in a subject, or reducing or preventing the formation of biofilms on or in an object. In certain embodiments, the kit includes a compound or pharmaceutical composition described herein (e.g., in a first container); and instructions for using the compound or pharmaceutical composition (e.g., instructions for administering the compound or pharmaceutical composition to the subject, instructions for contacting the cell, tissue, or biological sample with the compound or pharmaceutical composition). A kit described herein may also include information as required by a regulatory agency such as the U.S. Food and Drug Administration (FDA). In certain embodiments, the information included in the kits is prescribing information. In certain embodiments, the kits and instructions provide for chelating a metal (e.g., iron or another metal) in a subject, cell, tissue, or biological sample. In certain embodiments, the kits and instructions provide for treating a disease in a subject in need thereof. In certain embodiments, the kits and instructions provide for preventing a disease in a subject in need thereof. In certain embodiments, the kits and instructions provide for treating, reducing, or preventing the formation of biofilms in a subject. In certain embodiments, the kits and instructions provide for reducing or preventing the formation of biofilms on or in an object. A kit described herein may include one or more additional pharmaceutical agents described herein as a separate composition.

Methods of Treatment and Uses

The compounds of Formula (I) or Formula (II), and pharmaceutical compositions described herein, may be useful in chelating a metal (e.g., iron or another metal) in a subject, cell, tissue, or biological sample, treating a disease in a subject thereof, preventing a disease in a subject in need thereof, treating, reducing, or preventing the formation of biofilms in a subject, or reducing or preventing the formation of biofilms on or in an object.

The compounds of the invention are thought to be metal chelators. The compounds are advantageous over known metal chelators at least because the compounds described herein are "metabolically programmed" metal chelators, e.g., lipophilic, absorbable (e.g., orally absorbable), and effective metal chelators that are quickly converted (e.g., converted in vivo) to their hydrophilic, nontoxic counterparts. Hydrophilic compounds (e.g., compounds of Formula (I) or Formula (II) that include two or more carboxyl groups) typically cannot easily pass the cell membrane and/or are poorly absorbable (e.g., orally absorbable). Lipophilic compounds (e.g., compounds of Formula (I) or Formula (II) that include zero or one carboxyl group) typically are able to easily pass the cell membrane and/or are absorbable (e.g., orally absorbable). Moreover, lipophilic compounds are typically more effective in chelating metal than the hydrophilic compounds. However, the lipophilic compounds typically are more toxic than the hydrophilic compounds. Therefore, by "metabolically programing" the hydrophilic compounds, e.g., structurally modifying the hydrophilic compounds into lipophilic compounds that can easily pass the cell membrane and in turn are metabolically converted back to the hydrophilic compounds, metal chelators with balanced properties, such as being absorbable, effective, and non-toxic, are achieved.

In certain embodiments, the metal is iron (e.g., Fe(II) or Fe(III)). In certain embodiments, the metal is not iron. In certain embodiments, the metal is aluminum, thallium (e.g., Tl(I) or Tl(III)), chromium (e.g., Cr(III) or Cr(VI)), magnesium, calcium, strontium, nickel (e.g., Ni(II)), manganese (e.g., Mn(II)), cobalt (e.g., Co(II) or Co(III)), copper (e.g., Cu(I) or Cu(II)), zinc, silver (e.g., Ag(I)), sodium, potassium, cadmium (e.g., Cd(II)), mercury (e.g., Hg(I) or Hg(II)), lead (e.g., Pb(II) or Pb(IV)), antimony (e.g., Sb(III) or Sb(V)), molybdenum (e.g., Mo(III) or Mo(VI)), tungsten (e.g., W(VI)), a lanthanide (e.g., cerium, such as Ce(III) or Ce(IV)), or an actinide (e.g., uranium, such as U(VI)). In certain embodiments, the metal is a trivalent metal (e.g., Fe(III) or aluminum). In certain embodiments, the trivalent metal is Tl(III), Cr(III), Co(III), Sb(III), Mo(III), or Ce(III). In certain embodiments, the metal is a monovalent metal (e.g., Tl(I), Cu(I), Ag(I), Na(I), K(I), or Hg(I)). In certain embodiments, the metal is a divalent metal (e.g., Fe(II), Mg(II), Ca(II), Sr(II), Ni(II), Mn(II), Co(II), Cu(II), Zn(II), Cd(II), Hg(II), or Pb(II)). In certain embodiments, the metal is a tetravalent metal (e.g., Pb(IV) or Ce(IV)). In certain embodiments, the metal is a pentavalent metal (e.g., Sb(V)). In certain embodiments, the metal is a hexavalent metal (e.g., Cr(VI), Mo(VI), W(VI), or U(VI)).

In another aspect, provided herein are methods of chelating a metal (e.g., iron or another metal) in a subject, the methods including administering to the subject an effective amount (e.g., therapeutically effective amount) of a compound or pharmaceutical composition described herein.

In another aspect, provided herein are methods of chelating a metal (e.g., iron or another metal) in a cell, tissue, or biological sample, the methods including contacting the cell, tissue, or biological sample with an effective amount of a compound or pharmaceutical composition described herein.

In another aspect, provided herein are methods of treating a disease in a subject in need thereof, the methods including administering to the subject an effective amount (e.g., therapeutically effective amount) of a compound or pharmaceutical composition described herein.

In another aspect, provided herein are methods of preventing a disease in a subject in need thereof, the methods including administering to the subject an effective amount (e.g., prophylactically effective amount) of a compound or pharmaceutical composition described herein.

In another aspect, provided herein are methods of treating a disease in a subject in need thereof, the methods including mixing blood or a component thereof (e.g., red blood cells) with an effective amount (e.g., therapeutically effective amount) of a compound or pharmaceutical composition described herein to form a mixture; and administering the mixture to the subject.

In another aspect, provided herein are methods of preventing a disease in a subject in need thereof, the methods including mixing blood or a component thereof (e.g., red blood cells) with an effective amount (e.g., prophylactically effective amount) of a compound or pharmaceutical composition described herein to form a mixture; and administering the mixture to the subject.

The blood may be whole blood or a fluid comprising one or more components of whole blood (e.g., red blood cells, white blood cells, plasma, clotting factors, and platelets). In certain embodiments, the mixture is administered intravenously to the subject.

In another aspect, provided are the compounds described herein for use in a method described herein (e.g., method of chelating a metal (e.g., iron or another metal) in a subject, cell, tissue, or biological sample, method of treating a disease in a subject thereof, or method of preventing a disease in a subject in need thereof).

In another aspect, provided are the pharmaceutical compositions described herein for use in a method described herein (e.g., method of chelating a metal (e.g., iron or another metal) in a subject, cell, tissue, or biological sample, method of treating a disease in a subject thereof, or method of preventing a disease in a subject in need thereof).

The present invention stems from the recognition that the pathogenesis of various diseases. In certain embodiments, the disease is oxidative stress, transfusional iron overload, thalassemia, primary hemochromatosis, secondary hemochromatosis, diabetes, liver disease, heart disease, cancer, radiation injury, neurological or neurodegenerative disorder, Friedreich's ataxia (FRDA), macular degeneration, closed head injury, irritable bowel disease, or reperfusion injury. These diseases involve free iron and the generation of reactive oxygen species (ROS), including superoxide anion, hydrogen peroxide, hypochlorous acid, and hydroxyl radicals, and other longer lived, free radicals. Such radicals are now realized to be important contributors to these diseases. Free iron is known to contribute to the formation of reactive oxygen species. For example, $Fe^{+2}$ ions in biological systems react with oxygen species to produce highly reactive hydroxyl radicals via the Fenton reaction. The hydroxyl radical is a highly effective oxidizing agent, reacting at a diffusion-controlled rate with most organic species, such as nucleic acids, proteins, and lipids. Furthermore, superoxide anions or a biological reductant (e.g., ascorbic acid) can reduce the resulting $Fe^{+3}$ ion back to $Fe^{+2}$ for continued peroxide reduction, thus a problematic cycle.

Therefore, diseases that lead to bleeding and/or an inflammatory response involve the possibility that reactive oxygen species will come in contact with $Fe^{+2}$ ions to produce highly reactive and damaging hydroxyl radicals. That is, the iron released from red blood cells react with oxygen species produced by inflammatory cells such as neutrophils to produce hydroxyl radicals that cause cell and tissue injury. The solution, therefore, is chelation and removal of the unmanaged iron.

In certain embodiments, the subject is a mammal. In certain embodiments, the subject is a human. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is an experimental animal such as a rodent or non-human primate. In certain embodiments, the subject is diagnosed with cystic fibrosis. In certain embodiments, the subject is immunocompromised.

In certain embodiments, the cell is in vitro. In certain embodiments, the cell is in vivo.

In certain embodiments, the cell is a blood cell. In certain embodiments, the cell is a liver cell, lung cell, or spleen cell. In certain embodiments, the cell is a cancer cell.

In certain embodiments, the tissue is a target tissue (e.g., heart, lungs, liver, pancreas, kidneys, brain, or spleen).

In certain embodiments, the disease that is treated or prevented by a method described herein is an infectious disease. Infectious diseases are typically caused by microbial pathogens (e.g., viruses, bacteria, parasites (e.g., protozoa and multicellular parasites), and fungi) into the cells ("host cells") of a subject ("host"). Iron is an oxidant as well as a nutrient for many microorganisms. To survive and replicate, microbial pathogens must acquire iron from their host. Highly virulent microbial strains usually possess powerful mechanisms for obtaining iron from their host. Depriving the pathogenic microbes of iron may inhibit their activities and may be useful for the treatment and/or prevention of the infectious diseases caused by microbes. In certain embodiments, the infectious disease is responsive to the chelation or sequestration of a metal. In certain embodiments, the disease that is treated and/or prevented by the compounds, pharmaceutical compositions, and methods of the invention is a viral infection. In certain embodiments, the disease is a bacterial infection. In certain embodiments, the bacterial infection is caused by a Gram-positive bacterium.

Exemplary Gram-positive bacteria include, but are not limited to, species of the genera *Staphylococcus, Streptococcus, Micrococcus, Peptococcus, Peptostreptococcus, Enterococcus, Bacillus, Clostridium, Lactobacillus, Listeria, Erysipelothrix, Propionibacterium, Eubacterium,* and *Corynebacterium*. In certain embodiments, the Gram-positive bacterium is a bacterium of the phylum *Firmicutes*. In certain embodiments, the bacterium is a member of the phylum *Firmicutes* and the genus *Enterococcus*, i.e., the bacterial infection is an *Enterococcus* infection. Exemplary *Enterococci* bacteria include, but are not limited to, *E. avium, E. durans, E. faecalis, E. faecium, E. gallinarum, E. solitarius, E. casseliflavus,* and *E. raffinosus*. In certain embodiments, the *Enterococcus* infection is an *E. faecalis* infection. In certain embodiments, the *Enterococcus* infection is an *E. faecium* infection. In certain embodiments, the bacteria is a member of the phylum *Firmicutes* and the genus *Staphylococcus*, i.e., the bacterial infection is a *Staphylococcus* infection. Exemplary *Staphylococci* bacteria include, but are not limited to, *S. arlettae, S. aureus, S. auricularis, S. capitis, S. caprae, S. carnous, S. chromogenes, S. cohii, S. condimenti, S. croceolyticus, S. delphini, S. devriesei, S. epidermis, S. equorum, S. felis, S. fluroettii, S. gallinarum, S. haemolyticus, S. hominis, S. hyicus, S. intermedius, S. kloosii, S. leei, S. lenus, S. lugdunesis, S. lutrae, S. lyticans, S. massiliensis, S. microti, S. muscae, S. nepalensis, S. pasteuri, S. penttenkoferi, S. piscifermentans, S. psuedointermedius, S. psudolugdensis, S. pulvereri, S. rostri, S. saccharolyticus, S. saprophyticus, S. schleiferi, S. sciuri, S. simiae, S. simulans, S. stepanovicii, S. succinus, S. vitulinus, S. warneri,* and *S. xylosus*. In certain embodiments, the *Staphylococcus* infection is an *S. aureus* infection. In certain embodiments, the *Staphylococcus* infection is an *S. epidermis* infection. In certain embodiments, the Gram-positive bacterium is selected from the group consisting of *Staphylococcus aureus, Staphylococcus auricularis, Staphylococcus capitis, Staphylococcus cohnii, Staphylococcus epidermidis, Staphylococcus haemolyticus, Staphylococcus hominis, Staphylococcus lugdanensis, Staphylococcus saccharolyticus, Staphylococcus saprophyticus, Staphylococcus schleiferi, Staphylococcus similans, Staphylococcus warneri, Staphylococcus xylosus, Streptococcus agalactiae, Streptococcus anginosus, Streptococcus bovis, Streptococcus canis, Streptococcus equi, Streptococcus milleri, Streptococcus mitior, Streptococcus mutans, Streptococcus pneumoniae, Streptococcus pyogenes, Streptococcus salivarius, Streptococcus sanguis, Bacillus anthracis, Clostridium botulinum, Clostridium perfringens, Clostridium tetani, Corynebacterium diphtheriae, Corynebacterium jeikeium, Enterococcus faecalis, Enterococcus faecium, Erysipelothrix rhusiopathiae, Gardnerella vaginalis, Gemella morbillorum, Mycobacterium abcessus, Mycobacterium chelonae, Mycobacterium fortuitum, Mycobacterium haemophilium, Mycobacterium kansasii, Mycobacterium leprae, Mycobacterium marinum, Mycobacterium scrofulaceum, Mycobacterium smegmatis, Mycobacterium terrae, Mycobacterium tuberculosis, Mycobacterium ulcerans,* and *Peptococcus niger*.

In certain embodiments, the bacterial infection is an infection caused by a Gram-negative bacterium. Exemplary Gram-negative bacteria include, but are not limited to, *Escherchia coli, Caulobacter crescentus, Pseudomonas, Agrobacterium tumefaciens, Branhamella catarrhalis, Citrobacter diversus, Enterobacter aerogenes, Klebsiella pneumoniae, Proteus mirabilis, Salmonella typhimurium, Neisseria meningitidis, Serratia marcescens, Shigella sonnei, Neisseria gonorrhoeae, Acinetobacter baumannii, Salmonella enteriditis, Fusobacterium nucleatum, Veillonella parvula, Bacteroides forsythus, Actinobacillus actinomycetemcomitans, Aggregatibacter actinomycetemcomitans, Porphyromonas gingivalis, Helicobacter pylori, Francisella tularensis, Yersinia pestis, Morganella morganii, Edwardsiella tarda,* and *Haemophilus influenzae*. In certain embodiments, the Gram-negative bacteria species is *Pseudomonas*. In certain embodiments, the Gram-negative bacteria species is *Pseudomonas aeruginosa*.

In certain embodiments, the bacterial infection is a chronic bacterial infection. A "chronic bacterial infection" is a bacterial infection that is of a long duration or frequent recurrence. For example, a chronic middle ear infection, or otitis media, can occur when the Eustachian tube becomes blocked repeatedly due to allergies, multiple infections, ear trauma, or swelling of the adenoids. The definition of "long duration" will depend upon the particular infection. For example, in the case of a chronic middle ear infection, it may last for weeks to months. Exemplary chronic bacterial infections include, but are not limited to, urinary tract infection (e.g., urinary tract infection caused by *Escherichia coli* and/or *Staphylococcus saprophyticus*), gastritis (e.g., gastritis caused by *Helicobacter pylori*), respiratory infection (e.g., respiratory infection afflicting patents with cystic fibrosis and respiratory infection caused by *Pseudomonas aeuroginosa*), cystitis (e.g., cystitis caused by *Escherichia coli*), pyelonephritis (e.g., pyelonephritis caused by *Proteus* species, *Escherichia coli* and/or *Pseudomonas* sp), osteomyelitis (e.g., osteomyelitis caused by *Staphylococcus aureus* and/or by *Escherichia coli*), bacteremia, skin infection, rosacea, acne, chronic wound infection, infectious kidney stones (e.g., infectious kidney stones caused by *Proteus mirabilis*), bacterial endocarditis, and sinus infection.

In certain embodiments, the bacterial infection is caused by an organism resistant to one or more antibiotics. In certain embodiments, the bacterial infection is caused by an organism resistant to penicillin. In certain embodiments, the bacterial infection is caused by an organism resistant to vancomycin (VR). In certain embodiments, the bacterial infection is caused by vancomycin-resistant *E. faecalis*. In certain embodiments, the bacterial infection is caused by vancomycin-resistant *E. faecium*. In certain embodiments, the bacterial infection is caused by vancomycin-resistant *Staphylococcus aureus* (VRSA). In certain embodiments, the bacterial infection is caused by vancomycin-resistant *Enterococci* (VRE). In certain embodiments, the bacterial infection is caused by a methicillin-resistant (MR) organism. In certain embodiments, the bacterial infection is caused by methicillin-resistant *S. aureus* (MRSA). In certain embodiments, the bacterial infection is caused by methicillin-resistant *Staphylococcus epidermidis* (MRSE). In certain embodiments, the bacterial infection is caused by penicillin-resistant *Streptococcus pneumonia*. In certain embodiments, the bacterial infection is caused by quinolone-resistant *Staphylococcus aureus* (QRSA). In certain embodiments, the bacterial infection is caused by multi-drug resistant *Mycobacterium tuberculosis*.

In some embodiments, the bacterial infection is one or more infections selected from the group consisting of urinary tract infection, gastritis, respiratory infection, cystitis, pyelonephritis, osteomyelitis, bacteremia, skin infection, rosacea, acne, chronic wound infection, infectious kidney stones, bacterial endocarditis, and sinus infection. In certain embodiments, the infectious diseases is pneumonia, urinary tract infection, complicated intra-abdominal infection, or complicated skin/skin structure infection. In certain embodiments, the infectious diseases is nosocomial pneumonia, community-acquired pneumonia, urinary tract infection, complicated intra-abdominal infection, complicated skin/skin structure infection, infectious exacerbations of cystic fibrosis, sepsis, or melioidosis. In certain embodiments, the bacterial infection is respiratory infection. In certain embodiments, the bacterial infection is upper respiratory infection. In certain embodiments, the bacterial infection is pneumonia. In certain embodiments, the bacterial infection is bronchitis. In certain embodiments, the disease is a parasitic infection. In certain embodiments, the disease is a protozoan infection. In certain embodiments, the disease is malaria. Malaria is typically caused by parasites of the genus *Plasmodium* (phylum *Apicomplexa*), including, but not limited to, the species *P. falciparum, P. malariae, P. ovale, P. vivax*, and *P. knowlesi*. In certain embodiments, the disease is a multicellular-parasitic infection. In certain embodiments, the disease is a fungal infection.

In certain embodiments, the disease that is treated or prevented by a method described herein is a metal overload. The amount of free metal (e.g., a trivalent metal, such as iron(III) or aluminum) may be elevated in the subject (e.g., in the serum or in a cell), such as when there is insufficient storage capacity for the metal or an abnormality in the metal storage system that leads to metal release. In certain embodiments, the metal overload is iron overload (e.g., Fe(III) overload or Fe(II) overload).

Iron overload conditions or diseases can be characterized by global iron overload or focal iron overload. Global iron overload conditions generally involve an excess of iron in multiple tissues or excess iron located throughout an organism. Global iron overload conditions can result from excess uptake of iron by a subject, excess storage and/or retention of iron, from, for example, dietary iron or blood transfusions. One global iron overload condition is primary hemochromatosis, which is typically a genetic disorder. A second global iron overload condition is secondary hemochromatosis, which is typically the result of receiving multiple (chronic) blood transfusions. Blood transfusions are often required for subjects suffering from thalassemia or sickle cell anemia. A type of dietary iron overload is referred to as Bantu siderosis, which is associated with the ingestion of homebrewed beer with high iron content. In certain embodiments, the disease that is treated and/or prevented by a method described herein is global iron overload. In certain embodiments, the disease is focal iron overload. In certain embodiments, the disease is primary hemochromatosis. In certain embodiments, the disease is secondary hemochromatosis. In certain embodiments, the disease is Bantu siderosis.

In focal iron overload conditions, the excess iron is limited to one or a few cell types or tissues or a particular organ. Alternatively, symptoms associated with the excess iron are limited to a discrete organ, such as the heart, lungs, liver, pancreas, kidneys, or brain. It is believed that focal iron overload can lead to neurological or neurodegenerative disorders such as Parkinson's disease, Alzheimer's disease, Huntington's disease, neuroferritinopathy, amyotrophic lateral sclerosis, and multiple sclerosis. Diseases that benefit from metal chelation are often associated with deposition of the metal in the tissues of a subject. Deposition can occur globally or focally. In certain embodiments, the disease is a neurological or neurodegenerative disorder. In certain embodiments, the disease is Parkinson's disease, Alzheimer's disease, Huntington's disease, neuroferritinopathy, amyotrophic lateral sclerosis, or multiple sclerosis.

While humans have a highly efficient iron management system in which they absorb and excrete about 1 mg of iron daily, there is no conduit for the excretion of excess metal. Transfusion-dependent anemias, like thalassemia, lead to a buildup of iron in the liver, heart, pancreas, and elsewhere resulting in (i) liver disease that may progress to cirrhosis (Angelucci et al., "Hepatic Iron Concentration and Total Body Iron Stores in Thalassemia Major." *N. Engl. J. Med.* 2000, 343, 327-331; Bonkovsky et al., "Iron-Induced Liver Injury." *Clin. Liver Dis.* 2000, 4, 409-429; Peitrangelo, "Mechanism of Iron Toxicity." *Adv. Exp. Med. Biol.* 2002, 509, 19-43), (ii) diabetes related both to iron-induced decreases in pancreatic beta-cell secretion and to increases in hepatic insulin resistance (Cario et al., "Insulin Sensitivity and β-Cell Secretion in Thalassemia Major with Secondary Haemochromatosis: Assessment by Oral Glucose Tolerance Test." *Eur. J. Pediatr.* 2004, 162, 139-146; Wojcik et al., "Natural History of C282Y Homozygotes for Haemochromatosis." *Can. J. Gastroenterol.* 2002, 16, 297-302), and (iii) heart disease. Relative excess iron has been associated with increased risk of heart disease. Cardiac failure is still the leading cause of death in thalassemia major and related forms of transfusional iron overload (Brittenham, "Disorders of Iron Metabolism: Iron Deficiency and Overload." In: Hoffman et al., editors. *Hematology: Basic Principles and Practice*. 3. Churchill Livingstone; New York: 2000. pp. 397-428; Brittenham et al., "Efficacy of Deferoxamine in Preventing Complications of Iron Overload in Patients with Thalassemia Major." *N. Engl. J. Med.* 1994, 331, 567-573; Zurlo et al., "Survival and Causes of Death in Thalassemia Major." *Lancet.* 1989, 2, 27-30). There is a strong correlation between serum ferritin levels, inflammatory biomarkers such as C-reactive protein and interleukin-1, and mortality is a subset of patients with peripheral arterial disease; phlebotomy and iron chelation has been used to mitigate that risk. Treatment with an iron chelator would reduce iron stores, reduce serum ferritin and potentially reduce the incidence of heart disease and stroke. In certain embodiments, the disease that is treated and/or prevented by a method described herein is transfusional iron overload. In certain embodiments, the disease is transfusion-dependent anemia. In certain embodiments, the disease is thalassemia. In certain embodiments, the disease a liver disease (e.g., hepatitis B, hepatitis C, and liver cirrhosis), heart disease (e.g., cardiomyopathy, coronary heart disease, inflammatory heart disease, ischemic heart disease, valvular heart disease, hypertensive heart disease, and atherosclerosis), or pancreas disease. In certain embodiments, the disease is diabetes.

Moreover, the compounds, pharmaceutical compositions, and methods of the present invention may be useful in the treatment and/or prevention of metal overload where the metal is not iron. In certain embodiments, the metal overload is aluminum overload, chromium overload, magnesium overload, calcium overload, strontium overload, nickel overload, manganese overload, cobalt overload, copper overload, zinc overload, silver overload, sodium overload, potassium overload, cadmium overload, mercury overload, lead overload, molybdenum overload, tungsten overload, or actinide overload (e.g., uranium overload). In certain embodiments, the metal overload is trivalent metal overload. In certain embodiments, the metal overload is aluminum overload. In certain embodiments, the trivalent metal overload is Cr(III) overload, Mo(III) overload, or Co(III) overload). In certain embodiments, the metal overload is monovalent metal overload (e.g., Cu(I) overload, Ag(I) overload, Na(I) overload, K(I) overload, or Hg(I) overload). In certain embodiments, the metal overload is divalent metal overload (e.g., Mg(II) overload, Ca(II) overload, Sr(II) overload, Ni(II) overload, Mn(II) overload, Co(II) overload, Cu(II) overload, Zn(II) overload, Cd(II) overload, Hg(II) overload, or Pb(II) overload). In certain embodiments, the metal overload is tetravalent metal overload (e.g., Pb(IV) overload). In certain embodiments, the metal overload is pentavalent metal overload. In certain embodiments, the metal overload is hexavalent metal overload (e.g., Cr(VI) overload, Mo(VI) overload, W(VI) overload, or U(VI) overload).

In certain embodiments, the disease that is treated or prevented by a method described herein is metal poisoning. Metal poisoning may be caused by metal toxicity to a subject. For example, metals with little or no endogenous function may find their way into the body of a subject and cause damage. Heavy metal ions such as Hg(II) can replace ions such as Zn(II) in metalloproteins and render them inactive, resulting in serious acute or chronic toxicity that can end in a patient's death or in birth defects. Even more significantly, radioactive isotopes of the lanthanide (e.g., cerium) and actinide (e.g., uranium) series can cause grave illness on an individual exposed to them by mouth, air, or skin contact. Such exposure could result not only from the detonation of a nuclear bomb or a "dirty bomb" composed of nuclear waste, but also from the destruction of a nuclear power facility. In certain embodiments, the metal poisoning is iron poisoning, aluminum poisoning, thallium poisoning, chromium poisoning, magnesium poisoning, calcium poisoning, strontium poisoning, nickel poisoning, manganese poisoning, cobalt poisoning, copper poisoning, zinc poisoning, silver poisoning, sodium poisoning, potassium poisoning, cadmium poisoning, mercury poisoning, lead poisoning, antimony poisoning, molybdenum poisoning, tungsten poisoning, lanthanide poisoning (e.g., cerium poisoning), or actinide poisoning (e.g., uranium poisoning). In certain embodiments, the metal poisoning is iron poisoning (e.g., Fe(II) poisoning or Fe(III) poisoning). In certain embodiments, the metal poisoning is aluminum poisoning. In certain embodiments, the metal poisoning is trivalent metal poisoning (e.g., Fe(III) poisoning, Al(III) poisoning, Tl(III) poisoning, Cr(III) poisoning, Co(III) poisoning, Sb(III) poisoning, Mo(III) poisoning, or Ce(III) poisoning). In certain embodiments, the metal poisoning is monovalent metal poisoning (e.g., Tl(I) poisoning, Cu(I) poisoning, Ag(I) poisoning, Na(I) poisoning, K(I) poisoning, or Hg(I) poisoning). In certain embodiments, the metal poisoning is divalent metal poisoning (e.g., Fe(II) poisoning, Mg(II) poisoning, Ca(II) poisoning, Sr(II) poisoning, Ni(II) poisoning, Mn(II) poisoning, Co(II) poisoning, Cu(II) poisoning, Zn(II) poisoning, Cd(II) poisoning, Hg(II) poisoning, or Pb(II) poisoning). In certain embodiments, the metal poisoning is tetravalent metal poisoning (e.g., Pb(IV) or Ce(IV) poisoning). In certain embodiments, the metal poisoning is pentavalent metal poisoning (e.g., Sb(V) poisoning). In certain embodiments, the metal poisoning is hexavalent metal poisoning (e.g., Cr(VI) poisoning, Mo(VI) poisoning, W(VI) poisoning, or U(VI) poisoning).

In certain embodiments, the disease that is treated or prevented by a method described herein is oxidative stress. In a subject who suffers from oxidative stress and thus needs oxidative stress reduction, the iron released from red blood cells of the subject may react with oxygen species produced by inflammatory cells such as neutrophils to produce hydroxyl radicals that cause cell and tissue injury. Chelation and removal of the unmanaged iron may prevent or impede these harmful reactions and, therefore, reduce oxidative stress. A subject in need of oxidative stress reduction can have one or more of the following conditions: decreased levels of reducing agents, increased levels of reactive oxygen species, mutations in or decreased levels of antioxidant enzymes (e.g., Cu/Zn superoxide dismutase, Mn superoxide dismutase, glutathione reductase, glutathione peroxidase, thioredoxin, thioredoxin peroxidase, DT-diaphorase), mutations in or decreased levels of metal-binding proteins (e.g., transferrin, ferritin, ceruloplasmin, albumin, metallothionein), mutated or overactive enzymes capable of producing superoxide (e.g., nitric oxide synthase, NADPH oxidases, xanthine oxidase, NADH oxidase, aldehyde oxidase, dihydroorotate dehydrogenase, cytochrome c oxidase), and radiation injury. Increased or decreased levels of reducing agents, reactive oxygen species, and proteins are determined relative to the amount of such substances typically found in healthy persons. A subject in need of oxidative stress reduction can be suffering from an ischemic episode. Ischemic episodes can occur when there is mechanical obstruction of the blood supply, such as from arterial narrowing or disruption. Myocardial ischemia, which can give rise to angina pectoris and myocardial infarctions, results from inadequate circulation of blood to the myocardium, usually due to coronary artery disease. Ischemic episodes in the brain that resolve within 24 hours are referred to as transient ischemic attacks. A longer-lasting ischemic episode, a stroke, involves irreversible brain damage, where the type and severity of symptoms depend on the location and extent of brain tissue whose access to blood circulation has been compromised. A subject at risk of suffering from an ischemic episode typically suffers from atherosclerosis, other disorders of the blood vessels, increased tendency of blood to clot, or heart disease.

A subject in need of oxidative stress reduction can be suffering from inflammation Inflammation is a fundamental pathologic process consisting of a complex of cytologic and chemical reactions that occur in blood vessels and adjacent tissues in response to an injury or abnormal stimulation caused by a physical, chemical, or biologic agent. Inflammatory disorders are characterized inflammation that lasts for an extended period (e.g., chronic inflammation) or that damages tissue. Such inflammatory disorders can affect a wide variety of tissues, such as respiratory tract, joints, bowels, and soft tissue. The compounds or pharmaceutical compositions of the invention can be used to treat these diseases. Not wishing to be bound by any theory, it is believed that the compounds of the invention derive their ability to reduce oxidative stress through various mechanisms. In one mechanism, the compound binds to a metal, particularly a redox-active metal (e.g., iron), and fills all of the coordination sites of the metal. When all of the metal coordination sites are filled, it is believed that oxidation and/or reducing agents have a diminished ability to interact with the metal and cause redox cycling. In another mechanism, the compound stabilizes the metal in a particular oxidation state, such that it is less likely to undergo redox cycling. In yet another mechanism, the compound itself has antioxidant activity (e.g., free radical scavenging, scavenging of reactive oxygen or nitrogen species). Desferrithiocin and desazadesferrithiocin, and their derivatives and analogs, are known to have intrinsic antioxidant activity, as described in U.S. Application Publication No. 2004/0044220, published Mar. 4, 2004 and now abandoned; U.S. Application Publication No. 2004/0132789 and now abandoned, published Jul. 8, 2004; International PCT Application Publication No. WO 2004/017959, published Mar. 4, 2004; U.S. Application Publication No. 2005/0234113, published Oct. 20, 2005 and now abandoned; U.S. Application Publication No. 2008/0255081, published Oct. 16, 2008 and now abandoned; U.S. Application Publication No. 2003/0236417, published Dec. 25, 2003 and now abandoned; U.S. Patent Application Ser. No. 61/576,920, filed Dec. 16, 2011; U.S. Patent Application Ser. No. 61/576,913, filed Dec. 16, 2011; and U.S. Pat. Nos. 6,083,966, 6,559,315, 6,525,080, 6,521,652, 7,126,004, 7,531,563, and 8,008,502; each of which are incorporated herein by reference. The compounds of the invention can be used to treat these diseases. In certain embodiments, the disease that is treated or prevented by a method described herein is oxidative stress. In certain embodiments, oxidative stress is reduced by a method described herein. In certain embodiments, the disease is radiation injury. In certain embodiments, the disease is inflammation.

In certain embodiments, the disease that is treated or prevented by a method described herein is macular degeneration. Without wishing to be bound by a particular theory, the compounds and pharmaceutical compositions described herein are able to get into the eye. See, e.g., U.S. Patent Application Ser. No. 61/576,920, filed Dec. 16, 2011; U.S. Patent Application Ser. No. 61/576,913, filed Dec. 16, 2011, International PCT Application Publication No. WO 2013/090750, published Jun. 20, 2013; and International PCT Application Publication No. WO 2013/090766, published Jun. 20, 2013. The compounds of the invention are then able to chelate and remove iron from the eye thereby preventing $Fe^{+2}$ from generating reactive oxygen species. The local accumulation of iron is thought to contribute to macular degeneration. Therefore, the removal of iron from the eye (including the retina) can prevent and treat macular degeneration. In the treatment of macular degeneration, the compound or pharmaceutical composition described herein may be administered systemically or ocularly. In certain embodiments, the compound or pharmaceutical composition is administered orally. In other embodiments, the compound or pharmaceutical composition is administered to the eye using eye drops or an ointment suitable for ocular administration.

In certain embodiments, the disease that is treated or prevented by a method described herein is head injury, such as those involving bleeding into the brain or other parts of the central nervous system. Without wishing to be bound by any particular theory, the compounds and pharmaceutical compositions described herein are thought to chelate the iron from red blood cells the blood resulting from the head injury, thereby preventing iron ions from generating reactive oxygen species. In the case of head injury resulting in bleeding into the central nervous system where the vasculature has been compromised a compound being used may or may not have the ability to cross the blood brain barrier. In certain embodiments, the compound being used to treat a head injury in a subject is able to cross the blood brain barrier. In other embodiments, the compounds are not able to cross the blood brain barrier. Certain compounds of the invention have been found in the CSF after systemic administration (orally and subcutaneously).

Head injuries come in various forms and results from various causes. In certain embodiments, the head injury is an injury to the head that penetrates the skull. In other embodiments, the head injury is a closed head injury, which does penetrate the skull. Closed head injuries results from a variety of causes including accidents including vehicular accidents, falls, and assaults. Types of closed head injuries include concussions, brain contusions, diffuse axonal injury, and hemtoma. In certain embodiments, the closed head injury is closed head injuries that result in blood outside the blood vessels of the brain. The local accumulation of iron from the bleeding is thought to contribute to after effects associated with closed head injury. By assisting the clearance of iron from the brain the effects of the bleeding are minimized. In the treatment or prevention of closed head injury, the compound or pharmaceutical composition described herein may be administered systemically, for example, parenterally (e.g., intravenously) or orally.

Reactive oxygen species have been implicated in the pathogenesis of inflammatory bowel disease (IBD). Grisham et al., "Neutophil-mediated mucosal injury. Role of reactive oxygen metabolites." *Dig. Dis. Sci.* 33:6S-15S, 1988; Allgayer "Clinical relevance of oxygen radicals in inflammatory bowel disease—facts and fashion." *Klin. Wochenschr.* 69:1001-1003, 1991; Ymamada et al. "Role of neutrophil-derived oxidants in the pathogenesis of intestinal inflammation." *Klin. Wocheschr.* 69:988-944, 1991; Babbs, "Oxygen radicals in ulcerative colitis." *Free Radic. Biol. Med.* 13:169-181, 1992. The present invention provides for the treatment or preventon of IBD. DFO, an iron chelator, has been discovered to prevent acetic acid-induced colitis in rats, an animal model of IBD. See, e.g., U.S. Patent Application Ser. No. 61/576,920, filed Dec. 16, 2011; U.S. Patent Application Ser. No. 61/576,913, filed Dec. 16, 2011; Bergeron et al., "Prevention of Acetic Acid-Induced Colitis by Desferrithiocin Analgos in a Rat Model." *Digestive Diseases and Sciences,* 48(2):399-407, February 2003. The compounds and pharmaceutical compositions described herein are thought to prevent or eliminate the generation of reactive oxygen species or other longer-lived, more stable radicals that may be responsible for the tissue damage and inflammation seen in subjects with IBD. Another possible mechanism of action of the compounds useful in the invention is the chelation of metal, such as iron, which may contribute to the generation of reactive oxygen species, such as hydroxyl radicals and hydrogen peroxide, that cause cell damage. The present invention may also be useful in treating a subject diagnosed with IBD. The treatment may be used to treat the subject long term or may be used to treat a subject with a fare up of IBD. In certain embodiments, treatment with a compound or pharmaceutical composition described herein leads to reduced levels of reactive oxygen species in the intestines, specifically the intestinal mucosa. In the treatment of IBD, the compound or pharmaceutical composition may be administered systemically, for example, parenterally (e.g., intravenously), orally, or rectally.

In certain embodiments, the disease that is treated or prevented by a method described herein is stroke. The inventive treatment typically leads to a better and/or faster recovery from stroke. The stroke being treated may be either an ischemic stroke or a hemorrhagic stroke. In the treatment of an ischemic stroke, a compound or pharmaceutical composition described herein is administered to a subject to prevent or minimize the damage due to reperfusion injury after the blood supply to the affected part of the brain is restored. The compound and pharmaceutical composition are thought to prevent the generation of reactive oxygen species by either chelating iron responsible for the generation of such species and/or quenching such radical species when they do occur. In hemorrhagic stroke, the compound and pharmaceutical composition are thought to work by similar mechanisms although the sequestering of iron from the blood in the brain is probably the predominate mechanism by which the inventive treatment works. The mechanism of action of the compound or pharmaceutical composition is similar to that in the treatment of head injury. The compound being used in the treatment may have the ability to cross the blood brain barrier. In certain embodiments, when the subject has been diagnosed with an ischemic stroke, the compound used in the treatment can pass through the blood brain barrier.

Moreover, the present invention may be useful in treating a subject after the subject has been diagnosed with having a stroke, or a subject who is susceptible to having a stroke may be administered a compound or pharmaceutical composition thereof to prevent or minimize the stroke's effects. In certain embodiments, the compound or pharmaceutical composition is administered as quickly as possible after a subject has been diagnosed with having a stroke. In certain embodiments, the compound is administered to the subject while the stroke is still occurring. In certain embodiments, the compound or pharmaceutical composition is administered to a subject who has a history of strokes or is susceptible to having a stroke because of the subject's underlying medical condition. In the treatment of stroke the compound or pharmaceutical composition may be administered systemically, for example, parenterally (e.g., intravenously) or orally.

In certain embodiments, the disease that is treated or prevented by a method described herein is reperfusion injury. Reperfusion injury may occur in any area of the body where the blood supply has been compromised. In certain embodiments, the reperfusion injury being treated occurs in the heart. In other embodiments, the reperfusion injury occurs in the brain, for example, as discussed above in the context of a stroke. The inventive treatment minimizes reperfusion injury once the blood supply to the affects organ or tissue is restored. In the treatment and/or prevention of reperfusion injury, a compound or pharmaceutical composition described herein is administered to a subject who is suffering from ischemia of a tissue or organ. Without wishing to be bound by any particular theory, the compound or pharmaceutical composition is thought to prevent the generation of reactive oxygen species by either chelating iron responsible for the generation of such species and/or quenching such radical species when they do occur.

The present invention may be useful in treating a subject after the subject has been diagnosed with ischemia of a particular organ or tissue. In certain embodiments, the compound or pharmaceutical composition described herein is administered as quickly as possible after a subject has been diagnosed with ischemia. In certain embodiments, the compound or pharmaceutical composition is administered to the subject at risk of ischemia. In certain embodiments, the compound pharmaceutical composition is administered to a subject who is about to undergo a procedure that may lead to ischemia of an organ or tissue (e.g., cardiac surgery). In certain embodiments, the compound or pharmaceutical composition is used to prevent reperfusion injury in a transplanted organ. In certain embodiments, the compound or pharmaceutical composition is used to perfuse an isolated organ being prepared for donation. In the prevention or treatment of reperfusion injury, the compound or pharmaceutical composition may be administered systemically, for example, parenterally (e.g., intravenously) or orally. In certain embodiments, the compound or pharmaceutical composition is administered locally to the organ or tissue suffering from ischemia.

In certain embodiments, the disease that is treated or prevented by a method described herein is a neoplastic disease or preneoplastic condition. In certain embodiments, the disease is a benign neoplastic disease. In certain embodiments, the disease is cancer. In certain embodiments, the disease is a preneoplastic disease.

Imaging or examining one or more organs, tissues, tumors, or a combination thereof can be conducted after a metal salt of a compound or pharmaceutical composition described herein is administered to a subject. The methods of imaging and examining are intended to encompass various instrumental techniques used for diagnosis, such as x-ray methods (including CT scans and conventional x-ray images), magnetic imaging (magnetic resonance imaging, electron paramagnetic resonance imaging) and radiochemical methods. Typically, the metal salts used in imaging or examining serve as a contrast agent. Therefore in one embodiment the metal complexes or metal salts of compounds of the present invention can be used as contrast agents for example in imaging or examining one or more organs, for example, the gastrointestinal tract. Metals that can serve as contrast agents include gadolinium, iron, manganese, chromium, dysprosium, technetium, scandium, barium, aluminum and holmium, preferably as trications. Radioactive metal salts can be made from isotopes including $^{241}$Am, $^{51}$Cr, $^{60}$Co, $^{57}$Co, $^{58}$Co, $^{64}$Cu, $^{153}$Gd, $^{67}$Ga, $^{198}$Au, $^{113m}$In, $^{111}$In, $^{59}$Fe, $^{55}$Fe, $^{197}$Hg, $^{99m}$Tc, $^{201}$Ti, and $^{169}$Yb, again preferably when the metal is present as a trivalent cation.

In another aspect, the present disclosure provides methods of treating or preventing biofilm formation comprising administering to a subject in need thereof a therapeutically effective amount of a compound or pharmaceutical composition described herein. In certain embodiments, the method of treating or preventing biofilm formation treats, cleans, or disinfects a wound. In certain embodiments, the wound is a chronic wound, acute wound, surgical wound, surgical site, second or third degree burn, stasis ulcer, tropic lesion, decubitus ulcer, severe cut, or abrasion.

In another aspect, the present disclosure provides methods of reducing or preventing biofilm formation comprising contacting object with an effective amount of a compound jor pharmaceutical composition described herein. In certain embodiments, the provided methods inhibit, reduce, or remove biofilms on or in an object. In certain embodiments, the provided method inhibits or removes the biofilm on the surface of the object. In certain embodiments, the surface is a hard, rigid surface. In certain embodiments, the surface is selected from the group consisting of a drainpipe, glaze ceramic, porcelain, glass, metal, wood, chrome, plastic, vinyl, and formica. In certain embodiments, the surface is a soft, flexible surface. In certain embodiments, the surface is selected from the group consisting of shower curtains and liners, upholstery, laundry, and carpeting. In certain embodiments, the surface is a food preparation surface, such as a kitchen counter, cutting board, sink, stove, refrigerator surface, or on a sponge. In certain embodiments, the surface is a bathroom surface such as a toilet, sink, bathtub, shower, or drain. In certain embodiment, the surface is a medical device surface.

In some embodiment, the contacting of the compound or pharmaceutical composition described herein with the object is carried out by wiping, sponging, or soaking, or laundering means.

In some embodiments, the provided methods prevent or remove biofilm as a dentifrice, a mouthwash, a compound for the treatment of dental caries, acne treatment, cleaning and disinfecting contact lenses, and medically implanted devices that are permanent such as an artificial heart valve or hip joint, and those that are not permanent such as indwelling catheters, pacemakers, and surgical pins. In some embodiments, the provided methods prevent or remove biofilm in situations involving bacterial infection of a subject, for example, in a topical dressing for burn patients. An example of such a situation is the infection by *P. aeruginosa* of superficial wounds such as those found in burn patients or in the lung of a subject with cystic fibrosis. In some embodiments, the provided methods control or prevent the development of biofilm in the process of manufacturing integrated circuits, circuit boards, or other electronic or microelectronic devices.

In certain embodiments, the bacterium is contacted with the compound or pharmaceutical composition in vitro. In certain embodiments, the bacterium is contacted with the compound or pharmaceutical composition in vivo. In certain embodiments, the bacterium is subsequently contacted with an antibiotic.

In some embodiments, the compound or pharmaceutical composition is administered with one or more additional pharmaceutical agents (e.g., biocides, e.g., antimicrobials, e.g., antibiotics).

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Design of the Compounds

Figure 2A:
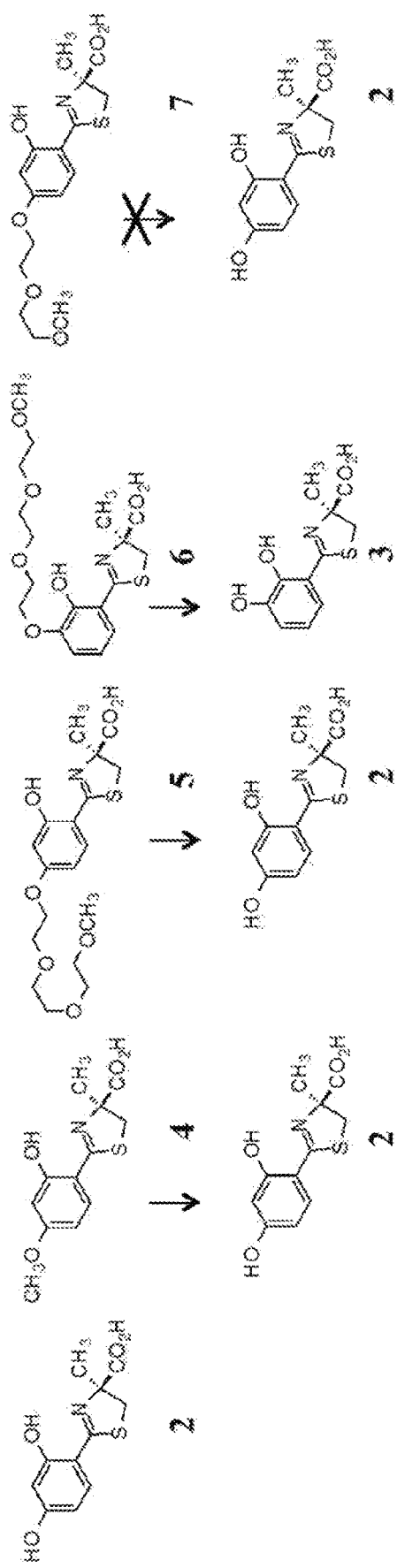
FIGS. 2A-2B show the tissue metabolism/distribution of compounds 2 and 4-7 in rat liver. The rats (n=3 per group) were given the compounds subcutaneously at a dose of 300 mol/kg. The concentration data of the compounds (y-axis) are expressed as nmol/g wet weight of the liver. "Admin. Cmpd.": administered compound.
Figure 2B:
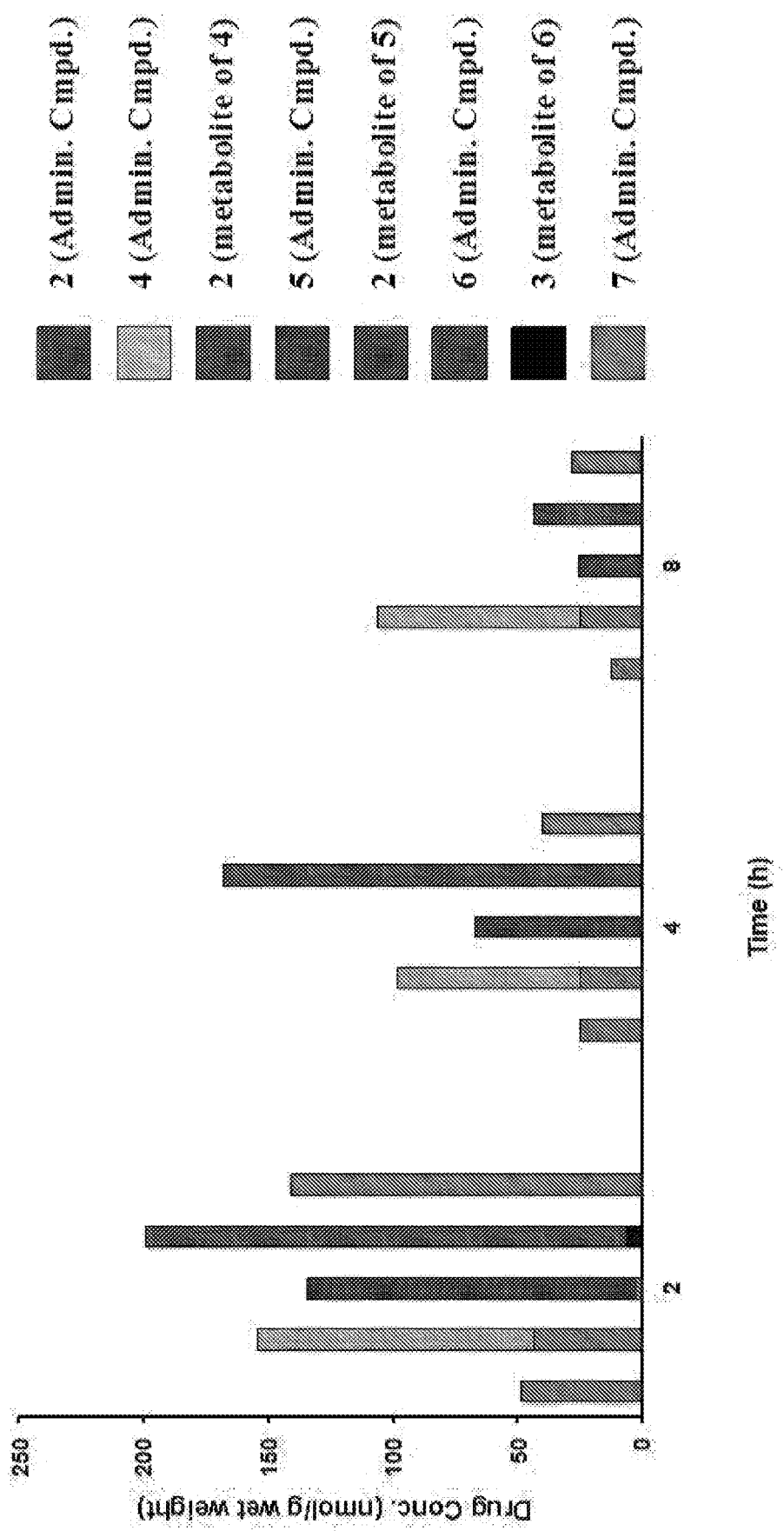

The design concept is to fix a lipophilic fragment to a chelator that will promote its gastrointestinal absorption. Once absorbed, it should be quickly converted to its hydrophilic, nontoxic counterpart. The metabolic profiles of the current chelators will thus set the structural boundary conditions for the future design strategies. Early metabolic studies with (S)-4'-($CH_3O$)-DADFT (4), in which the ligand was given subcutaneously to rats at a dose of 300 mol/kg, revealed that it was demethylated in the liver (Kem et al., Mol. Pharmacol. 65 (2004) 56-67), producing (S)-4'-(HO)-DADFT (2, FIG. 2).[42] At 2 hours post drug exposure, about 30% of the (S)-4'-($CH_3O$)-DADFT (4) is demethylated to 2, and the metabolite remains at fairly high levels through the 8-hour time point (FIG. 2). This observation encouraged a similar assessment of the polyethers (S)-4'-(HO)-DADFT-PE (5) and (S)-3'-(HO)-DADFT-PE (6). If, for example, 5 were converted to 2 to any great extent, this would preclude it being given b.i.d. as renal toxicity might be expected over a long-term exposure. The lack of toxicity of 5 and 6, even when given b.i.d., suggests that cleavage to 2 was either absent or very modest. Accordingly, chelators 5 and 6 were given to rats subcutaneously at a dose of 300 mol/kg. The tissues that were evaluated included the plasma, liver, kidney, heart, and pancreas. The only organ that presented with any 4'- or 3'-polyether cleavage was the liver (FIG. 2). At 2 hours, 2% of 5 was converted to 2, and 2.6% of 6 was metabolized to the corresponding 3. The metabolites were not detected at the 4 and 8 hours time points.[45]

When 7 was given subcutaneously to rats under the same experimental protocol as described for 5 and 6, there was no cleavage to 2 (FIG. 2). However, based on studies with other drugs, e.g., glycodiazine, in which of ether fragments were appended,[64-68] there was a need to determine whether or not the terminal methyl of 7 was being cleaved.

Figure 3:
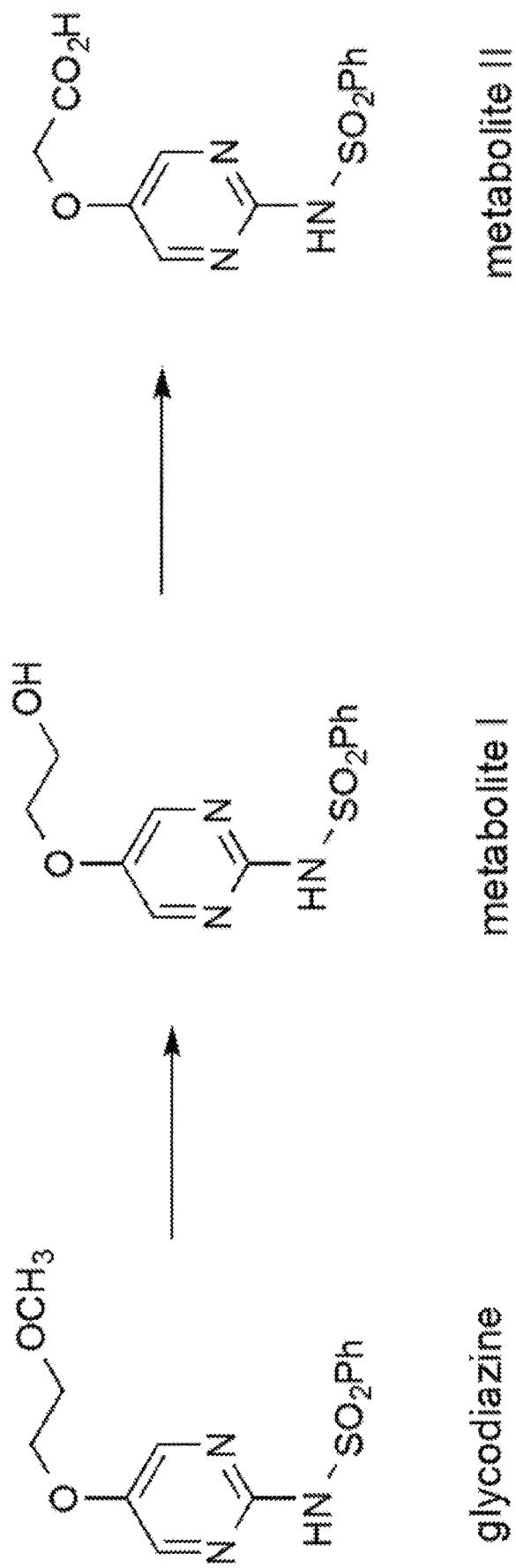
FIG. 3 shows the dealkylation of the methyl ether of glycodiazine, first to an alcohol (metabolite I), which is then oxidized to a carboxylic acid (metabolite II).

With glycodiazine (FIG. 3), the methyl ether was dealkylated to an alcohol (metabolite I) (Platzer et al., *Europ. J. Clin. Pharmacol.* 14 (1978) 293-299), which was oxidized to a carboxylic acid (metabolite II). If this were the case with 7, for example, this would lead first to the corresponding alcohol (S)-4,5-dihydro-2-[2-hydroxy-4-(5-hydroxy-3-oxapentyloxy)phenyl]-4-methyl-4-thiazolecarboxylic acid [(S)-4'-(HO)-DADFT-PEA, 8] and then to the acid (S)-4,5-dihydro-2-[2-hydroxy-4-(4-carboxy-3-oxabutyloxy) phenyl]-4-methyl-4-thiazolecarboxylic acid [(S)-4'-(HO)-DADFT-PEAA, 9], FIG. 4. Both of these metabolic products would be expected to be very hydrophilic. This increase in hydrophilicity, based on previous studies, would further be expected to minimize ligand toxicity.[37,43,45] If indeed such a demethylation-oxidation scenario is occurring with 7, it could support a novel approach to "metabolically programmed" iron chelators, e.g., highly lipophilic, orally absorbable ligands that are quickly converted to hydrophilic, likely nontoxic metabolites.

The two putative metabolites of (S)-4'-(HO)-DADFT-norPE (7), the alcohol (S)-4'-(HO)-DADFT-PEA (8) and the carboxylic acid (S)-4'-(HO)-DADFT-PEAA (9), were assembled. These two synthetic chelators allowed us to develop an analytical high-pressure liquid chromatography (HPLC) method to follow the potential conversion of 7 to its metabolites in the organs of animals treated with the parent chelator 7. Furthermore, it provided an opportunity to evaluate the lipophilicity (log $P_{app}$), and the ICE values of 8 and 9 when the chelators were given to the rats and primates orally and/or subcutaneously.

Preparation of the Compounds

The compounds provided herein can be prepared from readily available starting materials using the following general methods and procedures. Where typical or preferred process conditions (e.g., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Exemplary materials and methods employed in Examples 1 to 2 are shown below. Reagents were purchased from Aldrich Chemical Co. (Milwaukee, Wis.). Fisher Optima grade solvents were routinely used. DMF was dried over 4 Å molecular sieves. Potassium carbonate was flame activated and cooled in a desiccator over Drierite. Reactions were run under a nitrogen atmosphere, and organic extracts were dried with sodium sulfate and filtered. Silica gel 40-63 from SiliCycle, Inc. (Quebec City, Quebec, Canada) was used for column chromatography. Glassware that was presoaked in 3 N HCl for 15 minutes, washed with distilled water and distilled EtOH, and oven-dried was used during the isolation of 8-14. Melting points are uncorrected. Optical rotations were run at 589 nm (sodium D line) and 20° C. on a Perkin-Elmer 341 polarimeter, with c being concentration in grams of compound per 100 mL of solution ($CHCl_3$ not indicated). NMR spectra were obtained at 400 MHz ($^1$H) or 100 MHz ($^{13}$C). Chemical shifts (δ) for $^1$H spectra are given in parts per million downfield from tetramethylsilane for organic solvents ($CDCl_3$ not indicated) or sodium 3-(trimethylsilyl)propionate-2,2,3,3-$d_4$ for $D_2O$. Chemical shifts (δ) for $^{13}$C spectra are given in parts per million referenced to $CH_3OH$ (δ 49.50) in $D_2O$ or to the residual solvent resonance in $CDCl_3$ (δ 77.16) (not indicated) or DMSO-$d_6$ (δ 39.52). The base peaks are reported for the ESI-FTICR mass spectra. Elemental analyses were performed by Atlantic Microlabs (Norcross, Ga.) and were within ±0.4% of the calculated values. The purity of all compounds was confirmed by elemental analysis. Furthermore, the purity of 8-14 was ≥95% by HPLC analysis.

Example 1

Synthesis of Compounds 8 and 9

Assembly of alcohol 8 and the carboxylic acid 9 (Scheme 1) began with alkylation of deferitrin ethyl ester (15) at the 4'-hydroxyl.[52] Specifically, reaction of 15 with 2-(2-chloroethoxy)ethanol (16), $K_2CO_3$ and KI in DMF at 100° C. provided the alcohol ester 17 in 62% yield. Treatment of 17 with 50% NaOH in $CH_3OH$ led to the alcohol 8 in 97% yield. Alkylating 15 with ethyl 2-chloroethoxyacetate (18)[69] under the above conditions gave the diester 19 in 35% yield. Saponification of 19 furnished the diacid 9 as its monosodium salt in 98% yield.

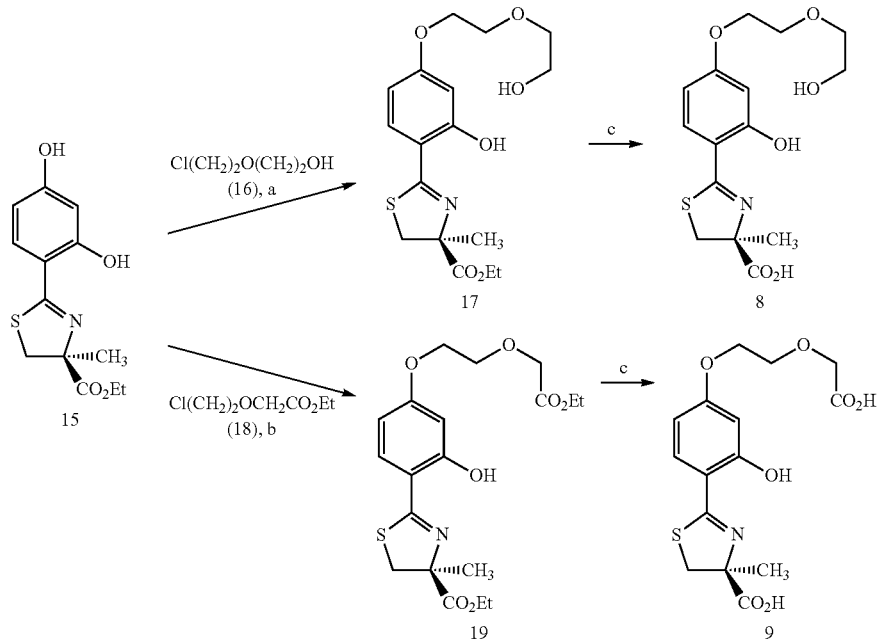 [SMILES: CCOC(=O)[C@@]1(C)CSC(c2ccc(O)cc2O)=N1 ; CCOC(=O)COCCOc1ccc(C2=N[C@@](C)(C(=O)OCC)CS2)c(O)c1 ; CCOC(=O)[C@@]1(C)CSC(c2ccc(OCCOCCO)cc2O)=N1 ; C[C@]1(C(=O)O)CSC(c2ccc(OCCOCC(=O)O)cc2O)=N1 ; C[C@]1(C(=O)O)CSC(c2ccc(OCCOCCO)cc2O)=N1]

Scheme 1. Synthesis of (S)-4,5-dihydro-2-[2-hydroxy-4-(5-hydroxy-3-oxapentyloxy)phenyl]-4-methyl-4-thiazolecarboxylic acid (8) and (S)-4,5-dihydro-2-[2-hydroxy-4-(4-carboxy-3-oxabutyloxy)phenyl]-4-methyl-4-thiazolecarboxylic acid (9)[a]

[a]Reagents and conditions: (a) $K_2CO_3$ (2.0 equiv), KI, DMF, 100° C., 1 d, 62%; (b) $K_2CO_3$ (2.1 equiv), NaI, DMF, 95° C., 22 hours, 35%; (c) 50% NaOH (aq), $CH_3OH$, 97% (8), 98% (9 as its monosodium salt).

Ethyl (5)-4,5-Dihydro-2-[2-hydroxy-4-(5-hydroxy-3-oxapentyloxy)phenyl]-4-methyl-4-thiazolecarboxylate (17). Potassium carbonate (2.76 g, 20.0 mmol) and KI (200 mg, 1.2 mmol) were added to a mixture of 15 (Bergeron et al., J. Med. Chem. 48 (2005) 4120-4137) (2.81 g, 10 mmol) in DMF (100 mL). A solution of 16 (1.24 g, 10 mmol) in DMF (10 mL) was added to the reaction mixture, which was heated at 100° C. for 24 hours. After cooling to room temperature, $H_2O$ (100 mL) was added followed by extraction with EtOAc (2×100 mL). Organic layers were combined, washed with $H_2O$ (100 mL) and 6 M NaCl (100 mL), and solvent was removed in vacuo. Column chromatography using 30% EtOAc/$CH_2Cl_2$ furnished 2.30 g of 17 (62%) as a viscous oil: [α] +48.0° (c 0.15). $^1H$ NMR δ 12.70 (br s, 1H), 7.30 (d, J=8.8 Hz, 1H), 6.50 (d, J=2.4 Hz, 1H), 6.47 (dd, J=8.8, 2.4 Hz, 1H), 4.24 (dq, J=7.6, 1.6 Hz, 2H), 4.15-4.17 (m, 2H), 3.83-3.88 (m, 3H), 3.76-3.79 (m, 2H), 3.66-3.69 (m, 2H), 3.20 (d, J=10.8 Hz, 1H), 1.66 (s, 3H), 1.3 (t, J=7.2 Hz, 3H). $^{13}C$ NMR δ 172.96, 170.92, 162.95, 161.32, 131.87, 110.14, 107.39, 101.51, 83.25, 72.73, 69.54, 67.61, 62.05, 61.89, 39.98, 24.61, 14.23. HRMS m/z calcd for $C_{17}H_{24}NO_6S$, 370.1319 (M+H); found, 370.1323. Anal. Calc'd for $C_{17}H_{23}NO_6S$: C, 55.27; H, 6.28; N, 3.79. Found: C, 54.99; H, 6.24; N, 3.75.

Ethyl (S)-4,5-Dihydro-2-[2-hydroxy-4-[(4-ethoxycarbonyl)-3-oxabutyloxy]-phenyl]-4-methyl-4-thiazolecarboxylate (19). Sodium iodide (0.5527 g, 3.69 mmol) and $K_2CO_3$ (5.1304 g, 37.12 mmol) were added to 15 (5.08 g, 18.1 mmol) and 18[69] (3.31 g, 19.9 mmol) in DMF (46 mL), and the reaction mixture was heated at 95° C. for 22 hours. The mixture was cooled, filtered, washing the solids with acetone (100 mL, 2×50 mL). Solvents were removed in vacuo, and the concentrate was treated with 1:1 0.5 N HCl/6 M NaCl (120 mL) followed by extraction with EtOAc (100 mL, 2×50 mL). Organic layers were combined, washed with 1% $NaHSO_3$ (75 mL), $H_2O$ (75 mL) and 6 M NaCl (55 mL), and solvent was removed by rotary evaporation. Flash column chromatography using 8.4:25:66.5 EtOAc/petroleum ether/$CH_2Cl_2$ gave 2.574 g of 19 (35%) as a yellow oil: [α] +41.0° (c 0.68).

$^1H$ NMR δ 12.70 (s, 1H), 7.29 (d, J=8.6 Hz, 1H), 6.50 (d, J=2.3 Hz, 1H), 6.47 (dd, J=8.8, 2.5 Hz, 1H), 4.17-4.28 (m+s, 8H), 3.92-3.97 (m, 2H), 3.84 (d, J=11.3 Hz, 1H), 3.20 (d, J=11.3 Hz, 1H), 1.66 (s, 3H), 1.298 (t, J=7.2 Hz, 3H), 1.290 (t, J=7.0 Hz, 3H). $^{13}C$ NMR δ 172.96, 170.92, 170.42, 162.88, 161.29, 131.84, 110.13, 107.34, 101.52, 83.25, 69.94, 69.02, 67.71, 62.05, 61.10, 39.97, 24.60, 14.33, 14.22. HRMS m/z calcd for $C_{19}H_{26}NO_7S$, 412.1424 (M+H); found, 412.1440. Anal. Calc'd for $C_{19}H_{25}NO_7S$: C, 55.46; H, 6.12; N, 3.40. Found: C, 55.66; H, 6.21; N, 3.44.

(S)-4,5-Dihydro-2-[2-hydroxy-4-(5-hydroxy-3-oxapentyloxy)phenyl]-4-methyl-4-thiazolecarboxylic Acid (8). A solution of 50% (w/w) NaOH (3.0 mL, 57 mmol) in CH$_3$OH (25 mL) was added slowly to a solution of 17 (2.0 g, 5.4 mmol) in CH$_3$OH (50 mL) at 0° C. The reaction mixture was stirred at room temperature for 16 hours, and the bulk of the solvent was removed under reduced pressure. The residue was dissolved in dilute NaCl (50 mL) and was extracted with Et$_2$O (2×30 mL). The aqueous layer was cooled in ice, acidified with cold 6 N HCl to pH=2, and extracted with EtOAc (8×30 mL). The combined EtOAc layers were concentrated in vacuo to furnish 1.78 g of 8 (97%) as a yellow oil: [α] +25.3° (c 0.88). $^1$H NMR δ 7.9 (br s, 1H), 7.21 (d, J=8.8 Hz, 1H), 6.50 (d, J=2.4 Hz, 1H), 6.47 (dd, J=8.8, 2.4 Hz, 1H), 4.15-4.19 (m, 2H), 3.74-3.92 (m, 5H), 3.65-3.70 (m, 2H), 3.20 (d, J=10.8 Hz, 1H), 1.68 (s, 3H). $^{13}$C NMR δ 176.29, 171.96, 163.02, 161.32, 131.97, 109.79, 107.69, 101.49, 82.68, 72.57, 69.19, 67.56, 61.78, 39.78, 24.61. HRMS m/z calc'd for C$_{15}$H$_{20}$NO$_6$S, 342.1006 (M+H), C$_{15}$H$_{19}$NNaO$_6$S, 364.0825 (M+Na); found, 342.1014, 364.0826. Anal. Calc'd for C$_{15}$H$_{19}$NO$_6$S: C, 52.78; H, 5.61; N, 4.10. Found: C, 52.93; H, 5.83; N, 4.02.

(S)-4,5-Dihydro-2-[2-hydroxy-4-(4-carboxy-3-oxabutyloxy)phenyl]-4-methyl-4-thiazolecarboxylic Acid (9). A solution of 50% (w/w) NaOH (2.88 mL, 55.1 mmol) in CH$_3$OH (30 mL) was added to a mixture of 19 (2.27 g, 5.52 mmol) in CH$_3$OH (62 mL) over 5 min at 0° C. The reaction mixture was stirred at room temperature for 17 hours, and the bulk of the solvent was removed by rotary evaporation. The residue was dissolve in 3 M NaCl (70 mL) and was extracted with Et$_2$O (3×40 mL). The aqueous layer was cooled in ice, treated with cold 2 N HCl (30 mL) and extracted with EtOAc (100 mL, 4×50 mL). Organic layers were combined, washed with 6 M NaCl (80 mL) and concentrated by rotary evaporation. The residue was combined with H$_2$O (43 mL) and 0.1050 N NaOH (52.76 mL, 5.540 mmol), heated on the steam bath and hot suction filtered, washing with H$_2$O (18 mL). The filtrate was diluted with H$_2$O (34 mL) and lyophilized. Solid was dried under high vacuum at 72° C., furnishing 2.05 g of 9 as its sodium salt (98%) as an amorphous yellow solid: [α] +124.3° (c 0.73, H$_2$O). $^1$H NMR (D$_2$O) δ 7.57 (d, J=9.0 Hz, 1H), 6.61 (dd, J=9.0, 2.3 Hz, 1H), 6.52 (d, J=2.3 Hz, 1H), 4.26-4.30 (m, 2H), 4.06 (s, 2H), 3.90-3.95 (m, 3H), 3.53 (d, J=11.7 Hz, 1H), 1.74 (s, 3H). $^{13}$C NMR (D$_2$O) δ 178.94, 177.92, 177.62, 166.41, 162.21, 134.11, 109.15, 107.12, 102.09, 78.41, 70.23, 69.43, 68.45, 39.67, 23.98. HRMS m/z calcd for C$_{15}$H$_{15}$NNaO$_7$S, 376.0472 (M−H), C$_{15}$H$_{16}$NO$_7$S, 354.0653 (M−Na); found, 376.0479, 354.0663. A sample (1.00 g) was recrystallized from EtOH (aq) to give 0.631 g of 9 (Na salt). Anal. Calc'd for C$_{15}$H$_{16}$NNaO$_7$S: C, 47.75; H, 4.27; N, 3.71. Found: C, 47.82; H, 4.43; N, 3.75.

Example 2

Synthesis of Deferitrin Hexamethylene Methyl Ether, (S)-4'-(HO)-DADFT-HXME (10), the Corresponding Alcohol Analogue, (S)-4'-(HO)-DADFT-HXA (11), and its Putative Metabolites 12, 13, and 14

Synthesis of the methyl ether-containing chelator 10 required first generating 6-iodo-1-methoxyhexane (21)[70] from 1,6-diiodohexane (20) in 28% yield by employing 25% NaOCH$_3$ (1 equivalent) in DMF at 63° C. (Scheme 2). Alkylation of deferitrin ethyl ester (15) with 21 using K$_2$CO$_3$ in DMF at 62° C., generated intermediate 22 in 59% yield. Alkaline cleavage of ester 22 provided (S)-4'-(HO)-DADFT-HXME (10) in 97% yield. The synthesis of alcohol 11 involved first alkylating the ester of deferitrin (15) with 6-iodohexyl acetate (23)[71] utilizing K$_2$CO$_3$ in DMF at 70° C., giving diester 24 in 53% yield (Scheme 2). Alkaline hydrolysis of 24 provided the final product 11 in 91% recrystallized yield.

Synthesis of the anticipated metabolites of alcohol 11 (12-14) followed methodology similar to that of polyether acid 9 (Scheme 3). The DADFT ester 15 was selectively alkylated with one of three ethyl ω-bromoalkanoates (25, 26, or 27) in DMF in the presence of K$_2$CO$_3$ and catalytic iodide salt. The corresponding diesters 28, 29, and 30 were obtained in 61, 72, and 66% yields. Once again, these diesters were cleaved in 50% NaOH in CH$_3$OH, giving the required acids 12, 13, and 14 in 99, 90, and 98% yields, respectively.

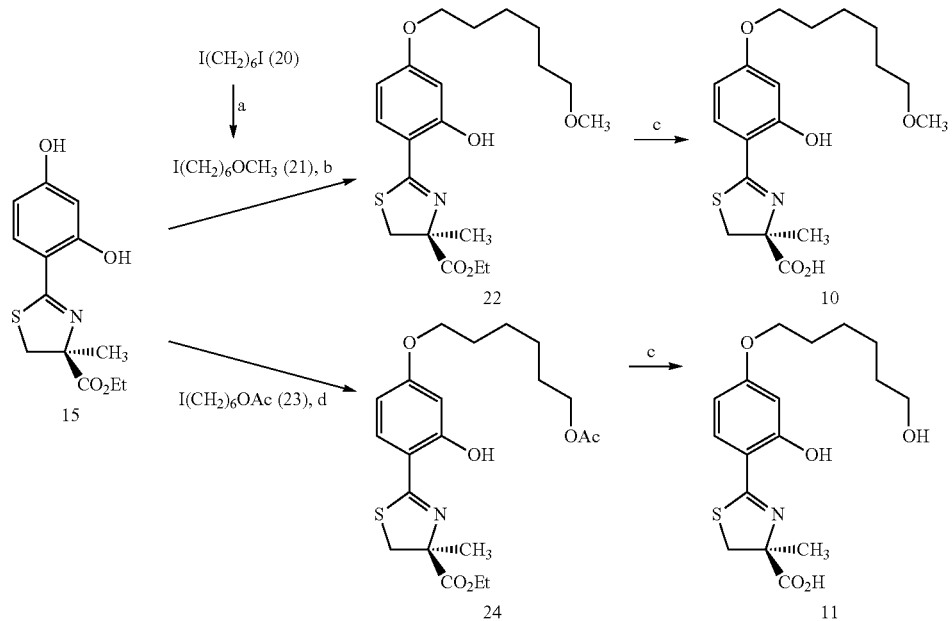 [SMILES: CCOC(=O)[C@@]1(C)CSC(c2ccc(O)cc2O)=N1 ; "I(CH2)6I (20)" ; CCOC(=O)[C@@]1(C)CSC(c2ccc(OCCCCCCOC(C)=O)cc2O)=N1 ; CCOC(=O)[C@@]1(C)CSC(c2ccc(OCCCCCCOC)cc2O)=N1 ; COCCCCCCOc1ccc(C2=N[C@@](C)(C(=O)O)CS2)c(O)c1 ; C[C@]1(C(=O)O)CSC(c2ccc(OCCCCCCO)cc2O)=N1]

Scheme 2. Synthesis of (S)-4,5-dihydro-2-[2-hydroxy-4-(6-methoxyhexyloxy)phenyl]-4-methyl-4-thiazolecarboxylic acid (10) and (S)-4,5-dihydro-2-[2-hydroxy-4-(6-hydroxyhexyloxy)phenyl]-4-methyl-4-thiazolecarboxylic acid (11)[a]

[a]Reagents and conditions: (a) 25% NaOCH$_3$ (1.0 equiv), DMF, 63° C., 17 hours, 28%; (b) K$_2$CO$_3$ (2.0 equiv), DMF, 62° C., 22 hours, 59%; (c) 50% NaOH (aq), CH$_3$OH, 97% (10) (d) K$_2$CO$_3$ (1.9 equiv), DMF, 70° C., 18 hours, 53%; (c) 50% NaOH (aq), CH$_3$OH, 91% (11).

1-Iodo-6-methoxyhexane (21). Sodium methoxide (25 weight %, 5.5 mL, 24.1 mmol) was added by syringe to 20 (4.0 mL, 24.3 mmol) in DMF (10 mL) over 20 minutes. The reaction solution was heated at 63° C. for 17 hours. After cooling to 0° C., the reaction solution was treated with 3:1 cold 0.5 N HCl/6 M NaCl (200 mL) and was extracted with EtOAc (2×150 mL, 50 mL). The organic extracts were washed with 1% NaHSO$_3$ (150 mL), H$_2$O (2×150 mL) and 6 M NaCl (100 mL), and solvent was removed by rotary evaporation. Flash column chromatography using 4% then 6% EtOAc/petroleum ether furnished 1.61 g of 21[70] (28%) as a liquid: $^1$H NMR δ 3.37 (t, J=6.4 Hz, 2H), 3.33 (s, 3H), 3.19 (t, J=7.0 Hz, 2H), 1.83 (quintet, J=7.1 Hz, 2H), 1.54-1.62 (m, 2H), 1.33-1.46 (m, 4H). $^{13}$C NMR δ 72.78, 58.72, 33.58, 30.46, 29.57, 25.26, 7.25. HRMS m/z calc'd for C$_7$H$_{19}$INO, 260.0506 (M+NH$_4$); found, 260.0515. Anal. Calcd for C$_7$H$_{15}$IO: C, 34.73; H, 6.25. Found: C, 34.44; H, 6.19.

Ethyl (S)-4,5-Dihydro-2-[2-hydroxy-4-(6-methoxyhexyloxy)phenyl]-4-methyl-4-thiazolecarboxylate (22). Potassium carbonate (1.81 g, 13.1 mmol) was added to 15 (1.77 g, 6.29 mmol) and 21 (1.56 g, 6.44 mmol) in DMF (32 mL), and the reaction mixture was heated at 62° C. for 22 hours. After cooling in an ice bath, cold 0.5 N HCl (100 mL) was added followed by extraction with EtOAc (120 mL, 2×50 mL). Organic layers were combined and washed with 1% NaHSO$_3$ (100 mL), H$_2$O (3×100 mL) and 6 M NaCl (80 mL), and solvent was removed by rotary evaporation. Flash column chromatography using 10% EtOAc/petroleum ether then 1:3:6 EtOAc/petroleum ether/CH$_2$Cl$_2$ gave 1.47 g of 22 (59%) as a viscous yellow oil: [α] +43.3° (δ 0.72). $^1$H NMR δ 12.68 (s, 1H), 7.28 (d, J=8.6 Hz, 1H), 6.47 (d, J=2.3 Hz, 1H), 6.43 (dd, J=8.8, 2.5 Hz, 1H), 4.18-4.29 (m, 2H), 3.97 (t, J=6.6 Hz, 2H), 3.83 (d, J=11.3 Hz, 1H), 3.38 (t, J=6.4 Hz, 2H), 3.34 (s, 3H), 3.19 (d, J=11.3 Hz, 1H), 1.75-1.83 (m, 2H), 1.65 (s, 3H), 1.56-1.64 (m, 2H), 1.37-1.53 (m, 4H), 1.30 (t, J=7.0 Hz, 3H). $^{13}$C NMR δ 173.02, 170.92, 163.50, 161.34, 131.77, 109.71, 107.40, 101.36, 83.23, 72.86, 68.19, 62.02, 58.70, 39.96, 29.69, 29.14, 26.03, 25.99, 24.61, 14.22. HRMS m/z calcd for C$_{20}$H$_{30}$NO$_5$S, 396.1839 (M+H); found, 396.1858. Anal. Calc'd for C$_{20}$H$_{29}$NO$_5$S: C, 60.74; H, 7.39; N, 3.54. Found: C, 60.59; H, 7.29; N, 3.60.

Ethyl (S)-4,5-Dihydro-2-[2-hydroxy-4-(6-acetoxyhexyloxy)phenyl]-4-methyl-4-thiazolecarboxylate (24). Potassium carbonate (3.42 g, 24.8 mmol) was added to 15 (3.255 g, 11.57 mmol) and 23 [75] (3.44 g, 12.7 mmol) in DMF (60 mL), and the mixture was heated at 70° C. for 21 hours. After cooling to 0° C., cold 0.5 M HCl (150 mL) was added followed by extraction with EtOAc (150 mL, 2×80 mL). Organic layers were combined, washed with 1% NaHSO$_3$ (150 mL), H$_2$O (3×150 mL) and 6 M NaCl (100 mL), and solvent was removed by rotary evaporation. Flash column chromatography using 1:3:6 EtOAc/petroleum ether/CH$_2$Cl$_2$ gave 2.60 g of 24 (53%) as a white solid: mp 58.5-60° C., [α] +40.1° (c 0.98). $^1$H NMR δ 12.69 (s, 1H), 7.29 (d, J=9.0 Hz, 1H), 6.47 (d, J=2.3 Hz, 1H), 6.43 (dd, J=8.8, 2.5 Hz, 1H), 4.20-4.28 (m, 2H), 4.07 (t, J=6.6 Hz, 2H), 3.97 (t, J=6.4 Hz, 2H), 3.84 (d, J=11.3 Hz, 1H), 3.19 (d, J=11.3 Hz, 1H), 2.05 (s, 3H), 1.76-1.84 (m, 2H), 1.62-1.70 (m, 2H), 1.66 (s, 3H), 1.38-1.54 (m, 4H), 1.30 (t, J=7.0 Hz, 3H). $^{13}$C NMR δ 173.01, 171.39, 170.93, 163.45, 161.36, 131.79, 109.76, 107.40, 101.35, 83.23, 68.10, 64.58, 62.03, 39.98, 29.07, 28.66, 25.84, 25.83, 24.62, 21.16, 14.23. HRMS m/z calc'd for C$_{21}$H$_{30}$NO$_6$S, 424.1788 (M+H); found, 424.1798. Anal. Calc'd for C$_{21}$H$_{29}$NO$_6$S: C, 59.56; H, 6.90; N, 3.31. Found: C, 59.71; H, 6.81; N, 3.33.

(S)-4,5-Dihydro-2-[2-hydroxy-4-(6-methoxyhexyloxy)phenyl]-4-methyl-4-thiazolecarboxylic Acid (10). A solution of 50% (w/w) NaOH (1.87 mL, 35.8 mmol) in CH$_3$OH (40 mL) was added over 4 min to a solution of 22 (1.41 g, 3.56 mmol) in CH$_3$OH (80 mL) at 0° C. The reaction mixture was stirred at room temperature for 15 hours, and the bulk of the solvent was removed under reduced pressure. The residue was diluted in 2 M NaCl (120 mL) and was extracted with Et$_2$O (3×50 mL). The aqueous layer was cooled in ice, acidified with cold 2 N HCl (30 mL), and extracted with EtOAc (100 mL, 3×50 mL). The combined EtOAc extracts were washed with 6 M NaCl (60 mL) and concentrated in vacuo to generate 1.275 g of 10 (97%) as a waxy, light tan solid: mp 68-68.5° C., [α] +48.8° (c 0.80, DMF). $^1$H NMR (DMSO-d$_6$) δ 13.17 (s, 1H), 12.74 (s, 1H), 7.31 (d, J=8.6 Hz, 1H), 6.52 (dd, J=2.3, 8.6 Hz, 1H), 6.50 (d, J=2.3 Hz, 1H), 4.00 (t, J=6.6 Hz, 2H), 3.79 (d, J=11.3 Hz, 1H), 3.36 (d, J=11.3 Hz, 1H), 3.30 (t, J=6.4 Hz, 2H), 3.21 (s, 3H), 1.66-1.74 (m, 2H), 1.58 (s, 3H), 1.47-1.54 (m, 2H), 1.29-1.45 (m, 4H). $^{13}$C NMR (DMSO-d$_6$) δ 173.73, 170.03, 162.96, 160.49, 131.57, 108.97, 107.27, 101.13, 82.45, 71.82, 67.80, 57.79, 28.97, 28.47, 25.42, 25.28, 24.11. HRMS m/z calcd for C$_{18}$H$_{26}$NO$_5$S, 368.1526 (M+H); found, 368.1540.

Anal. Calc'd for C$_{18}$H$_{25}$NO$_5$S: C, 58.84; H, 6.86; N, 3.81. Found: C, 58.55; H, 6.81; N, 3.80.

(S)-4,5-Dihydro-2-[2-hydroxy-4-(6-hydroxyhexyloxy)phenyl]-4-methyl-4-thiazole-carboxylic Acid (11). A solution of 50% (w/w) NaOH (3.12 mL, 59.7 mmol) in CH$_3$OH (95 mL) was added to a mixture of 24 (2.53 g, 5.97 mmol) in CH$_3$OH (100 mL) over 32 min at 0° C. The reaction mixture was stirred at room temperature for 1 d, and the bulk of the solvent was removed under reduced pressure. The residue was treated with 2 M NaCl (150 mL) and was extracted with Et$_2$O (3×50 mL). The aqueous layer was cooled in ice, treated with cold 2 N HCl (50 mL) and extracted with EtOAc (2×100 mL, 50 mL). Organic layers were combined, washed with 6 M NaCl (65 mL) and concentrated by rotary evaporation. The residue was recrystallized from EtOAc/hexanes. Solid was collected and dried under high vacuum at 58° C., providing 1.917 g of 11 (91%) as pale yellow crystals: mp 116-116.5° C., [α] +50.1° (c 0.83, DMF). $^1$H NMR (DMSO-d$_6$) δ 13.20 (s, 1H), 12.73 (s, 1H), 7.32 (d, J=9.0 Hz, 1H), 6.52 (dd, J=8.6, 2.3 Hz, 1H), 6.50 (d, J=2.3 Hz, 1H), 4.35 (br s, 1H), 4.00 (t, J=6.4 Hz, 2H), 3.79 (d, J=11.3 Hz, 1H), 3.36-3.42 (m, 2H), 3.36 (d, J=11.3 Hz, 1H), 1.66-1.75 (m, 2H), 1.58 (s, 3H), 1.29-1.48 (m, 6H). $^{13}$C NMR (DMSO-d$_6$) δ 173.76, 170.04, 162.97, 160.50, 131.59, 108.97, 107.28, 101.13, 82.45, 67.85, 60.64, 32.48, 28.56, 25.35, 25.27, 24.12. HRMS m/z calcd for C$_{17}$H$_{24}$NO$_5$S, 354.1370 (M+H); found, 354.1384. Anal. Calc'd for C$_{17}$H$_{23}$NO$_5$S: C, 57.77; H, 6.56; N, 3.96. Found: C, 57.94; H, 6.50; N, 3.93.

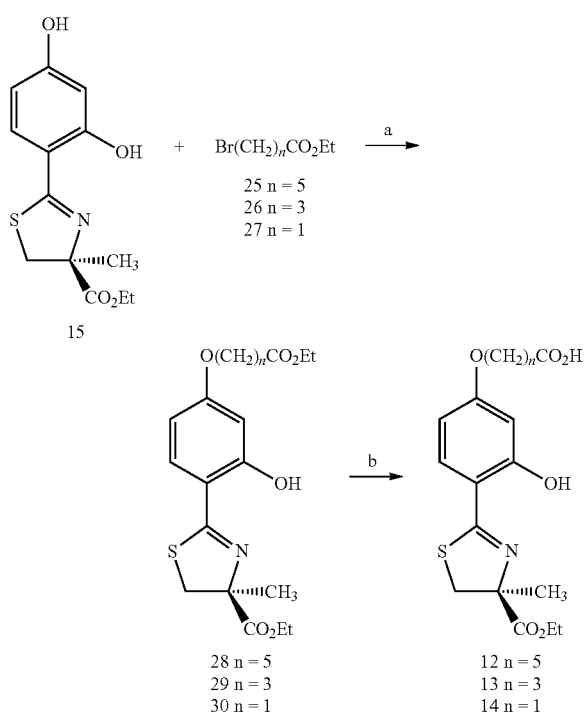

Scheme 3. Synthesis of (S)-4,5-dihydro-2-[2-hydroxy-4-(5-carboxypentyloxy)phenyl]-4-methyl-4-thiazolecarboxylic acid (12), (S)-4,5-dihydro-2-[2-hydroxy-4-(3-carboxypropyloxy)phenyl]-4-methyl-4-thiazolecarboxylic acid (13), and (S)-4,5-dihydro-2-[2-hydroxy-4-(carboxymethoxy)phenyl]-4-methyl-4-thiazolecarboxylic acid (14)[a]

[a]Reagents and conditions: (a) $K_2CO_3$ (1.3 equiv), NaI, DMF, 65° C., 5 d, 61% (28); $K_2CO_3$ (1.3 equiv), NaI, DMF, 100° C., 2 d, 72% (29); $K_2CO_3$ (2.1 equiv), NaI, DMF, 70° C., 20 hours, 66% (30); (b) 50% NaOH (aq), $CH_3OH$, 99% (12), 90% (13), 98% (14).

Ethyl (S)-4,5-Dihydro-2-[2-hydroxy-4-[5-(ethoxycarbonyl)pentyloxy]phenyl]-4-methyl-4-thiazolecarboxylate (28). Potassium carbonate (3.19 g, 23.1 mmol), NaI (0.351 g, 2.34 mmol), and a solution of 25 (4.46 g, 20.0 mmol) in DMF (25 mL) were added to a solution of 15 (5.0 g, 17.8 mmol) in DMF (100 mL). The reaction mixture was heated at 65° C. for 5 days. After cooling to room temperature, the solvent was removed by rotary evaporation. The residue was treated with cold 0.5 M HCl (200 mL) and was extracted with EtOAc (150 mL, 2×50 mL). The organic extracts were washed with 1% $NaHSO_3$ (100 mL), $H_2O$ (100 mL), 6 M NaCl (50 mL), and solvent was removed in vacuo. Column chromatography using 30% EtOAc/petroleum ether furnished 4.586 g of 28 (61%) as an off-white solid: mp 61-62° C., [α] +40.94° (c 0.171). $^1$H NMR δ 12.68 (s, 1H), 7.28 (d, J=8.4 Hz, 1H), 6.47 (d, J=2.4 Hz, 1H), 6.42 (dd, J=8.8, 2.4 Hz, 1H), 4.24 (dq, J=7.2, 2.0 Hz, 2H), 4.13 (q, J=7.2 Hz, 2H), 3.97 (t, J=6.4 Hz, 2H), 3.84 (d, J=11.2 Hz, 1H), 3.19 (d, J=11.2 Hz, 1H), 2.33 (t, J=7.6 Hz, 2H), 1.77-1.84 (m, 2H), 1.67-1.73 (m, 2H), 1.66 (s, 3H), 1.46-1.54 (m, 2H), 1.30 (t, J=7.2 Hz, 3H), 1.26 (t, J=7.2 Hz, 3H). $^{13}$C NMR δ 173.70, 172.96, 170.88, 163.38, 161.31, 131.75, 109.73, 107.32, 101.33, 83.20, 67.93, 61.99, 60.37, 39.93, 34.31, 28.85, 25.68, 24.78, 24.58, 14.36, 14.20. HRMS m/z calcd for $C_{21}H_{30}NO_6S$, 424.1788 (M+H); found, 424.1784. Anal. Calc'd for $C_{21}H_{29}NO_6S$: C, 59.56; H, 6.90; N, 3.31. Found: C, 59.69; H, 6.78; N, 3.24.

Ethyl (S)-4,5-Dihydro-2-[2-hydroxy-4-[3-(ethoxycarbonyl)propyloxy]phenyl]-4-methyl-4-thiazolecarboxylate (29). Potassium carbonate (4.41 g, 32.0 mmol) and NaI (182 mg, 1.2 mmol) were added to a mixture of 15 (6.90 g, 24.5 mmol) and 26 (5.27 g, 27.0 mmol) in DMF (150 mL). The reaction mixture was stirred at room temperature for 6 hours and then heated at 100° C. for 48 hours. After cooling to room temperature, the solvent was removed by rotary evaporation under high vacuum, and the residue was treated with 0.2 M HCl/6 M NaCl (50 mL) followed by extraction with EtOAc (4×30 mL). The organic extracts were washed with 1% $NaHSO_3$ (150 ml), $H_2O$ (150 mL) and 6 M NaCl (150 mL), and solvent was removed in vacuo. Column chromatography using 30% EtOAc/$CH_2Cl_2$ gave 6.94 g of 29 (72%) as a light yellow viscous oil: [α] +44.35° (c 0.372). $^1$H NMR δ 12.65 (s, 1H), 7.28 (d, J=8.4 Hz, 1H), 6.47 (d, J=2.4 Hz, 1H), 6.42 (dd, J=8.8, 2.0 Hz, 1H), 4.24 (dq, J=7.2, 1.6 Hz, 2H), 4.15 (q, J=7.6 Hz, 2H), 4.03 (t, J=6.4 Hz, 2H), 3.84 (d, J=11.2 Hz, 1H), 3.19 (d, J=11.2 Hz, 1H), 2.51 (t, J=7.6 Hz, 2H), 2.11 (quintet, J=6.2 Hz, 2H), 1.66 (s, 3H), 1.30 (t, J=7.6 Hz, 3H), 1.26 (t, J=7.2 Hz, 3H). $^{13}$C NMR δ 173.21, 172.98, 170.90, 163.15, 161.32, 131.81, 109.91, 107.24, 101.44, 83.23, 67.02, 62.02, 60.63, 39.96, 30.84, 24.60, 24.55, 14.35, 14.22. HRMS m/z calcd for $C_{19}H_{26}NO_6S$, 396.1475 (M+H); found, 396.1475. Anal. Calc'd for $C_{19}H_{25}NO_6S$: C, 57.71; H, 6.37; N, 3.54. Found: C, 57.72; H, 6.23; N, 3.52.

Ethyl (S)-4,5-Dihydro-2-[2-hydroxy-4-(ethoxycarbonylmethoxy)phenyl]-4-methyl-4-thiazolecarboxylate (30). Potassium carbonate (5.29 g, 38.3 mmol) and NaI (0.498 g, 3.32 mmol) were added to 15 (5.035 g, 17.90 mmol) in DMF (75 mL). The mixture was stirred for several minutes, 27 (2.2 mL, 19.8 mmol) was introduced, and the contents were heated at 70° C. for 3.5 d. After cooling to 0° C., cold 0.5 M HCl (200 mL) was added followed by extraction with EtOAc (200 mL, 2×100 mL). Organic layers were combined, washed with 1% $NaHSO_3$ (200 mL), $H_2O$ (2×200 mL) and 6 M NaCl (130 mL) and solvent was removed in vacuo. Flash column chromatography using 1% EtOAc/$CH_2Cl_2$ then 6% acetone/$CH_2Cl_2$ generated 4.37 g of 30 (66%) as a viscous yellow oil: [α] +45.1° (c 0.88). $^1$H NMR δ 12.73 (s, 1H), 7.32 (d, J=8.6 Hz, 1H), 6.50 (d, J=2.7 Hz, 1H), 6.47 (dd, J=6.8, 2.5 Hz, 1H), 4.63 (s, 2H), 4.20-4.31 (m, 4H), 3.84 (d, J=11.3 Hz, 1H), 3.20 (d, J=11.3 Hz, 1H), 1.66 (s, 3H), 1.305 (t, J=7.2 Hz, 3H), 1.298 (t, J=7.0 Hz, 3H). $^{13}$C NMR δ 172.89, 170.92, 168.39, 161.91, 161.29, 132.00, 110.74, 107.18, 101.71, 83.28, 65.27, 62.07, 61.68, 40.00, 24.59, 14.28, 14.22. HRMS m/z calcd for $C_{17}H_{22}NO_6S$, 368.1162 (M+H); found, 368.1172. Anal. Calc'd for $C_{17}H_{21}NO_6S$: C, 55.57; H, 5.76; N, 3.81. Found: C, 55.72; H, 5.72; N, 3.82.

(S)-4,5-Dihydro-2-[2-hydroxy-4-(5-carboxypentyloxy)phenyl]-4-methyl-4-thiazolecarboxylic Acid (12). A solution of 50% (w/w) NaOH (5.00 mL, 95.6 mmol) in $CH_3OH$ (50 mL) was added to a mixture of 28 (4.434 g, 10.47 mmol) in $CH_3OH$ (120 mL) over 7 min at 0° C. The reaction mixture was stirred at room temperature for 2 d, and the bulk of the solvent was removed under reduced pressure. The residue was dissolved in 3 M NaCl (110 mL) and was extracted with $Et_2O$ (2×100 mL). The aqueous layer was cooled in ice, treated with cold 2 N HCl (54 mL) and extracted with EtOAc (150 mL, 2×60 mL). Organic layers were combined, washed with 6 M NaCl (100 mL), and concentrated by rotary evaporation. The residue was dried under high vacuum at 57° C. for 16 hours to afford 3.80 g of 12 (99%) as light colored crystals: mp 153.5-155° C., [α] +47.5° (c 0.76, DMF). $^1$H NMR (DMSO-$d_6$) δ 12.72 (s, 2H), 7.31 (d, J=8.6 Hz, 1H), 6.52 (dd, J=8.6, 2.3 Hz, 1H), 6.49 (d, J=2.3 Hz, 1H), 4.00 (t, J=6.4 Hz, 2H), 3.79 (d, J=11.3 Hz, 1H), 3.36 (d, J=11.3 Hz, 1H), 2.23 (t, J=7.2 Hz, 2H), 1.66-1.75 (m, 2H), 1.58 (s, 3H), 1.51-1.60 (m, 2H), 1.36-1.45 (m, 2H). $^{13}$C NMR (DMSO-$d_6$) δ 174.46, 173.76, 170.05, 162.96, 160.50, 131.60, 108.98, 107.29, 101.16, 82.46, 67.76, 33.61, 28.26, 25.08, 24.25, 24.12. HRMS m/z calcd for $C_{17}H_{22}NO_6S$, 368.1162 (M+H); found, 368.1169. Anal. Calc'd for $C_{17}H_{21}NO_6S$: C, 55.57; H, 5.76; N, 3.81. Found: C, 55.58; H, 5.79; N, 3.78.

(S)-4,5-Dihydro-2-[2-hydroxy-4-(3-carboxypropyloxy) phenyl]-4-methyl-4-thiazolecarboxylic Acid (13). A solution of 50% (w/w) NaOH (6.34 mL, 0.121 mol) in $CH_3OH$ (100 mL) was added dropwise to a solution of 29 (6.56 g, 16.6 mmol) in $CH_3OH$ (50 mL) at 0° C. The reaction mixture was stirred at room temperature for 36 hours, and the bulk of the solvent was removed under reduced pressure. The residue was dissolved in dilute NaCl (150 mL) and was washed with $Et_2O$ (2×100 mL). The aqueous layer was cooled at 0° C., acidified with 6 N HCl to pH=2. Solid was filtered and washed with cold water. Crystallization in hot $CH_3OH$ and EtOAc afforded 5.06 g of 13 (90%) as a white solid: mp 202-204° C., [α] +22.1° (c 0.086, $CH_3OH$). $^1$H NMR (DMSO-$d_6$) δ 7.32 (d, J=8.4 Hz, 1H), 6.53 (dd, J=8.4, 2.0 Hz, 1H), 6.50 (d, J=2.4 Hz, 1H), 4.03 (t, J=6.4 Hz, 2H), 3.79 (d, J=11.2 Hz, 1H), 3.35 (d, J=11.2 Hz, 1H), 2.38 (t, J=7.2 Hz, 2H), 1.93 (quintet, J=7.2 Hz, 2H), 1.57 (s, 3H). $^{13}$C NMR (DMSO-$d_6$) δ 177.42, 177.11, 173.34, 166.13, 163.85, 135.00, 112.48, 110.60, 104.58, 85.86, 70.38, 33.42, 27.51, 27.43. HRMS m/z calcd for $C_{15}H_{18}NO_6S$, 340.0849 (M+H); found, 340.0849. Anal. Calcd for $C_{15}H_{17}NO_6S$: C, 53.09; H, 5.05; N, 4.13. Found: C, 52.81; H, 5.17; N, 4.09.

(S)-4,5-Dihydro-2-[2-hydroxy-4-(carboxymethoxy)phenyl]-4-methyl-4-thiazole-carboxylic Acid (14). A solution of 50% (w/w) NaOH (5.60 mL, 0.107 mol) in $CH_3OH$ (75 mL) was added to a solution of 30 (4.32 g, 11.76 mmol) in $CH_3OH$ (120 mL) over 10 min at 0° C. The reaction mixture was stirred at room temperature for 2 d, and the bulk of the solvent was removed under reduced pressure. The residue was dissolved in $H_2O$ (120 mL) and was extracted with $Et_2O$ (2×100 mL). The aqueous layer was cooled in ice, treated with 2 N HCl (60 mL) and extracted with EtOAc (150 mL, 2×100 mL). Organic layers were combined, washed with 6 M NaCl (100 mL) and concentrated by rotary evaporation. The residue was dried under high vacuum to afford 3.589 g of 14 (98%) as a pale yellow solid: mp 206-206.5° C. (dec), [α] +56.3° (c 0.76, DMF). $^1$H NMR (DMSO-$d_6$) δ 13.14 (s, 2H), 12.75 (s, 1H), 7.34 (d, J=8.6 Hz, 1H), 6.53 (dd, J=8.6, 2.3 Hz, 1H), 6.47 (d, J=2.3 Hz, 1H), 4.75 (s, 2H), 3.79 (d, J=11.3 Hz, 1H), 3.37 (d, J=11.3 Hz, 1H), 1.58 (s, 3H). $^{13}$C NMR (DMSO-$d_6$) δ 173.71, 170.04, 169.72, 161.94, 160.33, 131.62, 109.52, 107.17, 101.46, 82.47, 64.57, 39.34, 24.09. HRMS m/z calcd for $C_{13}H_{14}NO_6S$, 312.0536 (M+H); found, 312.0546. Anal. Calcd for $C_{13}H_{13}NO_6S$: C, 50.16; H, 4.21; N, 4.50. Found: C, 50.06; H, 4.38; N, 4.41.

Biological Assays of the Compounds

Exemplary materials and methods employed in Examples 3 to 10 are shown below.

Materials. Male Cebus apella monkeys were obtained from World Wide Primates (Miami, Fla.). Male Sprague-Dawley rats were procured from Harlan Sprague-Dawley (Indianapolis, Ind.). Ultra-pure salts were obtained from Johnson Matthey Electronics (Royston, UK). All hematological and biochemical studies were performed by Antech Diagnostics (Tampa, Fla.). Histopathological analysis was carried out by Florida Vet Path (Bushnell, Fla.). Atomic absorption (AA) measurements were made on a Perkin-Elmer model 5100 PC (Norwalk, Conn.).

Biological Methods. All animal experimental treatment protocols were reviewed and approved by the University of Florida's Institutional Animal Care and Use Committee.

Cannulation of Bile Duct in Non Iron-Overloaded Rats. The cannulation has been described previously.[38,40] Bile samples were collected from male Sprague-Dawley rats (400-450 g) at 3 hours intervals for up to 48 hours. The urine sample(s) was taken at 24 hours intervals. Sample collection and handling are as previously described.[38,40]

Iron Loading of Cebus apella Monkeys. The monkeys (3.5-6.5 kg) were iron overloaded with intravenous iron dextran as specified in earlier publications to provide about 500 mg of iron per kg of body weight; the serum transferrin iron saturation rose to between 70 and 80%.[38,40] At least 20 half-lives, 60 days, elapsed before any of the animals were used in experiments evaluating iron-chelating agents.

Primate Fecal and Urine Samples. Fecal and urine samples were collected at 24 hours intervals and processed as described previously[38,40,74] Briefly, the collections began 4 days prior to the administration of the test drug and continued for an additional 5 days after the drug was given. Iron concentrations were determined by flame absorption spectroscopy as presented in other publications.[38,40]

Drug Preparation and Administration. In the iron clearing experiments, the rats were given 8-14 orally at a dose of 300 μmol/kg. Ligand 9 and 12-14 were also given subcutaneously at the same dose. The primates were given 8-9 and 11-14 orally at a dose of 75 μmol/kg. Ligand 9 and 12-14 were also given subcutaneously at the same dose. The chelators were administered as their monosodium salts (prepared by the addition of 1 equiv of NaOH to a suspension of the free acid in distilled water).

Calculation of Chelator Iron Clearing Efficiency (ICE). The term "ICE" is used as a measure of the amount of iron excretion induced by a chelator. The ICE, expressed as a percent, is calculated as (ligand-induced iron excretion/theoretical iron excretion)×100. To illustrate, the theoretical iron excretion after administration of 1 mmol of DFO, a hexadentate chelator that forms a 1:1 complex with Fe(III), is 1 milli-g-atom of iron. The theoretical iron outputs of the chelators were generated on the basis of a 2:1 ligand:iron complex. The efficiencies in the rats and monkeys were calculated as set forth elsewhere.[37] Data are presented as the mean±the standard error of the mean; p-values were generated via a one-tailed Student's t-test in which the inequality of variances was assumed, and a p-value of <0.05 was considered significant. The p-values for the monkeys that were given 9 and 12-14 orally and subcutaneously were generated via a one-tailed, paired Student's t-test; a p-value of <0.05 was considered significant.

Collection of Chelator Tissue Distribution Samples from Rodents. Male Sprague-Dawley rats (250-350 g) were given a single subcutaneously injection of the monosodium salts of 8 and 11 prepared as described above at a dose of 300 mol/kg. At times 0.5, 1, 2, 4 and 8 hours after dosing (n=3 rats per time point), the animals were euthanized by exposure to $CO_2$ gas. Blood was obtained via cardiac puncture into vacutainers containing sodium citrate. The blood was centrifuged, and the plasma was separated for analysis. The liver, kidney, heart, and pancreas were removed from the animals and frozen.

Tissue Analytical Methods. Tissue samples of animals treated with 8 were prepared for HPLC analysis by homogenizing them in $H_2O$ at a ratio of 1:1 (w/v). Then, as a rinse, $CH_3OH$ at a ratio of 1:3 (w/v) was added, and the mixture was stored at −20° C. for 30 min. This homogenate was centrifuged. The supernatant was diluted with $H_2O$, vortexed, and filtered with a 0.2 μm membrane. Analytical separation was performed on a Supelco Discovery RP Amide C16 HPLC system with UV detection at 310 nm as described previously.[44,75] Mobile phase and chromatographic conditions were as follows: solvent A, 5% $CH_3CN$/95% buffer (25 mM $KH_2PO_4$+2.5 mM 1-octanesulfonic acid, pH 3.0); solvent B, 60% $CH_3CN$/40% buffer.

Tissue samples of animals treated with 11 were prepared for HPLC analysis by homogenizing them in 0.5 N $HClO_4$ at a ratio of 1:3 (w/v). Then, as a rinse, $CH_3OH$ at a ratio of 1:3 (w/v) was added, and the mixture was stored at −20° C. for 30 min. This homogenate was centrifuged. The supernatant was diluted with 95% buffer (25 mM $KH_2PO_4$, pH 3.0)/5% $CH_3CN$, vortexed, and filtered with a 0.2 μm membrane. Analytical separation was performed on a Supelco Ascentis Express RP-Amide HPLC system with UV detection at 310 nm as described previously [47,80]. Mobile phase and chromatographic conditions were as for 8.

Ligand concentrations were calculated from the peak area fitted to calibration curves by nonweighted least-squares linear regression with Shimadzu Class-VP 7.4 software. The method had a detection limit of 0.25 μm and was reproducible and linear over a range of 1-1000 μn. Tissue distribution data are presented as the mean; p-values were generated via a one-tailed student's t-test, in which the inequality of variances was assumed; a p-value of <0.05 was considered significant.

Toxicity Assessment of (S)-4'-(HO)-DADFT-HXA (11) in Rats. A 10-day toxicity trial on ligand 11 was performed in rodents. Male Sprague-Dawley rats (n=5, 375-400 g) were given the drug, administered as its monosodium salt, orally once daily for 10 days at a dose of 384 μmol/kg/day. Note that this dose is equivalent to 100 mg/kg/day of DFT (1) as its sodium salt. The rats were housed in individual metabolic cages and were weighed each day. A baseline (day 0) urine sample was collected and assessed for its Kim-1 content (Bergeron et al., *J. Med. Chem.* 57 (2014) 9259-9291; Bergeron et al., *Biometals* 24 (2011) 239-258); each animal served as its own control. Chilled urine was collected from the metabolic cages at 24-hour intervals as previously described (Bergeron et al., *Biometals* 24 (2011) 239-258) to allow for the determination of Kim-1 levels. The rats were fasted overnight and were given the chelator first thing in the morning. The rodents were fed ~3 hours post-drug and had access to food for ~5 hours before being fasted overnight. The animals were euthanized one day post drug (day 11). Blood was collected for the performance of a routine CBC and serum chemistries (Bergeron et al., *Blood* 79 (1992) 1882-1890). Extensive tissues (Bergeron et al., *J. Med. Chem.* 42 (1999) 2432-2440) were collected and submitted to an outside laboratory for histopathological analysis. Additional age-matched rats served as untreated controls for the CBC and serum chemistries and histopathology. No urine was collected from these animals. The studies were performed on rats with normal iron stores.

Example 3

Tissue Distribution/Metabolism of (S)-4'-(HO)-DADFT-norPE (7)

As described above, when 7 was given subcutaneously to rats at a dose of 300 mol/kg, there was no cleavage to 2 (FIG. 2). When the tissues were subjected to further analysis via HPLC for the presence of 8 or 9, cleavage of the terminal methyl of 7 to the corresponding alcohol 8 did occur (FIG. 5). However, carboxylic acid 9 was not detected, probably because the extent of the metabolism of the parent 7 to 8 was so minor. In order to verify that conversion of the alcohol 8 to the acid 9 could occur efficiently, rodents were given synthetic alcohol 8 subcutaneously at a dose of 300 μmol/kg. The rats were euthanized 0.5, 1, 2, 4, and 8 hours post drug. The animals' plasma, liver, kidney, heart and pancreas were removed and assessed for the presence of 8 and its putative metabolite 9. The extent and rapidity of oxidation of 8 to 9 that unfolded was surprising (FIG. 5). In the plasma at 0.5 hour post drug, nearly 60% of 8 had been converted to 9. At 2 hour post dosing, 88% of the drug is in the form of the metabolite. Neither the parent 8 nor the metabolite 9 was found at the 8 hour time point. A similar story unfolds in the liver (FIG. 5). At 0.5 hour post drug, only 53% of the drug (parent+metabolite) is in the form of the parent 8. At 1 hour, the metabolite 9 comprises 59% of the total. The parent vs metabolite ratio is similar at the 2 and 4 hour time points. At 8 hours, very little parent alcohol 8 and no metabolite 9 remains. The kidney, heart and pancreas also demonstrated a similar and significant conversion of 8 to 9 (FIG. 5).

Example 4

Chelator-Induced Iron Clearance of 2 and 7-9 in Non-iron-Overloaded, Bile Duct-Cannulated Rodents The ICE values for compounds 2 and 7 (Table 2) are historical and included for comparative purposes. The chelators were given to the rats orally at a dose of 300 μmol/kg; 9 was also given subcutaneously at the same dose. Compound 2 (log $P_{app}$=−1.05) was the least effective ligand, with an ICE of 1.1±0.8%.[50] Analogue 7 (log $P_{app}$=−0.89) was the most effective, with an ICE of 26.7±4.7%.[59] Ligands 8 (log $P_{app}$=−0.53) and 9 (log $P_{app}$=−1.63), the two putative metabolites of 7, were significantly less active than the parent drug 7 when given orally. The ICE of 8 was 15.4±5.6% (p<0.02), while the ICE of 9 was and 6.2±1.7% (p<0.005). As ligand 9 is very hydrophilic (log $P_{app}$=−1.63) the lack of activity on orally administration was likely due to its poor oral absorption. Indeed, when 9 was given to the rats subcutaneously at a dose of 300 mol/kg, its ICE, 11.3±3.4%, was nearly twice that when the drug was dosed orally (p<0.05).

TABLE 1

Iron Clearing Efficiency of Iron Chelators given to Rats and *Cebus apella* Primates, and the Log $P_{app}$ of the Compounds

| Compound | Route | [a]Log $P_{app}$ | [b]Rodent ICE (%) | [d]Primate ICE (%) |
|---|---|---|---|---|
| Desferrioxamine (DFO) | sc | <−3.2 | 2.5 ± 0.7 [74/26] | 5.5 ± 0.9 [45/55] |

TABLE 1-continued
Iron Clearing Efficiency of Iron Chelators given to Rats and *Cebus apella* Primates, and the Log $P_{app}$ of the Compounds
| Compound | Route | [a]Log $P_{app}$ | [b]Rodent ICE (%) | [d]Primate ICE (%) |
|---|---|---|---|---|
| 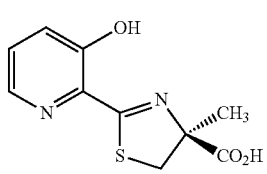 [SMILES: C[C@]1(C(=O)O)CSC(c2ncccc2O)=N1] (S)-Desferrithiocin (1) | po | −1.77 | 5.5 ± 3.2 [93/7] | 16.1 ± 8.5 [78/22] |
| 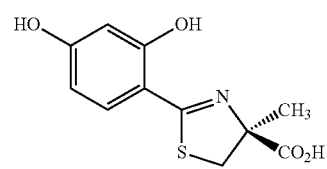 [SMILES: C[C@]1(C(=O)O)CSC(c2ccc(O)cc2O)=N1] (S)-4'-(HO)-DADFT (2) | po | −1.05 | 1.1 ± 0.8 [100/0] | 16.8 ± 7.2 [88/12] |
| 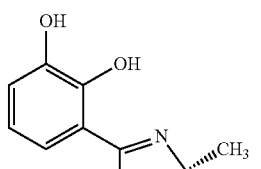 (S)-3'-(HO)-DADFT (3) | po | −1.17 | 4.6 ± 0.9 [98/2] | 23.1 ± 5.9 [83/17] |
| 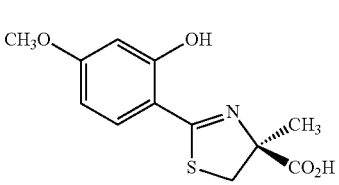 (S)-4'-($CH_3O$)-DADFT (4) | po | −0.70 | 6.6 ± 2.8 [98/2] | 24.4 ± 10.8 [91/9] |
| 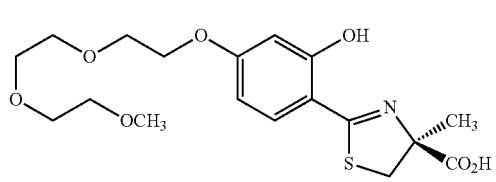 [SMILES: COCCOCCOCCOc1ccc(C2=N[C@@](C)(C(=O)O)CS2)c(O)c1] (S)-4'-(HO)-DADFT-PE (5) | po | −1.10 | 5.5 ± 1.9 [90/10] | 25.4 ± 7.4 [96/4] |
| 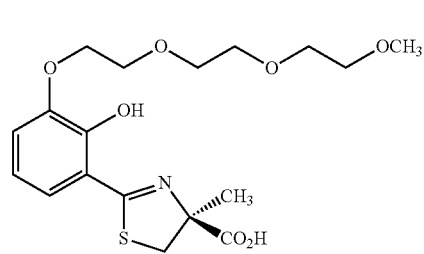 [SMILES: COCCOCCOCCOc1cccc(C2=N[C@@](C)(C(=O)O)CS2)c1O] | po | −1.22 | 10.6 ± 4.4[c] [95/5] | 23.0 ± 4.1 [95/5] |

TABLE 1-continued

Iron Clearing Efficiency of Iron Chelators given to Rats and *Cebus apella* Primates, and the Log $P_{app}$ of the Compounds

| Compound | Route | [a]Log $P_{app}$ | [b]Rodent ICE (%) | [d]Primate ICE (%) |
|---|---|---|---|---|
| (S)-3'-(HO)-DADFT-PE (6) | | | | |
| (S)-4'-(HO)-DADFT-norPE (7) [structure shown] | po | −0.89 | 26.7 ± 4.7[c] [97/3] | 26.3 ± 9.9[e] [93/7] 28.7 ± 12.4[f] [83/17] |

[a]Data are expressed as the log of the fraction of the chelator seen in the octanol layer (log $P_{app}$); measurements were done in TRIS buffer, pH 7.4, using a "shake flask" direct method.
[b]In the rodents n = 3 (7), 4 (3-6), 5 (1), 6 (DFO) or 8 (2). The drugs were given orally (po) or subcutaneously (sc) as indicated in the table at a dose of 150 (Desferal and 1) or 300 μmol/kg (2-7) The drugs were solubilized in 40% Cremophor RH-40/water (DFO and 1), distilled water (5), administered in capsules (7), or were given as their monosodium salts, prepared by the addition of 1 equiv of NaOH to a suspension of the free acid in distilled water (2-4, 6). The efficiency of each compound was calculated by subtracting the iron excretion of control animals from the iron excretion of the treated animals. The number was then divided by the theoretical output; the result is expressed as a percent.
[c]ICE is based on a 48 hour sample collection period. The relative percentages of the iron excreted in the bile and urine are in brackets.
[d]In the primates n = 3 (6), 4 (1, 3-5, 7 in capsules[d]), 5 (DFO), or 7 (2, 7 as its monosodium salt[e]).
The chelators were given orally or subcutaneously at a dose of 75 (7) or 150 μmol/kg (DFO, 1-6). The ligands were solubilized in 40% Cremophor RH-40/water (1, 3, 4), distilled water (DFO, 5), administered in capsules (7[d]), or were given as their monosodium salts, prepared by the addition of 1 equiv of NaOH to a suspension of the free acid in distilled water (2, 6, 7[f]). The ICE was calculated by averaging the iron output for 4 days before the drug, subtracting these numbers from the 2-day iron clearance after the administration of the drug, and then dividing by the theoretical output; the result is expressed as a percent. The relative percentages of the iron excreted in the feces and urine are in brackets.

TABLE 2

Iron Clearing Efficiency of Iron Chelators given to Rats and *Cebus apella* Primates, and the Log $P_{app}$ of the Compounds

| Compound | Log $P_{app}$ | [b]Rat ICE (%) [bile/urine] | Rat n = | [d]Cebus ICE (%) [bile/urine] | Primate n = | [g]Performance Ratio (PR) |
|---|---|---|---|---|---|---|
| [structure] 2 | −1.05 | 1.1 ± 0.8 [100/0] | 8 | 16.8 ± 7.2 [88/12] | 7 | 15.3 |
| [structure] 7 | −0.89 | 26.7 ± 4.7[c] [97/3] | 3 | 26.3 ± 9.9[e] [93/7] 28.7 ± 12.4[f] [83/17] | 4 6 | 1.0 1.1 |

TABLE 2-continued
Iron Clearing Efficiency of Iron Chelators given to Rats and *Cebus apella* Primates, and the Log $P_{app}$ of the Compounds
| Compound | Log $P_{app}$ | [b]Rat ICE (%) [bile/urine] | Rat n = | [d]Cebus ICE (%) [bile/urine] | Primate n = | [g]Performance Ratio (PR) |
|---|---|---|---|---|---|---|
| 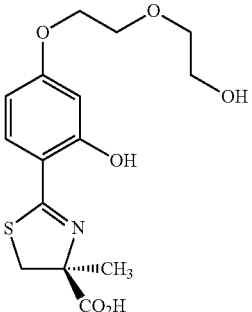 8 | −0.53 | 15.4 ± 5.6 [98/2] | 8 | 9.8 ± 3.4 [54/46] | 4 | 0.6 |
| 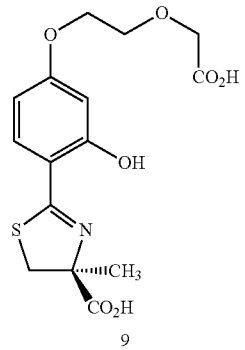 9 | −1.63 | 6.2 ± 1.7 (po) [100/0] 11.3 ± 3.4 (sc) [99/1] | 3 3 | 1.7 ± 1.4 (po) [51/49] 17.4 ± 9.7 (sc) [84/16] | 4 4 | 0.3 1.5 |
| 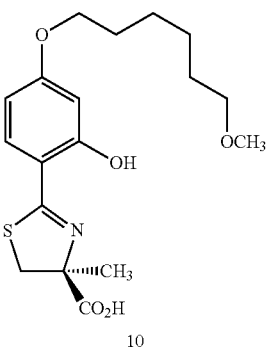 10 | 0.95 | 15.8 ± 3.7 (po) [99/1] | 4 | Toxic in Rats | | |
| 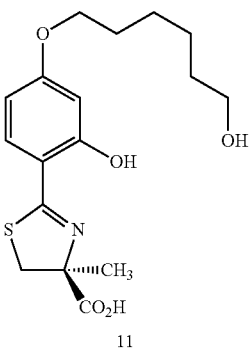 11 | 0.21 | 9.9 ± 0.8 (po) [96/4] | 4 | 21.9 ± 3.6 (po) [90/10] | 3 | 2.2 |

TABLE 2-continued

Iron Clearing Efficiency of Iron Chelators given to Rats and *Cebus apella* Primates, and the Log $P_{app}$ of the Compounds

| Compound | Log $P_{app}$ | [b]Rat ICE (%) [bile/urine] | Rat n = | [d]Cebus ICE (%) [bile/urine] | Primate n = | [g]Performance Ratio (PR) |
|---|---|---|---|---|---|---|
| 12 (structure) | −1.90 | 8.8 ± 1.8 (po) [94/6]<br>6.5 ± 1.5 (sc) [96/4] | 5<br>4 | 10.6 ± 4.0 (po) [82/18]<br>18.8 ± 8.7 (sc) [69/31] | 4<br>4 | 1.2<br>4.4 |
| 13 (structure) | −2.21 | 3.7 ± 1.7 (po) [89/11]<br>4.3 ± 1.1 (sc) [95/5] | 5<br>4 | 5.4 ± 1.5 (po) [97/3]<br>18.1 ± 7.5 (sc) [78/22] | 4<br>4 | 1.5<br>4.2 |
| 14 (structure) | −1.98 | 2.6 ± 1.6 (po) [89/11]<br>6.0 ± 1.9 (sc) [94/6] | 3<br>3 | 3.0 ± 2.7 (po) [60/40]<br>15.9 ± 4.3 (sc) [53/47] | 4<br>4 | 1.2<br>2.7 |

[a]Data are expressed as the log of the fraction of the chelator seen in the octanol layer (log $P_{app}$); measurements were done in TRIS buffer, pH 7.4, using a "shake flask" direct method.
[b]In the rodents the drugs were given orally (po) or subcutaneously (sc) at a dose of 300 μmol/kg. The drugs were administered in capsules (7), or were given as their monosodium salts, prepared by the addition of 1 equiv of NaOH to a suspension of the free acid in distilled water (2, 8-14). The efficiency of each compound was calculated by subtracting the iron excretion of control animals from the iron excretion of the treated animals. The number was then divided by the theoretical output; the result is expressed as a percent.
[c]ICE is based on a 48 hour sample collection period. The relative percentages of the iron excreted in the bile and urine are in brackets.
[d]In the primates the chelators were given orally or subcutaneously at a dose of 75 μmol/kg (7-9, 11-14) or 150 μmol/kg (2). The drugs were administered in capsules (2[e]), or were given as their monosodium salts, prepared by the addition of 1 equiv of NaOH to a suspension of the free acid in distilled water (2[f]). The efficiency was calculated by averaging the iron output for 4 days before the drug, subtracting these numbers from the 2-day iron clearance after the administration of the drug, and then dividing by the theoretical output; the result is expressed as a percent. The relative percentages of the iron excreted in the feces and urine are in brackets.
[g]Performance ratio (PR) is defined as the mean $ICE_{primates}/ICE_{rodents}$.

Example 5

Chelator-Induced Iron Clearance of 2 and 7-9 in Iron-Overloaded Primates

The primate iron clearance data are provided in Table 2. The ICE values for compounds 2 and 7 are historical and included for comparative purposes. The chelators were given to the monkeys orally at a dose of 75 (7-9) or 150 μmol/kg (2); 9 was also given to the primates subcutaneously at a dose of 75 μmol/kg. The ICE of ligand 2 was 16.8±7.2%.[50] As with the rats, compound 7 was the most effective iron decorporation agent, with an ICE of 26.3±9.9% when it was given orally in capsules, and an ICE of 28.7±12.4% when it was administered orally as its monosodium salt.[59] Although 8, the putative metabolite of 7, is more lipophilic than 7, log $P_{app}$=−0.53 vs −0.89, its ICE was lower, 9.8±3.4% (p<0.003, Table 2). The ICE of 9 given orally was even lower, only 1.7±1.4%. When 9 was administered subcutaneously to the same group of monkeys that had been given the drug orally, the ICE increased by more than 10-fold, to 17.4±9.7% (p<0.03). This is in keeping with the idea that highly charged ligands like 9 (log $P_{app}$=−1.63) do not make it across the intestinal mucosa, but hydrophilic metabolic precursors do.

Example 6

Metabolically Programmed Iron Chelators

Figure 4:
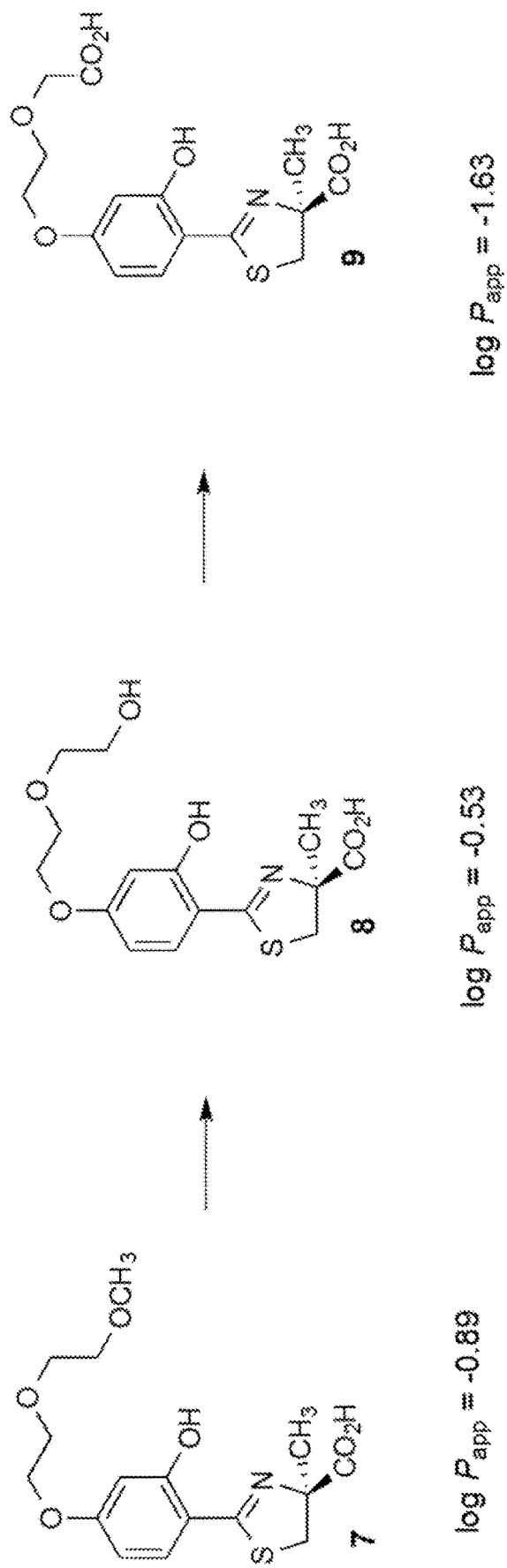
FIG. 4 shows the a putative metabolism of compound 7 into compounds 8 and 9, and the lipophilicity (log $P_{app}$) of compounds 7 to 9.
Figure 5A:
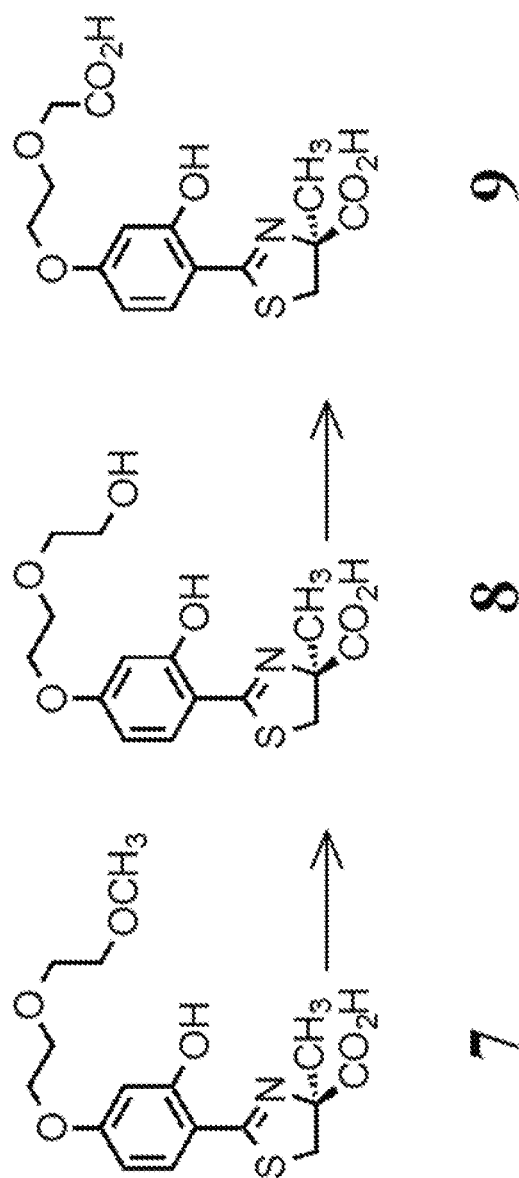
FIG. 5A shows the tissue metabolism/distribution of compounds 7 and 8 in rat plasma, liver, kidney, heart, and pancreas.
Figure 5B:
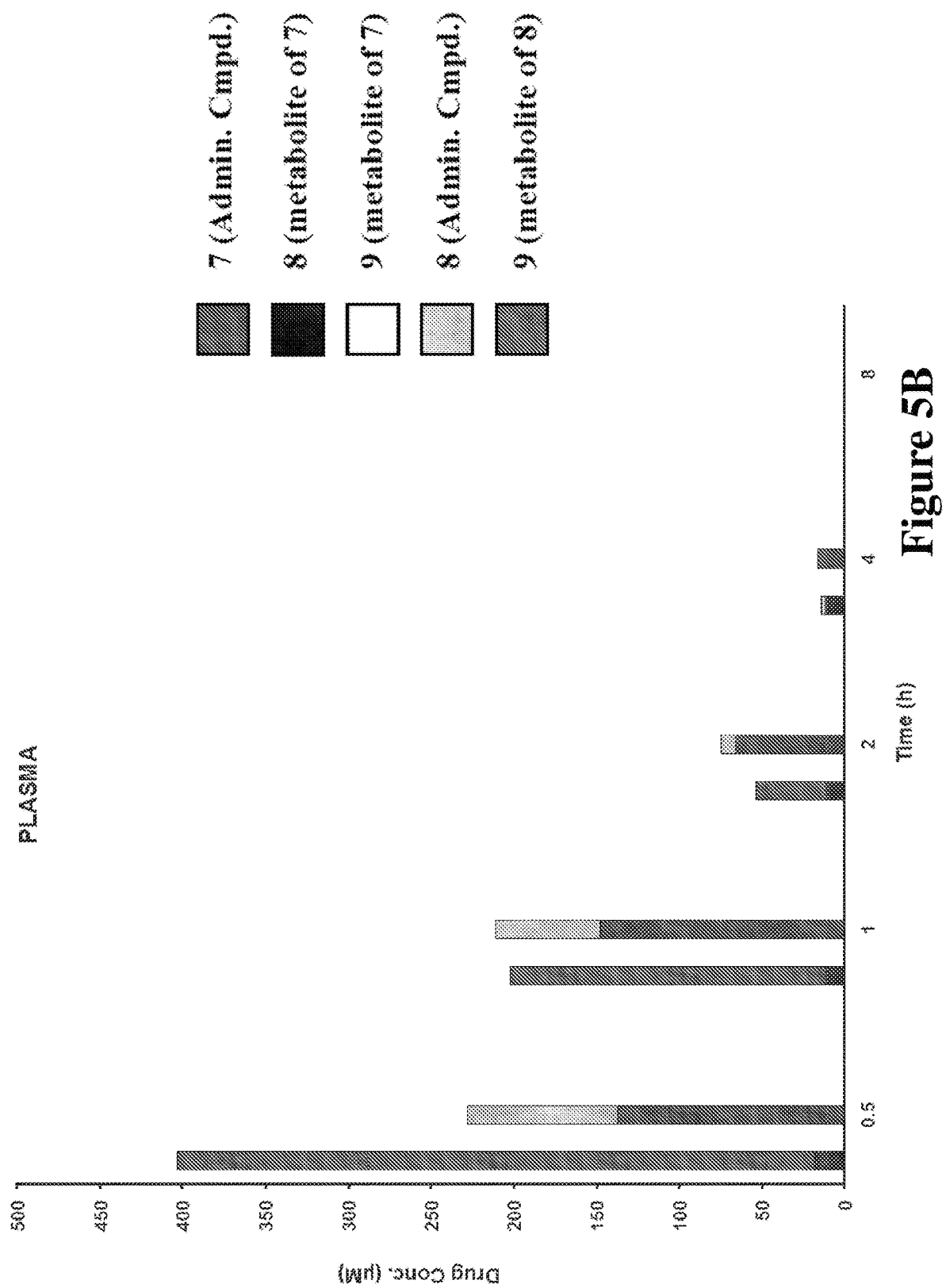
FIG. 5B shows the tissue metabolism/distribution of compounds 7 and 8 in rat plasma.
Figure 5C:
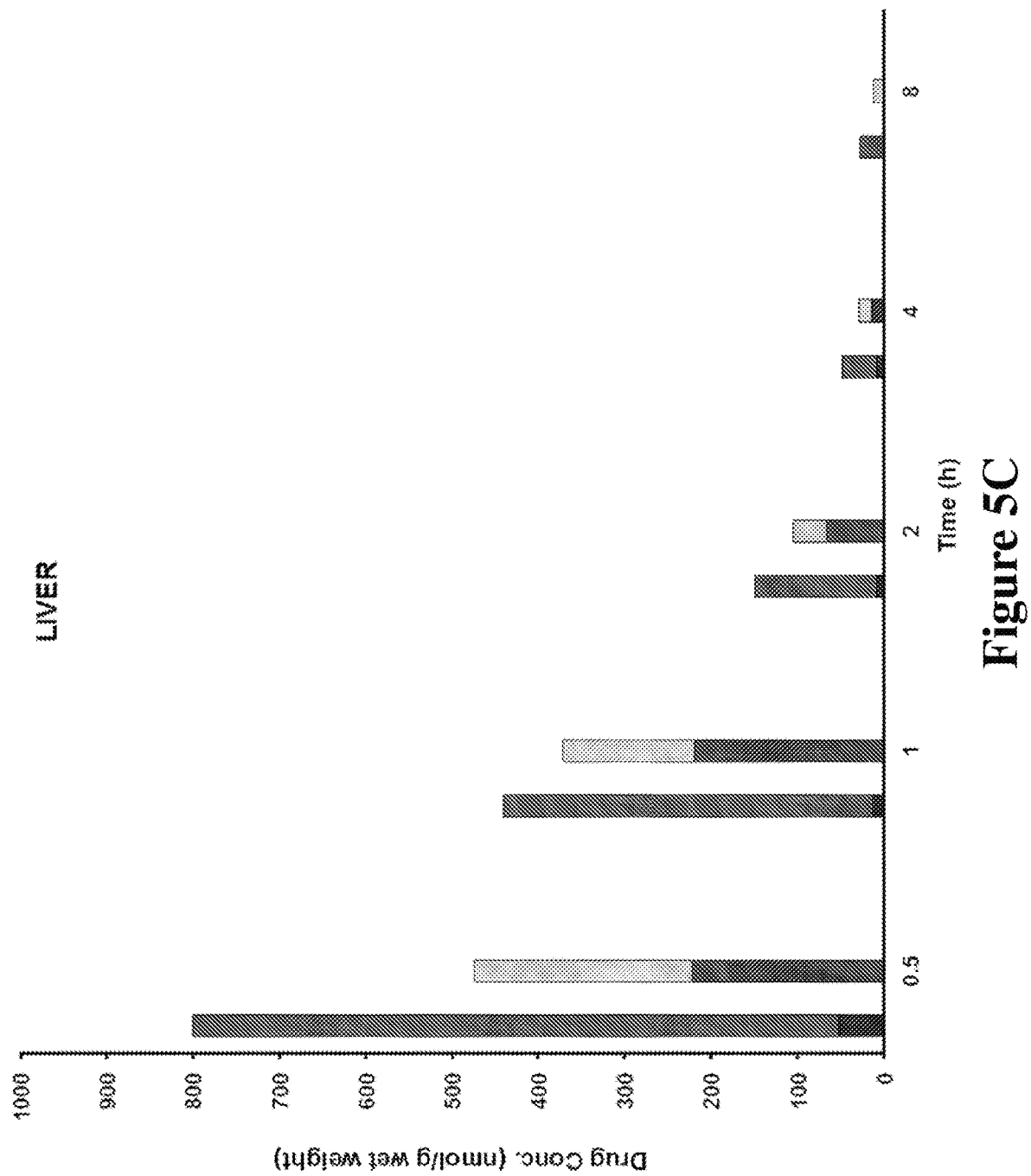
FIG. 5C shows the tissue metabolism/distribution of compounds 7 and 8 in rat liver.
Figure 5D:
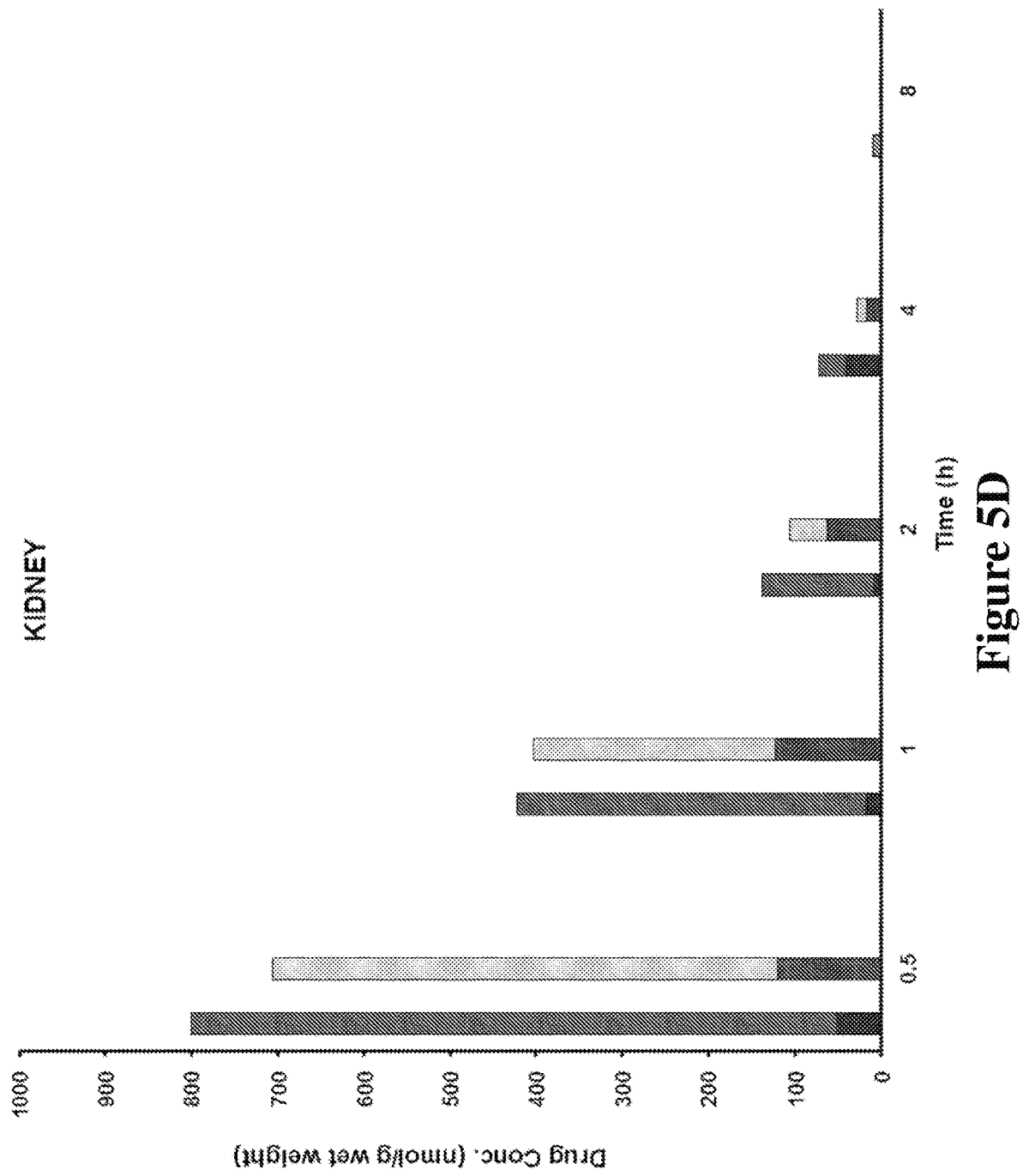
FIG. 5D shows the tissue metabolism/distribution of compounds 7 and 8 in rat kidney.
Figure 5E:
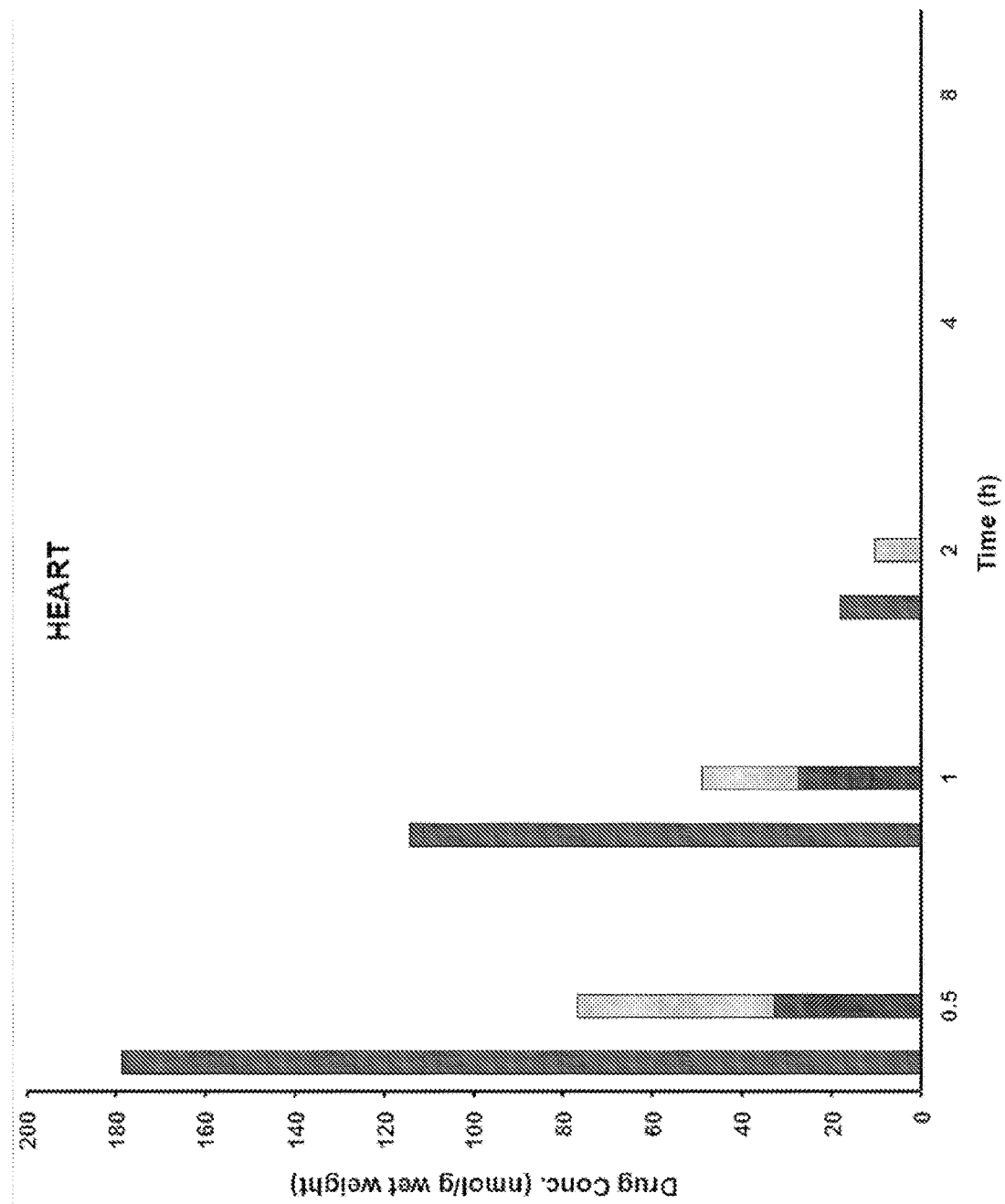
FIG. 5E shows the tissue metabolism/distribution of compounds 7 and 8 in rat heart.
Figure 5F:
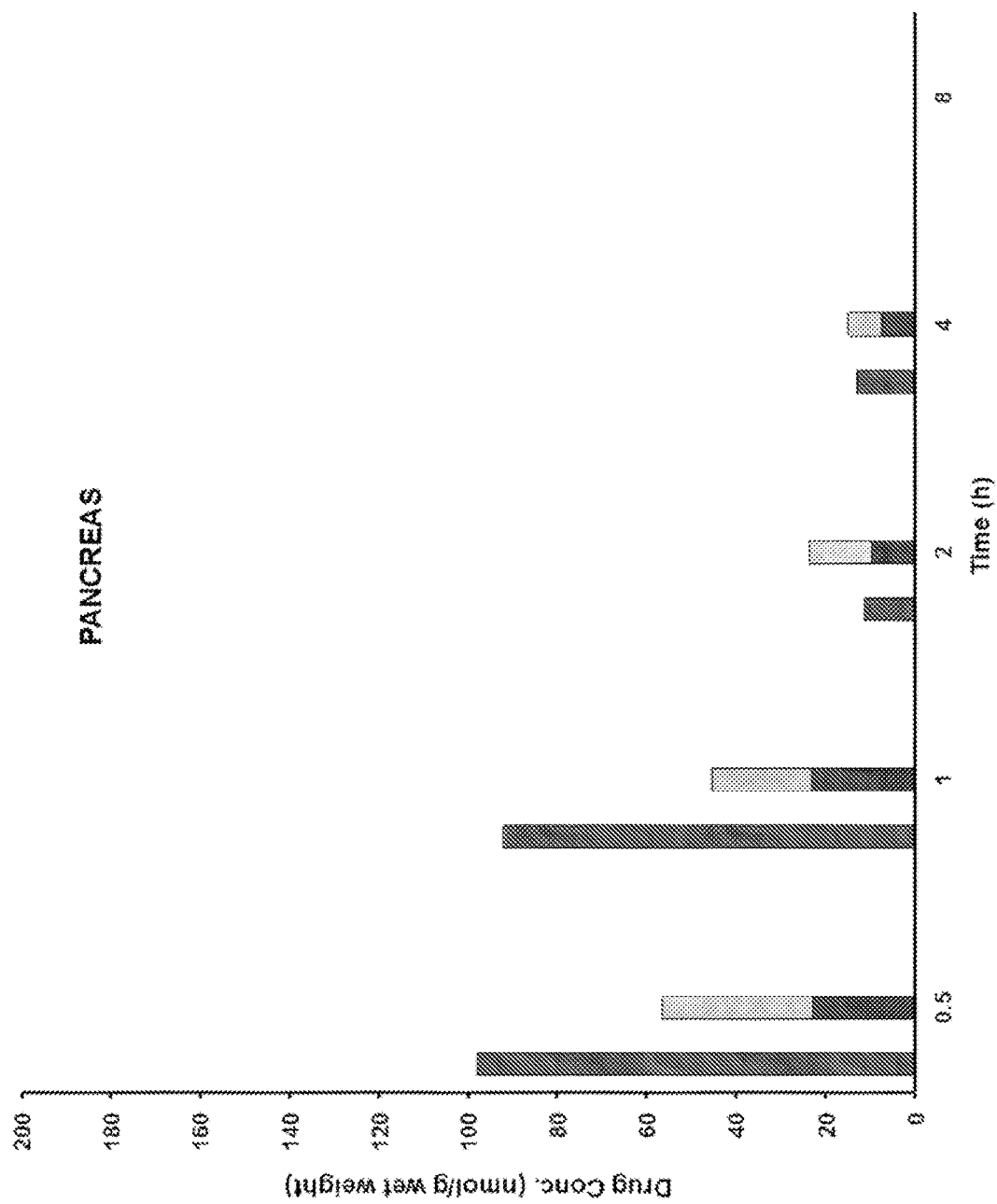
FIG. 5F shows the tissue metabolism/distribution of compounds 7 and 8 in rat pancreas. The rats (n=3 per group) were given the compounds subcutaneously at a dose of 300 μmol/kg. The concentration data (y-axis) of the compounds are expressed as nmol/g wet weight of the organ (e.g., liver, kidney, heart, pancreas), or as μM (plasma). "Admin. Cmpd.": administered compound.

The design of metabolically programmed iron chelators is thus derived from the observation that alcohol 8 is very efficiently oxidized to carboxylic acid 9 (FIGS. 4 and 5). The corollary to all of this is that the replacement of the 3,6-dioxaheptyl group of the parent polyether (S)-4'-(HO)-DADFT-norPE (7) with a long chain alcohol should provide a highly lipophilic chelator with good oral absorption. Once absorbed, the ligand is likely to be metabolized to its less lipophilic, less toxic acid counterparts. This metabolic programming represents an innovative way to exploit the delicate balance seen between enhanced chelator lipophilicity and ICE, and ameliorate the concomitant increase in toxicity usually associated with increases in lipophilicity.

Accordingly, five different ligands predicated on the (S)-4'-(HO)-DADFT platform were assembled (Schemes 2 and 3): 1) the hexamethylene analogue of 7, (S)-4,5-dihydro-2-[2-hydroxy-4-(6-methoxyhexyloxy)phenyl]-4-methyl-4-thiazolecarboxylic acid [(S)-4'-(HO)-DADFT-HXME, 10]; 2) the corresponding alcohol of 10, (S)-4,5-dihydro-2-[2-hydroxy-4-(6-hydroxyhexyloxy)phenyl]-4-methyl-4-thiazolecarboxylic acid [(S)-4'-(HO)-DADFT-HXA, 11]; 3) the putative first metabolite of 11, (S)-4,5-dihydro-2-[2-hydroxy-4-(5-carboxypentyloxy)phenyl]-4-methyl-4-thiazolecarboxylic acid [(S)-4'-(5-carboxypentyloxy)-DADFT, 12]; 4) the β-oxidation product of 11, (S)-4,5-dihydro-2-[2-hydroxy-4-(3-carboxypropyloxy)phenyl]-4-methyl-4-thiazolecarboxylic acid [(S)-4'-(3-carboxypropyloxy)-DADFT, 13], and 5) the second β-oxidation product of 11, (S)-4,5-dihydro-2-[2-hydroxy-4-(carboxymethoxy)phenyl]-4-methyl-4-thiazolecarboxylic acid [(S)-4'-(carboxymethoxy)-DADFT, 14]. The conversion of the parent alcohol 11 to its putative metabolites 12-14 (FIG. 6) was assessed in rats given 11 subcutaneously at a dose of 300 mol/kg. In addition, the ligands were evaluated for their log $P_{app}$, and their ICE in rats and primates (Table 2).

Example 7

Tissue Distribution/Metabolism of (S)-4'-(HO)-DADFT-HXA (11): A Metabolically Programmed Ligand In order to verify that conversion of the alcohol 11 to its putative metabolites 12-14 (FIG. 6) was occurring in vivo, rats were given the parent alcohol 11 subcutaneously at a dose of 300 μmol/kg. The rats were euthanized 0.5, 1, 2, 4, and 8 hours post drug. The conversion of 11→12-14 was assessed in the animals' plasma, liver, kidney, heart and pancreas. Significant conversion of 11→12-14 was found in all of the tissues examined (FIG. 7). The extent and rapidity of metabolism of 11→12-14 that unfolded was surprising. Chelator 11 and its metabolites achieve a concentration of 400 μM in the plasma at 0.5 hour post drug. This tissue concentration is very similar to that seen with the 4-nor-polyether 7 (FIG. 5). However, with 7, the parent represented 95% of the total drug concentration, while its metabolite (8) only accounted for 5% of the total drug. In the case of 11 in the plasma at 0.5 hour, only 22% of the total (parent+metabolites) was in the form of the parent 11 (FIG. 7). The first β-oxidation product 13 comprised 62% of the total, while the second β-oxidation product 14 represented 16% of the total. The ratio of the parent 11 to its metabolites 13 and 14 was similar at the 1 and 2 hour time points. By 4 hours post dosing, the parent 11 was no longer detectable, and metabolites 13 and 14 each accounted for 50% of the total. At 8 hours post dosing, the total plasma drug concentration had decreased to 23 μM. Metabolite 13 accounted for 65% of this quantity, while the remainder was in the form of metabolite 14. None of the first oxidation product of alcohol 11, the dicarboxylic acid 12, was detected in the plasma.

Significant conversion of 11→12-14 also occurred in the liver (FIG. 7). Interestingly, the parent 11 was not found in the liver at any of the time points. However, unlike the plasma, small quantities of first oxidation product of alcohol 11, the dicarboxylic acid 12, were found in the liver 0.5 and 1 hour post drug. At 0.5 hour, 12 represented 11% of the total drug (parent+metabolites); the first β-oxidation product 13 comprised 71% of the total, while the second β-oxidation product 14 represented 18% of the total. At 1 hour post dosing, the concentration of metabolites 12 and 13 in the liver had decreased to 2% and 59% of the total, respectively, while the proportion of 14 had increased to 39% (FIG. 7). Ligand 12 was not detected in the liver 2, 4, or 8 hours post dosing. Metabolite 13 accounted for 66% of the total drug (metabolites) at 2 hours, and 70% of the total at 4 hours. By 8 hours post dosing, no 13 remained in the liver, and only trace amounts of 14 were detected.

The parent drug 11 was found in the kidney in trace amounts 0.5 hour post drug, and the carboxylic acid 12 was found at 0.5 and 1 hour post drug. Metabolite 13, the first β-oxidation product, achieves very high levels in the kidney, ~300 nmol/g wet weight at 0.5 and 1 hour, but is not detectable 8 hours post dosing. Metabolite 14, the second β-oxidation product, also reached high levels in the kidney at 0.5, 1, and 2 hours, 156, 201, and 161 nmol/g wet weight, respectively, but had decreased to only 5 nmol/g wet weight at 8 hours.

The parent drug 11 was found in the heart at 0.5 hour post drug, 26 nmol/g wet weight. The dicarboxylic acid 12 was not found in the cardiac tissue at any of the time points. The concentration of metabolite 13 in the heart was ~46 nmol/g wet weight 0.5 and 1 hour post drug, but was not found in the later time points. Metabolite 14 was found in the heart 0.5 and 1 hour post dosing, 17 and 23 nmol/g wet weight, respectively, but was not found in the 2-8 hour time points (FIG. 7).

In the pancreas, the parent 11 was only found 0.5 hour post drug, <5 nmol/g wet weight. Metabolite 12 was not found at any of the time points. Ligand 13 was present in the 0.5 and 1 hour samples, 19 and 23 nmol/g wet weight, respectively (FIG. 7). Trace amounts of 14 were found at 0.5, 1, and 2 hours post dosing. Ligands 11-14 were not detected in the pancreas at 4 or 8 hours post drug.

Example 8

Chelator-Induced Iron Clearance of 10-14 in Non-iron-Overloaded, Bile Duct-Cannulated Rodents Ligands 10-14 were administered to the rats orally at a dose of 300 μmol/kg; 12-14 were given to the animals subcutaneously at the same dose. The first chelator evaluated in the rats was 10, the methyl ether analogue of 11. Ligand 10 is very lipophilic (log $P_{app}$=0.95), and is also profoundly toxic. When it was given orally to bile duct-cannulated rats, one of animals died about 22 hours post drug. The remaining rodents were euthanized 24 hours post dosing due to their rapidly deteriorating condition. We had seen this same scenario with (S)-2-(4-butoxy-2-hydroxyphenyl)-4,5-dihydro-4-thiazolecarboxylic acid, the 4'-butoxy analogue of 2 (log $P_{app}$=1.02), with deaths occurring within 24 hours.[72] Nonetheless, 10 was a very active decorporation agent. The baseline iron output for rats treated with 10 was 5 µg/kg of iron. The drug-induced iron excretion peaked 6 hours post drug, 300 µg/kg of iron, and was still 80 µg/kg of iron when the rodents were euthanized 24 hours post dosing. The ICE of the drug was 15.8±3.7% (Table 2), and clearly would have been higher had the animals survived. The ICE of 10 was not assessed in the primates due to the overt toxicity seen with the rodents. The ICE and toxicity of 10 is in keeping with the molecule's lipophilicity. Next, 11, the O-demethylated, metabolically labile analog of 10 was evaluated.

Figure 6:
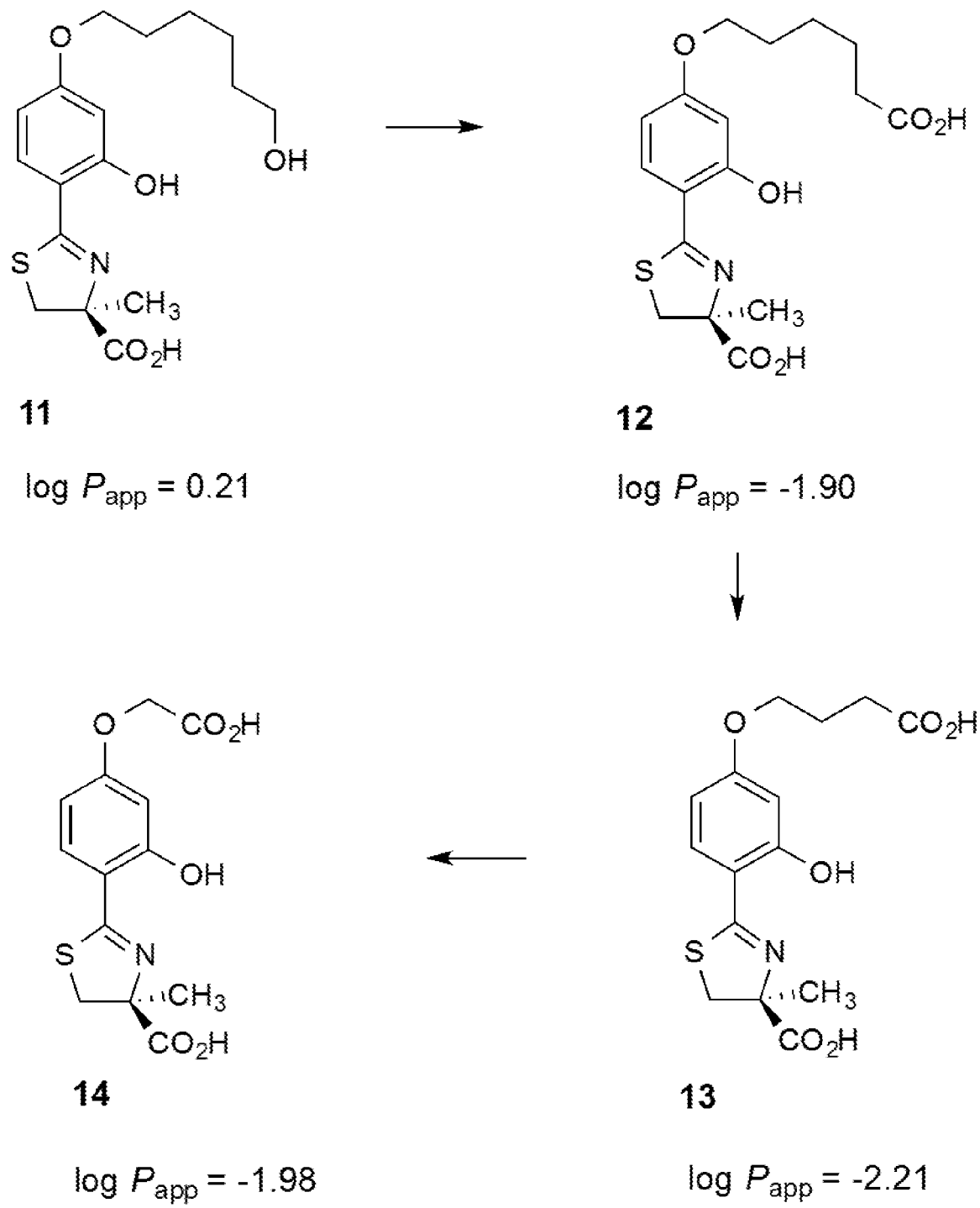
FIG. 6 shows a putative metabolism of compound 11 into compounds 12 to 14, and the lipophilicity (log $P_{app}$) of the compounds 11 to 14.
Figure 7A:
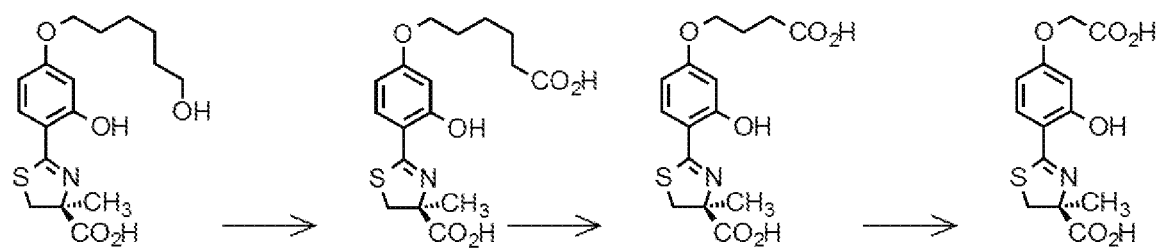
FIG. 7A shows the tissue metabolism/distribution of compound 11 in rat heart.
Figure 7A:
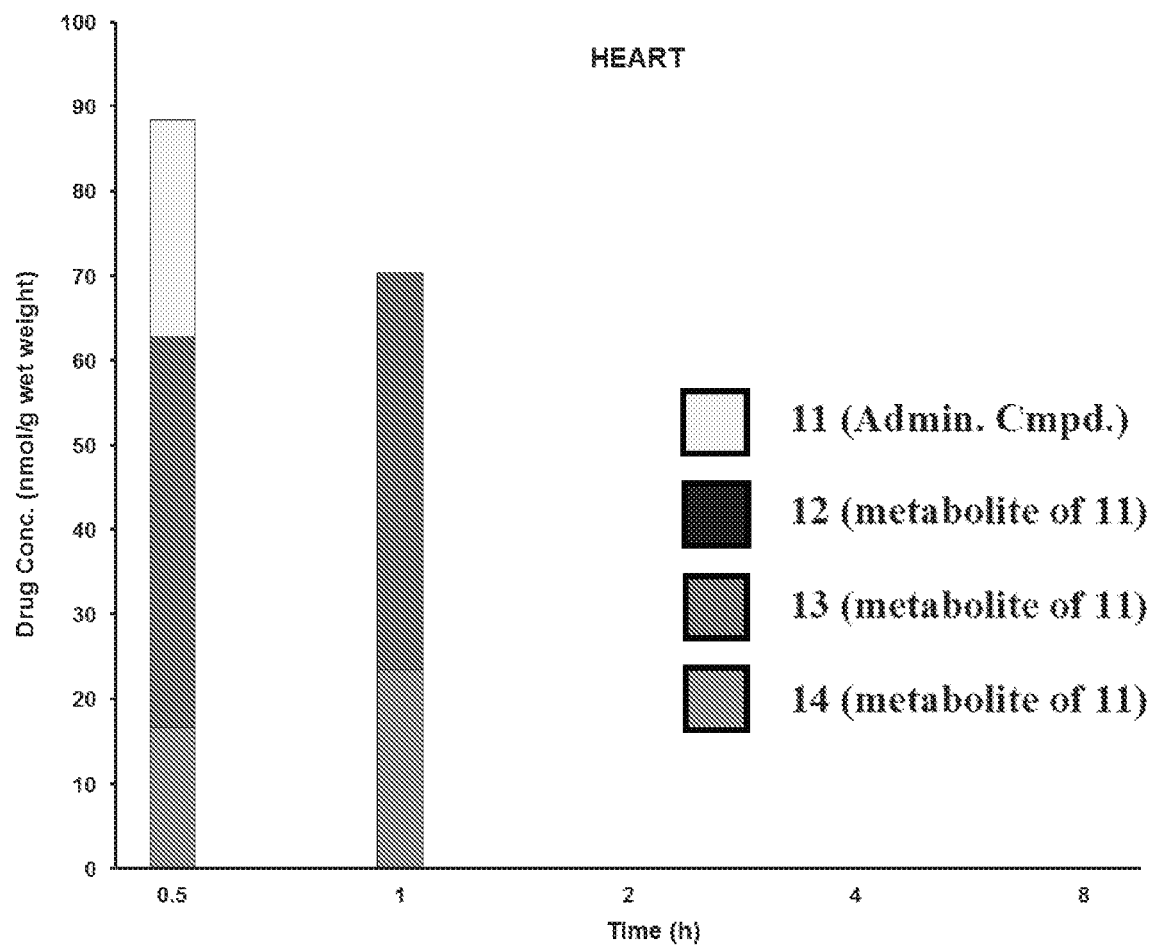
Figure 7B:
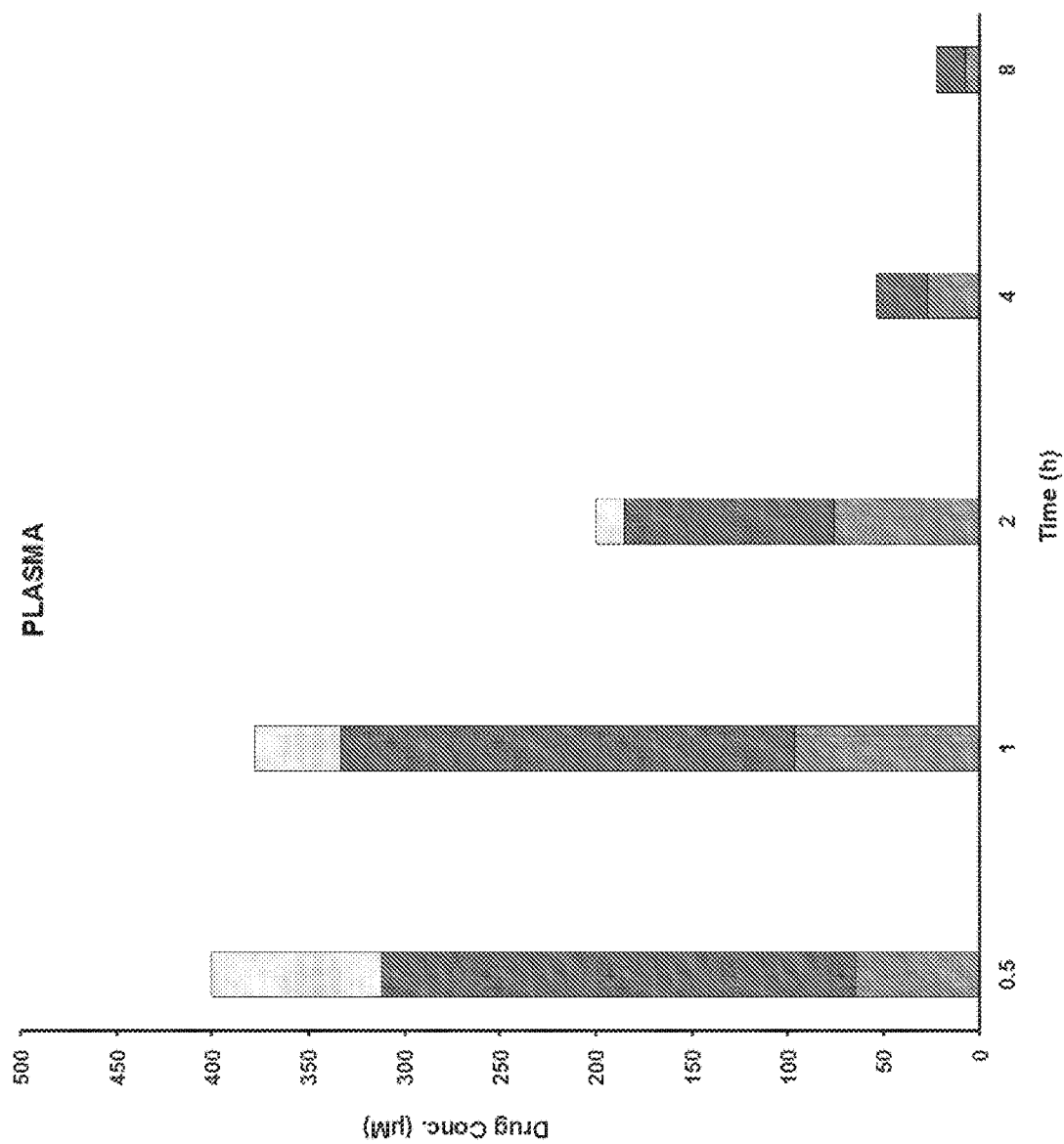
FIG. 7B shows the tissue metabolism/distribution of compound 11 in rat plasma.
Figure 7C:
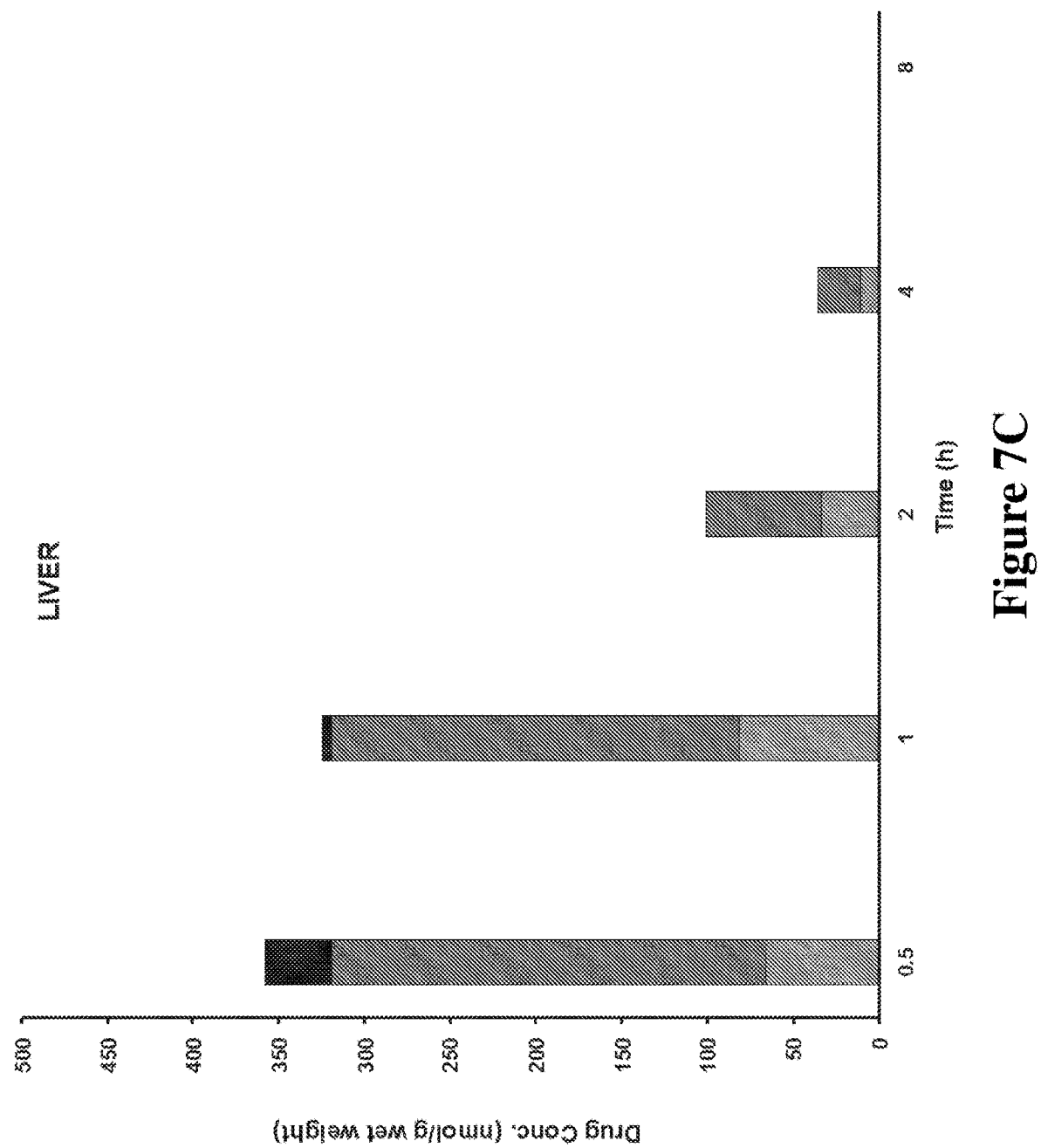
FIG. 7C shows the tissue metabolism/distribution of compound 11 in rat liver.
Figure 7D:
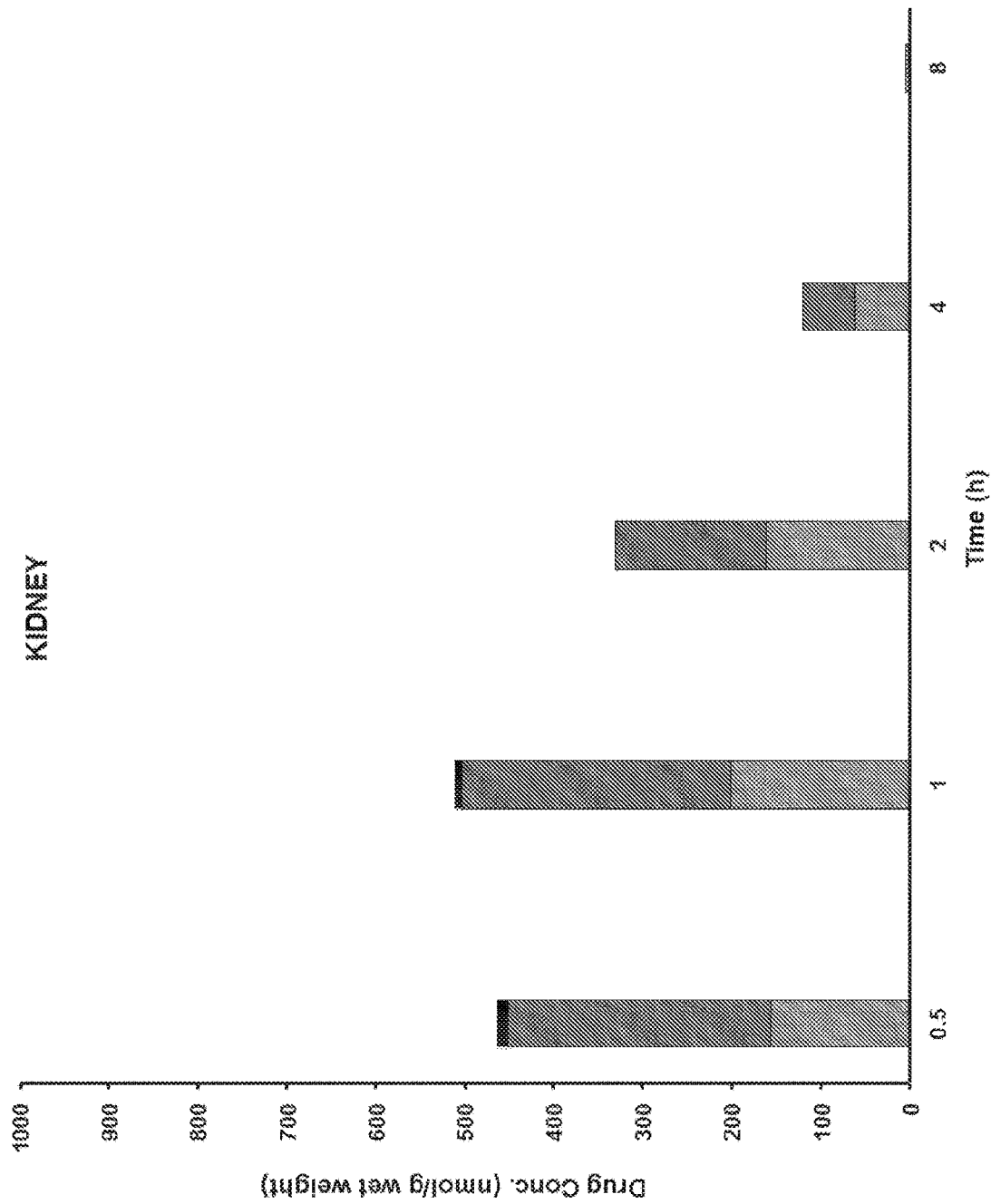
FIG. 7D shows the tissue metabolism/distribution of compound 11 in rat kidney.
Figure 7E:
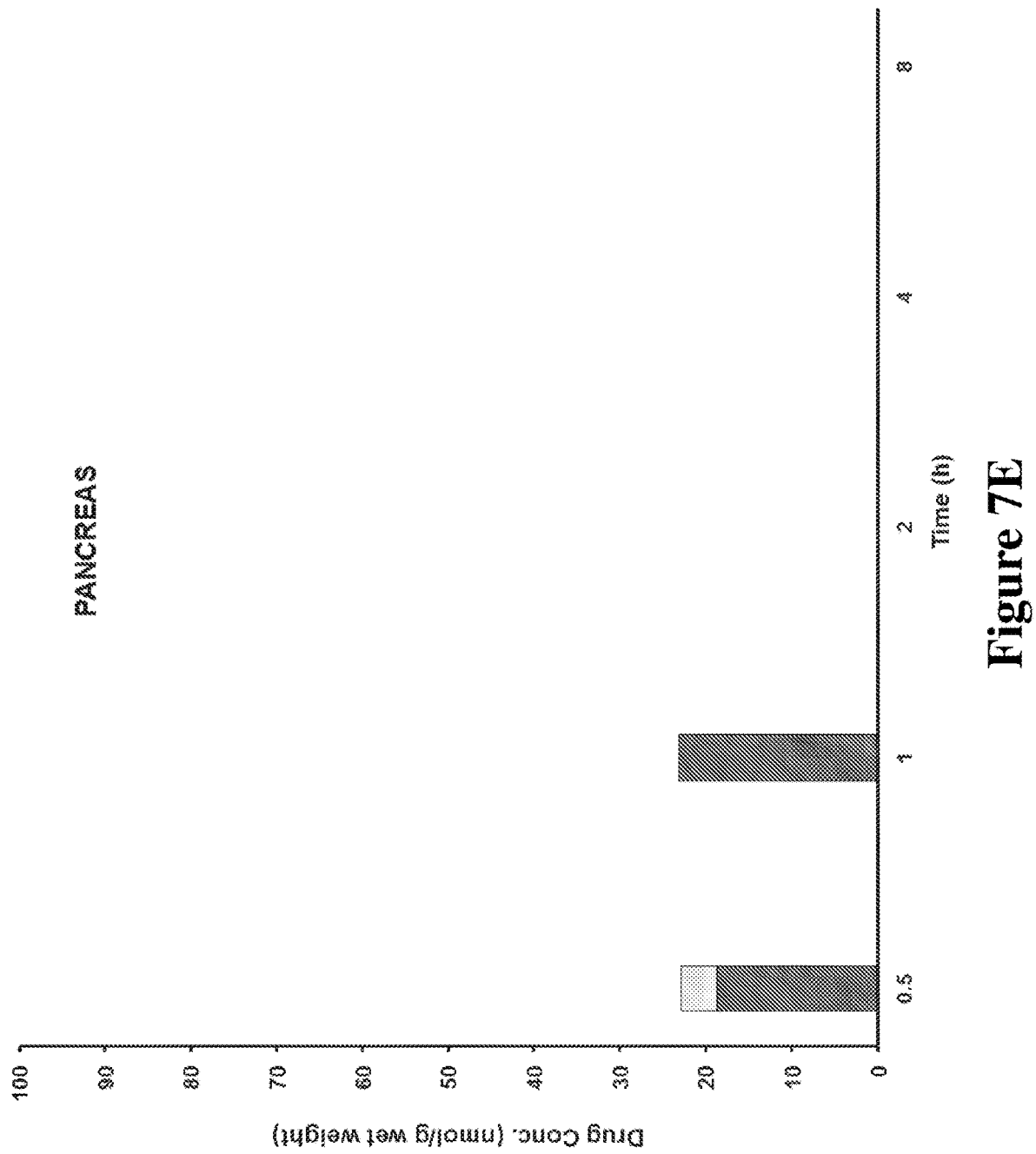
FIG. 7E shows the tissue metabolism/distribution of compound 11 in rat pancreas. The rats (n=3 per group) were given compound 11 subcutaneously at a dose of 300 µmol/kg. The concentration data (y-axis) of compound 11 are expressed as nmol/g wet weight or the organ (e.g., liver, kidney, heart, pancreas), or as µM (plasma). "Admin. Cmpd.": administered compound.

An alkanol, e.g., a 6-(HO) hexyl fragment, was fixed to the 4'-(HO) position of 15 leading to 11 (Scheme 2). This resulted in a less lipophilic, log $P_{app}$=0.21, less toxic ligand than 10. Chelator 11 was given to the rats orally at a dose of 300 mol/kg. The drug was well absorbed, had an ICE of 9.9±0.8%, and did not present with any overt toxicity. As described above, when ligand 11 was given to rats subcutaneously, it was quickly converted to the corresponding hydrophilic metabolites, carboxylic acid (12, log $P_{app}$=-1.90),[64,66] with β-oxidations[73] to acids 13 log $P_{app}$=-2.21 and acid 14 log $P_{app}$=-1.98 (FIG. 6). The ICEs of 12-14 were determined in rodents given the drugs orally and subcutaneously at a dose of 300 mol/kg. The oral ICE of the putative first metabolite, 12, was similar to that of 11, 8.8±1.8% (p>0.05). However, the oral ICEs of 13 and 14 were significantly less than 11, 3.7±1.7% (p<0.001) and 2.6±1.6% (p<0.005), respectively. When 12 and 13 were given to the rats subcutaneously, their ICEs were within error of when the drugs were dosed orally (Table 2). In contrast, the ICE of 14 given subcutaneously (6.0±1.9%) was more than twice that of when the drug was given orally (2.6±1.6%, p<0.05).

Example 9

Chelator-Induced Iron Clearance of 11-14 in Iron-Overloaded Primates

Ligand 11 was administered to the primates orally at a dose of 75 µmol/kg; 12-14 were given orally and subcutaneously at the same dose. Ligand 11, in which a 6-(HO)-hexyl fragment was fixed to the 4'-(HO) position of 2, was very lipophilic (log $P_{app}$=0.21). The ICE of this compound given to the monkeys orally was 21.9±3.6% (Table 2). The ICEs of the much more hydrophilic metabolites of 11, 12-14, given orally to the monkeys, were all significantly less than the parent. The first oxidation product of alcohol 11, the dicarboxylic acid 12 (log $P_{app}$=-1.90), had an ICE of 10.6±4.0% in primates when it was given orally (p<0.01). The first and second β-oxidation products, 13 (log $P_{app}$=-2.21) and 14 (log $P_{app}$=-1.98), were also significantly less effective than 11 when they were administered orally, 5.4±1.5% (p<0.005) and 3.0±2.7% (p<0.002), respectively. Again, the reason for the substantial reduction in the efficacy of 12-14 dosed orally was likely due to the poor GI absorption of the dicarboxylic acids because of their charge: they are dianions at physiological pH. In order to confirm this, ligands 12-14 were given to the primates subcutaneously. In each case, the same animals that had been given the drugs orally were also given the chelators subcutaneously.

The oral ICE of 12 in the monkeys was 10.6±4.0%; the ICE increased to 18.8±8.7% when the ligand was given subcutaneously, but the increase was not significant (p=0.06). The ICE of 13 increased significantly in the primates, from 5.4±1.5% when it was dosed orally to 18.1±7.5% when it was administered subcutaneously (p<0.03). Finally, the ICE of the second β-oxidation product 14 in the primates was 3.0±2.7% when it was given orally. The ICE increased significantly, to 15.9±4.3%, when it was given to the same animals subcutaneously (p<0.001). Thus, the importance of ligand charge, log $P_{app}$, takes on a much more significant role in the primate model.

Example 10

ICE Observations

Several generalizations can be derived from Table 2. The performance ratio (PR), $ICE_{primate}/ICE_{rodent}$, show that although 8 and 9 (orally) were more effective at iron decorporation in the rats than in primates, the remaining ligands 11-14 are either as effective or better at iron clearance in the primates. In the rodents, 9 and 14 were approximately twice as effective subcutaneously as when they were dosed orally. There was also a dramatic difference in the subcutaneously vs oral ICEs of 9, 13, and 14 in the primates: their subcutaneously ICEs were 10.2, 3.4, and 5.3 times higher, respectively. The ICE of 12 was also increased upon subcutaneously dosing, but the increase was not significant (p=0.06).

Example 11

Toxicology Profile of (S)-4'-(HO)-DADFT-HXA (11), A Metabolically Programmed Chelator The concept behind the development of metabolically programmed iron chelators is predicated on the administration of highly lipophilic drugs that will be well absorbed orally, present with excellent ICE properties, and, to minimize potential toxicity, must be quickly metabolized to less lipophilic but still active deferration agents. For example, deferitrin analog 10 (Table 2), with a non-metabolizable terminal methyl ether, was highly lipophilic and was an effective iron clearing agent in the bile duct-cannulated rats. Unfortunately, the chelator was profoundly toxic. Conversely, the corresponding demethylated compound, alcohol 11, which is also lipophilic, had excellent ICE properties in rodents and primates and did not display any overt toxicity. As described above, ligand 11 was well absorbed, and, in a tissue distribution/metabolism study, was shown to be quickly converted to the corresponding hydrophilic acids 12, 13, and 14 (FIG. 6).

Aten-day toxicity trial of 11 was carried out in male Sprague-Dawley rats. The animals were housed in individual metabolic cages. Ligand 11 was given orally by gavage once daily for ten days at a dose of 384 mol/kg/day. Note that this dose is equivalent to 100 mg/kg/day of DFT (1) as its sodium salt. Urine was collected from the metabolic cages at 24-hour intervals and assessed for its Kim-1 content. The studies were performed on rats with normal iron stores; each animal served as its own control. Additional age-matched rats served as untreated controls for the CBC and serum chemistry assessments and histopathology.

All of the rats treated with 11 survived the exposure to the drug. The animals were bright, alert and responsive at the beginning of the study and remained that way throughout the course of the experiment. The rodents' baseline urinary Kim-1 excretion was <20 ng/kg/24 hours and did not exceed this level at any time during the 10-day exposure to the chelator. The rats were sacrificed 24 hours post drug. Blood was submitted for routine CBC and serum chemistry analysis. The BUN of the treated rats, 20±4 mg/dl, was within error of that of the untreated controls, 21±2 mg/dl (p>0.05). In addition, the SCr for both groups was 0.5±0.1 mg/dl (p>0.05). Note that these values are well within the normal range for this species: 9-30 mg/dl for BUN, and 0.4-1.0 mg/dl for SCr (Antech Diagnostics (2015), www.antechdiagnostics.com, accessed April 2015). Extensive tissues (25/rat) were submitted to an outside lab for assessment of histopathology. The pathologist did not identify any drug-related abnormalities.

Taken together, these results demonstrate that metabolically programmed ligands that are highly effective deferration agents can be successfully designed. As predicted, the parent in this case, a lipophilic alcohol, 11, was well absorbed and was quickly metabolized to hydrophilic ligands that, collectively, have excellent ICEs with little to no discernable toxicity.

Conclusions

A number of notable outcomes derived from the metabolic studies of (S)-4'-(HO)-DADFT-norPE (7). First, ligand 7 does not sustain metabolic cleavage at the 4'-(HO) to yield 2 (FIG. 2). However, what remained unclear is whether or not the terminal methyl on the polyether fragment of 7 is metabolically labile. If this were the case, it would likely be converted first to the corresponding alcohol, 8, and then to the carboxylic acid, 9, FIG. 4. Both of these metabolic products would be expected to be very hydrophilic. This increase in hydrophilicity, based on previous studies, could further be expected to minimize ligand toxicity.[37,43,45] If indeed such a demethylation-oxidation scenario is occurring with 7, it could support a novel approach to "metabolically programmed" iron chelators, e.g., highly lipophilic chelators that would be absorbed well orally, but would then be quickly metabolized to hydrophilic, nontoxic ligands.

The putative metabolites of 7, 8 and 9, were assembled. The alcohol 8 has a 3-oxa-5-hydroxypentyl fragment fixed to the 4'-(HO); the acid 9 has a 3-oxa-4-carboxybutyl group on the 4'-(HO). These two synthetic chelators allowed us to develop an analytical HPLC method to follow the potential metabolism of 7. When the tissues of rats treated with 7 subcutaneously were subjected to further analysis via HPLC for the presence of 8 or 9, cleavage of the terminal methyl of 7 to the corresponding alcohol 8 did occur (FIG. 5). However, carboxylic acid 9 was not detected, probably because the extent of the metabolism of the parent 7 to 8 was so minor. However, when synthetic alcohol 8 was given subcutaneously to rats, it was very efficiently converted to acid 9.

Rodents were administered the synthetic alcohol 8 subcutaneously at a dose of 300 mol/kg. Indeed, alcohol 8 was very quickly oxidized to 9 (FIG. 5).

When given orally to rodents and primates, neither of the synthetic metabolites of 7, alcohol 8 nor the acid 9, had ICE values as high as the parent ligand. The acid 9, given orally, was particularly ineffective. However, when given subcutaneously, the ICE of 9 doubled in rodents, and was 10 times higher in primates than when it was given to the same monkeys orally (Table 2). This is in keeping with the idea that highly charged ligands do not make it across the intestinal mucosa. Taken collectively, the data suggested that fixing a lipophilic alcohol fragment to the 4'-(HO) of 2 would provide a chelator that should be lipophilic, orally absorbed, and quickly converted to hydrophilic acid metabolites.

Initially, a 6-methoxyhexyl group was appended to the 4'-(HO) of 2, providing methyl ether 10. This ligand was very lipophilic (log $P_{app}$=0.95), had an ICE of 15.8±3.7% in the rats, and was very toxic. We had seen this scenario before with a 4'-butoxy analogue of 2 (log $P_{app}$=1.02), with deaths occurring within 24 hours.[72] Nevertheless, this ligand did serve to identify the upper boundary of the lipophilicity/toxicity relationship for this structural family.

Subsequently, a metabolizable 6-hydroxyhexyl group was fixed to the 4'-(HO) of 2, providing alcohol 11 (Table 2). Ligand 11 is still very lipophilic, log $P_{app}$=0.21, but it did not elicit any signs of overt toxicity. As predicted, each of the metabolites of 11 (12, 13, and 14) are very hydrophilic, moving from a log $P_{app}$=0.21 for the parent to −1.90 for acid 12, −2.21 for acid 13, and −1.98 for acid 14 (FIG. 6). When given to rats subcutaneously, 11 is very quickly converted to the corresponding acid (12), and by β-oxidation to acid 13 and finally to acid 14 (FIG. 7).

Figure 8:
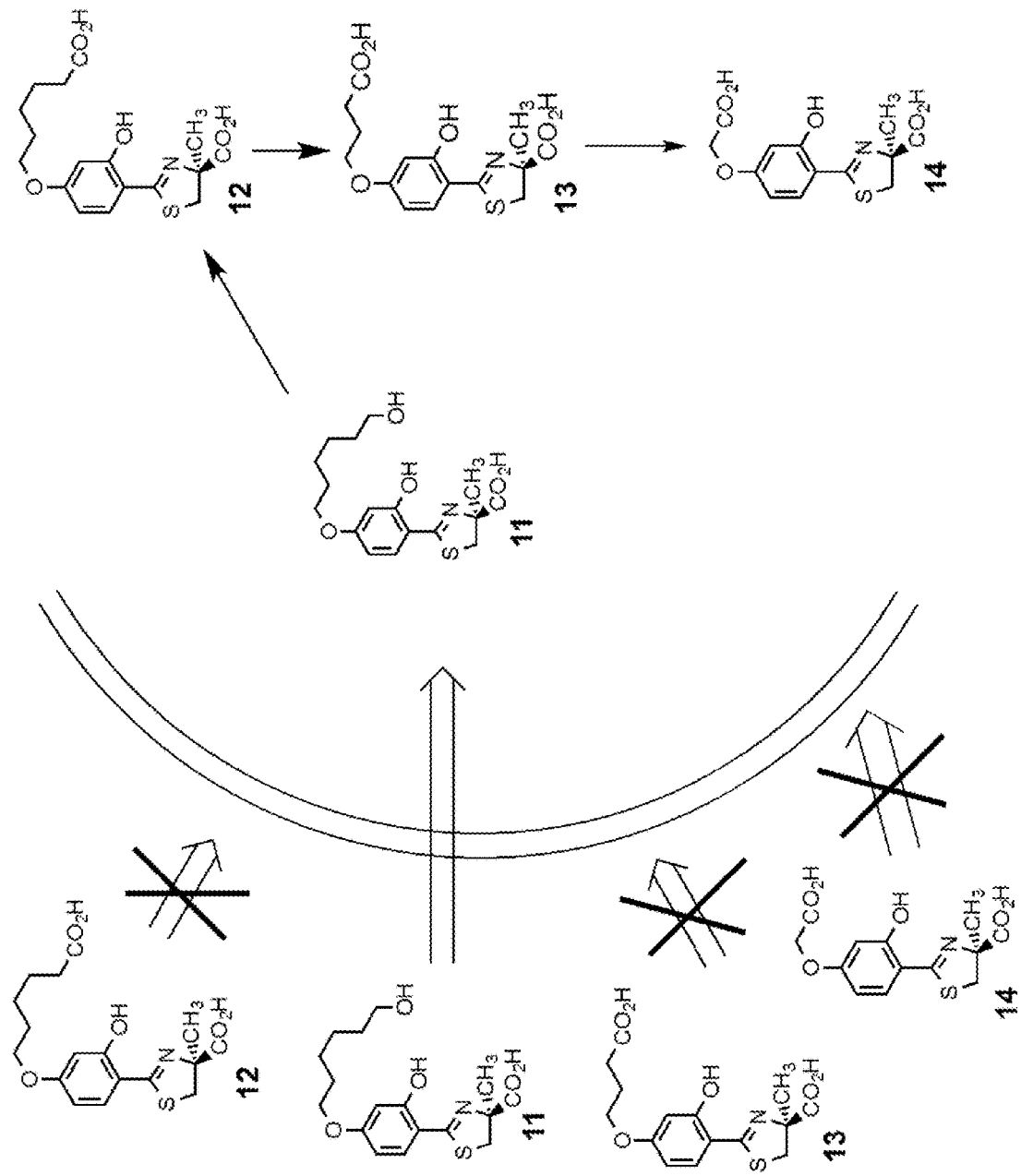
FIG. 8 is a schematic representation of the oral absorption of compound 11, and the rapid metabolism of compound 11 into compounds 12 to 14. Compound 11 is highly lipophilic, and compounds 12 to 14 are hydrophilic.

The oral ICE of ligand 11 in the rats is 9.9±0.8%. The oral ICE of 12 was similar, while the oral ICEs of 13 and 14 were significantly less. In the primates, the oral ICE of the parent 11 was 21.9±3.6%. The oral ICEs of the hydrophilic metabolites, 12-14, were all significantly less in the monkeys than the parent alcohol 11 (Table 2). Again, this is in keeping with the idea that highly charged ligands do not make it across the intestinal mucosa. To confirm this, ligands 12-14 were given subcutaneously to the rodents and primates. In the rats, the subcutaneously ICEs of 12 and 13 were within error of their oral values, while that of 14 subcutaneously was significantly greater than when the drug was given orally. In the monkeys, the subcutaneously ICE of 12 did increase vs oral dosing, but the increase was not significant. In contrast, the subcutaneously ICEs of 13 and 14 were 3.4 and 5.3 times greater, respectively, than when the drugs were given to the same animals orally (Table 2). The most notable finding was the lack of toxicity with ligand 11 when given to rodents once daily for 10 days at a dose of 384 mol/kg/day. The toxicity difference between 10 and 11 was profound. This substantiates the idea that the lipophilic parent chelator is quickly converted to hydrophilic, nontoxic deferration metabolites. Thus, the concept of developing "metabolically programmed" chelators, e.g., highly lipophilic, orally absorbable and effective molecules that are quickly converted to their hydrophilic counterparts, is indeed a credible approach in the design of highly effective iron chelators. FIG. 8 illustrates the concept established in this study.

REFERENCES (1) Mladenka, P.; Hrdina, R.; HüM, M.; Simunek, T. The Fate of Iron in the Organism and Its Regulatory Pathways. *Acta Medica.* 2005, 48, 127-135.

(2) Bauer, I.; Knolker, H-J. Iron Complexes in Organic Chemistry. In *Iron Catalysis in Organic Chemistry.* Plietker, B. Ed. Wiley-VCH: Weinheim, 2008; pp. 1-28.

(3) Saha, R.; Saha, N.; Donofrio, R. S.; Bestervelt, L. L. Microbial Siderophores: A Mini Review. *J. Basic Microbiol.* 2013, 53, 303-317.

(4) Abergel, R. J.; Wilson, M. K.; Arceneaux, J. E. L.; Hoette, T. M.; Strong, R. K.; Byers, B. R. Anthrax Pathogen Evades the Mammalian Immune System Through Stealth Siderophore Production. *Proc. Nat. Acad. Sci.,* 2006, 103, 18499-18503.

(5) Raymond, K. N.; Dertz, E. A.; Kim, S. S. Enterobactin: An Archetype for Microbial Iron Transport. *Proc. Natl. Acad. Sci.* 2003, 100, 3584-3588.

(6) Gkouvatsos, K.; Papanikolaou, G.; Pantopoulos, K. Regulation of Iron Transport and the Role of Transferrin. *Biochim. Biophys. Acta.* 2012, 1820, 188-202.

(7) Li, L.; Fang, C. J.; Ryan, J. C.; Niemi, E. C.; Lebron, J. A.; Bjorkman, P. J.; Arase, H.; Torti, F. M.; Torti, S. V.; Nakamura, M. C.; Seaman, W. E. Binding and Uptake of H-ferritin are Mediated by Human Transferrin Receptor-1. *Proc. Natl. Acad. Sci. U.S.A.* 2010, 107, 3505-3510.

(8) Andrews, N. C.; Schmidt, P. J. Iron Homeostasis. *Annu. Rev. Physiol.* 2007, 69, 69-85.

(9) Whittington, C. A.; Kowdley, K. V. Review Article: Haemochromatosis. *Aliment Pharmacol. Ther.* 2002, 16, 1963-1975.

(10) Peters, M.; Heijboer, H.; Smiers, F.; Giordano, P. C. Diagnosis and Management of Thalassemia. *B. M. J.* 2012, 344:e228. doi: 10.1136/bmj.e228.

(11) Cappellini, M. D.; Cohen, A. R.; Eleftheriou, A.; Piga, A.; Porter, J.; Taher, A. T. *Guidelines for the Clinical Management of Thalassemia.* $2^{nd}$ Ed. Thalassemia International Foundation, 2008.

(12) Conrad, M. E.; Umbreit, J. N.; Moore, E. G. Iron Absorption and Transport. *Am. J. Med. Sci.* 1999, 318, 213-229.

(13) Lieu, P. T.; Heiskala, M.; Peterson, P. A.; Yang, Y. The Roles of Iron in Health and Disease. *Mol. Aspects Med.* 2001, 22, 1-87.

(14) Bonkovsky, H. L.; Lambrecht, R. W. Iron-Induced Liver Injury. *Clin. Liver Dis.* 2000, 4, 409-429, vi-vii.

(15) Wojcik, J. P.; Speechley, M. R.; Kertesz, A. E.; Chakrabarti, S.; Adams, P. C. Natural History of C282Y Homozygotes for Haemochromatosis. *Can. J. Gastroenterol.* 2002, 16, 297-302

(16) Brittenham, G. M. Disorders of Iron Metabolism: Iron Deficiency and Overload. In *Hematology: Basic Principles and Practice,* 3rd Edn.; Hoffman, R.; Benz, E. J.; Shattil, S. J.; Furie, B.; Cohen, H. J., Eds.; Churchill Livingstone: New York, 2000; pp 397-428.

(17) Brissot, P.; Ropert, M.; Le Lan, C.; Loreal, O. Non-Transferrin Bound Iron: A Key Role in Iron Overload and Iron Toxicity. *Biochim. Biophys. Acta.* 2012, 1820, 403-410.

(18) Chua, A. C. G.; Olynyk, J. K.; Leedman, P. J.; Trinder, D. Nontransferrin-Bound Iron Uptake by Hepatocytes is Increased in the Hfe Knockout Mouse Model of Hereditary Hemochromatosis. *Blood* 2004, 104, 1519-1525.

(19) Bolli, R.; Patel, B. S.; Jeroudi, M. O.; Li, X. Y.; Triana, J. F.; Lai, E. K.; McCay, P. B. Iron-Mediated Radical Reactions upon Reperfusion Contributes to Myocardial "Stunning" *Am. J. Physiol.* 1990, 259, 1901-1911.

(20) Milian, M.; Sobrino, T.; Arenillas, J. F.; Rodriguez-Yañez, M.; Garcia, M.; Nombela, F.; Castellanos, M.; de la Ossa, N. P.; Cuadras, P.; Serena, J.; Castillo, J.; Davalos, A. Biological Signatures of Brain Damage Associated with High Serum Ferritin Levels in Patients with Acute Ischemic Stroke and Thrombolytic Treatment. *Dis. Markers.* 2008, 25, 181-188.

(21) Carr, A.; Frei, B. Does Vitamin C Act as a Pro-Oxidant Under Physiological Conditions? *FASEB J.* 1999, 13, 1007-1024.

(22) Jomova, K.; Valko, M. Advances in Metal-Induced Oxidative Stress and Human Disease. *Toxicology,* 2011, 283, 65-87.

(23) Hazen, S. L.; d'Avignon, A.; Anderson, M. M.; Hsu, F. F.; Heáinecke, J. W. Human Neutrophils Employ the Myeloperoxidase-Hydrogen Peroxide-Chloride System to Oxidize α-Amino Acids to a Family of Reactive Aldehydes. Mechanistic Studies Identifying Labile Intermediates along the Reaction Pathway. *J. Biol. Chem.* 1998, 273, 4997-5005.

(24) Bergeron, R. J.; Wiegand, J.; McManis, J. S.; Perumal, P. T. Synthesis and Biological Evaluation of Hydroxamate-Based Iron Chelators. *J. Med. Chem.* 1991, 34, 3182-3187.

(25) Balfour, J. A. B.; Foster, R. H. Deferiprone A Review of its Clinical Potential in Iron Overload in β-Thalassemia Major and Other Transfusion-Dependent Diseases. *Drugs.* 1999, 58, 553-578.

(26) Richardson, D. R. The Controversial Role of Deferiprone in the Treatment of Thalassemia. *J. Lab. Clin. Med.* 2001, 137, 324-329.

(27) Nick, H.; Wong, A.; Acklin, P.; Faller, B.; Jin, Y. Lattmann, R.; Sergejew, T.; Hauffe, S.; Thomas, H.; Schnebli, H. P. ICL670A: Preclinical Profile. *Adv. Exp. Med. Biol.* 2002, 509, 185-203.

(28) Yacobovich, J.; Stark, P.; Barzilai-Birenbaum, S.; Krause, I.; Yaniv, I.; Tamary, H. Acquired Proximal Renal Tubular Dysfunction in Beta-Thalassemia Patients Treated with Deferasirox. *J. Pediatr. Hematol. Oncol.* 2010, 32, 564-567.

(29) Cappellini, M. D.; Pattoneri, P. Oral Iron Chelators. *Annu. Rev. Med.* 2009, 60, 25-38.

(30) Bergeron, R. J.; Pegram, J. J. An Efficient Total Synthesis of Desferrioxamine B. *J. Org. Chem.* 1988, 53, 3131-3134.

(31) Cunningham, M. J.; Nathan, D. G. New Developments in Iron Chelators. *Curr. Opin. Hematol.* 2005, 12, 129-134.

(32) Olivieri, N. F.; Koren, G.; Hermann, C.; Bentur, Y.; Chung, D.; Klein, J.; St Louis, P.; Freedman, M. H.; McClelland, R. A.; Templeton, D. M. Comparison of Oral Iron Chelator L1 and Desferrioxamine in Iron-Loaded Patients. *Lancet* 1990, 336, 1275-1279.

(33) *Exjade Prescribing Information;* Novartis Pharmaceuticals Corporation: East Hanover, N.J., December, 2014; www.pharma.us. novartis.com/product/pi/pdf/exjade.pdf.

(34) Naegeli, H.-U.; Zahner, H. Metabolites of Microorganisms. Part 193. Ferrithiocin. *Helv. Chim. Acta* 1980, 63, 1400-1406.

(35) Anderegg, G.; Räber, M. Metal Complex Formation of a New Siderophore Desferrithiocin and of Three Related Ligands. *J. Chem. Soc., Chem. Commun.* 1990, 1194-1196.

(36) Bergeron, R. J.; Wiegand, J.; Dionis, J. B.; Egil-Karmakka, M.; Frei, J.; Huxley-Tencer, A.; Peter, H. H. Evaluation of Desferrithiocin and its Synthetic Analogues as Orally Effective Iron Chelators. *J. Med Chem.* 1991, 34, 2072-2078.

(37) Bergeron R. J.; Wiegand, J.; McManis, J. S.; McCosar, B. H.; Weimar, W. R.; Brittenham, G. W.; Smith, R. E. Effects of C-4 Stereochemistry and C-4' Hydroxylation on the Iron Clearing Efficiency and Toxicity of Desferrithiocin Analogues. *J. Med. Chem.* 1999, 42, 2432-2440.

(38) Bergeron, R. J.; Streiff, R. R.; Wiegand, J.; Vinson, J. R. T.; Luchetta, G.; Evans, K. M.; Peter, H.; Jenny, H-B.

(39) Wolfe, L. C.; Nicolosi, R. J.; Renaud, M. M.; Finger, J.; Hegsted, M.; Peter, H.; Nathan, D. G. A Non-Human Primate Model for the Study of Oral Iron Chelators. *Br. J. Hematol.* 1989, 72, 456-461.

(40) Bergeron, R. J.; Streiff, R. R.; Creary, E. A.; Daniels, R. D. Jr.; King, W.; Luchetta, G.; Wiegand, J.; Moerker, T.; Peter, H. H. A Comparative Study of the Iron-Clearing Properties of Desferrithiocin Analogues with Desferrioxamine B in a Cebus Monkey Model. *Blood* 1993, 81, 2166-2173.

(41) Baker, E.; Wong, A.; Peter, H.; Jacobs, A. Desferrithiocin is an Effective Iron Chelator in vivo and in vitro but Ferrithiocin is Toxic. *Br. J. Haematol.* 1992, 81, 424-431.

(42) Bergeron, R. J.; Wiegand, J.; McManis, J. S.; Weimar, W. R.; Park, J. H.; Eiler-McManis, E.; Bergeron, J.; Brittenham, G. M. Partition-Variant Desferrithiocin Analogues: Organ Targeting and Increased Iron Clearance. *J. Med. Chem.* 2005, 48, 821-831.

(43) Bergeron, R. J.; Wiegand, J.; McManis, J. S.; Bussenius, J.; Smith, R. E.; Weimar, W. R. Methoxylation of Desazadesferrithiocin Analogues: Enhanced Iron Clearing Efficiency. *J. Med. Chem.* 2003, 46, 1470-1477.

(44) Bergeron, R. J.; Wiegand, J.; Weimar, W. R.; McManis, J. S.; Smith, R. E.; Abboud, K. A. Iron Chelation Promoted by Desazadesferrithiocin Analogs: An Enantioselective Barrier. *Chirality* 2003, 15, 593-599.

(45) Bergeron, R. J.; Wiegand, J.; McManis, J. S.; Bharti, N. Desferrithiocin: A Search for Clinically Effective Iron Chelators. *J. Med. Chem.* 2014, pubs.acs.org/doi/pdf/10.1021/jm500828f.

(46) Donovan, J. M.; Plone, M.; Dagher, R.; Bree, M.; Marquis, J. Preclinical and Clinical Development of Deferitrin, a Novel, Orally Available Iron Chelator. *Ann. N.Y. Acad. Sci.* 2005, 1054, 492-494.

(47) Brittenham, G. M. Pyridoxal Isonicotinoyl Hydrazone (PIH): Effective Iron Chelation after Oral Administration. *Ann. N.Y. Acad. Sci.* 1990, 612, 315-326.

(48) Galanello, R.; Forni, G.; Jones, A.; Kelly, A.; Willemsen, A.; He, X.; Johnston, A.; Fuller, D.; Donovan, J.; Piga, A. A Dose Escalation Study of the Pharmacokinetics, Safety, and Efficacy of Deferitrin, an Oral Iron Chelator in Beta Thalassaemia Patients. *ASH Annu. Meet. Abstr.* 2007, 110, 2669.

(49) Sangster, J. *Octanol-Water Partition Coefficients: Fundamentals and Physical Chemistry*; John Wiley and Sons: West Sussex, England, 1997; Vol. 2.

(50) Bergeron, R. J.; Wiegand, J.; McManis, J. S.; Vinson, J. R. T.; Yao, H.; Bharti, N.; Rocca, J. R. (S)-4,5-Dihydro-2-(2-hydroxy-4-hydroxyphenyl)-4-methyl-4-thiazolecarboxylic Acid Polyethers: A Solution to Nephrotoxicity. *J. Med. Chem.* 2006, 49, 2772-2783.

(51) Bergeron, R. J.; Wiegand, J.; Bharti, N.; Singh, S.; Rocca, J. R. Impact of the 3,6,9-Trioxadecyloxy Group on Desazadesferrithiocin Analogue Iron Clearance and Organ Distribution. *J. Med. Chem.* 2007, 50, 3302-3313.

(52) Bergeron, R. J.; Wiegand, J.; McManis, J. S.; Bharti, N.; Singh, S. Design, Synthesis, and Testing of Non-Nephrotoxic Desazadesferrithiocin Polyether Analogues. *J. Med. Chem.* 2008, 51, 3913-3923.

(53) Rienhoff, H. Y. Jr.; Virakasit, V.; Tay, L.; Harmatz, P.; Vichinsky, E.; Chirnomas, D.; Kwiatkowski, J. L.; Tapper, A.; Kramer, W.; Porter, J. B.; Neufeld, E. J. A Phase-1 Dose-Escalation Study: Safety, Tolerability, and Pharmacokinetics of FBS0701, a Novel Oral Iron Chelator for the Treatment of Transfusional Overload. *Haematologica.* 2011, 96, 521-525.

(54) Neufeld, E. J.; Galanello, R.; Viprakasit, V.; Aydinok, Y.; Piga, A.; Harmatz, P.; Forni, G. L.; Shah, F. T.; Grace, R E. F.; Porter, J. B.; Wood, J. C.; Peppe, J. Jones, A.; Rienhoff, H. Y. Jr. A Phase 2 Study of the Safety, Tolerability, and Pharmacodynamics of FBS0701, a Novel Oral Iron Chelator, in Transfusional Iron Overload. *Blood* 2012, 119, 3263-3268.

(55) Suk, O. J. Paradoxical Hypomagnesemia Caused by Excessive Ingestion of Magnesium Hydroxide. *Am. J. Emerg. Med.* 2008, 26, 837.e1-837.e2.

(56) Durlach, J.; Durlach, V.; Bac, P.; Bara, M.; Guiet-Bara, A. Magnesium and Therapeutics. *Magnes. Res.* 1994, 7, 313-328.

(57) Randall, R. E. Jr. Magnesium Toxicity. *Ann. Intern. Med.* 1963, 58, 744.

(58) Bergeron, R. J.; Wiegand, J.; Bharti, N.; McManis, J. S.; Singh, S. Desferrithiocin Analogue Iron Chelators: Iron Clearing Efficiency, Tissue Distribution, and Renal Toxicity. *Biometals* 2011, 24, 239-258.

(59) Bergeron, R. J.; Bharti, N.; Wiegand, J.; McManis, J. S.; Singh, S.; Abboud, K. A. The Impact of Polyether Chain Length on the Iron Clearing Efficiency and Physiochemical Properties of Desferrithiocin Analogues. *J. Med. Chem.* 2010, 53, 2843-2853.

(60) Han, W. K.; Bailly, V.; Abichandani, R.; Thadhani, R.; Bonventre, J. V. Kidney Injury Molecule-1 (KIM-1): A Novel Biomarker for Human Renal Proximal Tubule Injury. *Kidney Int.* 2002, 62, 237-244.

(61) Bonventre, J. V. Kidney Injury Molecule-1 (KIM-1): A Urinary Biomarker and Much More. *Nephrol. Dial. Transpl.* 2009, 24, 3265-3268.

(62) Zhou, Y.; Vaidya, V. S.; Brown, R. P.; Zhang, J.; Rosenzweig, B. A.; Thompson, K. L.; Miller, T. J.; Bonventre, J. V.; Goering, P. L. Comparison of Kidney Injury Molecule-1 and Other Nephrotoxicity Biomarkers in Urine and Kidney Following Acute Exposure to Gentamicin, Mercury, and Chromium. *Toxicol. Sci.* 2008, 101, 159-170.

(63) Vaidya, V. S.; Ramirez, V.; Ichimura, T.; Bobadilla, N. A.; Bonventre, J. V. Urinary Kidney Injury Molecule-1: A Sensitive Quantitative Biomarker for Early Detection of Kidney Tubular Injury. *Am. J. Physiol. Renal Physiol.* 2006, 290, F517-F529.

(64) Rosse, G. Metabolites of the Pyrimidine Amine Preladenant as Adenosine A2a Receptor Antagonists. *ACS Med. Chem. Lett.* 2013, 4, 5-6.

(65) Zhao, M.; He, P.; Rudek, M. A.; Hidalgo, M.; Baker, S. D. Specific Method for Determination of OSI-774 and its Metabolite OSI-420 in Human Plasma by Using Liquid Chromatography-Tandem Mass Spectrometry. *J. Chromatogr.* 2003, 793, 413-420.

(66) Platzer, R.; Galeazzi, R. L.; Karlaganis, G.; Bircher, J. Rate of Drug Metabolism in Man Measured by $^{14}CO_2$-Breath Analysis. *Europ. J. Clin. Pharmacol.* 1978, 14, 293-299.

(67) Li, X.-Q.; Zhong, D.-F.; Huang, H.-H.; Wu, S.-D. Demethylation Metabolism of Roxithromycin in Humans and Rats. *Acta Pharmacol. Sin.* 2001, 22, 469-474.

(68) Zeng, Z.; Andrew, N. W.; Halley, B. A. Identification of Cytochrome P4503A as the Major Enzyme Sub-Family Responsible for the Metabolism of 22, 23-Dihydro-13-O-[(2-methoxyethoxy)methyl]-Avermectin $B_1$ Aglycone by Rat Liver Microsomes. *Xenobiotica* 1997, 27, 985-994.

(69) He, H.; Jenkins, K.; Lin, C. A Fluorescent Chemosensor for Calcium with Excellent Storage Stability in Water. *Anal. Chim. Acta* 2008, 197-204.

(70) Jouany, M.; Coustal, S.; Frappier, F.; Marquet, A. Novel Synthesis of Dethiobiotin. *J. Chem. Research (S)* 1982, 114.

(71) Doláková, P.; Dračínský, M.; Fanfrlík, J.; Hol, A. Synthesis of Analogues of Acyclic Nucleoside Diphosphates Containing a (Phosphonomethyl)phosphanyl Moiety and Studies of Their Phosphorylation. *Eur. J. Org. Chem.* 2009, 1082-1092.

(72) Bergeron, R. J.; Wiegand, J.; McManis, J. S.; Bharti, N.; Singh, S. Desferrithiocin Analogues and Nephrotoxicity. *J. Med. Chem.* 2008, 51, 5993-6004.

(73) Dover, G. J.; Brusilow, S.; Samid, D. Increased Fetal Hemoglobin in Patients Receiving Sodium 4-Phenylbutyrate. *N. Engl. J. Med.* 1992, 327, 569-570.

(74) Bergeron, R. J.; Wiegand, J.; Brittenham, G. M. HBED: A Potential Alternative to Deferoxamine for Iron-Chelating Therapy. *Blood.* 1998, 91, 1446-1452.

(75) Bergeron, R. J.; Wiegand, J.; Ratliff-Thompson, K.; Weimar, W. R. The Origin of the Differences in (R)- and (S)-Desmethyldesferrithiocin: Iron-Clearing Properties. *Ann. N.Y. Acad. Sci.* 1998, 850, 202-216.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

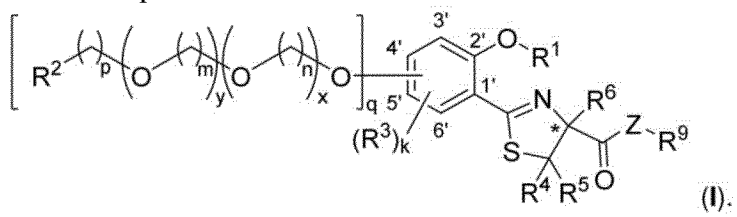

What is claimed is:

1. A compound of Formula (I):

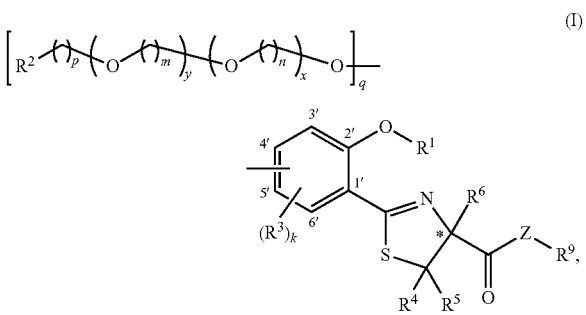

or a pharmaceutically acceptable salt thereof, wherein:
$R^1$ is hydrogen, substituted or unsubstituted alkyl, substituted or unsubstituted acyl, an oxygen protecting group,

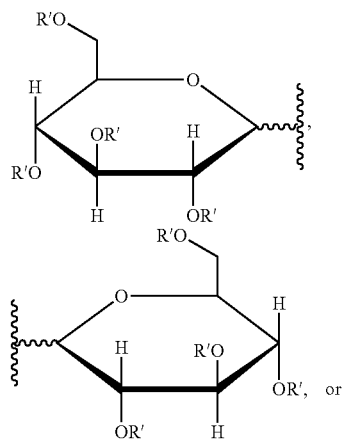

-continued

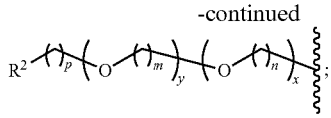

each instance of R' is independently hydrogen, substituted or unsubstituted alkyl, or an oxygen protecting group;
each instance of x is independently 0;
each instance of y is independently 0;
each instance of p is independently an integer between 1 and 10, inclusive;
q is 0 or 1, provided that when q is 0, then $R^1$ is of the formula:

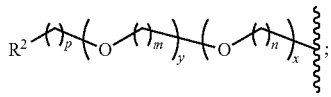

each instance of $R^2$ is independently —C(=O)OH, or —C(=O)OR$^{2a}$, wherein each instance of $R^{2a}$ is independently substituted or unsubstituted alkyl or an oxygen protecting group;
each instance of $R^3$ is independently halogen, substituted or unsubstituted alkyl, or —OR$^8$, wherein each instance of $R^8$ is independently hydrogen, substituted or unsubstituted alkyl, substituted or unsubstituted acyl, an oxygen protecting group,

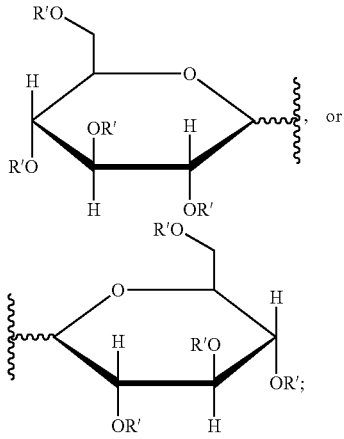

k is 0, 1, 2, 3, or 4;
$R^4$ is hydrogen or substituted or unsubstituted alkyl;
$R^5$ is hydrogen or substituted or unsubstituted alkyl;
$R^6$ is hydrogen or substituted or unsubstituted alkyl;
Z is —O— or —S—; and
$R^9$ is hydrogen, substituted or unsubstituted alkyl,

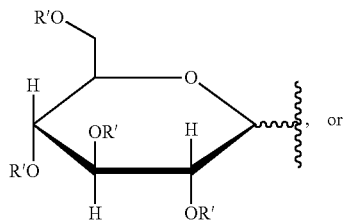

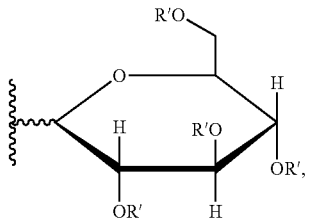

an oxygen protecting group when attached to an oxygen atom, or a sulfur protecting group when attached to a sulfur atom.

2. The compound of claim 1, wherein the compound is of the formula:

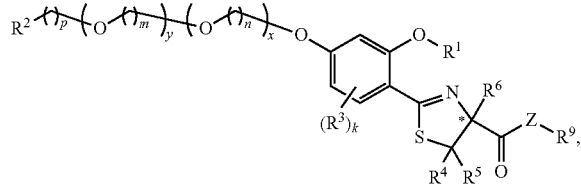

or a pharmaceutically acceptable salt thereof.

3. The compound of claim 2, wherein the compound is of the formula:

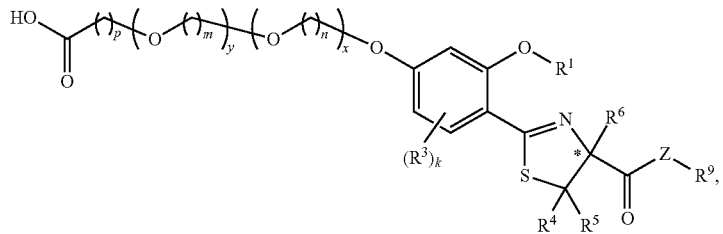

or a pharmaceutically acceptable salt thereof.

4. The compound of claim 2, wherein the compound is of the formula:

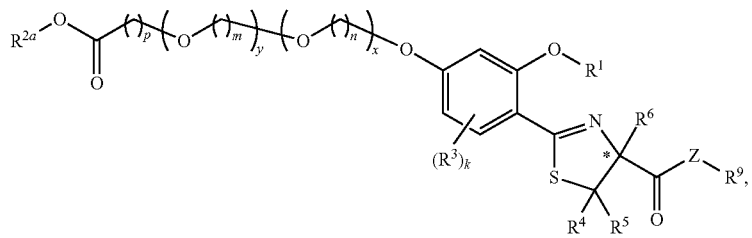

or a pharmaceutically acceptable salt thereof.

5. The compound of claim 1, wherein the compound is of the formula:

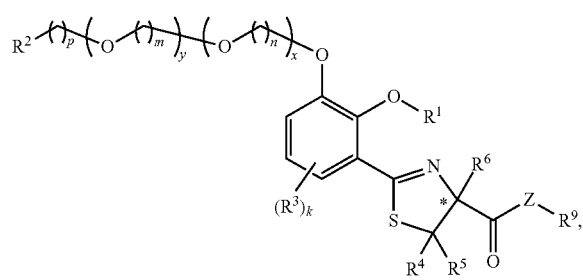

or a pharmaceutically acceptable salt thereof.

6. The compound of claim 1, wherein at least one instance of p is 1, 2, 3, 4, or 5.

7. The compound of claim 1, wherein at least one instance of $R^2$ is —C(=O)OH.

8. The compound of claim 1, wherein at least one instance of $R^2$ is —C(=O)OR$^{2a}$.

9. A compound of the formula:

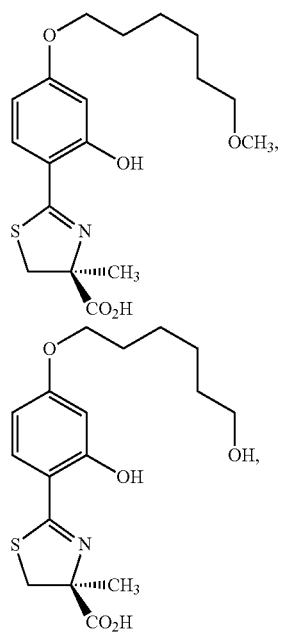

-continued

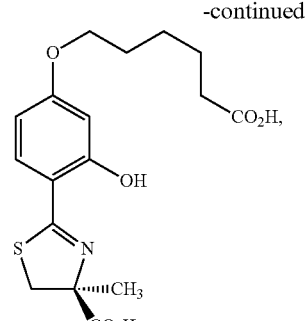

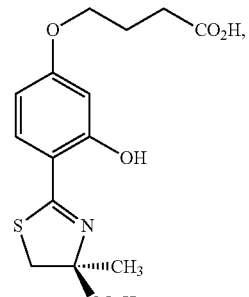 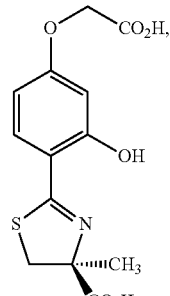

or a pharmaceutically acceptable salt thereof.

10. The compound of claim 1, wherein the pharmaceutically acceptable salt is a pharmaceutically acceptable alkali or alkaline earth metal salt.

11. A pharmaceutical composition comprising a compound of claim 1 and optionally a pharmaceutically acceptable excipient.

12. A method of treating a disease in a subject in need thereof, the method comprising administering to the subject an effective amount of a compound of claim 1, wherein the disease is iron overload, aluminum overload, lanthanide overload, actinide overload, oxidative stress, transfusional iron overload, thalassemia, primary hemochromatosis, secondary hemochromatosis, diabetes, liver disease, heart disease, cancer, radiation injury, neurological or neurodegenerative disorder, Friedreich's ataxia (FRDA), macular degeneration, closed head injury, irritable bowel disease, reperfusion injury, an infectious disease, or metal poisoning.

13. A method of reducing the formation of biofilms in a subject in need thereof, the method comprising administering to the subject an effective amount of a compound of claim 1.

14. The compound of claim 2, wherein the compound is of the formula:

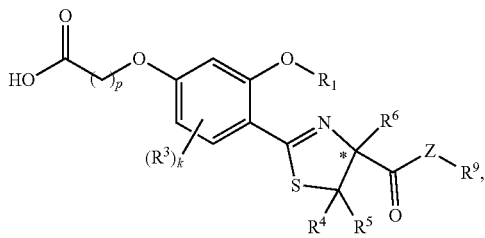

or a pharmaceutically acceptable salt thereof.

15. The compound of claim 1, wherein each of $R^4$ and $R^5$ is hydrogen.

16. The compound of claim 1, wherein Z is —O—.

17. The compound of claim 1, wherein $R^6$ is substituted or unsubstituted $C_{1-6}$ alkyl.

18. The compound of claim 1, wherein p is 3.

19. The compound of claim 1, wherein $R^9$ is hydrogen.

20. A compound of Formula (I):

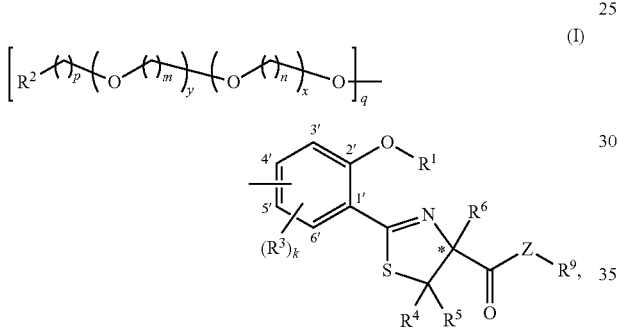

or a pharmaceutically acceptable salt thereof, wherein:
$R^1$ is hydrogen, substituted or unsubstituted alkyl, substituted or unsubstituted acyl, an oxygen protecting group,

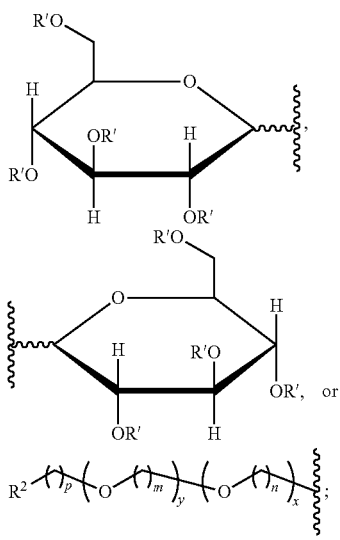

each instance of R' is independently hydrogen, substituted or unsubstituted alkyl, or an oxygen protecting group;

each instance of x is independently 0;
each instance of y is independently 0;
each instance of p is independently 5, 6, 7, 8, 9, or 10;
q is 0 or 1, provided that when q is 0, then $R^1$ is of the formula:

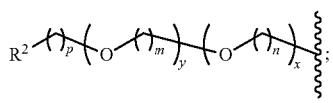

each instance of $R^2$ is independently —CH$_2$OH, —C(=O)OH, or —C(=O)OR$^{2a}$, wherein each instance of $R^{2a}$ is independently substituted or unsubstituted alkyl or an oxygen protecting group;

each instance of $R^3$ is independently halogen, substituted or unsubstituted alkyl, or —OR$^8$, wherein each instance of $R^8$ is independently hydrogen, substituted or unsubstituted alkyl, substituted or unsubstituted acyl, an oxygen protecting group,

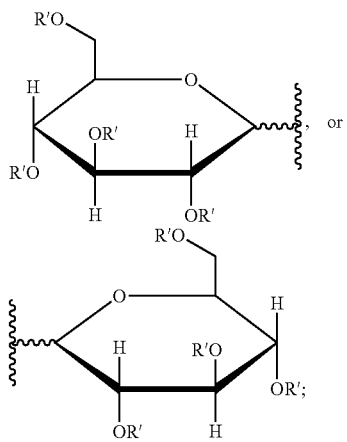

k is 0, 1, 2, 3, or 4;
$R^4$ is hydrogen or substituted or unsubstituted alkyl;
$R^5$ is hydrogen or substituted or unsubstituted alkyl;
$R^6$ is hydrogen or substituted or unsubstituted alkyl;
Z is —O— or —S—; and
$R^9$ is hydrogen, substituted or unsubstituted alkyl,

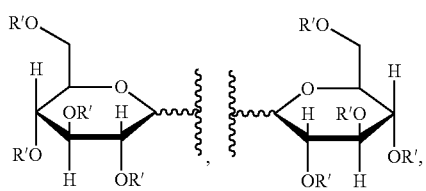

an oxygen protecting group when attached to an oxygen atom, or a sulfur protecting group when attached to a sulfur atom.

* * * * *

UNITED STATES PATENT AND TRADEMARK OFFICE
CERTIFICATE OF CORRECTION

PATENT NO. : 10,570,104 B2  
APPLICATION NO. : 15/569750  
DATED : February 25, 2020  
INVENTOR(S) : Bergeron, Jr.

Page 1 of 2

It is certified that error appears in the above-identified patent and that said Letters Patent is hereby corrected as shown below:

In the Claims

In Claim 1, at Column 150, Lines 30-44, the formula:

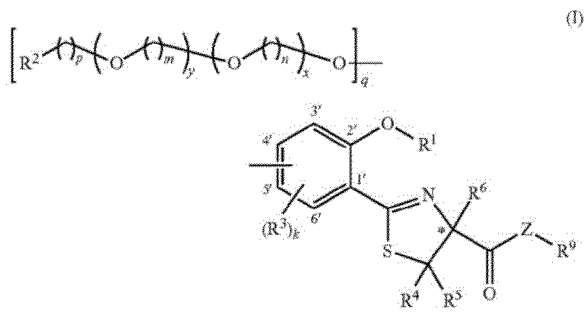

Should be replaced with the formula:

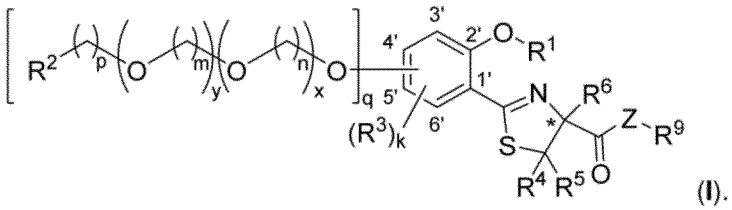

In Claim 14, at Column 155, in Lines 3-14, the formula:

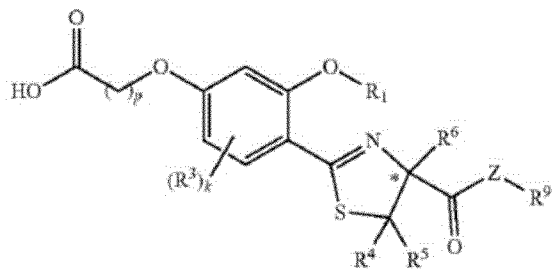

Signed and Sealed this  
Twenty-first Day of December, 2021

Drew Hirshfeld  
*Performing the Functions and Duties of the*  
*Under Secretary of Commerce for Intellectual Property and*  
*Director of the United States Patent and Trademark Office*

CERTIFICATE OF CORRECTION (continued)
U.S. Pat. No. 10,570,104 B2

Should be replaced with the formula:

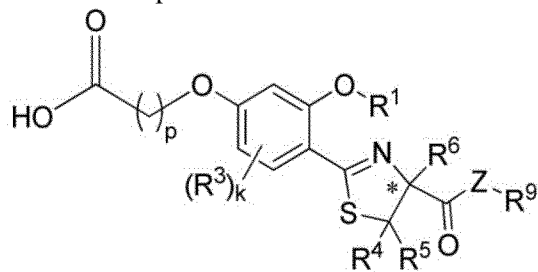

In Claim 20, at Column 155, Lines 25-38, the formula:

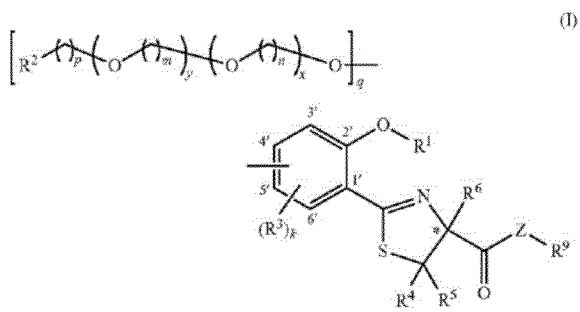

Should be replaced with the formula: